US012091412B2

(12) United States Patent
Bettigole et al.

(10) Patent No.: US 12,091,412 B2
(45) Date of Patent: Sep. 17, 2024

(54) HETEROCYCLIC INHIBITORS OF ENPP1

(71) Applicant: Volastra Therapeutics, Inc., New York, NY (US)

(72) Inventors: Sarah Bettigole, New York, NY (US); Michael Su, New York, NY (US); Derek A. Cogan, New York, NY (US); Leon Van Berkom, Nijmegen (NL); Piotr Nieczypor, Nijmegen (NL); Gydo Van Der Heijden, Nijmegen (NL); Prashanna Vijayachandran, Nijmegen (NL)

(73) Assignee: Volastra Therapeutics, Inc., New York, NY (US)

( * ) Notice: Subject to any disclaimer, the term of this patent is extended or adjusted under 35 U.S.C. 154(b) by 36 days.

(21) Appl. No.: 17/348,607

(22) Filed: Jun. 15, 2021

(65) Prior Publication Data

US 2023/0036933 A1 Feb. 2, 2023

Related U.S. Application Data

(60) Provisional application No. 63/132,322, filed on Dec. 30, 2020, provisional application No. 63/039,923, filed on Jun. 16, 2020.

(51) Int. Cl.
| | | |
|---|---|---|
| *C07D 487/04* | (2006.01) | |
| *C07D 471/04* | (2006.01) | |
| *C07D 519/00* | (2006.01) | |
| *C07F 5/02* | (2006.01) | |
| *C07F 9/6561* | (2006.01) | |

(52) U.S. Cl.
CPC ......... *C07D 487/04* (2013.01); *C07D 471/04* (2013.01); *C07D 519/00* (2013.01); *C07F 5/025* (2013.01); *C07F 9/6561* (2013.01); *C07B 2200/05* (2013.01)

(58) Field of Classification Search
CPC .................................................. C07D 487/04
See application file for complete search history.

(56) References Cited

U.S. PATENT DOCUMENTS

| | | |
|---|---|---|
| 5,846,514 A | 12/1998 | Foster et al. |
| 6,334,997 B1 | 1/2002 | Foster et al. |
| 8,759,400 B2 | 6/2014 | Georgopapadakou et al. |
| 8,796,330 B2 | 8/2014 | Deziel et al. |
| 9,868,749 B2 | 1/2018 | Alexander et al. |
| 11,780,849 B2 | 10/2023 | Cogan et al. |
| 2014/0024608 A1 | 1/2014 | Deziel et al. |
| 2014/0378408 A1 | 12/2014 | Fischet et al. |
| 2019/0201423 A1 | 7/2019 | Deb et al. |
| 2019/0282703 A1 | 9/2019 | Gallatin et al. |
| 2023/0002406 A1 | 1/2023 | Cogan et al. |

FOREIGN PATENT DOCUMENTS

| | | | |
|---|---|---|---|
| CN | 104650116 A1 * | 5/2015 | |
| EP | 1 963 258 | 9/2008 | |
| EP | 2 003 132 | 12/2008 | |
| EP | 2 573 069 | 3/2013 | |
| EP | 3 080 115 | 10/2016 | |
| JP | 2020-015670 | 1/2020 | |
| JP | 2020015670 A * | 1/2020 | |
| WO | WO-1991008211 A1 * | 6/1991 | |
| WO | WO 2007/072179 | 6/2007 | |
| WO | WO 2008/074132 | 6/2008 | |
| WO | WO 2012/032513 | 3/2012 | |
| WO | WO 2012/116137 | 8/2012 | |
| WO | WO 2014/134772 | 9/2014 | |
| WO | WO 2015/086506 | 6/2015 | |
| WO | WO 2016/090296 | 6/2016 | |
| WO | WO 2017/198756 | 11/2017 | |
| WO | WO 2018/119325 | 6/2018 | |
| WO | WO 2019/046778 | 3/2019 | |
| WO | WO 2019/051269 | 3/2019 | |
| WO | WO 2019/149660 | 8/2019 | |
| WO | WO-2019149660 A1 * | 8/2019 | ........... A61K 31/519 |
| WO | WO 2019/177971 | 9/2019 | |
| WO | WO 2019/191504 | 10/2019 | |
| WO | WO 2020/035052 | 2/2020 | |
| WO | WO 2020/140001 | 7/2020 | |
| WO | WO 2020/160333 | 8/2020 | |
| WO | WO 2020/190912 | 9/2020 | |
| WO | WO 2021/061803 | 4/2021 | |
| WO | WO-2021225969 A1 * | 11/2021 | |
| WO | WO 2023/076866 | 5/2023 | |

OTHER PUBLICATIONS

Wislicenus, J. "Adolph Strecker's Short Textbook of Organic Chemistry" 1881, Spottiswoode: London, pp. 38-39.*
STN-Chemical database registry RN 949716-61-4 for N-Hydroxy-5,7-dimethyl[1,2,4]triazolo[1,5-a]pyrimidine-6-propanamide, Entered STN: Oct. 9, 2007, LC STN Files: CHEMCATS.*
STN-Chemical database registry RN 2172070-37-8 for 3-methyl-Imidazo[1,2-a]pyridine-6-sulfonamide, Entered STN: Jan. 31, 2018, LC STN Files: CHEMCATS.*
Zimmermann "Cellular function and molecular structure of ecto-nucleotidases" Purinergic Signalling (2012), 8(3), 437-502.*
Lee "Nucleotide pyrophosphatase/phosphodiesterase 1 (NPP1) and its inhibitors" Med. Chem. Commun., 2017, 8, 823.*
Mornet "Hypophosphatasia" Orphanet Journal of Rare Diseases 2007, 2:40, 1-8.*
Roberts "ENPP1 in the Regulation of Mineralization and Beyond" Trends in Biochemical Sciences, Jul. 2019, vol. 44, No. 7 616-628.*
Bae, Cancer Targeted Drug Delivery, Springer: New York, 2013, p. v.*
Carlo C. Maley and Mel Greaves Frontiers in Cancer Research Springer: 2016, pp. 18-19.*

(Continued)

*Primary Examiner* — David K O'Dell
(74) *Attorney, Agent, or Firm* — MORRISON & FOERSTER LLP

(57) ABSTRACT

The present disclosure relates generally to inhibitors of ectonucleotide pyrophosphatase/phosphodiesterase 1 (ENPP1), compositions thereof, and methods of using said compounds and compositions thereof. More specifically, the present disclosure relates to triazolopyrimidine and imidazolopyrimidine inhibitors of ENPP1 and methods of their use for treating disease mediated by ENPP1.

24 Claims, No Drawings

(56) References Cited

OTHER PUBLICATIONS

Damia "Contemporary pre-clinical development of anticancer agents—What are the optimal preclinical models?" European Journal of Cancer 2009, 45, 2768-2781.*

Sharma "Cell line-based platforms to evaluate the therapeutic efficacy of candidate anticancer agents" Nature Reviews Cancer Apr. 2010, vol. 10, 241-253.*

Ocana, A. "Preclinical development of molecular targeted agents for cancer" Nat. Rev. Clin. Oncol. 2011, 8, 200-209.*

Ledford "US cancer institute overhauls cell lines" Nature Feb. 25, 2016 vol. 530 p. 391.*

Johnson, et al. "Relationships between drug activity in NCI preclinical in vitro and in vivo models and early clinical trials." British Journal of Cancer 2001, 84, 1424-1431.*

Muller and Kräusslich in "Antiviral Strategies" Handbook of Experimental Pharmacology 2009, vol. 189 Chapter 1, pp. 1-24.*

Berge et al., "Pharmaceutical Salts," J Pharmaceutical Sciences (1977) 66(1):1-19.

Carozza et al., "Structure-Aided Development of Small-Molecule Inhibitors of ENPP1, the Extracellular Phosphodiesterase of the Immunotransmitter cGAMP," Cell Chem Biol (2020) 27:1347-1358.

Danino et al., "Inhibition of nucleotide pyrophosphatase/ phosphodiesterase 1: implications for developing a calcium pyrophosphate deposition disease modifying drug," Rheumatology (2018) 57:1472-1480.

Dean et al., "Recent Advances in the Synthesis and Applications of Radiolabeled Compounds for Drug Discovery and Development," Curr Pharm Des (2000) 6(10).

Dennis et al., "Crystal structures of human ENPP1 in apo and bound forms," Acta Crystallogr Sect D 76, 889-898 (2020).

Evans et al., "Synthesis of radiolabeled compounds," J Radioanal Xhem (1981) 64(1-2):9-32.

Hessle et al., "Tissue-nonspecific alkaline phosphatase and plasma cell membrane glycoprotein-1 are central antagonistic regulators of bone mineralization," PNAS (2002) 99(14):9445-9449.

Jafari et al., Synthesis of 2-arylated thiadiazolopyrimidones by Suzuki-Miyaura cross-coupling: a new class of nucleotide pyrophosphatase (NPPs) inhibitors. Rsc Adv 6:107556-107571 (2016).

Kabalka et al., "The Synthesis of Radiolabeled Compounds via Organometallic Intermediates," Tetrahedron (1989) 45(21): 6601-21.

Kawaguchi et al., "Development of an ENPP1 Fluorescence Probe for Inhibitor Screening, Cellular Imaging, and Prognostic Assessment of Malignant Breast Cancer," Journal of Medicinal Chemistry (2019) 62(20), 9254-9269.

Lee et al., "Substrate-dependence of competitive nucleotide pyrophosphatase/phosphodiesterase1 (NPP1) inhibitors," Frontiers Pharma (2017) 8:Article 54.

Mardjuki et al., "Development of cGAMP-Luc, a sensitive and precise coupled enzyme assay to measure cGAMP in complex biological samples," J Biol Chem (2020) 295(15):4881-4892.

Onyedibe et al., "ENPP1, an Old Enzyme with New Functions, and Small Molecule Inhibitors-A STING in the Tale of ENPP1," Molecules (2019) 24:4192.

Patel et al., "Quinazolin-4-Piperidin-4-Methyl Sulfamide PC-1 Inhibitors: Alleviating HERG Interactions through Structure Based Design," Bioorganic Med. Chem. Lett. (2009) 19 (12):3339-3343.

Rosenthal et al., "Calcium Pyrophosphate Deposition Disease," N Engl J Med (2016) 374(26):2575-2584.

Shayhidin et al., "Quinazoline-4-Piperidine Sulfamides Are Specific Inhibitors of Human NPP1 and Prevent Pathological Mineralization of Valve Interstitial Cells," Br. J. Pharmacol. (2015) 172 (16): 4189-4199.

Ullah et al., "Synthesis, biological evaluation, and docking studies of new pyrazole-based thiourea and sulfonamide derivatives as inhibitors of nucleotide pyrophosphatase/phosphodiesterase," Bioorg Chem (2020) 99:103783.

Zelikman et al., "Highly Selective and Potent Ectonucleotide Pyrophosphatase-1 (NPP1) Inhibitors Based on Uridine 5'-P α,α -Dithiophosphate Analogues," J Med Chem (2018) 61:3939-3951.

* cited by examiner

HETEROCYCLIC INHIBITORS OF ENPP1

CROSS-REFERENCE TO RELATED APPLICATIONS

This application claims priority to and the benefit of U.S. Provisional Application No. 63/039,923, filed on Jun. 16, 2020, and U.S. Provisional Application No. 63/132,322, filed on Dec. 30, 2020, the disclosures of each of which are incorporated herein by reference in their entireties.

FIELD

The present disclosure relates generally to inhibitors of ectonucleotide pyrophosphatase/phosphodiesterase 1 (ENPP1), compositions thereof, and methods of using said compounds and compositions thereof. More specifically, the present disclosure relates to triazolopyrimidine and imidazolopyrimidine inhibitors of ENPP1 and methods of their use for treating disease mediated by ENPP1.

BACKGROUND

In certain human diseases, maintenance of the phosphorylated nucleotides can be dysregulated resulting in poor outcomes, severe complications, and even death. Ectonucleotide Pyrophosphatase/Phosphodiesterase 1 (ENPP1), also known as ARHR2, COLED, M6S1, NPP1, NPPS, PC-1, PCA1 and PDNP1, is an enzyme that hydrolyzes phosphorylated nucleotides, including adenosine triphosphate (ATP) and 2',3'-cyclic adenosine monophosphate-guanidine monophosphate (cGAMP). In some cases, ENPP1 consumes substrates preventing their role in resolving disease. The concomitant increase in hydrolysis products can also have detrimental effects. Therefore, inhibitors of ENNP1's enzyme activity will have a beneficial effect in certain human diseases.

Cells detecting aberrant DNA in the cytosol generate cGAMP, which is an activator of the immune response via the STING pathway. ATP activates immune cells via purinergic receptor signaling. ENPP1 can be expressed as a mechanism to degrade cGAMP and ATP and evade the immune response. Such expression of ENPP1 has been identified in cancers with especially poor prognosis. Therefore, ENPP1 inhibition can be an effective treatment in cancers, especially in cases where ENPP1 expression is high or cytosolic DNA levels are elevated. Adenosine monophosphate (AMP) is also a product of both ATP and cGAMP hydrolysis. Adenosine is generated from AMP by enzymes such as CD73, and further suppresses the immune response and supports tumor survival by adenosine receptor pathways.

ENPP1 has also been implicated in bacterial or viral infections, insulin resistance and type II diabetes, chondrocalcinosis, calcium pyrophosphate deposition disorder (CPPD), or hypophosphatasia. Therefore, ENPP1 inhibition can be used to treat any of these disorders.

BRIEF SUMMARY

The present disclosure provides compounds of Formula (I), compositions thereof, and methods of using said compounds and compositions thereof for the treatment of diseases or conditions associated with ENPP1. In one aspect, provided is a compound of Formula (I)

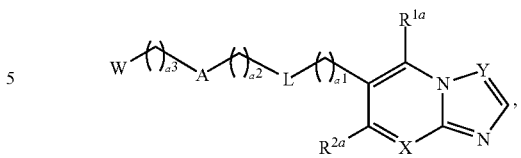

(I)

or a pharmaceutically acceptable salt thereof, wherein: X is —N— or —CR$^{3a}$—; Y is —N— or —CR$^{4a}$—; R$^{1a}$ is hydrogen, halogen, cyano, C$_{1-3}$ alkyl, C$_{1-3}$ haloalkyl, —NR$^{1b}$R$^{2b}$, aryl, heteroaryl, cycloalkyl, cycloalkenyl, heterocycloalkyl, or heterocycloalkenyl, wherein the C$_{1-3}$ alkyl, aryl, heteroaryl, cycloalkyl, cycloalkenyl, heterocycloalkyl, or heterocycloalkenyl of R$^{1a}$ is optionally substituted; R$^{2a}$— R$^{4a}$ are each independently hydrogen, halogen, cyano, optionally substituted C$_{1-3}$ alkyl, C$_{1-3}$ haloalkyl, —NR$^{7b}$R$^{8b}$, cycloalkyl, or —OR$^{3b}$; L is a bond, —O—, —C(O)—, —NR$^{4b}$—, or —CR$^{5b}$R$^{6b}$—; A is a bond, aryl, heteroaryl, cycloalkyl, cycloalkenyl, heterocycloalkyl, or heterocycloalkenyl, each of which is optionally substituted; R$^{1b}$ and R$^{2b}$ are each independently hydrogen, optionally substituted C$_{1-3}$ alkyl, or cycloalkyl; R$^{3b}$—R$^{8b}$ are each independently hydrogen or optionally substituted C$_{1-3}$ alkyl; W is

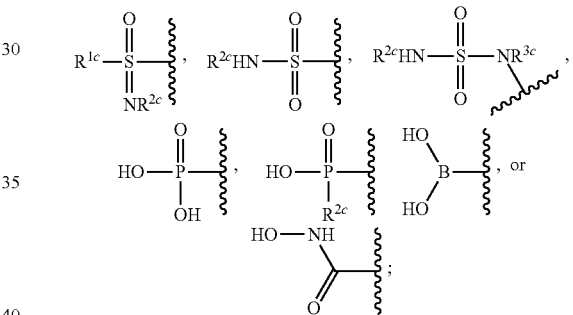

R$^{1c}$ is hydrogen, —NHR$^{1d}$, optionally substituted C$_{1-3}$ alkyl, C$_{1-3}$ haloalkyl, cycloalkyl, or heterocycloalkyl; R$^{2c}$, R$^{3c}$, and R$^{1d}$ are each independently hydrogen or optionally substituted C$_{1-3}$ alkyl; and a$^1$, a$^2$, and a$^3$ are each independently 0, 1, or 2.

In another aspect, provided are compounds of Formula (I-4):

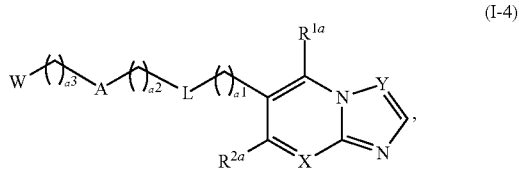

(I-4)

or a pharmaceutically acceptable salt thereof, wherein: X is —N— or —CR$^{3a}$—; Y is —N— or —CR$^{4a}$—; R$^{1a}$ is hydrogen, halogen, cyano, C$_{1-3}$ alkyl, C$_{1-3}$ haloalkyl, —NR$^{1b}$R$^{2b}$, aryl, heteroaryl, cycloalkyl, cycloalkenyl, heterocycloalkyl, or heterocycloalkenyl, wherein the C$_{1-3}$ alkyl, aryl, heteroaryl, cycloalkyl, cycloalkenyl, heterocycloalkyl, or heterocycloalkenyl of R$^{1a}$ is optionally substituted, wherein the C$_{1-3}$ alkyl is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, $-NR^{1a1}R^{1a2}$; $-OR^{1a3}$, $-NR^{1a4}C(O)R^{1a5}$, and $-C(O)OR^{1a6}$, wherein $R^{1a1}$-$R^{1a6}$ are each independently hydrogen or $C_{1-6}$ alkyl; $R^{2a}$ is hydrogen, halogen, cyano, optionally substituted $C_{1-3}$ alkyl, $C_{1-3}$ haloalkyl, $-NR^{7b}R^{8b}$, cycloalkyl, or $-OR^{3b}$; $R^{3a}$ is hydrogen, halogen, cyano, $C_{1-3}$ alkyl, $C_{1-3}$ haloalkyl, $-NR^{9b}R^{10b}$, cycloalkyl, or $-OR^{11b}$, wherein the $C_{1-3}$ alkyl is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, $-NR^{3a1}R^{3a2}$, $-OR^{3a3}$, $-NR^{3a4}C(O)R^{3a5}$, and $-C(O)OR^{3a6}$, wherein $R^{3a1}$-$R^{3a6}$ are each independently hydrogen or $C_{1-6}$ alkyl; $R^{4a}$ is hydrogen, halogen, cyano, $C_{1-3}$ alkyl, $C_{1-3}$ haloalkyl, $-NR^{12b}R^{13b}$ or $-OR^{14b}$, wherein the $C_{1-3}$ alkyl is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, $-NR^{4a1}R^{4a2}$; $-OR^{4a3}$; $-NR^{4a4}C(O)R^{4a5}$, and $-C(O)OR^{4a6}$, wherein $R^{4a1}$-$R^{4a6}$ are each independently hydrogen or $C_{1-6}$ alkyl; L is a bond, $-O-$, $-NR^{4b}-$, or $-CR^{5b}R^{6b}-$; A is a bond, aryl, heteroaryl, cycloalkyl, cycloalkenyl, heterocycloalkyl, or heterocycloalkenyl, each of which is optionally substituted with one, two, three, four, five, or more substituents selected from the group consisting of deuterium, halo, cyano, $C_{1-6}$ alkyl, $C_{3-10}$ cycloalkyl, $C_{3-10}$ cycloalkenyl, 3- to 18-membered heterocycloalkyl, $-NR^{41}R^{42}$; $-OR^{43}$; $-NR^{44}C(O)R^{45}$; and $-C(O)OR^{46}$, wherein $R^{41}-R^{46}$ are each independently hydrogen or $C_{1-6}$ alkyl; $R^{1b}$ and $R^{2b}$ are each independently hydrogen, optionally substituted $C_{1-3}$ alkyl, or cycloalkyl; $R^{3b}$-$R^{14b}$ are each independently hydrogen or optionally substituted $C_{1-3}$ alkyl; W is

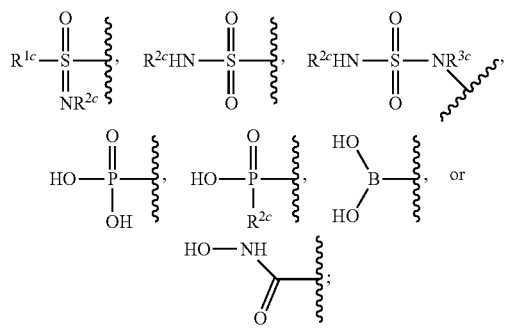

$R^{1c}$ is hydrogen, $-NHR^{1d}$ optionally substituted $C_{1-3}$ alkyl, $C_{1-3}$ haloalkyl, cycloalkyl, or heterocycloalkyl; $R^{2c}$, $R^{3c}$, and $R^{1d}$ are each independently hydrogen or optionally substituted $C_{1-3}$ alkyl; and $a^1$, $a^2$, and $a^3$ are each independently 0, 1, or 2, wherein when A is a bond and L is a bond, then $a^1$ is 1 or 2; and wherein when W is

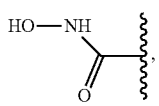

then A is not a bond and X is not CH.

In another aspect, provided is pharmaceutical composition comprising a compound of Formula (I), or a pharmaceutically acceptable salt thereof, and a pharmaceutically acceptable carrier or excipient.

In another aspect, provided is a method of inhibiting ENPP1 comprising contacting a cell with an effective amount of a compound of Formula (I), or a pharmaceutically acceptable salt thereof.

In another aspect, provided is a method of treating cancer, a bacterial and/or viral infection, insulin resistance, type II diabetes, chondrocalcinosis, calcium pyrophosphate deposition disorder (CPPD), or hypophosphatasia, in a subject in need thereof, comprising administering to the subject a therapeutically effective amount of a compound of Formula (I), or a pharmaceutically acceptable salt thereof.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown but are to be accorded the scope consistent with the claims.

As used in the present specification, the following words and phrases are generally intended to have the meanings as set forth below, except to the extent that the context in which they are used indicates otherwise.

Throughout this application, unless the context indicates otherwise, references to a compound of Formula (I) includes all subgroups of Formula (I) defined herein, such as Formula (I-1), (I-2), (I-3), (I-4), (Ia), (Ia1), (Ia2), (Ia3), (Ia4), (Ib), (Ib1), (Ic), (Ic1), (Id), (Ie), (If), or (Ig), including all substructures, subgenera, preferences, embodiments, examples and particular compounds defined and/or described herein. In some embodiments, references to a compound of Formula (I) and subgroups thereof, such as Formula (I-1), (I-2), (I-3), (I-4), (Ia), (Ia1), (Ia2), (Ia3), (Ia4), (Ib), (Ib1), (Ic), (Ic1), (Id), (Ie), (If), or (Ig), include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of Formula (I) and subgroups thereof, such as Formula (I-1), (I-2), (I-3), (I-4), (Ia), (Ia1), (Ia2), (Ia3), (Ia4), (Ib), (Ib1), (Ic), (Ic1), (Id), (Ie), (If), or (Ig), include polymorphs, solvates, co-crystals, isomers, tautomers and/or oxides thereof. In some embodiments, references to a compound of Formula (I) and subgroups thereof, such as Formula (I-1), (I-2), (I-3), (I-4), (Ia), (Ia1), (Ia2), (Ia3), (Ia4), (Ib), (Ib1), (Ic), (Ic1), (Id), (Ie), (If), or (Ig), include polymorphs, solvates, and/or co-crystals thereof. In some embodiments, references to a compound of Formula (I) and subgroups thereof, such as Formula (I-1), (I-2), (I-3), (I-4), (Ia), (Ia1), (Ia2), (Ia3), (Ia4), (Ib), (Ib1), (Ic), (Ic1), (Id), (Ie), (If), or (Ig), include isomers, tautomers and/or oxides thereof. In some embodiments, references to a compound of Formula (I) and subgroups thereof, such as Formula (I-1), (I-2), (I-3), (I-4), (Ia), (Ia1), (Ia2), (Ia3), (Ia4), (Ib), (Ib1), (Ic), (Ic1), (Id), (Ie), (If), or (Ig), include solvates thereof.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Aryl" indicates an aromatic carbocyclic ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl," as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluoro, chloro, bromo or iodo.

"Haloalkyl" refers to alkyl substituted with one or more halogen. A haloalkyl group may have a halogen substituent at any valence-permitted location on the alkyl and may have any number of halogen substituents ranging from one to the maximum valence-permitted number. Particular haloalkyl groups have 1, 2, or 3 halogen substituents. Examples of haloalkyl groups include, but are not limited to, —$CH_2F$, —$CHF_2$, —$CF_3$, —$CH_2CH_2F$, —$CH_2CHF_2$, —$CH_2CF_3$, —$CH_2C_1$, —$CHCl_2$, —$CCl_3$, —$CH_2CH_2C_1$, —$CH_2CHCl_2$, —$CH_2CCl_3$.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocycloalkyl, heterocycloalkenyl, aralkyl, aminosulfonyl, sulfonylamino, sulfonyl, oxo and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^2H$, $^3H$, $^{11}C$, $^{13}C$ and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, Curr. Pharm. Des., 2000; 6(10); Kabalka, G. et al., The Synthesis of Radiolabeled Compounds via Organometallic Intermediates, Tetrahedron, 1989, 45(21), 6601-21; and Evans, E., Synthesis of radiolabeled compounds, J. Radioanal. Chem., 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient, individual, or subject is a human, for example a human that has been or will be the object of treatment, observation or experiment. The compounds, compositions and methods described herein can be useful in both human therapy and veterinary applications.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation (e.g., inhibition) of ENPP1. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat," "treated," "treating") includes one or more of: inhibiting a disease or disorder; slowing or arresting the development of clinical symptoms of a disease or disorder; and/or relieving a disease or disorder (i.e., causing relief from or regression of clinical symptoms). The term covers both complete and partial reduction of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder.

It is understood that embodiments described herein as "comprising" include "consisting of" and "consisting essentially of" embodiments.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (I):

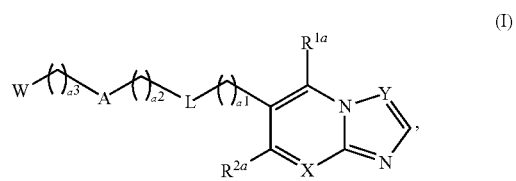

or a pharmaceutically acceptable salt thereof, wherein:

X is —N— or —$CR^{3a}$—;

Y is —N— or —$CR^{4a}$—;

$R^{1a}$ is hydrogen, halogen, cyano, $C_{1-3}$ alkyl, $C_{1-3}$ haloalkyl, —$NR^{1b}R^{2b}$ aryl, heteroaryl, cycloalkyl, cycloalkenyl, heterocycloalkyl, or heterocycloalkenyl, wherein the $C_{1-3}$ alkyl, aryl, heteroaryl, cycloalkyl, cycloalkenyl, heterocycloalkyl, or heterocycloalkenyl of $R^{1a}$ is optionally substituted;

$R^{2a}$—$R^{4a}$ are each independently hydrogen, halogen, cyano, optionally substituted $C_{1-3}$ alkyl, $C_{1-3}$ haloalkyl, —$NR^{7b}R^{8b}$, cycloalkyl, or —$OR^{3b}$;

L is a bond, —O—, —C(O)—, —$NR^{4b}$—, or —$CR^{5b}R^{6b}$—;

A is a bond, aryl, heteroaryl, cycloalkyl, cycloalkenyl, heterocycloalkyl, or heterocycloalkenyl, each of which is optionally substituted;

$R^{1b}$ and $R^{2b}$ are each independently hydrogen, optionally substituted $C_{1-3}$ alkyl, or cycloalkyl;

$R^{3b}$—$R^{8b}$ are each independently hydrogen or optionally substituted $C_{1-3}$ alkyl;

W is

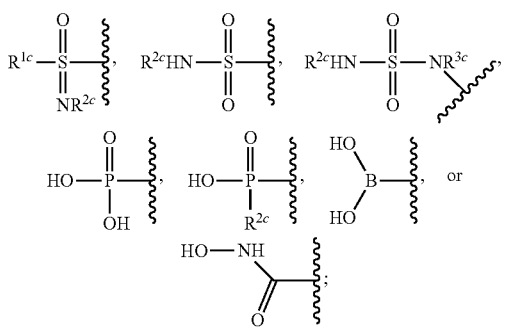

$R^{1c}$ is hydrogen, —$NHR^{1d}$, optionally substituted $C_{1-3}$ alkyl, $C_{1-3}$ haloalkyl, cycloalkyl, or heterocycloalkyl;

$R^{2c}$, $R^{3c}$, and $R^{1d}$ are each independently hydrogen or optionally substituted $C_{1-3}$ alkyl; and $a^1$, $a^2$, and $a^3$ are each independently 0, 1, or 2.

In some embodiments, provided herein is a compound of Formula (I-1)

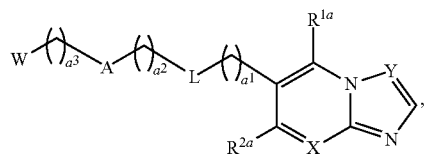

(I-1)

or a pharmaceutically acceptable salt thereof, wherein:
X is —N— or —CR$^{3a}$—;
Y is —N— or —CR$^{4a}$—;
R$^{1a}$ is hydrogen, halogen, cyano, C$_{1-3}$ alkyl, C$_{1-3}$ haloalkyl, —NR$^{1b}$R$^{2b}$ aryl, heteroaryl, cycloalkyl, cycloalkenyl, heterocycloalkyl, or heterocycloalkenyl, wherein the C$_{1-3}$ alkyl, aryl, heteroaryl, cycloalkyl, cycloalkenyl, heterocycloalkyl, or heterocycloalkenyl of R$^{1a}$ is optionally substituted;
R$^{2a}$—R$^{4a}$ are each independently hydrogen, halogen, cyano, optionally substituted C$_{1-3}$ alkyl, C$_{1-3}$ haloalkyl, or —OR$^{3b}$;
L is a bond, —O—, —C(O)—, —NR$^{4b}$—, or —CR$^{5b}$R$^{6b}$—;
A is a bond, aryl, heteroaryl, cycloalkyl, cycloalkenyl, heterocycloalkyl, or heterocycloalkenyl, each of which is optionally substituted;
R$^{1b}$—R$^{6b}$ are each independently hydrogen or optionally substituted C$_{1-3}$ alkyl;
W is

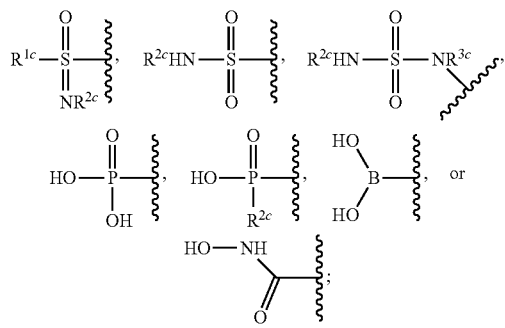

R$^{1c}$ is hydrogen, —NHR$^{1d}$, optionally substituted C$_{1-3}$ alkyl, or C$_{1-3}$ haloalkyl;
R$^{2c}$, R$^{3c}$, and R$^{1d}$ are each independently hydrogen or optionally substituted C$_{1-3}$ alkyl; and
a$^1$, a$^2$, and a$^3$ are each independently 0, 1, or 2.

In some embodiments, provided herein is a compound of Formula (I-2)

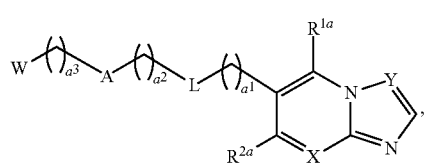

(I-2)

or a pharmaceutically acceptable salt thereof, wherein:
X is —N— or —CR$^{3a}$—;
Y is —N— or —CR$^{4a}$—;
R$^{1a}$ is hydrogen, halogen, cyano, C$_{1-3}$ alkyl, C$_{1-3}$ haloalkyl, —NR$^{1b}$R$^{2b}$, aryl, heteroaryl, cycloalkyl, cycloalkenyl, heterocycloalkyl, or heterocycloalkenyl, wherein the C$_{1-3}$ alkyl, aryl, heteroaryl, cycloalkyl, cycloalkenyl, heterocycloalkyl, or heterocycloalkenyl of R$^{1a}$ is optionally substituted;
R$^{2a}$—R$^{4a}$ are each independently hydrogen, halogen, cyano, optionally substituted C$_{1-3}$ alkyl, C$_{1-3}$ haloalkyl, cycloalkyl, or —OR$^{3b}$;
L is a bond, —O—, —C(O)—, —NR$^{4b}$—, or —CR$^{5b}$R$^{6b}$—,
A is a bond, aryl, heteroaryl, cycloalkyl, cycloalkenyl, heterocycloalkyl, or heterocycloalkenyl, each of which is optionally substituted;
R$^{1b}$ and R$^{2b}$ are each independently hydrogen, optionally substituted C$_{1-3}$ alkyl, or cycloalkyl;
R$^{3b}$—R$^{6b}$ are each independently hydrogen or optionally substituted C$_{1-3}$ alkyl;
W is

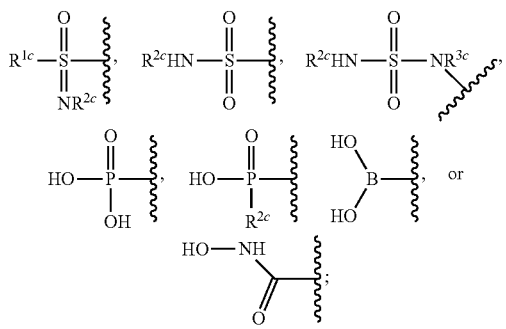

R$^{1c}$ is hydrogen, —NHR$^{1d}$, optionally substituted C$_{1-3}$ alkyl, C$_{1-3}$ haloalkyl, cycloalkyl, or heterocycloalkyl;
R$^{2c}$, R$^{3c}$, and R$^{1d}$ are each independently hydrogen or optionally substituted C$_{1-3}$ alkyl; and
a$^1$, a$^2$, and a$^3$ are each independently 0, 1, or 2.

In one aspect, provided are compounds of Formula (I-3):

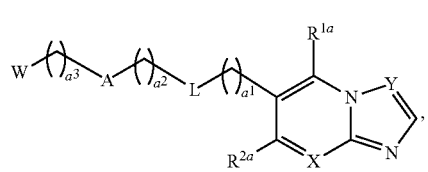

(I-3)

or a pharmaceutically acceptable salt thereof, wherein:
X is —N— or —CR$^{3a}$—;
Y is —N— or —CR$^{4a}$—; R$^{1a}$ is hydrogen, halogen, cyano, C$_{1-3}$ alkyl, C$_{1-3}$ haloalkyl, —NR$^{1b}$R$^{2b}$, aryl, heteroaryl, cycloalkyl, cycloalkenyl, heterocycloalkyl, or heterocycloalkenyl, wherein the C$_{1-3}$ alkyl, aryl, heteroaryl, cycloalkyl, cycloalkenyl, heterocycloalkyl, or heterocycloalkenyl of R$^{1a}$ is optionally substituted;
R$^{2a}$ is —NR$^{7b}$R$^{8b}$;
R$^{3a}$ and R$^{4a}$ are each independently hydrogen, halogen, cyano, optionally substituted C$_{1-3}$ alkyl, C$_{1-3}$ haloalkyl, cycloalkyl, or —OR$^{3b}$;

L is a bond, —O—, —C(O)—, —NR$^{4b}$—, or —CR$^{5b}$R$^{6b}$—;

A is a bond, aryl, heteroaryl, cycloalkyl, cycloalkenyl, heterocycloalkyl, or heterocycloalkenyl, each of which is optionally substituted;

R$^{1b}$ and R$^{2b}$ are each independently hydrogen, optionally substituted C$_{1-3}$ alkyl, or cycloalkyl;

R$^{3b}$—R$^{8b}$ are each independently hydrogen or optionally substituted C$_{1-3}$ alkyl;

W is

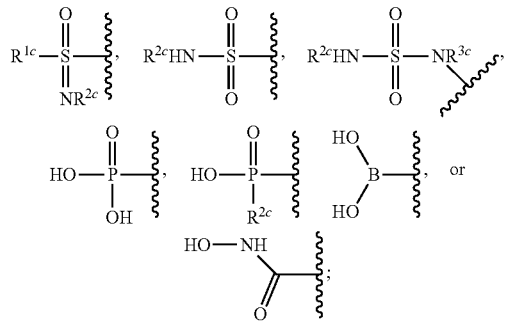

R$^{1c}$ is hydrogen, —NHR$^{1d}$, optionally substituted C$_{1-3}$ alkyl, C$_{1-3}$ haloalkyl, cycloalkyl, or heterocycloalkyl;

R$^{2c}$, R$^{3c}$, and R$^{1d}$ are each independently hydrogen or optionally substituted C$_{1-3}$ alkyl; and a$^1$, a$^2$, and a$^3$ are each independently 0, 1, or 2.

In one aspect, provided are compounds of Formula (I-4):

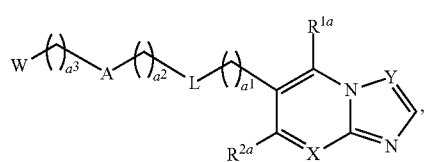

(I-4)

or a pharmaceutically acceptable salt thereof, wherein:

X is —N— or —CR$^{3a}$—;

Y is —N— or —CR$^{4a}$—;

R$^{1a}$ is hydrogen, halogen, cyano, C$_{1-3}$ alkyl, C$_{1-3}$ haloalkyl, —NR$^{1b}$R$^{2b}$ aryl, heteroaryl, cycloalkyl, cycloalkenyl, heterocycloalkyl, or heterocycloalkenyl, wherein the C$_{1-3}$ alkyl, aryl, heteroaryl, cycloalkyl, cycloalkenyl, heterocycloalkyl, or heterocycloalkenyl of R$^{1a}$ is optionally substituted, wherein the C$_{1-3}$ alkyl is optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, —NR$^{1a1}$R$^{1a2}$, —OR$^{1a3}$, —NR$^{1a4}$C(O)R$^{1a5}$, and —C(O)OR$^{1a6}$, wherein R$^{1a1}$—R$^{1a6}$ are each independently hydrogen or C$_{1-6}$ alkyl;

R$^{2a}$ is hydrogen, halogen, cyano, optionally substituted C$_{1-3}$ alkyl, C$_{1-3}$ haloalkyl, —NR$^{7b}$R$^{8b}$, cycloalkyl, or —OR$^{3b}$;

R$^{1a}$ is hydrogen, halogen, cyano, C$_{1-3}$ alkyl, C$_{1-3}$ haloalkyl, —NR$^{9b}$R$^{10b}$, cycloalkyl, or —OR$^{11b}$, wherein the C$_{1-3}$ alkyl is optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, —NR$^{3a1}$R$^{3a2}$, —OR$^{3a3}$, —NR$^{3a4}$C(O)R$^{3a5}$, and —C(O)OR$^{3a6}$, wherein R$^{3a1}$—R$^{3a6}$ are each independently hydrogen or C$_{1-6}$ alkyl;

R$^{4a}$ is hydrogen, halogen, cyano, C$_{1-3}$ alkyl, C$_{1-3}$ haloalkyl, —NR$^{12b}$R$^{13b}$ or —OR$^{14b}$ wherein the C$_{1-3}$ alkyl is optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, —NR$^{4a1}$R$^{4a2}$, —OR$^{4a3}$, —NR$^{4a4}$C(O)R$^{4a5}$, and —C(O)OR$^{4a6}$, wherein R$^{4a1}$—R$^{4a6}$ are each independently hydrogen or C$_{1-6}$ alkyl;

L is a bond, —O—, —NR$^{4b}$—, or —CR$^{5b}$R$^{6b}$—;

A is a bond, aryl, heteroaryl, cycloalkyl, cycloalkenyl, heterocycloalkyl, or heterocycloalkenyl, each of which is optionally substituted with one, two, three, four, five, or more substituents selected from the group consisting of deuterium, halo, cyano, C$_{1-6}$ alkyl, C$_{3-10}$ cycloalkyl, C$_{3-10}$ cycloalkenyl, 3- to 18-membered heterocycloalkenyl, —NR$^{A1}$R$^{A2}$, —OR$^{A3}$, —NR$^{A4}$C(O)R$^{A5}$, and —C(O)OR$^{A6}$, wherein R$^{A1}$—R$^{A6}$ are each independently hydrogen or C$_{1-6}$ alkyl;

R$^{1b}$ and R$^{2b}$ are each independently hydrogen, optionally substituted C$_{1-3}$ alkyl, or cycloalkyl;

R$^{3b}$—R$^{14b}$ are each independently hydrogen or optionally substituted C$_{1-3}$ alkyl;

W is

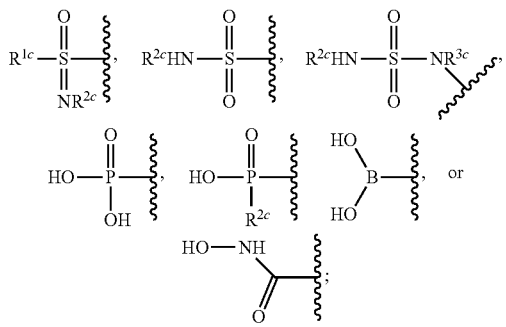

R$^{1c}$ is hydrogen, —NHR$^{1d}$, optionally substituted C$_{1-3}$ alkyl, C$_{1-3}$ haloalkyl, cycloalkyl, or heterocycloalkyl;

R$^{2c}$, R$^{3c}$, and R$^{1d}$ are each independently hydrogen or optionally substituted C$_{1-3}$ alkyl; and a$^1$, a$^2$, and a$^3$ are each independently 0, 1, or 2, wherein when A is a bond and L is a bond, then a$^1$ is 1 or 2; and wherein when W is

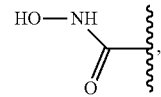

then A is not a bond and X is not CH.

In some embodiments of Formula (I), (I-1), (I-2), (I-3), (I-4), (Ia), (Ia2), (Ia3), (Ia4), (Ib), (Ib1), (Ic), (Ic1), (Id), (Ie), (If), or (Ig), or a pharmaceutically acceptable salt thereof, when $R^{3a}$ is $C_{1-6}$ alkyl, it is not substituted with —$OR^{3a7}$, wherein $R^{3a7}$ is optionally substituted aryl or optionally substituted heteroaryl. In some embodiments, when A is a bond and L is a bond, then $a^1$ is 1 or 2. In some embodiments, when W is

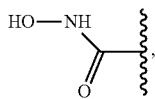

then A is not a bond and X is —N—. In some embodiments, A is not a bond. In some embodiments, L is not a bond. In some embodiments, when W is

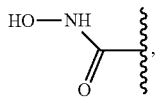

then X is not CH. In some embodiments, when W is

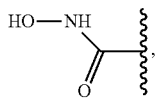

then A is not a bond and X is not CH. In some embodiments, A is not a bond and X is —N—. In some embodiments, X is not CH. In some embodiments, A is not a bond and X is not CH. In some embodiments, A is not spirocyclic.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, the compound is not (βS)-4-[[6-[4-(aminosulfonyl)-2-methylphenyl][1,2,4]triazolo[1,5-a]pyridin-8-yl]methoxy]-β-1-propyn-1-yl-benzenepropanoic acid; (βS)-4-[[6-[4-(aminosulfonyl)-2-methylphenyl][1,2,4]triazolo[1,5-a]pyridin-8-yl]methoxy]-(3-1-propyn-1-yl-benzenepropanoic acid ethyl ester; 2-fluoro-N-methyl-4-[3-[1-(6-quinolinyl)cyclopropyl]imidazo[1,2-a]pyrimidin-6-yl]-benzenesulfonamide; 2-methoxy-N-methyl-5-[3-(4-morpholinylcarbonyl)imidazo[1,2-a]pyridin-6-yl]-benzenesulfonamide; N-methyl-5-[3-(4-morpholinylcarbonyl)imidazo[1,2-a]pyridin-6-yl]-3-Pyridinesulfonamide; 6-(phosphonomethyl)-imidazo[1,2-a]pyridine-3-carboxylic acid; 3,4-dihydro-N-hydroxy-6-(5-methylimidazo[1,2-a]pyridin-6-yl)-spiro[2H-1-benzopyran-2,4'-piperidine]-1'-carboxamide; (2S)-3,4-dihydro-N-hydroxy-1'-imidazo[1,2-a]pyridin-6-yl-2'-oxo-spiro[naphthalene-2(1H),3'-pyrrolidine]-6-carboxamide; (2R)-3,4-dihydro-N-hydroxy-1'-imidazo[1,2-a]pyridin-6-yl-2'-oxo-spiro[naphthalene-2(1H),3'-pyrrolidine]-7-carboxamide; (2R)-3,4-dihydro-N-hydroxy-1'-imidazo[1,2-a]pyridin-6-yl-2'-oxo-spiro[naphthalene-2(1H),3'-pyrrolidine]-6-carboxamide; 1-[3-(5,7-dimethyl[1,2,4]triazolo[1,5-a]pyrimidin-6-yl)-1-oxopropyl]-3-pyrrolidinemethanesulfonamide; 4-(imidazo[1,2-a]pyridin-6-ylcarbonyl)-N-(1-methylethyl)-1-piperazinesulfonamide; N-methyl-1-([1,2,4]triazolo[1,5-a]pyridin-6-ylcarbonyl)-3-piperidinesulfonamide; 1-[3-(5,7-dimethyl[1,2,4]triazolo[1,5-a]pyrimidin-6-yl)-1-oxopropyl]-N-methyl-2-pyrrolidinemethanesulfonamide; 4-(imidazo[1,2-a]pyridin-6-ylcarbonyl)-1-piperazinesulfonamide; N[[1-(imidazo[1,2-a]pyridin-6-ylcarbonyl)-3-piperidinyl]methyl]-sulfamide; 1-(imidazo[1,2-a]pyridin-6-ylcarbonyl)-3-azetidinesulfonamide; 1-(imidazo[1,2-a]pyridin-6-ylcarbonyl)-N-methyl-2-pyrrolidinemethanesulfonamide; N-ethyl-1-([1,2,4]triazolo[1,5-a]pyridin-6-ylcarbonyl)-3-pyrrolidinesulfonamide; 1-[3-(5,7-dimethyl[1,2,4]triazolo[1,5-a]pyrimidin-6-yl)-1-oxopropyl]-N-ethyl-3-pyrrolidinesulfonamide; N-hydroxy-5,7-dimethyl-[1,2,4]triazolo[1,5-a]pyrimidine-6-propanamide; or N-hydroxy-4-(4-imidazo[1,2-a]pyridin-6-ylbutyl)-benzeneacetamide.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, W is

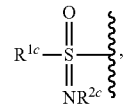

wherein $R^{1c}$ and $R^{2c}$ are as defined for Formula (I) or any variation or embodiment thereof. In some variations, W is

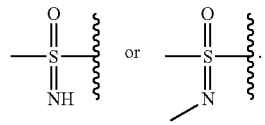

In some variations, W is

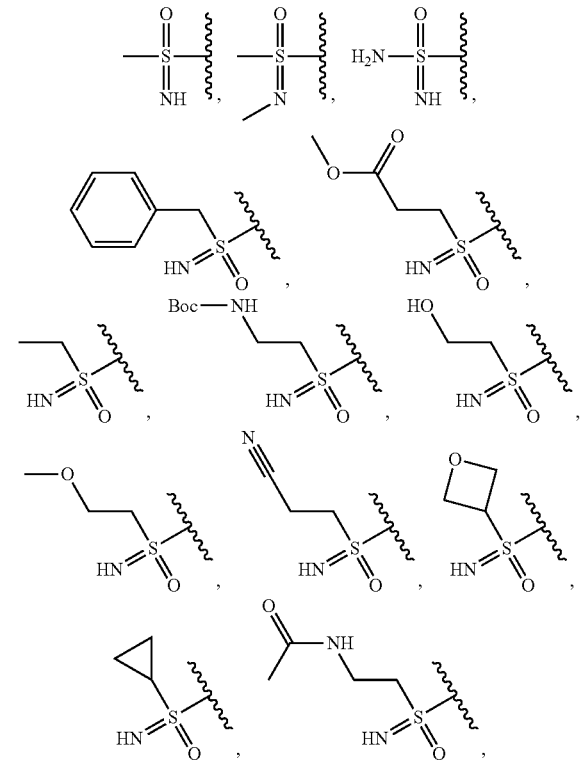

-continued

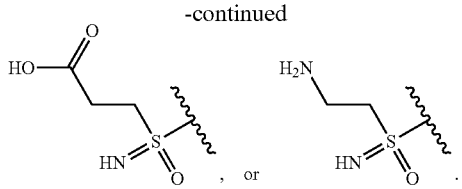

In some variations, W is

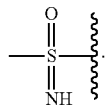

In some embodiments, $R^{1c}$ is optionally substituted $C_{1-3}$ alkyl, and $R^{2c}$ is hydrogen. In some variations, $R^{1c}$ is optionally substituted methyl and $R^{2c}$ is hydrogen. In some variations, $R^{1c}$ is methyl and $R^{2c}$ is hydrogen. In other variations, $R^{1c}$ is methyl substituted by —OH, $C_{1-3}$ alkoxy, —C(=O)OH, —C(=O)—OC$_{1-3}$ alkyl; —NC(=O)—CH$_3$, cyano, or phenyl. In some variations, $R^{1c}$ is methyl. In some variations, $R^{2c}$ is hydrogen. In some variations, $R^{1c}$ is optionally substituted ethyl and $R^{2c}$ is hydrogen. In some variations, In some variations, $R^{1c}$ is ethyl substituted by —OH, $C_{1-3}$ alkoxy, C(=O)OH, —C(=O)—OC$_{1-3}$ alkyl; —NC(=O)—CH$_3$, cyano, or phenyl. In still other embodiments, $R^{1c}$ is cycloalkyl or heterocycloalkyl. In some variations, $R^{1c}$ is cycloalkyl. In certain variations, $R^{1c}$ is cyclopropyl. In other variations, $R^{1c}$ is heterocycloalkyl. In certain variations, $R^{1c}$ is oxetanyl.

In some embodiments, $R^{1c}$ is $C_{1-3}$ alkyl optionally substituted with —OH, $C_{1-3}$ alkoxy, —C(=O)OH, —C(=O)—OC$_{1-3}$ alkyl; —NR$^{1c1}$C(=O)R$^{1c2}$, —NR$^{1c1}$C(=O)OR$^{1c2}$ cyano, or phenyl, wherein $R^{1c1}$ and $R^{1c2}$ are each independently hydrogen or $C_{1-6}$ alkyl. In some embodiments, $R^{1c}$ is $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —NR$^{1c1}$R$^{1c2}$, —OR$^{1c3}$, —NR$^{1c4}$C(O)R$^{1c5}$, —NR$^{1c6}$C(O)OR$^{1c7}$, and —C(O)OR$^{1c8}$, wherein $R^{1c1}$—$R^{1c6}$ are each independently hydrogen or $C_{1-6}$ alkyl.

In some embodiments, $R^2$ is $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —NR$^{2c1}$R$^{2c2}$, —OR$^{2c3}$, —NR$^{2c4}$C(O)R$^{2c5}$, and —C(O)OR$^{2c6}$, wherein $R^{2c1}$—$R^{2c6}$ are each independently hydrogen or $C_{1-6}$ alkyl.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, W is

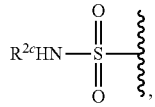

wherein $R^{2c}$ is as defined for Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or any variation or embodiment thereof. In some variations, W is

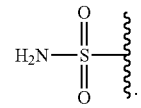

In some variations, $R^{2c}$ is hydrogen.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, W is

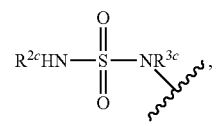

wherein $R^{2c}$ and $R^{3c}$ are as defined for Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or any variation or embodiment thereof. In some variations, W is

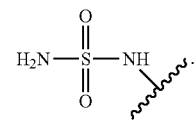

In some variations, $R^{2c}$ and $R^{3c}$ are each hydrogen. In some variations, $R^{2c}$ is hydrogen. In some variations, $R^{3c}$ is hydrogen.

In some embodiments, $R^{3c}$ is $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —NR$^{3c1}$R$^{3c2}$, —OR$^{3c3}$, —NR$^{3c4}$C(O)R$^{3c5}$ and —C(O)OR$^{3c6}$, wherein $R^{3c1}$—$R^{3c6}$ are each independently hydrogen or $C_{1-6}$ alkyl.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, W is

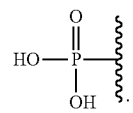

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, W is

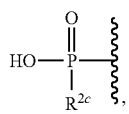

wherein $R^{2c}$ is as defined for Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or any variation or embodiment thereof. In some variations, W is

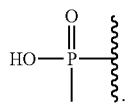

In some variations, $R^{2c}$ is methyl.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, W is

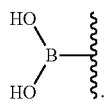

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, W is

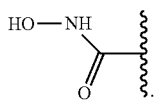

In another aspect, the compound of Formula (I) is a compound of Formula (Ia), (Ib), (Ic), (Id), (Ie), (If), or (Ig):

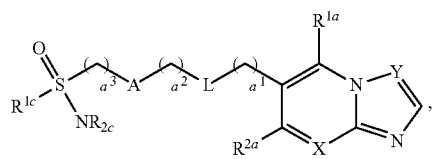
(Ia)

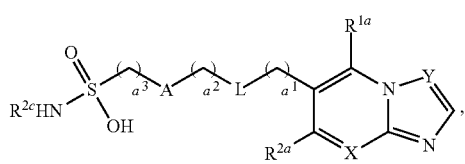
(Ib)

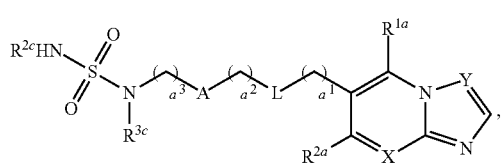
(Ic)

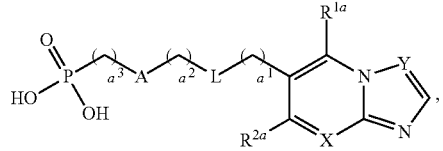
(Id)

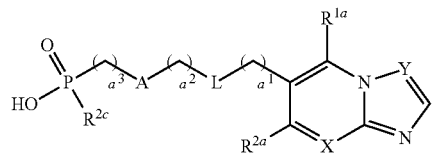
(Ie)

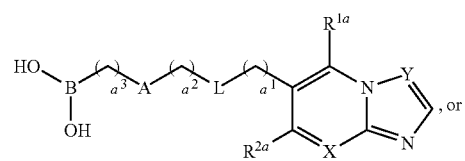
(If)

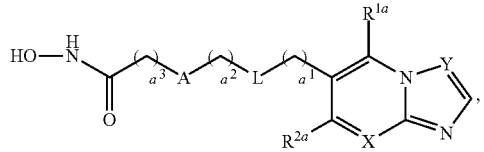
(Ig)

or a pharmaceutically acceptable salt thereof, wherein X, Y, $R^{1a}$, $R^{2a}$, L, A, $R^{1c}$—$R^{3c}$, and $a^1$-$a^3$ are as defined for Formula (I) or any variation or embodiment thereof.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, X is —N—. In some variations, X is —$CR^{3a}$—. In some variations, X is —CH—. In some variations, X is —C(CN)—. In some variations, Y is —N—. In some variations, Y is —$CR^{4b}$—. In some variations, Y is —CH—. In some variations, X is —N— and Y is —N—. In some variations, X is —N— and Y is —$CR^{4b}$—. In some variations, X is —N— and Y is —CH—. In some variations, X is —$C^{3a}$— and Y is —N—. In some variations, X is —CH— and Y is —N—. In some variations, X is —$C^{3a}$— and Y is —$CR^{4b}$—. In some variations, X is —CH— and Y is —CH—.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, the

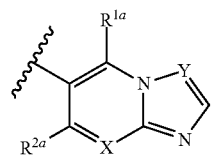

portion is [1,2,4]triazolo[1,5-α]pyrimidin-6-yl, [1,2,4]triazolo[1,5-α]pyridin-6-yl, or imidazo[1,2-a]pyrimidin-6-yl, each of which is optionally substituted. In some variations, the

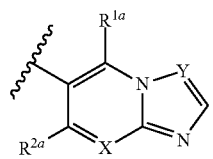

portion is 7-(dimethylamino)-5-methyl-[1,2,4]triazolo[1,5-α]pyrimidin-6-yl, 5-methyl-7-(pyrrolidin-1-yl)-[1,2,4]triazolo[1,5-α]pyrimidin-6-yl, 7-(azetidin-1-yl)-5-methyl-[1,2,4]triazolo[1,5-α]pyrimidin-6-yl, 7-(ethyl(methyl)amino)-5-methyl-[1,2,4]triazolo[1,5-α]pyrimidin-6-yl, 5-methyl-7-(piperidin-1-yl)-[1,2,4]triazolo[1,5-α]pyrimidin-6-yl, 5-methyl-7-(1H-pyrazol-1-yl)-[1,2,4]triazolo[1,5-α]pyrimidin-6-yl, 5-methyl-[1,2,4]triazolo[1,5-α]pyrimidin-6-yl, 7-(dimethylamino)-[1,2,4]triazolo[1,5-α]pyrimidin-6-yl, 5,7-dimethyl-[1,2,4]triazolo[1,5-α]pyrimidin-6-yl, 5-(dimethylamino)-7-methyl-[1,2,4]triazolo[1,5-α]pyridin-6-yl, 5-(dimethylamino)-7-methylimidazo[1,2-a]pyrimidin-6-yl, or 7-(dimethylamino)-5-ethyl-[1,2,4]triazolo[1,5-α]pyrimidin-6-yl. In some variations, the

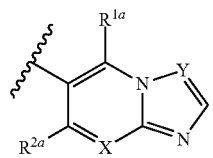

portion is 7-(dimethylamino)-5-methyl-[1,2,4]triazolo[1,5-α]pyrimidin-6-yl.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, the

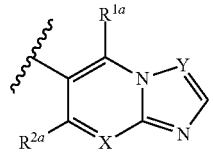

portion is

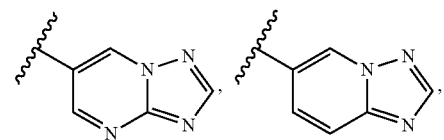

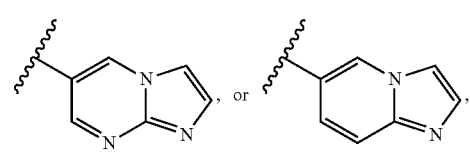

each of which is optionally substituted. In some variations,

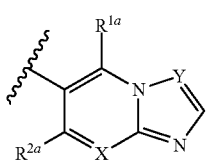

the portion is

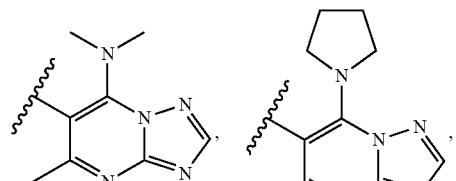

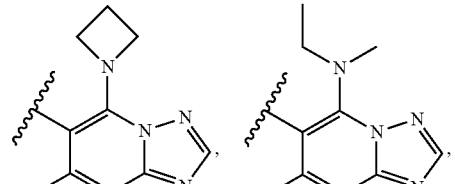

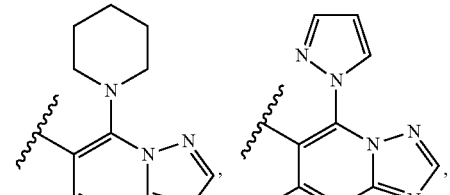

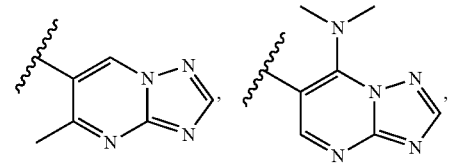

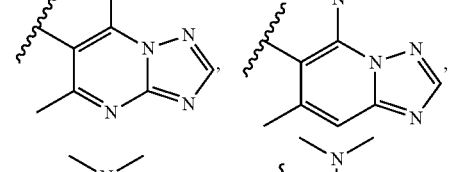

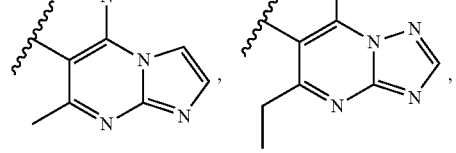

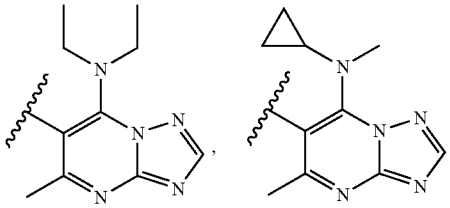

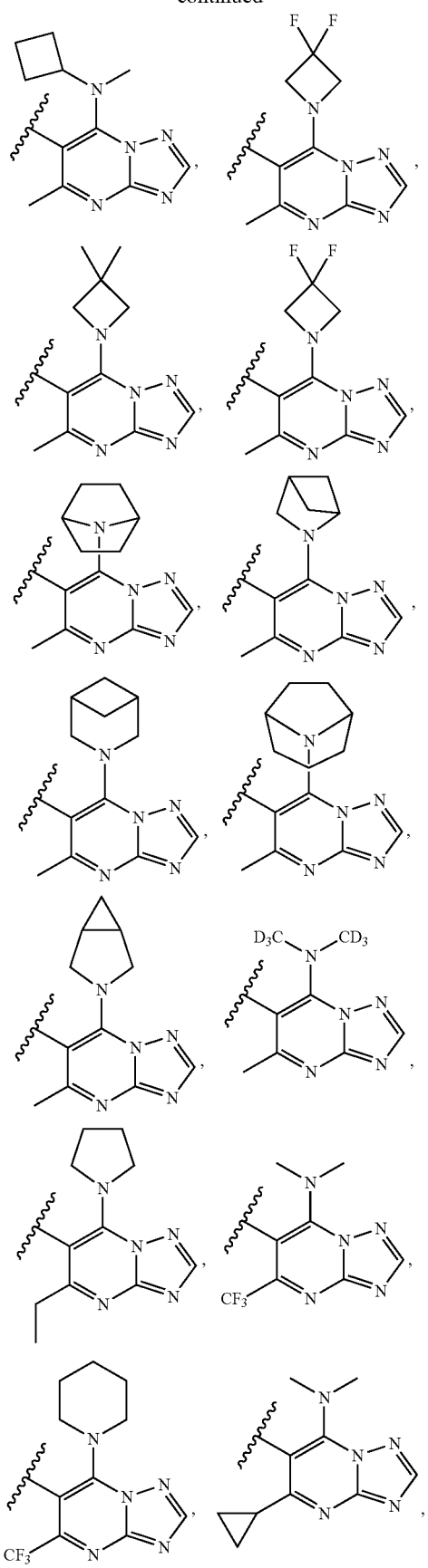
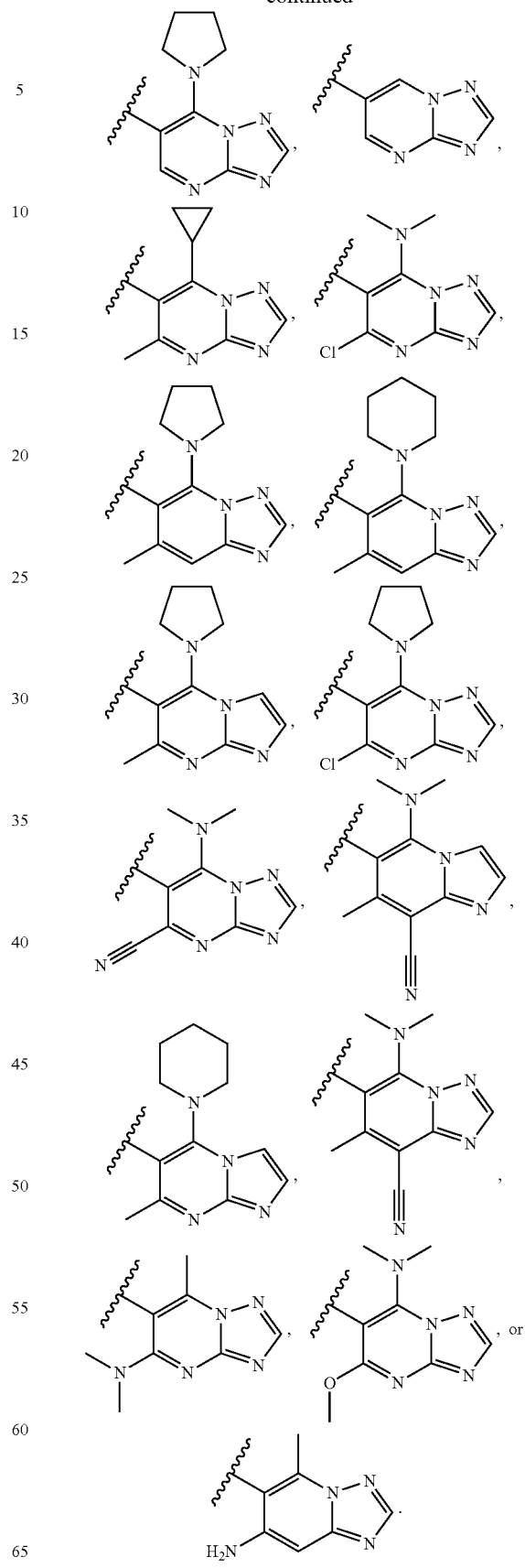

In some variations, the

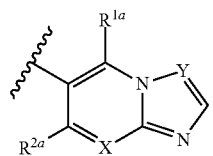

portion of Formula (I) is

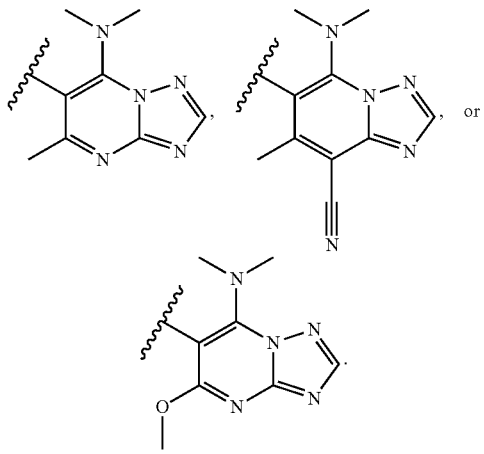

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, $R^{1a}$ is —$NR^{1b}R^{2b}$ or heterocycloalkyl. In some variations, $R^{1a}$ is —$NR^{1b}R^{2b}$. In some variations, $R^{1b}$ and $R^{2b}$ are each methyl. In some variations, $R^{1b}$ is methyl. In some variations, $R^{2b}$ is methyl. In some variations, $R^{1a}$ is dimethylamino. In some variations, $R^{1a}$ is optionally substituted cycloalkyl or optionally substituted heterocycloalkyl, such as a heterocycloalkyl containing one of more annular nitrogen atoms. In some embodiments, $R^{1a}$ is optionally substituted cycloalkyl. In some embodiments, $R^{1a}$ is cyclopropyl. In some embodiments, wherein $R^{1a}$ is an optionally substituted heterocycloalkyl, the heterocycloalkyl may be monocyclic or bicyclic, wherein the bicyclic heterocycloalkyl may be spirocyclic, fused, or bridged. In some variations, $R^{1a}$ is azetidinyl, pyrrolidinyl, piperidinyl, 3-azabicyclo[3.1.0]hexan-3-yl, 2-azabicyclo[2.1.1]hexan-2-yl, 7-azabicyclo[2.2.1]heptan-7-yl, 3-azabicyclo[3.1.1]heptan-3-yl, or 8-azabicyclo[3.2.1]octan-8-yl. In some variations, $R^{1a}$ is azetidinyl, pyrrolidinyl, or piperidinyl. In some variations, $R^{1a}$ is hydrogen, methyl, dimethylamino, ethyl(methyl)amino, azetidin-1-yl, pyrrolidin-1-yl, 1H-pyrazol-1-yl, or piperidin-1-yl.

In some embodiments, $R^{1a}$ is $C_{6-14}$ aryl, 4- to 14-membered heteroaryl, $C_{3-10}$ cycloalkyl, $C_{3-10}$ cycloalkenyl, 3- to 18-membered heterocycloalkyl, or 3- to 18-membered heterocycloalkenyl, each of which is optionally substituted. In some embodiments, $R^{1a}$ is 4- to 14-membered heteroaryl, 3- to 18-membered heterocycloalkyl, or 3- to 18-membered heterocycloalkenyl, each of which is optionally substituted, wherein the 4- to 14-membered heteroaryl, 3- to 18-membered heterocycloalkyl, or 3- to 18-membered heterocycloalkenyl contains one, two, three, four, five, or six heteroatoms. In some embodiments, each heteroatom is independently selected from nitrogen, oxygen, and sulfur.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, $R^{1a}$ is hydrogen, methyl,

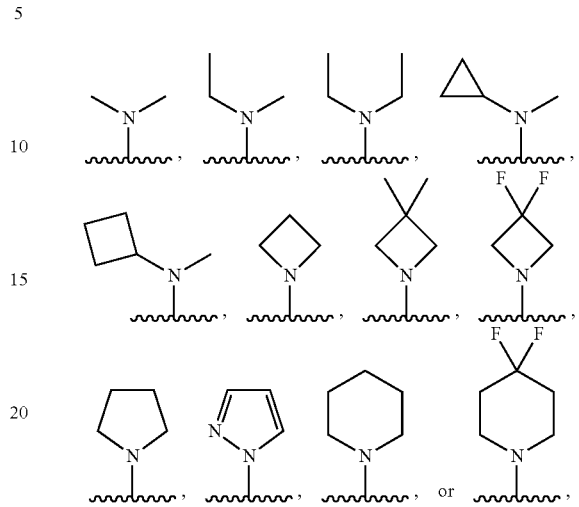

each of which is optionally substituted. In some embodiments, $R^{1a}$ is hydrogen, methyl,

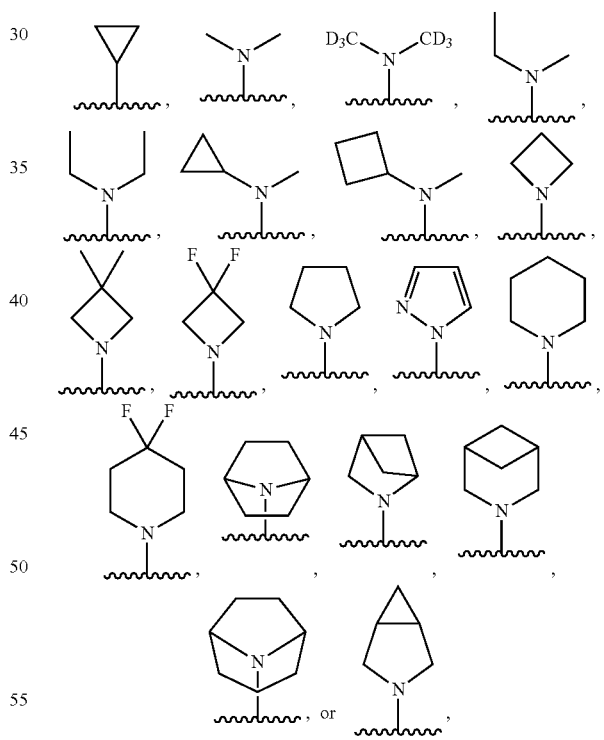

each of which is
optionally substituted. In some variations, $R^{1a}$ is

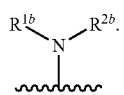

In some variations, $R^{1a}$ is

In some embodiments, when a variable or a chemical group is indicated as "substituted" or "optionally substituted," then the variable or the chemical group can be substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —$NR^{z1}R^{z2}$, —$OR^{z3}$, —$NR^{z4}C(O)R^{z5}$, —$NR^{z6}C(O)OR^{z7}$, and —$C(O)OR^{z8}$, wherein $R^{z1}$—$R^{z8}$ are each independently hydrogen or $C_{1-6}$ alkyl. In some embodiments, when a variable or a chemical group is indicated as "substituted" or "optionally substituted," then the variable or the chemical group can be substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, amino, —OH, and $C_{1-6}$ alkoxy. In some embodiments, when a variable or a chemical group is indicated as "substituted" or "optionally substituted," then the variable or the chemical group can be substituted with one, two, three, four, five, or more substituents selected from the group consisting of deuterium, halo, cyano, $C_{1-6}$ alkyl, $C_{3-10}$ cycloalkyl, amino, —OH, and $C_{1-6}$ alkoxy. In some embodiments, when a variable or a chemical group is indicated as "substituted" or "optionally substituted," then the variable or the chemical group can be substituted with one, two, three, four, five, or more substituents selected from the group consisting of deuterium, halo, cyano, $C_{1-6}$ alkyl, and —OH. In some embodiments, when a variable or a chemical group is indicated as "substituted" or "optionally substituted," then the variable or the chemical group can be substituted with halo or $C_{1-6}$ alkyl.

In some embodimnts, $R^{1a}$ is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —$NR^{1a4}C(O)R^{1a5}$, and —$C(O)OR^{1a6}$, wherein $R^{1a1}$—$R^{1a6}$ are each independently hydrogen or $C_{1-6}$ alkyl. In some embodiments, $R^{1a}$ is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, amino, —OH, and $C_{1-6}$ alkoxy. In some embodiments, $R^{1a}$ is optionally substituted with one, two, three, four, five, or more substituents selected from the group consisting of deuterium, halo, cyano, $C_{1-6}$ alkyl, $C_{3-10}$ cycloalkyl, $C_{3-10}$ cycloalkenyl, amino, —OH, and $C_{1-6}$ alkoxy. In some embodiments, $R^{1a}$ is optionally substituted with one, two, three, four, five, or more substituents selected from the group consisting of deuterium, halo, cyano, $C_{1-6}$ alkyl, amino, —OH, and $C_{1-6}$ alkoxy. In some embodiments, $R^{1a}$ optionally substituted with halo, $C_{1-6}$ alkyl, or $C_{3-6}$ cycloalkyl. In some embodiments, $R^{1a}$ is unsubstituted.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, $R^{2a}$ is hydrogen, methyl, or ethyl. In some variations, $R^{2a}$ is methyl. In other embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, $R^{2a}$ is halogen, or cyano, or $C_{1-3}$ haloalkyl. In some variations, $R^{2a}$ is chloro. In some variations, $R^{2a}$ is cyano. In still other embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, $R^{2a}$ is optionally substituted cycloalkyl. In some variations, $R^{2a}$ is cyclopropyl. In still other embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, $R^{2a}$ is $C_{1-3}$ haloalkyl. In some variations, $R^{2a}$ is —$CF_3$.

In some embodiments, $R^{2a}$ is hydrogen, halogen, cyano, optionally substituted $C_{1-3}$ alkyl, $C_{1-3}$ haloalkyl, —$NR^{7b}R^{8b}$, cycloalkyl, or —$OR^{3b}$. In some embodiments, $R^{2a}$ is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —$NR^{2a1}R^{2a2}$, —$OR^{2a3}$, —$NR^{2a4}C(O)R^{2a5}$, and —$C(O)OR^{2a6}$, wherein $R^{2a1}$—$R^{2a6}$ are each independently hydrogen or $C_{1-6}$ alkyl. In some embodiments, $R^{2a}$ is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, amino, —OH, and $C_{1-6}$ alkoxy. In some embodiments, $R^{2a}$ is optionally substituted with one, two, three, four, five, or more substituents selected from the group consisting of deuterium, halo, cyano, $C_{1-6}$ alkyl, $C_{3-10}$ cycloalkyl, $C_{3-10}$ cycloalkenyl, amino, —OH, and $C_{1-6}$ alkoxy. In some embodiments, $R^{2a}$ is optionally substituted with one, two, three, four, five, or more substituents selected from the group consisting of deuterium, halo, cyano, $C_{1-6}$ alkyl, amino, —OH, and $C_{1-6}$ alkoxy. In some embodiments, $R^{2a}$ is optionally substituted with halo, $C_{1-6}$ alkyl, or $C_{3-6}$ cycloalkyl. In some embodiments, $R^{2a}$ is unsubstituted.

In some embodiments, $R^{2a}$ is $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —$NR^{2a1}R^{2a2}$, —$OR^{2a3}$, $NR^{2a4}C(O)R^{2a5}$, and —$C(O)OR^{2a6}$, wherein $R^{2a1}$—$R^{2a6}$ are each independently hydrogen or $C_{1-6}$ alkyl. In some embodiments, $R^{2a}$ is $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, amino, —OH, and $C_{1-6}$ alkoxy. In some embodiments, $R^{2a}$ is $C_{1-3}$ alkyl optionally substituted with one, two, three, four, five, or more substituents selected from the group consisting of deuterium, halo, cyano, $C_{1-6}$ alkyl, $C_{3-10}$ cycloalkyl, $C_{3-10}$ cycloalkenyl, amino, —OH, and $C_{1-6}$ alkoxy. In some embodiments, $R^{2a}$ is $C_{1-3}$ alkyl optionally substituted with one, two, three, four, five, or more substituents selected from the group consisting of deuterium, halo, cyano, $C_{1-6}$ alkyl, amino, —OH, and $C_{1-6}$ alkoxy. In some embodiments, $R^{2a}$ is $C_{1-3}$ alkyl optionally substituted with halo, $C_{1-6}$ alkyl, or $C_{3-6}$ cycloalkyl. In some embodiments, $R^{2a}$ is unsubstituted $C_{1-3}$ alkyl.

In some embodiments, $R^{1a}$ is hydrogen, halogen, cyano, optionally substituted $C_{1-3}$ alkyl, $C_{1-3}$ haloalkyl, —$NR^{9b}R^{10b}$, cycloalkyl, or —$OR^{11b}$. In some embodiments, $R^{3a}$ is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —$NR^{3a1}R^{3a2}$, —$OR^{3a3}$, —$NR^{3a4}C(O)R^{3a5}$, and —$C(O)OR^{3a6}$, wherein $R^{3a1}$—$R^{3a6}$ are each independently hydrogen or $C_{1-6}$ alkyl. In some embodiments, $R^{3a}$ is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, amino, —OH, and $C_{1-6}$ alkoxy. In some embodiments, $R^{3a}$ is optionally substituted with one, two, three, four, five, or more substituents selected from the group consisting of deuterium, halo, cyano, $C_{1-6}$ alkyl, $C_{3-10}$ cycloalkyl, $C_{3-10}$ cycloalkenyl, amino, —OH, and $C_{1-6}$ alkoxy. In some embodiments, $R^{3a}$ is optionally substituted with one, two, three, four, five, or more substituents selected from the group consisting of deuterium, halo, cyano, $C_{1-6}$ alkyl, amino, —OH, and $C_{1-6}$ alkoxy. In some embodiments, $R^{3a}$ is optionally substituted with halo, cyano, $C_{1-6}$ alkyl, or $C_{3-6}$ cycloalkyl. In some embodiments, $R^{3a}$ is unsubstituted.

In some embodiments, $R^{3a}$ is $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —$NR^{3a1}R^{3a2}$, —$OR^{3a3}$, —$NR^{3a4}C(O)R^{3a5}$ and —$C(O)OR^{3a6}$, wherein $R^{3a1}$—$R^{3a6}$ are each independently hydrogen or $C_{1-6}$ alkyl. In some embodiments, $R^{3a}$ is $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, amino, —OH, and $C_{1-6}$ alkoxy. In some embodiments, $R^{3a}$ is $C_{1-3}$ alkyl optionally substituted with one, two, three, four, five, or more substituents selected from the group consisting of deuterium, halo, cyano, $C_{1-6}$ alkyl, $C_{3-10}$ cycloalkyl, $C_{3-10}$ cycloalkenyl, amino, —OH, and $C_{1-6}$ alkoxy. In some embodiments, $R^{3a}$ is $C_{1-3}$ alkyl optionally substituted with one, two, three, four, five, or more substituents selected from the group consisting of deuterium, halo, cyano, $C_{1-6}$ alkyl, amino, —OH, and $C_{1-6}$ alkoxy. In some embodiments, $R^{3a}$ is $C_{1-3}$ alkyl optionally substituted with halo, $C_{1-6}$ alkyl, or $C_{3-6}$ cycloalkyl. In some embodiments, $R^{3a}$ is unsubstituted $C_{1-3}$ alkyl.

In some embodiments, $R^{4a}$ is hydrogen, halogen, cyano, optionally substituted $C_{1-3}$ alkyl, $C_{1-3}$ haloalkyl, —$NR^{12b}R^{13b}$, or —$OR^{14b}$. In some embodiments, $R^{4a}$ is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —$NR^{4a1}R^{4a2}$, —$OR^{4a3}$, —$NR^{4a4}C(O)R^{4a5}$ and —$C(O)OR^{4a6}$, wherein $R^{4a1}$—$R^{4a6}$ are each independently hydrogen or $C_{1-6}$ alkyl. In some embodiments, $R^{4a}$ is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, amino, —OH, and $C_{1-6}$ alkoxy. In some embodiments, $R^{4a}$ is optionally substituted with one, two, three, four, five, or more substituents selected from the group consisting of deuterium, halo, cyano, $C_{1-6}$ alkyl, $C_{3-10}$ cycloalkyl, $C_{3-10}$ cycloalkenyl, amino, —OH, and $C_{1-6}$ alkoxy. In some embodiments, $R^{4a}$ is optionally substituted with one, two, three, four, five, or more substituents selected from the group consisting of deuterium, halo, cyano, $C_{1-6}$ alkyl, amino, —OH, and $C_{1-6}$ alkoxy. In some embodiments, $R^{4a}$ is optionally substituted with halo, cyano, $C_{1-6}$ alkyl, or $C_{3-6}$ cycloalkyl. In some embodiments, $R^{4a}$ is unsubstituted.

In some embodiments, $R^{4a}$ is $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —$NR^{4a1}R^{4a2}$, —$OR^{4a3}$, —$NR^{4a4}C(O)R^{4a5}$ and —$C(O)OR^{4a6}$, wherein $R^{4a1}$—$R^{4a6}$ are each independently hydrogen or $C_{1-6}$ alkyl. In some embodiments, $R^{4a}$ is $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, amino, —OH, and $C_{1-6}$ alkoxy. In some embodiments, $R^{4a}$ is $C_{1-3}$ alkyl optionally substituted with one, two, three, four, five, or more substituents selected from the group consisting of deuterium, halo, cyano, $C_{1-6}$ alkyl, $C_{3-10}$ cycloalkyl, $C_{3-10}$ cycloalkenyl, amino, —OH, and $C_{1-6}$ alkoxy. In some embodiments, $R^{4a}$ is $C_{1-3}$ alkyl optionally substituted with one, two, three, four, five, or more substituents selected from the group consisting of deuterium, halo, cyano, $C_{1-6}$ alkyl, amino, —OH, and $C_{1-6}$ alkoxy. In some embodiments, $R^{4a}$ is $C_{1-3}$ alkyl optionally substituted with halo, $C_{1-6}$ alkyl, or $C_{3-6}$ cycloalkyl. In some embodiments, $R^{4a}$ is unsubstituted $C_{1-3}$ alkyl.

In some embodiments, $R^{2a}$ is hydrogen, methyl, ethyl, —$CF_3$,

Cl, CN,

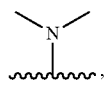

methoxy, or $NH_2$. In some embodiments, $R^{3a}$ is hydrogen or CN. In some embodiments, $R^{4a}$ is hydrogen.

In some embodiments, $R^{1b}$—$R^{14}$ are each independently optionally substituted $C_{1-3}$ alkyl. In some embodiments, $R^{1b}$—$R^{14}$ are each independently and optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, C$_{3-10}$ cycloalkenyl, 3- to 18-membered heterocycloalkyl, 3- to 18-membered heterocycloalkenyl, —NR$^{1b1}$R$^{1b2}$, —OR$^{1b3}$, —NR$^{1b4}$C(O)R$^{1b5}$, and —C(O)OR$^{1b6}$, wherein R$^{1b1}$—R$^{1b6}$ are each independently hydrogen or C$_{1-6}$ alkyl. In some embodiments, R$^{1b}$—R$^{14b}$ are each independently and optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, amino, —OH, and C$_{1-6}$ alkoxy. In some embodiments, R$^{1b}$—R$^{14b}$ are each independently and optionally substituted with one, two, three, four, five, or more substituents selected from the group consisting of deuterium, halo, cyano, C$_{1-6}$ alkyl, C$_{3-10}$ cycloalkyl, C$_{3-10}$ cycloalkenyl, amino, —OH, and C$_{1-6}$ alkoxy. In some embodiments, R$^{1b}$—R$^{14b}$ are each independently and optionally substituted with one, two, three, four, five, or more substituents selected from the group consisting of deuterium, halo, cyano, C$_{1-6}$ alkyl, amino, —OH, and C$_{1-6}$ alkoxy. In some embodiments, R$^{1b}$—R$^{14b}$ are each independently and optionally substituted with halo, C$_{1-6}$ alkyl, or C$_{3-6}$ cycloalkyl. In some embodiments, R$^{1b}$—R$^{14b}$ are unsubstituted.

In some embodiments, R$^{1b}$ and R$^{2b}$ are each independently hydrogen, C$_{3-10}$ cycloalkyl, or C$_{1-3}$ alkyl optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, —NR$^{1b1}$C(O)R$^{1b2}$, —OR$^{1b3}$, —NR$^{1b4}$C(O)R$^{1b5}$ and —C(O)OR$^{1b6}$, wherein R$^{1b1}$—R$^{1b6}$ are each independently hydrogen or C$_{1-6}$ alkyl. In some embodiments, R$^{1b}$ and R$^{2b}$ are each independently hydrogen, C$_{3-10}$ cycloalkyl, or C$_{1-3}$ alkyl optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, amino, —OH, and C$_{1-6}$ alkoxy. In some embodiments, R$^{1b}$ and R$^{2b}$ are each independently hydrogen, C$_{3-10}$ cycloalkyl, or C$_{1-3}$ alkyl optionally substituted with one, two, three, four, five, or more substituents selected from the group consisting of deuterium, halo, cyano, C$_{1-6}$ alkyl, C$_{3-10}$ cycloalkyl, C$_{3-10}$ cycloalkenyl, amino, —OH, and C$_{1-6}$ alkoxy. In some embodiments, R$^{1b}$ and R$^{2b}$ are each independently hydrogen, C$_{3-10}$ cycloalkyl, or C$_{1-3}$ alkyl optionally substituted with one, two, three, four, five, or more substituents selected from the group consisting of deuterium, halo, cyano, C$_{1-6}$ alkyl, amino, —OH, and C$_{1-6}$ alkoxy. In some embodiments, R$^{1b}$ and R$^{2b}$ are each independently hydrogen, C$_{3-10}$ cycloalkyl, or C$_{1-3}$ alkyl optionally substituted with halo, C$_{1-6}$ alkyl, or C$_{3-6}$ cycloalkyl. In some embodiments, R$^{1b}$ and R$^{2b}$ are each independently hydrogen, unsubstituted C$_{3-10}$ cycloalkyl, or unsubstituted C$_{1-3}$ alkyl.

In some embodiments, R$^{3b}$—R$^{14b}$ are each independently hydrogen or C$_{1-3}$ alkyl optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, —NR$^{3b1}$R$^{3b2}$, —OR$^{3b3}$, —NR$^{3b4}$C(O)R$^{3b5}$ and —C(O)OR$^{3b6}$, wherein R$^{3b1}$—R$^{3b6}$ are each independently hydrogen or C$_{1-6}$ alkyl. In some embodiments, R$^{3b}$—R$^{14b}$ are each independently hydrogen or C$_{1-3}$ alkyl optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, amino, —OH, and C$_{1-6}$ alkoxy. In some embodiments, R$^{3b}$—R$^{14b}$ are each independently hydrogen or C$_{1-3}$ alkyl optionally substituted with one, two, three, four, five, or more substituents selected from the group consisting of deuterium, halo, cyano, C$_{1-6}$ alkyl, C$_{3-10}$ cycloalkyl, C$_{3-10}$ cycloalkenyl, amino, —OH, and C$_{1-6}$ alkoxy. In some embodiments, R$^{3b}$—R$^{14b}$ are each independently hydrogen or C$_{1-3}$ alkyl optionally substituted with one, two, three, four, five, or more substituents selected from the group consisting of deuterium, halo, cyano, C$_{1-6}$ alkyl, amino, —OH, and C$_{1-6}$ alkoxy. In some embodiments, R$^{3b}$—R$^{14b}$ are each independently hydrogen or C$_{1-3}$ alkyl optionally substituted with halo, C$_{1-6}$ alkyl, or C$_{3-6}$ cycloalkyl. In some embodiments, R$^{3b}$—R$^{14b}$ are each independently hydrogen or unsubstituted C$_{1-3}$ alkyl.

In some embodiments, the 4- to 14-membered heteroaryl, 3- to 18-membered heterocycloalkyl, or 3- to 18-membered heterocycloalkenyl contains one, two, three, four, five, or six heteroatoms. In some embodiments, each heteroatom is independently selected from nitrogen, oxygen, and sulfur.

In some embodiments, R$^{1c}$ is hydrogen, C$_{1-3}$ haloalkyl, C$_{3-10}$ cycloalkyl, 3- to 18-membered heterocycloalkyl, or C$_{1-3}$ alkyl optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, —NR$^{1c1}$R$^{1c3}$, —OR$^{1c3}$, —NR$^{1c4}$C(O)R$^{1c5}$, —NR$^{1c6}$C(O)OR$^{1c7}$, and —C(O)OR$^{1c8}$, wherein R$^{1c1}$—R$^{1c6}$ are each independently hydrogen or C$_{1-6}$ alkyl. In some embodiments, the 4- to 14-membered heteroaryl, 3- to 18-membered heterocycloalkyl, or 3- to 18-membered heterocycloalkenyl contains one, two, three, four, five, or six heteroatoms. In some embodiments, each heteroatom is independently selected from nitrogen, oxygen, and sulfur. In some embodiments, R$^{1c}$ is methyl, ethyl, NH$_2$,

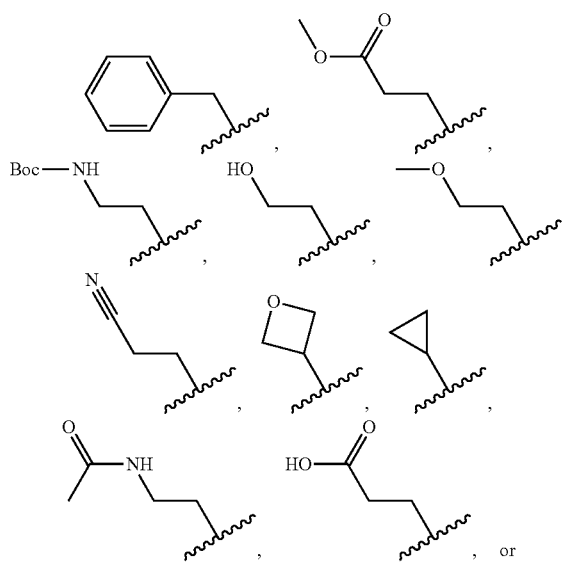

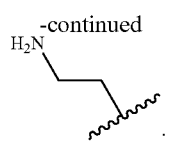

In some embodiments, $R^{1c}$ is hydrogen, $C_{1-3}$ haloalkyl, $C_{3-10}$ cycloalkyl, 3- to 18-membered heterocycloalkyl, or $C_{1-3}$ alkyl optionally substituted with one, two, three, four, five, or more substituents selected from the group consisting of deuterium, halo, cyano, $C_{1-6}$ alkyl, $C_{6-14}$ aryl, $C_{3-10}$ cycloalkyl, $C_{3-10}$ cycloalkenyl, 3- to 18-membered heterocycloalkyl, 3- to 18-membered heterocycloalkenyl, —$NR^{1c1}R^{1c2}$, —$OR^{1c3}$, —$NR^{1c4}C(O)R^{1c5}$, —$NR^{1c6}C(O)OR^{1c7}$, and —$C(O)OR^{1c8}$, wherein $R^{1c1}$—$R^{1c6}$ are each independently hydrogen or $C_{1-6}$ alkyl. In some embodiments, $R^{1c}$ is hydrogen, —$NHR^{1d}$, $C_{1-3}$ haloalkyl, $C_{3-10}$ cycloalkyl, 3- to 18-membered heterocycloalkyl, or $C_{1-3}$ alkyl optionally substituted with one, two, three, four, five, or more substituents selected from the group consisting of deuterium, halo, cyano, $C_{1-6}$ alkyl, $C_{6-14}$ aryl, $C_{3-10}$ cycloalkyl, 3- to 18-membered heterocycloalkyl, —$NR^{1c1}R^{1c2}$, —$OR^{1c3}$, —$NR^{1c4}C(O)R^{1c5}$, —$NR^{1c6}C(O)OR^{1c7}$, and —$C(O)OR^{1c8}$, wherein are each independently hydrogen or $C_{1-6}$ alkyl. In some embodiments, $R^{1c}$ is hydrogen, —$NHR^{1d}$, $C_{1-3}$ haloalkyl, $C_{3-10}$ cycloalkyl, 3- to 18-membered heterocycloalkyl, or $C_{1-3}$ alkyl optionally substituted with one, two, three, four, five, or more substituents selected from the group consisting of deuterium, halo, cyano, $C_{1-6}$ alkyl, $C_{3-10}$ cycloalkyl, amino, —OH, and $C_{1-6}$ alkoxy. In some embodiments, $R^{1c}$ is hydrogen, —$NHR^{1d}$, $C_{1-3}$ haloalkyl, $C_{3-10}$ cycloalkyl, 3- to 18-membered heterocycloalkyl, or $C_{1-3}$ alkyl optionally substituted with one, two, three, four, five, or more substituents selected from the group consisting of deuterium, halo, cyano, $C_{1-6}$ alkyl, amino, —OH, and $C_{1-6}$ alkoxy. In some embodiments, $R^{1c}$ is hydrogen, —$NHR^{1d}$, $C_{1-3}$ haloalkyl, $C_{3-10}$ cycloalkyl, 3- to 18-membered heterocycloalkyl, or $C_{1-3}$ alkyl optionally substituted with halo, $C_{1-6}$ alkyl, or $C_{3-6}$ cycloalkyl. In some embodiments, $R^{1c}$ is hydrogen, —$NHR^{1d}$, $C_{1-3}$ haloalkyl, $C_{3-10}$ cycloalkyl, 3- to 18-membered heterocycloalkyl, or unsubstituted $C_{1-6}$ alkyl.

In some embodiments, $R^{2c}$, $R^{3c}$, and $R^{1d}$ are each independently hydrogen or $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —$NR^{2c1}R^{2c2}$, —$OR^{2c3}$, —$NR^{2c4}C(O)R^{2c5}$, and —$C(O)OR^{2c6}$, wherein $R^{2c1}$-$R^{2c6}$ are each independently hydrogen or $C_{1-6}$ alkyl. In some embodiments, the 4- to 14-membered heteroaryl, 3- to 18-membered heterocycloalkyl, or 3- to 18-membered heterocycloalkenyl contains one, two, three, four, five, or six heteroatoms. In some embodiments, each heteroatom is independently selected from nitrogen, oxygen, and sulfur. In some embodiments, $R^{2c}$ is hydrogen or methyl. In some embodiments, $R^{2c}$ is hydrogen. In some embodiments, $R^{3c}$ is hydrogen.

In some embodiments, $R^{2c}$, $R^{3c}$, and $R^{1d}$ are each independently hydrogen or $C_{1-3}$ alkyl optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, amino, —OH, and $C_{1-6}$ alkoxy. In some embodiments, $R^{2c}$, $R^{3c}$, and $R^{1d}$ are each independently hydrogen or $C_{1-3}$ alkyl optionally substituted with one, two, three, four, five, or more substituents selected from the group consisting of deuterium, halo, cyano, $C_{1-6}$ alkyl, $C_{3-10}$ cycloalkyl, $C_{3-10}$ cycloalkenyl, amino, —OH, and $C_{1-6}$ alkoxy. In some embodiments, $R^{2c}$, $R^{3c}$, and $R^{1d}$ are each independently hydrogen or $C_{1-3}$ alkyl optionally substituted with one, two, three, four, five, or more substituents selected from the group consisting of deuterium, halo, cyano, $C_{1-6}$ alkyl, amino, —OH, and $C_{1-6}$ alkoxy. In some embodiments, $R^{2c}$, $R^{3c}$, and $R^{1d}$ are each independently hydrogen or $C_{1-3}$ alkyl optionally substituted with halo, $C_{1-6}$ alkyl, or $C_{3-6}$ cycloalkyl. In some embodiments, $R^{2c}$, $R^{3c}$, and $R^{1d}$ are each independently hydrogen or unsubstituted $C_{1-6}$ alkyl.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, L is a bond, —O—, —C(O)—, —$NR^{4b}$—, or —$CR^{5b}R^{6b}$—, wherein $R^{4b}$, $R^{5b}$ and $R^{6b}$ are as defined for Formula (I) or any variation or embodiment thereof. In some variations, L is a bond. In some variations, L is —$CR^{5b}R^{6b}$—. In some variations, L is —$CH(CH_3)$—. In some variations, L is —O—.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, A is a bond, aryl, heteroaryl, cycloalkyl, cycloalkenyl, heterocycloalkyl, or heterocycloalkenyl, each of which is optionally substituted. In some variations, A is aryl or heterocycloalkyl, each of which is optionally substituted. In some variations, A is phenyl, piperidinyl, or azetidinyl, each of which is optionally substituted. In some variations, A is phenyl. In some embodiments, A is not a bond.

In some embodiments, A is $C_{6-14}$ aryl, 4- to 14-membered heteroaryl, $C_{3-10}$ cycloalkyl, $C_{3-10}$ cycloalkenyl, 3- to 18-membered heterocycloalkyl, or 3- to 18-membered heterocycloalkenyl, each of which is optionally substituted. In some embodiments, A is 4- to 14-membered heteroaryl, 3- to 18-membered heterocycloalkyl, or 3- to 18-membered heterocycloalkenyl, each of which is optionally substituted, wherein the 4- to 14-membered heteroaryl, 3- to 18-membered heterocycloalkyl, or 3- to 18-membered heterocycloalkenyl contains one, two, three, four, five, or six heteroatoms. In some embodiments, each heteroatom is independently selected from nitrogen, oxygen, and sulfur.

In some embodiments of Formula (I), (I-1), (I-2), (I-3), (I-4), (Ia), (Ia2), (Ia3), (Ia4), (Ib), (Ib1), (Ic), (Ic1), (Id), (Ie), (If), or (Ig), or a pharmaceutically acceptable salt thereof, A is

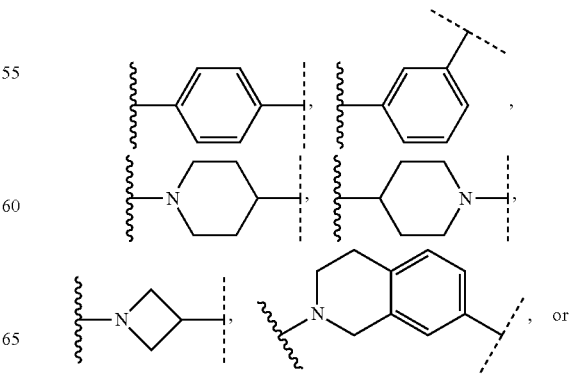

-continued

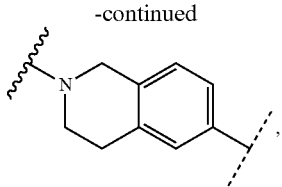

each of which is optionally substituted, wherein ⌇⌇⌇ denotes the point of attachment to

In some variations, A is

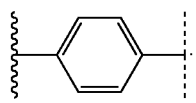

In some variations, A is

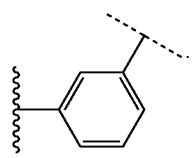

In some embodiments, polycyclic A groups such as

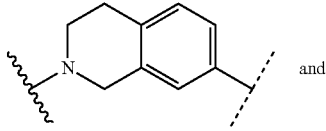 and

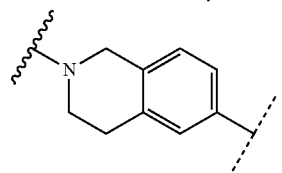

may be considered as either aryl or heterocycloalkyl as provided herein.

In some embodiments, A is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-membered heterocycloalkenyl, —$NR^{A1}R^{A2}$, —$OR^{A3}$, —$NR^{A4}C(O)R^{A5}$ and —$C(O)OR^{A6}$, wherein $R^{A1}$-$R^{A6}$ are each independently hydrogen or $C_{1-6}$ alkyl. In some embodiments, A is optionally substituted with one, two, three, four, five, or more substituents selected from the group consisting of deuterium, halo, cyano, $C_{1-6}$ alkyl, $C_{6-14}$ aryl, 4- to 14-membered heteroaryl, $C_{3-10}$ cycloalkyl, $C_{3-10}$ cycloalkenyl, 3- to 18-membered heterocycloalkyl, 3- to 18-mem- bered heterocycloalkenyl, amino, —OH, and $C_{1-6}$ alkoxy. In some embodiments, A is optionally substituted with one, two, three, four, five, or more substituents selected from the group consisting of deuterium, halo, cyano, $C_{1-6}$ alkyl, $C_{3-10}$ cycloalkyl, $C_{3-10}$ cycloalkenyl, amino, —OH, and $C_{1-6}$ alkoxy. In some embodiments, A is optionally substituted with one, two, three, four, five, or more substituents selected from the group consisting of deuterium, halo, cyano, $C_{1-6}$ alkyl, amino, —OH, and $C_{1-6}$ alkoxy. In some embodiments, A is optionally substituted with halo, $C_{1-6}$ alkyl, or $C_{3-6}$ cycloalkyl. In some embodiments, A is unsubstituted.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, $a^1$, $a^2$, and $a^3$ are each independently 0, 1, or 2. In some variations, $a^1$ is 0. In some variations, $a^1$ is 1. In some variations, $a^1$ is 2. In some variations, $a^2$ is 0. In some variations, $a^2$ is 1. In some variations, $a^2$ is 2. In some variations, $a^3$ is 0. In some variations, $a^3$ is 1. In some variations, $a^3$ is 2. In some variations, $a^1$ is 1 and $a^2$ is 0. In some variations, $a^1$ is 1, $a^2$ is 0, and L is a bond. In some variations, $a^1$ is 1, $a^2$ is 0, and $a^3$ is 0. In some variations, $a^1$ is 1, $a^2$ is 0, and $a^3$ is 1. In some variations, $a^1$ is 1, $a^2$ is 0, and $a^3$ is 2. In some variations, $a^1$ is 1, $a^2$ is 0, $a^3$ is 0, and L is a bond. In some variations, $a^1$ is 1, $a^2$ is 0, $a^3$ is 1, and L is a bond. In some variations, $a^1$ is 1, $a^2$ is 0, $a^3$ is 2, and L is a bond. In some variations, $a^1$ is 0, $a^2$ is 0, and $a^3$ is 2. In some variations, $a^1$ is 0, $a^2$ is 0, and $a^3$ is 0. In some variations, $a^1$ is 1, $a^2$ is 1, and $a^3$ is 2. In some variations, $a^1$ is 0, $a^2$ is 0, and $a^3$ is 1.

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, the

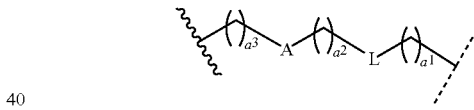

portion is

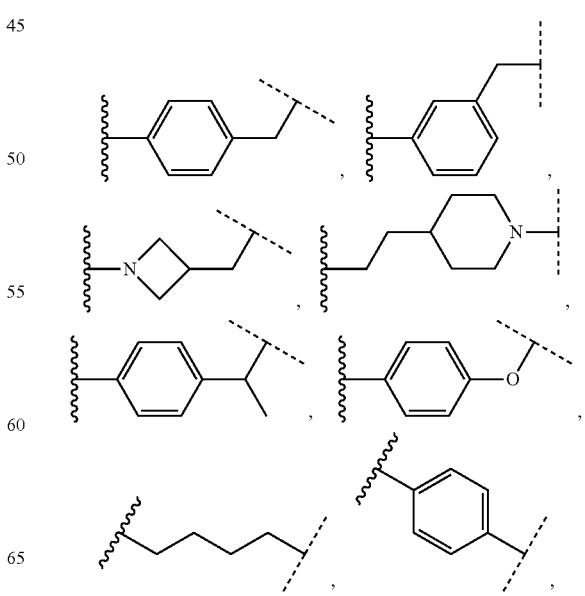

-continued

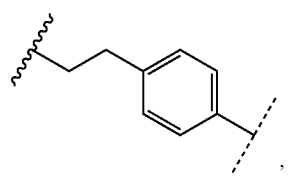

,

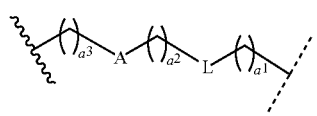

, or

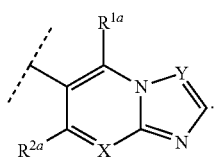

It will be understood that for the

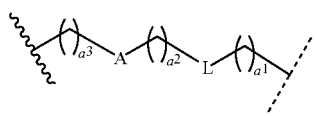

portion, the squiggly line ～ denotes the point of attachment to W, and the dotted line ----- denotes the point of attachment to

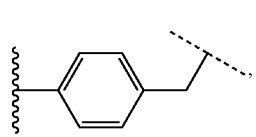

For example, when the

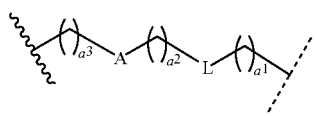

portion of Formula (I) is depicted as

the corresponding structure is

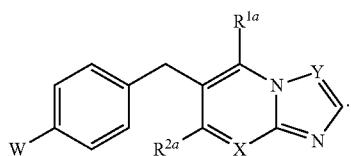

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, the

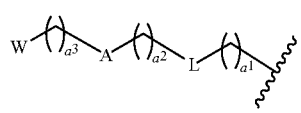

portion is

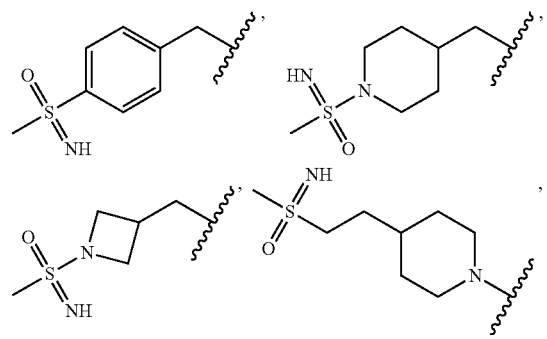

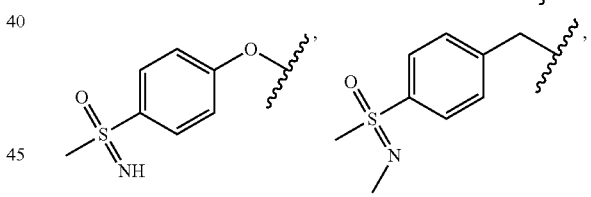

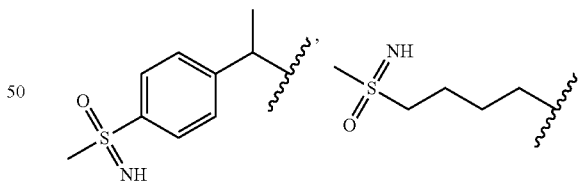

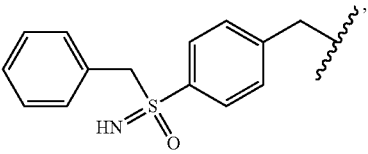

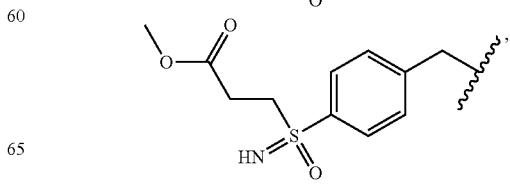

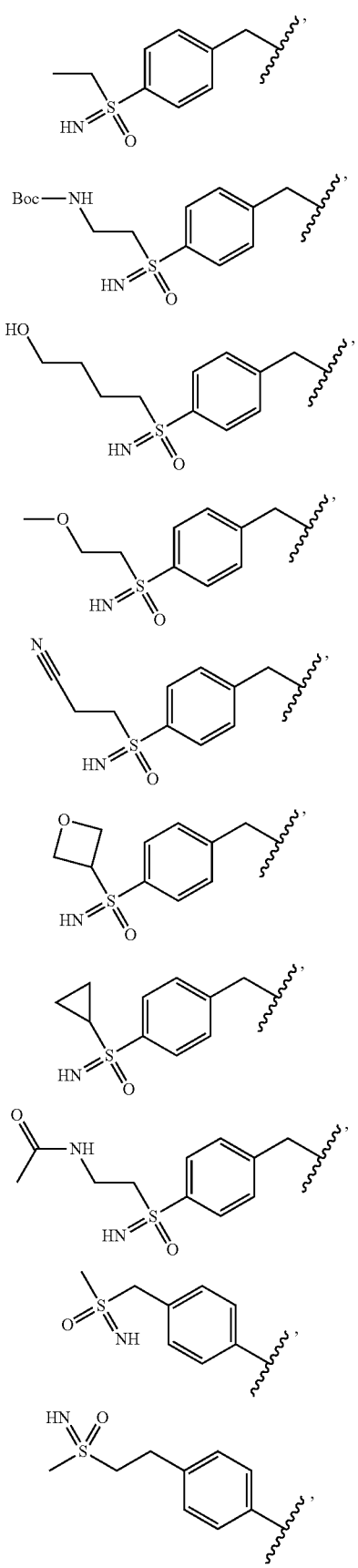
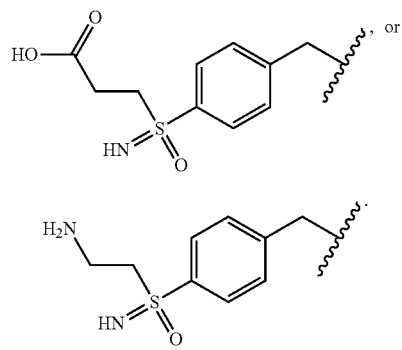
In some embodiments of Formula (I), or a pharmaceutically acceptable salt thereof, the
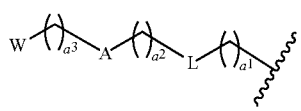
portion is
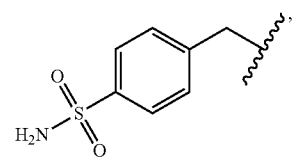
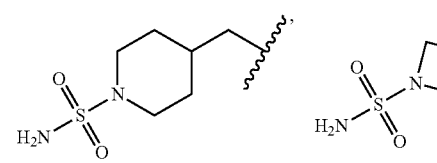
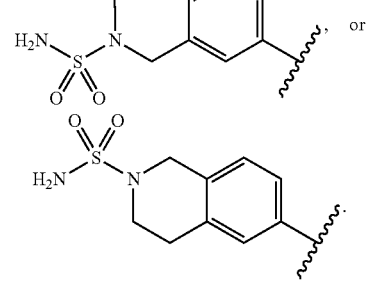
In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, the
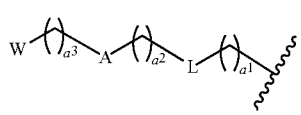

portion is

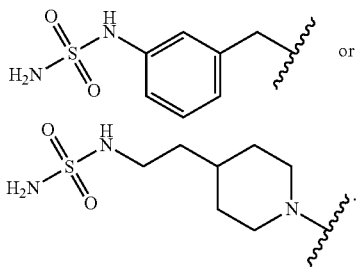

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, the

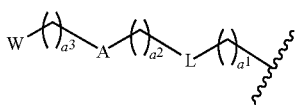

portion is

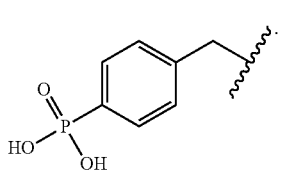 [SMILES: *Cc1ccc(P(=O)(O)O)cc1]

In some embodiments of Formula (I), (I-1), (I-2), (I-3), (I-4), (Ia), (Ia1), (Ia2), (Ia3),
(Ia4), (Ib), (Ib1), (Ic), (Ic1), (Id), (Ie), (If), or (Ig), or a pharmaceutically acceptable salt thereof, the

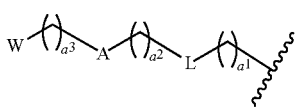

portion is

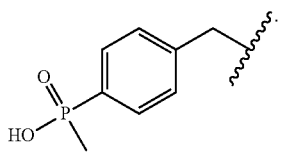 [SMILES: *Cc1ccc(P(C)(=O)O)cc1]

In some embodiments of Formula (I), (I-1), (I-2), (I-3), (I-4), (Ia), (Ia1), (Ia2), (Ia3),
(Ia4), (Ib), (Ib1), (Ic), (Ic1), (Id), (Ie), (If), or (Ig), or a pharmaceutically acceptable salt thereof, the

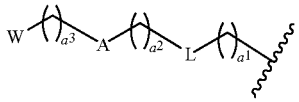

portion is

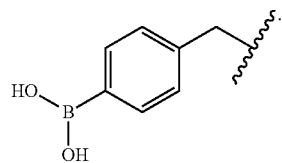

In some embodiments of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a pharmaceutically acceptable salt thereof, the

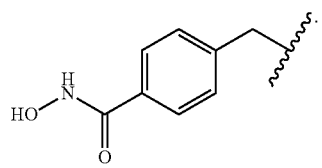 [SMILES: *Cc1ccc(C(=O)NO)cc1]

portion is

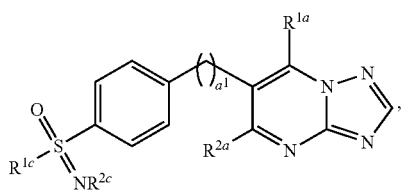

In one aspect, provided are compounds of Formula (Ia1):

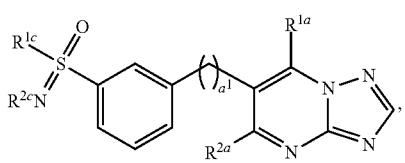

(Ia1)

or a pharmaceutically acceptable salt thereof, wherein $R^{1a}$, $R^{2a}$, $R^{1c}$, $R^{2c}$, and $a^1$ are as defined for Formula (I) or any variation or embodiment thereof.

In one aspect, provided are compounds of Formula (Ia2):

(Ia2)

or a pharmaceutically acceptable salt thereof, wherein $R^{1a}$, $R^{2a}$, $R^{1c}$, $R^{2c}$, and $a^1$ are as defined for Formula (I) or any variation or embodiment thereof.

In one aspect, provided are compounds of Formula (Ia3):

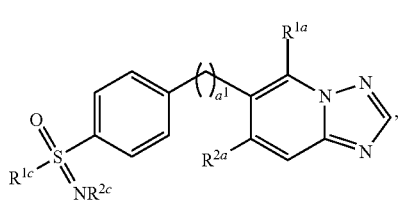

(Ia3)

or a pharmaceutically acceptable salt thereof, wherein $R^{1a}$, $R^{2a}$, $R^{1c}$, $R^{2c}$, and $a^1$ are as defined for Formula (I) or any variation or embodiment thereof.

In one aspect, provided are compounds of Formula (Ia4):

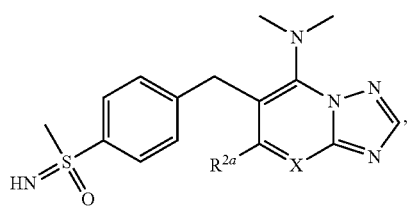

(Ia4)

or a pharmaceutically acceptable salt thereof, wherein $R^{2a}$ and X are as defined for Formula (I) or any variation or embodiment thereof.

In one aspect, provided are compounds of Formula (Ib1):

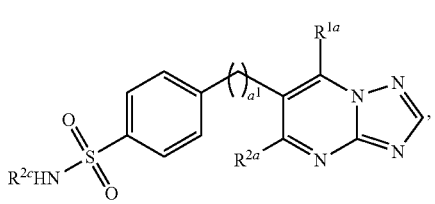

(Ib1)

or a pharmaceutically acceptable salt thereof, wherein $R^{1a}$, $R^{2a}$, $R^{2c}$, and $a^1$ are as defined for Formula (I) or any variation or embodiment thereof.

In one aspect, provided are compounds of Formula (Ic1):

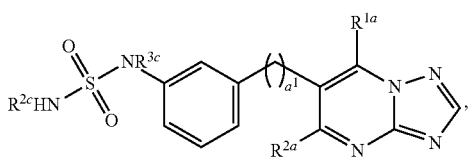

(Ic1)

or a pharmaceutically acceptable salt thereof, wherein $R^{1a}$, $R^{2a}$, $R^{2c}$, $R^{3c}$, and $a^1$ are as defined for Formula (I) or any variation or embodiment thereof.

In some embodiments, provided herein are compounds and salts thereof described in Table 1.

TABLE 1

| Compound No. | Structure | Name |
|---|---|---|
| 1 | ![structure] | (4-((7-(dimethylamino)-5-methyl-[1,2,4]triazolo[1,5-a]pyrimidin-6-yl)methyl)phenyl)(imino)(methyl)-$\lambda^6$-sulfanone |
| 1R | ![structure] | (R)-(4-((7-(dimethylamino)-5-methyl-[1,2,4]triazolo[1,5-a]pyrimidin-6-yl)methyl)phenyl)(imino)(methyl)-$\lambda^6$-sulfanone |
| 1S | ![structure] | (S)-(4-((7-(dimethylamino)-5-methyl-[1,2,4]triazolo[1,5-a]pyrimidin-6-yl)methyl)phenyl)(imino)(methyl)-$\lambda^6$-sulfanone |

TABLE 1-continued

| Compound No. | Structure | Name |
|---|---|---|
| 2 | 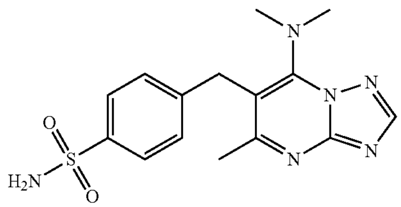 [SMILES: Cc1nc2ncnn2c(N(C)C)c1Cc1ccc(S(N)(=O)=O)cc1] | 4-((7-(dimethylamino)-5-methyl-[1,2,4]triazolo[1,5-a]pyrimidin-6-yl)methyl)benzenesulfonamide |
| 3 | 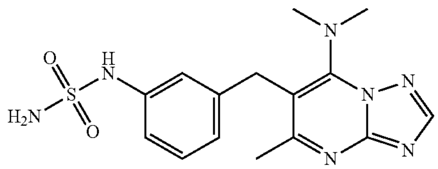 [SMILES: Cc1nc2ncnn2c(N(C)C)c1Cc1cccc(NS(N)(=O)=O)c1] | N-(3-{[7-(dimethylamino)-5-methyl-[1,2,4]triazolo[1,5-a]pyrimidin-6-yl]methyl}phenyl)aminosulfonamide |
| 4 | 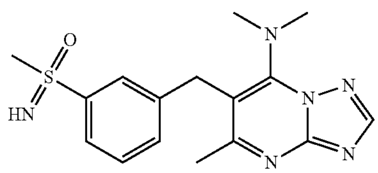 [SMILES: Cc1nc2ncnn2c(N(C)C)c1Cc1cccc(S(C)(=N)=O)c1] | (3-((7-(dimethylamino)-5-methyl-[1,2,4]triazolo[1,5-a]pyrimidin-6-yl)methyl)phenyl)(imino)(methyl)-$\lambda^6$-sulfanone |
| 5 | 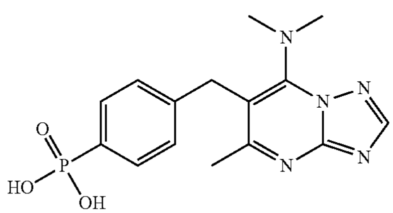 [SMILES: Cc1nc2ncnn2c(N(C)C)c1Cc1ccc(P(=O)(O)O)cc1] | (4-((7-(dimethylamino)-5-methyl-[1,2,4]triazolo[1,5-a]pyrimidin-6-yl)methyl)phenyl)phosphonic acid |
| 6 | 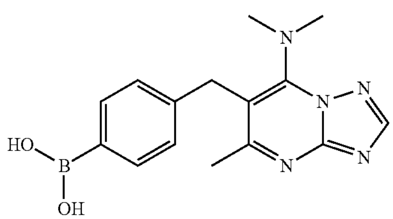 [SMILES: Cc1nc2ncnn2c(N(C)C)c1Cc1ccc(B(O)O)cc1] | imino(4-(7-methoxyquinolin-4-yl)phenethyl)(methyl)-$\lambda^6$-sulfanone |
| 7 | 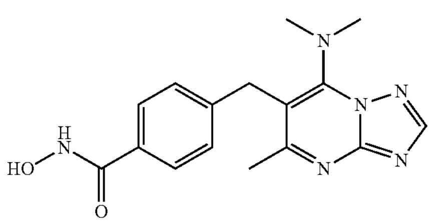 [SMILES: Cc1nc2ncnn2c(N(C)C)c1Cc1ccc(C(=O)NO)cc1] | 4-((7-(dimethylamino)-5-methyl-[1,2,4]triazolo[1,5-a]pyrimidin-6-yl)methyl)-N-hydroxybenzamide |
| 8 | 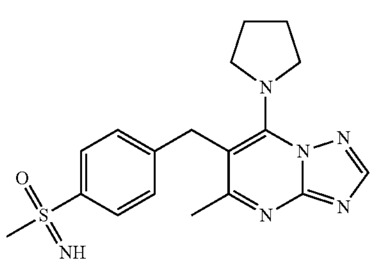 [SMILES: Cc1nc2ncnn2c(N2CCCC2)c1Cc1ccc(S(C)(=N)=O)cc1] | imino(methyl)(4-((5-methyl-7-(pyrrolidin-1-yl)-[1,2,4]triazolo[1,5-a]pyrimidin-6-yl)methyl)phenyl)-$\lambda^6$-sulfanone |

TABLE 1-continued

| Compound No. | Structure | Name |
| --- | --- | --- |
| 8R | 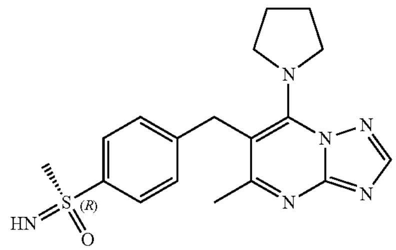 | (R)-imino(methyl)(4-((5-methyl-7-(pyrrolidin-1-yl)-[1,2,4]triazolo[1,5-a]pyrimidin-6-yl)methyl)phenyl)-λ⁶-sulfanone |
| 8S | 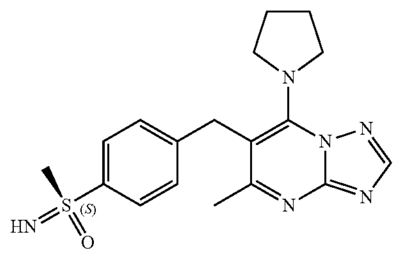 | (S)-imino(methyl)(4-((5-methyl-7-(pyrrolidin-1-yl)-[1,2,4]triazolo[1,5-a]pyrimidin-6-yl)methyl)phenyl)-λ⁶-sulfanone |
| 9 | 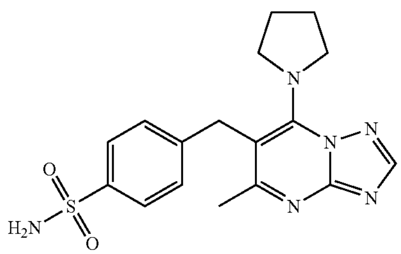 [SMILES: Cc1nc2ncnn2c(N2CCCC2)c1Cc1ccc(S(N)(=O)=O)cc1] | 4-((5-methyl-7-(pyrrolidin-1-yl)-[1,2,4]triazolo[1,5-a]pyrimidin-6-yl)methyl)benzenesulfonamide |
| 10 | 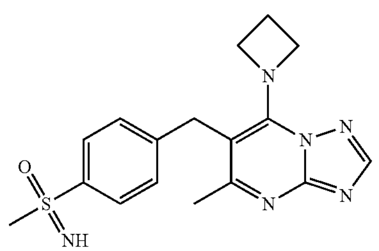 [SMILES: Cc1nc2ncnn2c(N2CCC2)c1Cc1ccc(S(C)(=N)=O)cc1] | (4-((7-(azetidin-1-yl)-5-methyl-[1,2,4]triazolo[1,5-a]pyrimidin-6-yl)methyl)phenyl)(imino)(methyl)-λ⁶-sulfanone |
| 11 | 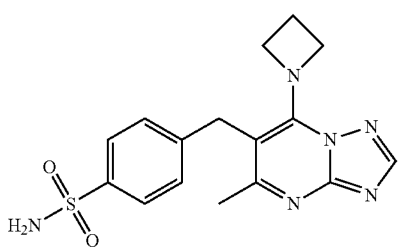 [SMILES: Cc1nc2ncnn2c(N2CCC2)c1Cc1ccc(S(N)(=O)=O)cc1] | 4-((7-(azetidin-1-yl)-5-methyl-[1,2,4]triazolo[1,5-a]pyrimidin-6-yl)methyl)benzenesulfonamide |
| 12 | 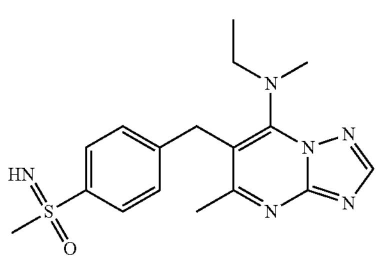 [SMILES: CCN(C)c1c(Cc2ccc(S(C)(=N)=O)cc2)c(C)nc2ncnn12] | (4-((7-(ethyl(methyl)amino)-5-methyl-[1,2,4]triazolo[1,5-a]pyrimidin-6-yl)methyl)phenyl)(imino)(methyl)-λ⁶-sulfanone |

TABLE 1-continued

| Compound No. | Structure | Name |
|---|---|---|
| 13 | 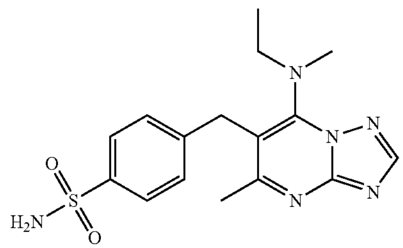 [SMILES: CCN(C)c1c(Cc2ccc(S(N)(=O)=O)cc2)c(C)nc2ncnn12] | 4-((7-(ethyl(methyl)amino)-5-methyl-[1,2,4]triazolo[1,5-a]pyrimidin-6-yl)methyl)benzenesulfonamide |
| 14 | 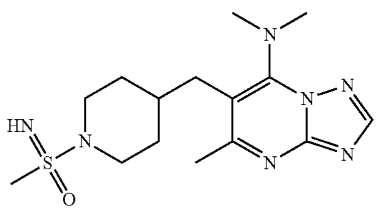 [SMILES: Cc1nc2ncnn2c(N(C)C)c1CC1CCN(S(C)(=N)=O)CC1] | N,N,5-trimethyl-6-((1-(S-methylsulfonimidoyl)piperidin-4-yl)methyl)-[1,2,4]triazolo[1,5-a]pyrimidin-7-amine |
| 15 | 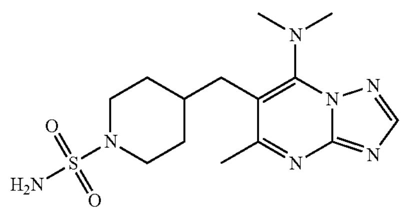 [SMILES: Cc1nc2ncnn2c(N(C)C)c1CC1CCN(S(N)(=O)=O)CC1] | 4-((7-(dimethylamino)-5-methyl-[1,2,4]triazolo[1,5-a]pyrimidin-6-yl)methyl)piperidine-1-sulfonamide |
| 16 | 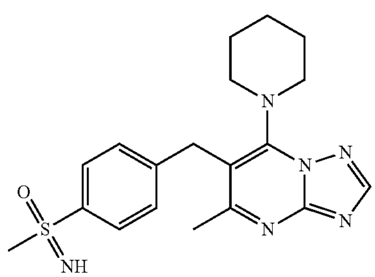 [SMILES: Cc1nc2ncnn2c(N2CCCCC2)c1Cc1ccc(S(C)(=N)=O)cc1] | imino(methyl)(4-((5-methyl-7-(piperidin-1-yl)-[1,2,4]triazolo[1,5-a]pyrimidin-6-yl)methyl)phenyl)-$\lambda^6$-sulfanone |
| 16R | 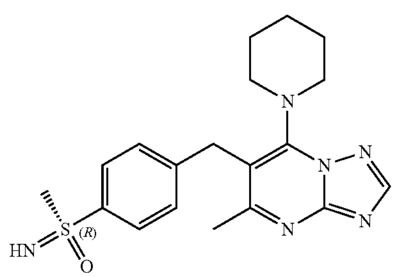 | (R)-imino(methyl)(4-((5-methyl-7-(piperidin-1-yl)[1,2,4]triazolo[1,5-a]pyrimidin-6-yl)methyl)phenyl)-$\lambda^6$-sulfanone |
| 16S | 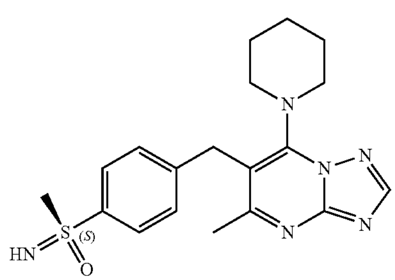 | (S)-imino(methyl)(4((5-methyl-7-(piperidin-1-yl)[1,2,4]triazolo[1,5-a]pyrimidin-6-yl)methyl)phenyl)-$\lambda^6$-sulfanone |

TABLE 1-continued

| Compound No. | Structure | Name |
|---|---|---|
| 17 | 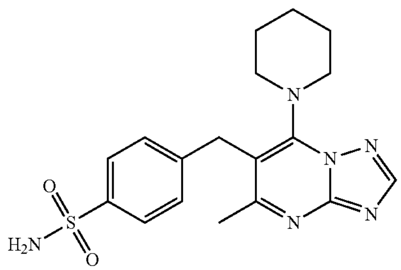 [SMILES: Cc1nc2ncnn2c(N2CCCCC2)c1Cc1ccc(S(N)(=O)=O)cc1] | 4-((5-methyl-7-(piperidin-1-yl)-[1,2,4]triazolo[1,5-a]pyrimidin-6-yl)methyl)benzenesulfonamide |
| 18 | 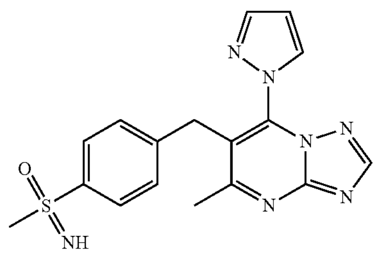 [SMILES: Cc1nc2ncnn2c(-n2cccn2)c1Cc1ccc(S(C)(=N)=O)cc1] | imino(methyl)(4-((5-methyl-7-(1H-pyrazol-1-yl)-[1,2,4]triazolo[1,5-a]pyrimidin-6-yl)methyl)phenyl)-$\lambda^6$-sulfanone |
| 19 | 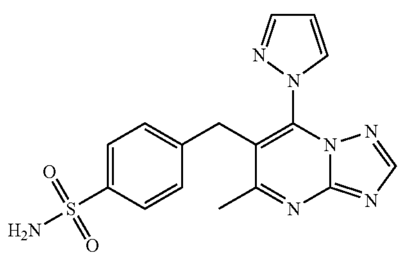 [SMILES: Cc1nc2ncnn2c(-n2cccn2)c1Cc1ccc(S(N)(=O)=O)cc1] | 4-((5-methyl-7-(1H-pyrazol-1-yl)-[1,2,4]triazolo[1,5-a]pyrimidin-6-yl)methyl)benzenesulfonamide |
| 20 | 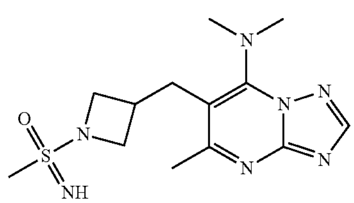 [SMILES: Cc1nc2ncnn2c(N(C)C)c1CC1CN(S(C)(=N)=O)C1] | N,N,5-trimethyl-6-((1-(S-methylsulfonimidoyl)azetidin-3-yl)methyl)-[1,2,4]triazolo[1,5-a]pyrimidin-7-amine |
| 21 | 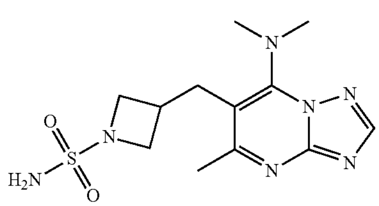 [SMILES: Cc1nc2ncnn2c(N(C)C)c1CC1CN(S(N)(=O)=O)C1] | 3-((7-(dimethylamino)-5-methyl-[1,2,4]triazolo[1,5-a]pyrimidin-6-yl)methyl)azetidine-1-sulfonamide |
| 22 | 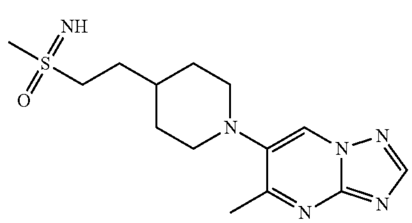 [SMILES: Cc1nc2ncnn2cc1N1CCC(CCS(C)(=N)=O)CC1] | imino(methyl)(2-(1-(5-methyl-[1,2,4]triazolo[1,5-a]pyrimidin-6-yl)piperidin-4-yl)ethyl)-$\lambda^6$-sulfanone |

TABLE 1-continued

| Compound No. | Structure | Name |
|---|---|---|
| 23 | 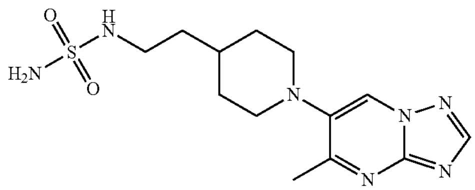 [SMILES: Cc1nc2ncnn2cc1N1CCC(CCNS(N)(=O)=O)CC1] | N-[2-(1-{5-methyl-[1,2,4]triazolo[1,5-a]pyrimidin-6-yl}pipendin-4-yl)ethyl]aminosulfonamide |
| 24 | 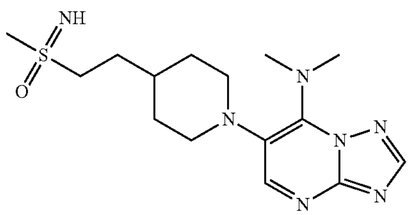 [SMILES: CN(C)c1c(N2CCC(CCS(C)(=N)=O)CC2)cnc2ncnn12] | (2-(1-(7-(dimethylamino)-[1,2,4]triazolo[1,5-a]pyrimidin-6-yl)piperidin-4-yl)ethyl)(imino)(methyl)-$\lambda^6$-sulfanone |
| 25 | 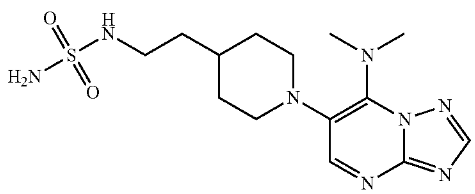 [SMILES: CN(C)c1c(N2CCC(CCNS(N)(=O)=O)CC2)cnc2ncnn12] | N-(2-{1-[7-(dimethylamino)-[1,2,4]triazolo[1,5-a]pyrimidin-6-yl]piperidin-4-yl}ethyl)aminosulfonamide |
| 26 | 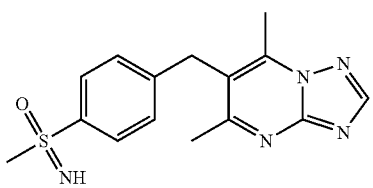 [SMILES: Cc1nc2ncnn2c(C)c1Cc1ccc(S(C)(=N)=O)cc1] | (4-((5,7-dimethyl-[1,2,4]triazolo[1,5-a]pyrimidin-6-yl)methyl)phenyl)(imino)(methyl)-$\lambda^6$-sulfanone |
| 27 | 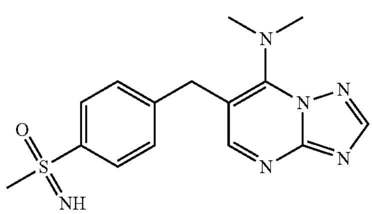 [SMILES: CN(C)c1c(Cc2ccc(S(C)(=N)=O)cc2)cnc2ncnn12] | (4-((7-(dimethylamino)-[1,2,4]triazolo[1,5-a]pyrimidin-6-yl)methyl)phenyl)(imino)(methyl)-$\lambda^6$-sulfanone |
| 28 | 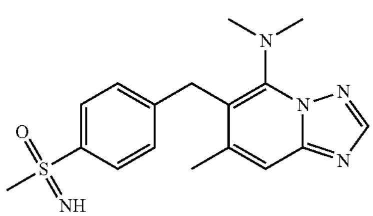 [SMILES: Cc1cc2ncnn2c(N(C)C)c1Cc1ccc(S(C)(=N)=O)cc1] | (4-((5-(dimethylamino)-7-methyl-[1,2,4]triazolo[1,5-a]pyridin-6-yl)methyl)phenyl)(imino)(methyl)-$\lambda^6$-sulfanone |
| 28R | 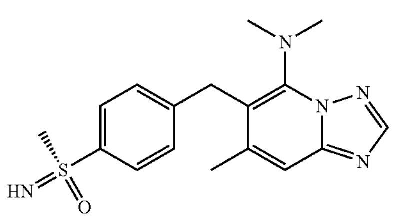 [SMILES: Cc1cc2ncnn2c(N(C)C)c1Cc1ccc([S@](C)(=N)=O)cc1] | (R)-(4-((5-(dimethylamino)-7-methyl-[1,2,4]triazolo[1,5-a]pyridin-6-yl)methyl)phenyl)(imino)(methyl)-$\lambda^6$-sulfanone |

TABLE 1-continued

| Compound No. | Structure | Name |
|---|---|---|
| 28S | 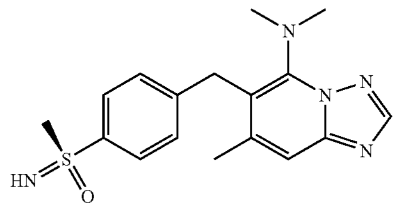 [SMILES: Cc1cc2ncnn2c(N(C)C)c1Cc1ccc([S@@](C)(=N)=O)cc1] | (S)-(4-((5-(dimethylamino)-7-methyl-[1,2,4]triazolo[1,5-a]pyridin-6-yl)methyl)phenyl)(imino)(methyl)-λ⁶-sulfanone |
| 29 | 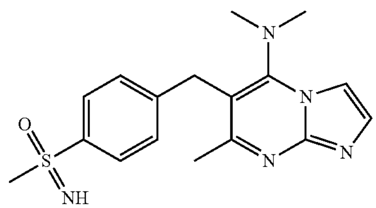 [SMILES: Cc1nc2nccn2c(N(C)C)c1Cc1ccc(S(C)(=N)=O)cc1] | (4-((5-(dimethylamino)-7-methylimidazo[1,2-a]pyrimidin-6-yl)methyl)phenyl)(imino)(methyl)-λ⁶-sulfanone |
| 29R | 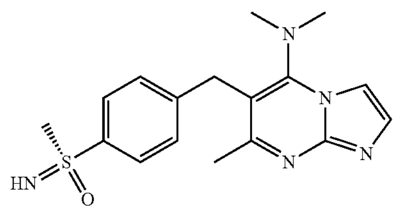 [SMILES: Cc1nc2nccn2c(N(C)C)c1Cc1ccc([S@](C)(=N)=O)cc1] | (R)-(4-((5-(dimethylamino)-7-methylimidazo[1,2-a]pyrimidin-6-yl)methyl)phenyl)(imino)(methyl)-λ⁶-sulfanone |
| 29S | 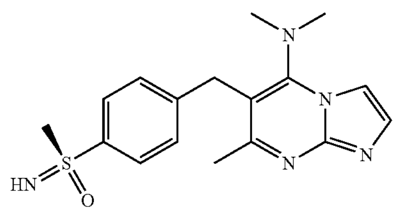 [SMILES: Cc1nc2nccn2c(N(C)C)c1Cc1ccc([S@@](C)(=N)=O)cc1] | (S)-(4-((5-(dimethylamino)-7-methylimidazo[1,2-a]pyrimidin-6-yl)methyl)phenyl)(imino)(methyl)-λ⁶-sulfanone |
| 30 | 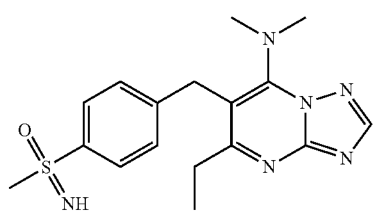 [SMILES: CCc1nc2ncnn2c(N(C)C)c1Cc1ccc(S(C)(=N)=O)cc1] | (4-((7-(dimethylamino)-5-ethyl-[1,2,4]triazolo[1,5-a]pyrimidin-6-yl)methyl)phenyl)(imino)(methyl)-λ⁶-sulfanone |
| 31 | 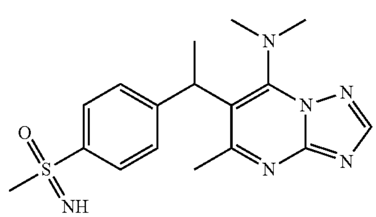 [SMILES: Cc1nc2ncnn2c(N(C)C)c1C(C)c1ccc(S(C)(=N)=O)cc1] | (4-(1-(7-(dimethylamino)-5-methyl-[1,2,4]triazolo[1,5-a]pyrimidin-6-yl)ethyl)phenyl)(imino)(methyl)-λ⁶-sulfanone |
| 32 | 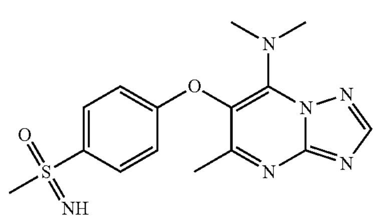 [SMILES: Cc1nc2ncnn2c(N(C)C)c1Oc1ccc(S(C)(=N)=O)cc1] | (4-((7-(dimethylamino)-5-methyl-[1,2,4]triazolo[1,5-a]pyrimidin-6-yl)oxy)phenyl)(imino)(methyl)-λ⁶-sulfanone |

TABLE 1-continued

| Compound No. | Structure | Name |
|---|---|---|
| 33 | 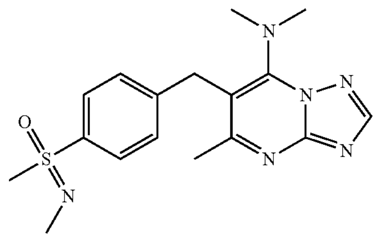 [SMILES: CN=S(C)(=O)c1ccc(Cc2c(C)nc3ncnn3c2N(C)C)cc1] | (4-((7-(dimethylamino)-5-methyl-[1,2,4]triazolo[1,5-a]pyrimidin-6-yl)methyl)phenyl)(methyl)(methylimino)-$\lambda^6$-sulfanone |
| 34 | 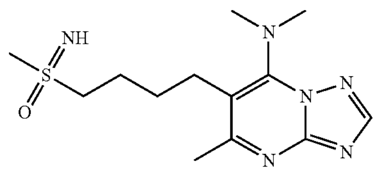 [SMILES: Cc1nc2ncnn2c(N(C)C)c1CCCCS(C)(=N)=O] | (4-((7-(dimethylamino)-5-methyl-[1,2,4]triazolo[1,5-a]pyrimidin-6-yl)butyl)(imino)(methyl)-$\lambda^6$-sulfanone |
| 35 | 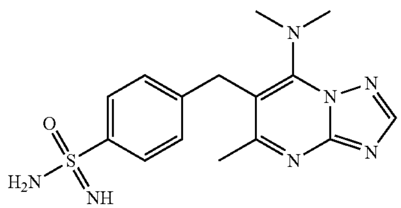 [SMILES: Cc1nc2ncnn2c(N(C)C)c1Cc1ccc(S(=N)(N)=O)cc1] | (4-((7-(dimethylamino)-5-methyl-[1,2,4]triazolo[1,5-a]pyrimidin-6-yl)methyl)benzenesulfonimidamide |
| 36 | 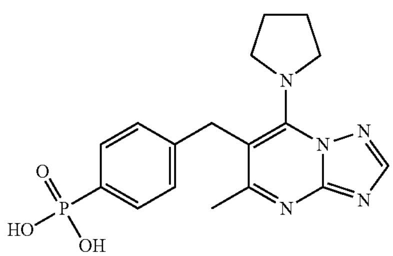 [SMILES: Cc1nc2ncnn2c(N2CCCC2)c1Cc1ccc(P(=O)(O)O)cc1] | (4-{[5-methyl-7-(pyrrolidin-1-yl)-[1,2,4]triazolo[1,5-a]pyrimidin-6-yl]methyl}phenyl)phosphinic acid |
| 37 | 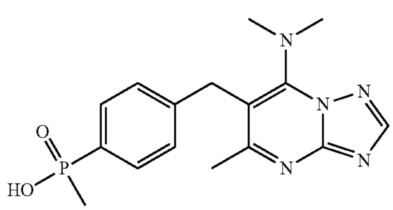 [SMILES: Cc1nc2ncnn2c(N(C)C)c1Cc1ccc(P(C)(=O)O)cc1] | (4-((7-(dimethylamino)-5-methyl-[1,2,4]triazolo[1,5-a]pyrimidin-6-yl)methyl)phenyl)(methyl)phosphinic acid |
| 38 | 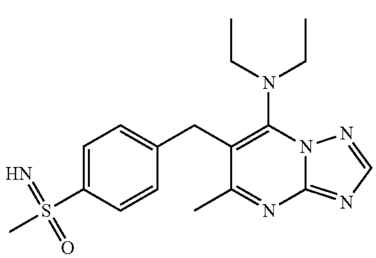 [SMILES: CCN(CC)c1c(Cc2ccc(S(C)(=N)=O)cc2)c(C)nc2ncnn12] | (4-{[7-(dimethylamino)-5-methyl-[1,2,4]triazolo[1,5-a]pyrimidin-6-yl]methy}phenyl)(imino)methyl-$\lambda^6$-sulfanone |

TABLE 1-continued

| Compound No. | Structure | Name |
|---|---|---|
| 39 | 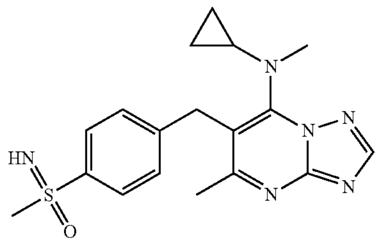 [SMILES: Cc1nc2ncnn2c(N(C)C2CC2)c1Cc1ccc(S(C)(=N)=O)cc1] | [4-({7-[cyclopropyl(methyl)amino]-5-methyl-[1,2,4]triazolo[1,5-a]pyrimidin-6-yl}methyl)phenyl](imino)methyl-$\lambda^6$-sulfanone |
| 40 | 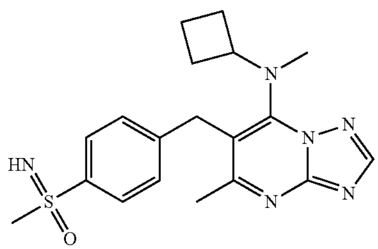 [SMILES: Cc1nc2ncnn2c(N(C)C2CCC2)c1Cc1ccc(S(C)(=N)=O)cc1] | [(4-({7-[cyclobutyl(methyl)amino]-5-methyl-[1,2,4]triazolo[1,5-a]pyrimidin-6-yl}methyl)phenyl](imino)methyl-$\lambda^6$-sulfanone |
| 41 | 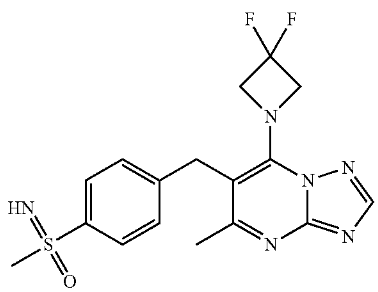 [SMILES: Cc1nc2ncnn2c(N2CC(F)(F)C2)c1Cc1ccc(S(C)(=N)=O)cc1] | (4-{[(7-(3,3-difluoroazetidin-1-yl)-5-methyl-[1,2,4]triazolo[1,5-a]pyrimidin-6-yl]methyl}phenyl)(imino)methyl-$\lambda^6$-sulfanone |
| 42 | 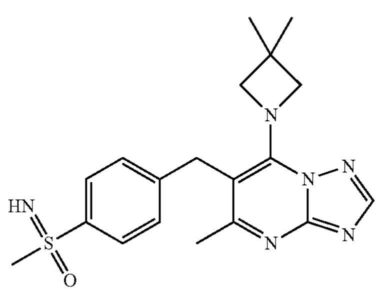 [SMILES: Cc1nc2ncnn2c(N2CC(C)(C)C2)c1Cc1ccc(S(C)(=N)=O)cc1] | (4-{[7-(3,3-dimethylazetidin-1-yl)-5-methyl-[1,2,4]triazolo[1,5-a]pyrimidin-6-yl]methyl}phenyl)(imino)methyl-$\lambda^6$-sulfanone |
| 43 | 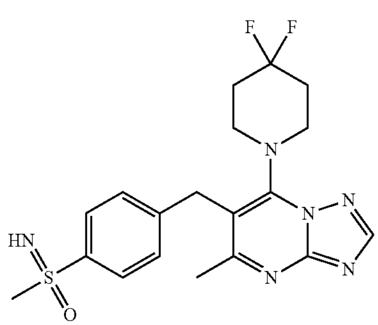 [SMILES: Cc1nc2ncnn2c(N2CCC(F)(F)CC2)c1Cc1ccc(S(C)(=N)=O)cc1] | (4-{[7-(4,4-difluoropiperidin-1-yl)-5-methyl-[1,2,4]triazolo[1,5-a]pyrimidin-6-yl]methyl}phenyl)(imino)methyl-$\lambda^6$-sulfanone |

TABLE 1-continued

| Compound No. | Structure | Name |
|---|---|---|
| 44 | 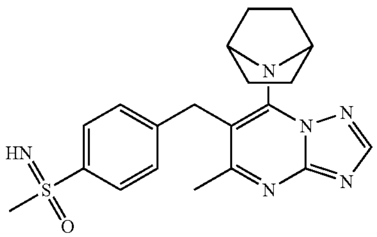 [SMILES: Cc1nc2ncnn2c(N2C3CCC2CC3)c1Cc1ccc(S(C)(=N)=O)cc1] | {4-[(7-{7-azabicyclo[2.2.1]heptan-7-yl}-5-methyl-[1,2,4]triazolo[1,5-a]pyrimidin-6-yl)methyl]phenyl}(imino)methyl-$\lambda^6$-sulfanone |
| 45 | 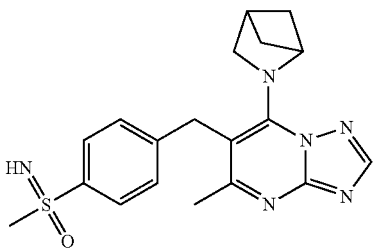 [SMILES: Cc1nc2ncnn2c(N2CC3CC2C3)c1Cc1ccc(S(C)(=N)=O)cc1] | {4-[(7-{2-azabicyclo[2.1.1]heptan-2-yl}-5-methyl-[1,2,4]triazolo[1,5-a]pyrimidin-6-yl)methyl]phenyl}(imino)methyl-$\lambda^6$-sulfanone |
| 46 | 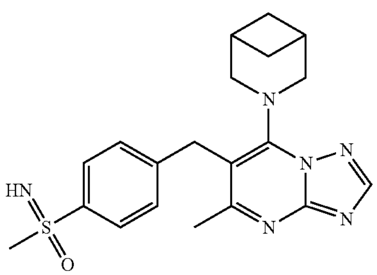 [SMILES: Cc1nc2ncnn2c(N2CC3CC(C3)C2)c1Cc1ccc(S(C)(=N)=O)cc1] | {4-[(7-{3-azabicyclo[3.1.1]heptan-3-yl}-5-methyl-[1,2,4]triazolo[1,5-a]pyrimidin-6-yl)methyl]phenyl}(imino)methyl-$\lambda^6$-sulfanone |
| 47 | 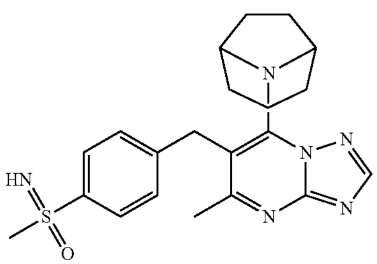 [SMILES: Cc1nc2ncnn2c(N2C3CCCC2CC3)c1Cc1ccc(S(C)(=N)=O)cc1] | [4-[{7-[(8-azabicyclo[3.2.1]heptan-8-yl]-5-methyl-[1,2,4]triazolo[1,5-a]pyrimidin-6-yl)methyl)phenyl](imino)methyl-$\lambda^6$-sulfanone |
| 48 | 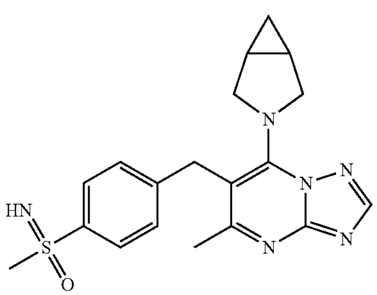 [SMILES: Cc1nc2ncnn2c(N2CC3CC3C2)c1Cc1ccc(S(C)(=N)=O)cc1] | {4-[(7-{3-azabicyclo[3.1.0]heptan-3-yl}-5-methyl-[1,2,4]triazolo[1,5-a]pyrimidin-6-yl)methyl]phenyl}(imino)methyl-$\lambda^6$-sulfanone |
| 49 | 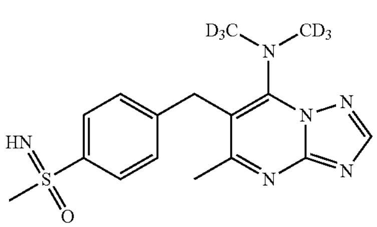 [SMILES: [2H]C([2H])([2H])N(c1c(Cc2ccc(S(C)(=N)=O)cc2)c(C)nc2ncnn12)C([2H])([2H])[2H]] | [4-[{7-[di($^2H_3$)methylamino]-5-methyl-[1,2,4]triazolo[1,5-a]pyrimidin-6-yl}methyl)phenyl](imino)methyl-$\lambda^6$-sulfanone |

TABLE 1-continued

| Compound No. | Structure | Name |
|---|---|---|
| 49R | 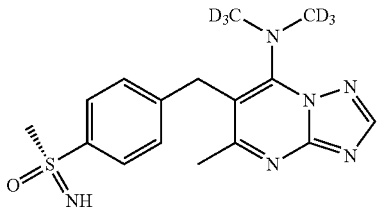 [SMILES: [2H]C([2H])([2H])N(c1c(Cc2ccc([S@@](C)(=N)=O)cc2)c(C)nc2ncnn12)C([2H])([2H])[2H]] | (R)-[4-({7-[di($^2$H$_3$)methylamino]-5-methyl-[1,2,4]triazolo[1,5-a]pyrimidin-6-yl}methyl)phenyl](imino)methyl-λ$^6$-sulfanone |
| 49S | 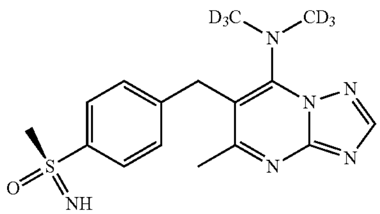 [SMILES: [2H]C([2H])([2H])N(c1c(Cc2ccc([S@](C)(=N)=O)cc2)c(C)nc2ncnn12)C([2H])([2H])[2H]] | (S)-[4-({7-[di($^2$H$_3$)methylamino]-5-methyl-[1,2,4]triazolo[1,5-a]pyrimidin-6-yl}methyl)phenyl](imino)methyl-λ$^6$-sulfanone |
| 50 | 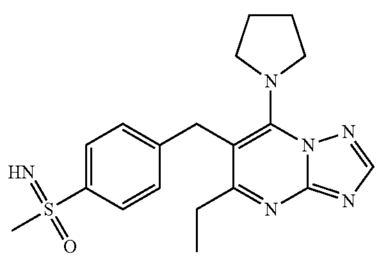 [SMILES: CCc1nc2ncnn2c(N2CCCC2)c1Cc1ccc(S(C)(=N)=O)cc1] | (4-{[5-ethyl-7-(pyrrolidin-1-yl)-[1,2,4]triazolo[1,5-a]pyrimidin-6-yl]methyl}phenyl)(imino)methyl-λ$^6$-sulfanone |
| 51 | 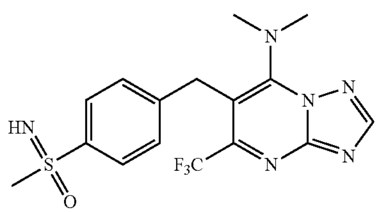 [SMILES: CN(C)c1c(Cc2ccc(S(C)(=N)=O)cc2)c(C(F)(F)F)nc2ncnn12] | (4-{[7-dimethylamino)-5-(trifluromethyl)-[1,2,4]triazolo[1,5-a]pyrimidin-6-yl]methyl}phenyl)(imino)methyl-λ$^6$-sulfanone |
| 52 | 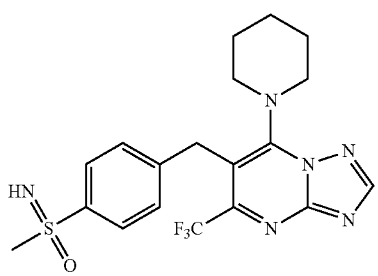 [SMILES: CS(=N)(=O)c1ccc(Cc2c(C(F)(F)F)nc3ncnn3c2N2CCCCC2)cc1] | imino(methyl)(4-{[7-(piperidin-1-yl-5-(trifluromethyl)-[1,2,4]triazolo[1,5-a]pyrimidin-6-yl]methyl}phenyl)-λ$^6$-sulfanone |
| 53 | 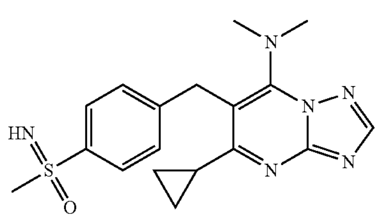 [SMILES: CN(C)c1c(Cc2ccc(S(C)(=N)=O)cc2)c(C2CC2)nc2ncnn12] | (4-{[5-cyclopropyl-7-(dimethylamino)-[1,2,4]triazolo[1,5-a]pyrimidin-6-yl]methyl}phenyl)(imino)methyl-λ$^6$-sulfanone |

TABLE 1-continued

| Compound No. | Structure | Name |
| --- | --- | --- |
| 54 | 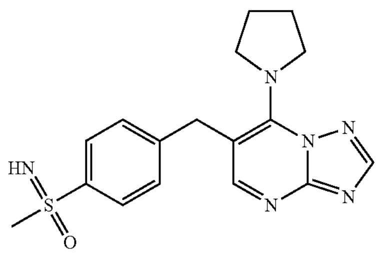 [SMILES: CS(=N)(=O)c1ccc(Cc2cnc3ncnn3c2N2CCCC2)cc1] | imino(methyl)(4-{[7-(piperidin-1-yl)-[1,2,4]triazolo[1,5-a]pyrimidin-6-yl]methyl}phenyl)-$\lambda^6$-sulfanone |
| 55 | 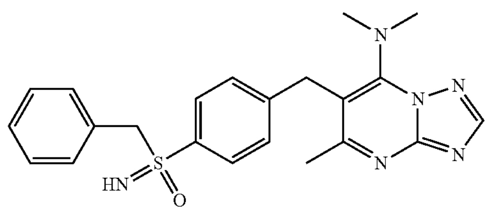 [SMILES: Cc1nc2ncnn2c(N(C)C)c1Cc1ccc(S(=N)(=O)Cc2ccccc2)cc1] | benzyl(4-((7-(dimethylamino)-5-methyl-[1,2,4]triazolo[1,5-a]pyrimidin-6-yl)methyl)phenyl)(imino)-$\lambda^6$-sulfanone |
| 56 | 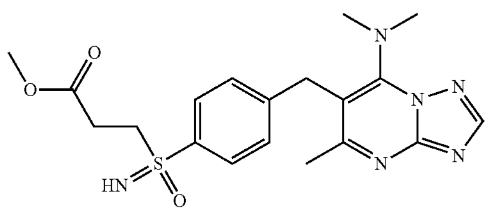 [SMILES: COC(=O)CCS(=N)(=O)c1ccc(Cc2c(C)nc3ncnn3c2N(C)C)cc1] | methyl 3-((4-((7-(dimethylamino)-5-methyl-[1,2,4]triazolo[1,5-a]pyrimidin-6-yl)methyl)phenyl)thio)propanoate |
| 57 | 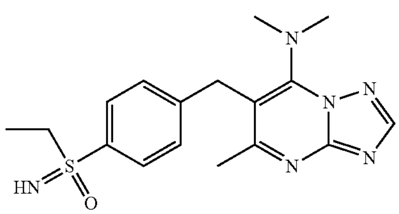 [SMILES: CCS(=N)(=O)c1ccc(Cc2c(C)nc3ncnn3c2N(C)C)cc1] | (4-{[7-(dimethylamino)-5-methyl-[1,2,4]triazolo[1,5-a]pyrimidin-6-yl]methyl}phenyl)(ethyl)imino-$\lambda^6$-sulfanone |
| 58 | 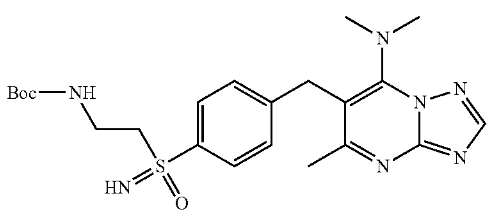 [SMILES: Cc1nc2ncnn2c(N(C)C)c1Cc1ccc(S(=N)(=O)CCNC(=O)OC(C)(C)C)cc1] | tert-butyl(2-(4-((7-(dimethylamino)-5-methyl-[1,2,4]triazolo[1,5-a]pyrimidin-6-yl)methyl)phenylsulfonimidoyl)ethyl)carbamate |
| 59 | 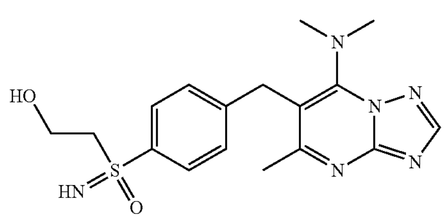 [SMILES: Cc1nc2ncnn2c(N(C)C)c1Cc1ccc(S(=N)(=O)CCO)cc1] | (4-{[7-(dimethylamino)-5-methyl-[1,2,4]triazolo[1,5-a]pyrimidin-6-yl]methyl}phenyl)(2-hydroxyethyl)imino-$\lambda^6$-sulfanone |
| 60 | 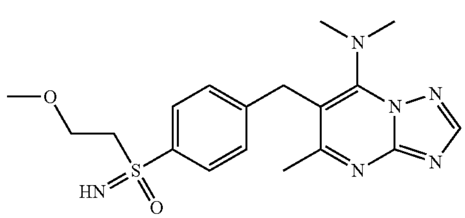 [SMILES: COCCS(=N)(=O)c1ccc(Cc2c(C)nc3ncnn3c2N(C)C)cc1] | (4-{[7-(dimethylamino)-5-methyl-[1,2,4]triazolo[1,5-a]pyrimidin-6-yl]methyl}phenyl)(imino)(2-methoxyethyl)-$\lambda^6$-sulfanone |

TABLE 1-continued

| Compound No. | Structure | Name |
|---|---|---|
| 61 | 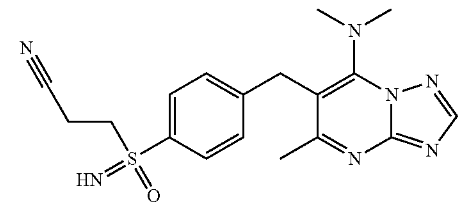 [SMILES: Cc1nc2ncnn2c(N(C)C)c1Cc1ccc(S(=N)(=O)CCC#N)cc1] | 3-[(4-{[7-(dimethylamino)-5-methyl-[1,2,4]triazolo[1,5-a]pyrimidin-6-yl]methyl}phenyl)(imino)oxo-λ⁶-sulfanyl]propanenitrile |
| 62 | 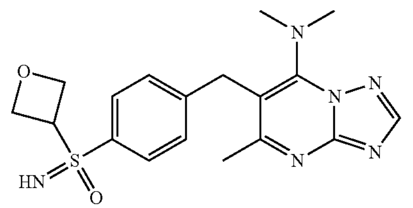 [SMILES: Cc1nc2ncnn2c(N(C)C)c1Cc1ccc(S(=N)(=O)C2COC2)cc1] | [(4-{[7-(dimethylamino)-5-methyl-[1,2,4]triazolo[1,5-a]pyrimidin-6-yl]methyl}phenyl)(oxetan-3-yl)imino-λ⁶-sulfanyl]one |
| 63 | 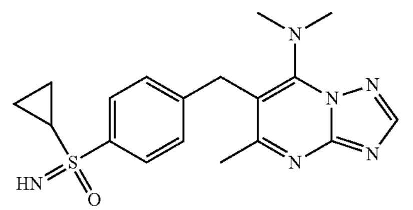 [SMILES: Cc1nc2ncnn2c(N(C)C)c1Cc1ccc(S(=N)(=O)C2CC2)cc1] | [cyclopropyl(4-{[7-(dimethylamino)-5-methyl-[1,2,4]triazolo[1,5-a]pyrimidin-6-yl]methyl}phenyl)imino-λ⁶-sulfanyl]one |
| 64 | 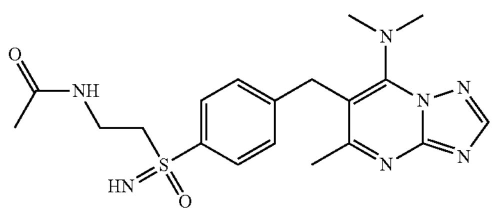 [SMILES: CC(=O)NCCS(=N)(=O)c1ccc(Cc2c(C)nc3ncnn3c2N(C)C)cc1] | N-{2-[(4-{[7-(dimethylamino)-5-methyl-[1,2,4]triazolo[1,5-a]pyrimidin-6-yl]methyl}phenyl)(imino)oxo-λ⁶-sulfanyl]ethyl}acetamide |
| 65 | 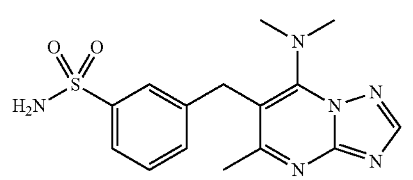 [SMILES: Cc1nc2ncnn2c(N(C)C)c1Cc1cccc(S(N)(=O)=O)c1] | 3-{[7-(dimethylamino)-5-methyl-[1,2,4]triazolo[1,5-a]pyrimidin-6-yl]methyl}benzene-1-sulfonamide |
| 66 | 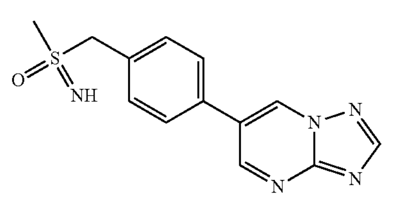 [SMILES: CS(=N)(=O)Cc1ccc(-c2cnc3ncnn3c2)cc1] | imino(methyl)[(4-{[1,2,4]triazolo[1,5-a]pyrimidin-6-yl}phenyl)methyl]-λ⁶-sulfanone |
| 67 | 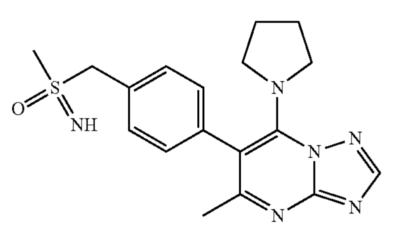 [SMILES: Cc1nc2ncnn2c(N2CCCC2)c1-c1ccc(CS(C)(=N)=O)cc1] | imino(methyl)({4-[5-methyl-7-(pyrrolidin-1-yl)-[1,2,4]triazolo[1,5-a]pyrimidin-6-yl]phenyl}methyl)-λ⁶-sulfanone |

TABLE 1-continued

| Compound No. | Structure | Name |
|---|---|---|
| 68 | 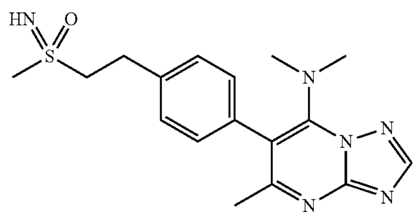 [SMILES: Cc1nc2ncnn2c(N(C)C)c1-c1ccc(CCS(C)(=N)=O)cc1] | (2-{4-[7-(dimethylamino)-5-methyl-[1,2,4]triazolo[1,5-a]pyrimidin-6-yl]phenyl}ethyl)(imino)methyl-λ⁶-sulfanone |
| 69 | 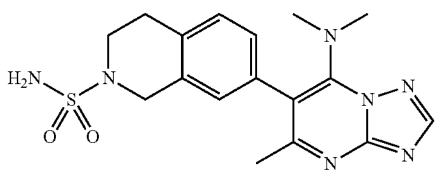 [SMILES: Cc1nc2ncnn2c(N(C)C)c1-c1ccc2c(c1)CN(S(N)(=O)=O)CC2] | 7-[7-(dimethylamino)-5-methyl-[1,2,4]triazolo[1,5-a]pyrimidin-6-yl]-1,2,3,4-tetrahydroisoquinoline-2-sulfonamide |
| 70 | 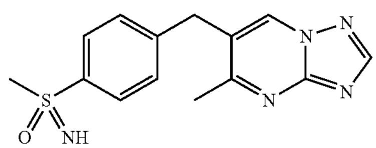 [SMILES: Cc1nc2ncnn2cc1Cc1ccc(S(C)(=N)=O)cc1] | imino(methyl)[4-({5-methyl-[1,2,4]triazolo[1,5-a]pyrimidin-6-yl}methyl)phenyl]-λ⁶-sulfanone |
| 71 | 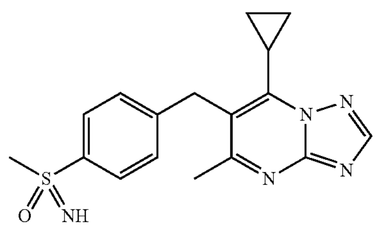 [SMILES: Cc1nc2ncnn2c(C2CC2)c1Cc1ccc(S(C)(=N)=O)cc1] | [4-({7-cyclopropyl-5-methyl-[1,2,4]triazolo[1,5-a]pyrimidin-6-yl}methyl)phenyl](imino)methyl-λ⁶-sulfanone |
| 72 | 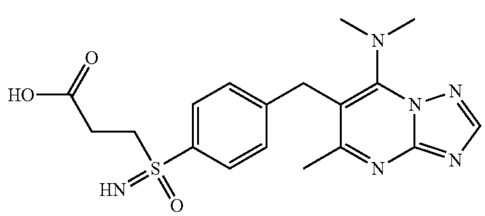 [SMILES: Cc1nc2ncnn2c(N(C)C)c1Cc1ccc(S(=N)(=O)CCC(=O)O)cc1] | 3-[(4-{[7-(dimethylamino)-5-methyl-[1,2,4]triazolo[1,5-a]pyrimidin-6-yl]methyl}phenyl)(imino)oxo-λ⁶-sulfanyl]propanoic acid |
| 72R | 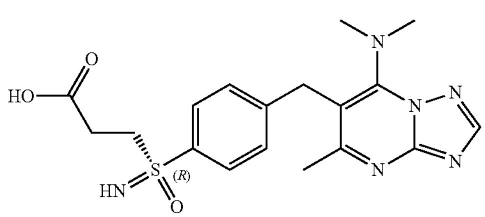 | (R)-3-[(4-{[7-(dimethylamino)-5-methyl-[1,2,4]triazolo[1,5-a]pyrimidin-6-yl]methyl}phenyl)(imino)oxo-λ⁶-sulfanyl]propanoic acid |
| 72S | 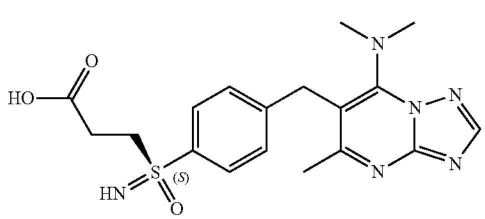 | (S)-3-[(4-{[7-(dimethylamino)-5-methyl-[1,2,4]triazolo[1,5-a]pyrimidin-6-yl]methyl}phenyl)(imino)oxo-λ⁶-sulfanyl]propanoic acid |

TABLE 1-continued

| Compound No. | Structure | Name |
|---|---|---|
| 73 | 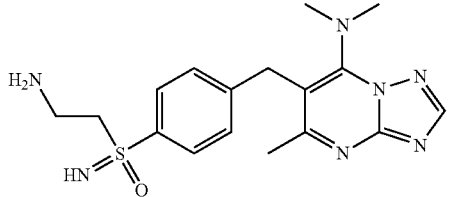 [SMILES: Cc1nc2ncnn2c(N(C)C)c1Cc1ccc(S(=N)(=O)CCN)cc1] | (2-aminoethyl)(4-{[7-(dimethylamino)-5-methyl-[1,2,4]triazolo[1,5-a]pyrimidin-6-yl]methyl}phenyl)imino-$\lambda^6$-sulfanone |
| 74 | 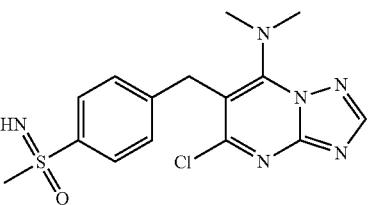 [SMILES: CN(C)c1c(Cc2ccc(S(C)(=N)=O)cc2)c(Cl)nc2ncnn12] | (4-{[5-chloro-7-(dimethylamino)-[1,2,4]triazolo[1,5-a]pyrimidin-6-yl]methyl}phenyl)(imino)methyl-$\lambda^6$-sulfanone |
| 74R | 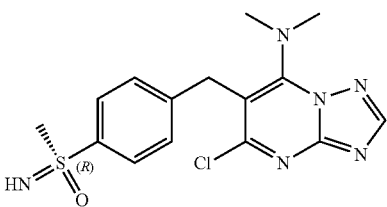 | (R)-(4-{[5-chloro-7-(dimethylamino)-[1,2,4]triazolo[1,5-a]pyrimidin-6-yl]methyl}phenyl)(imino)methyl-$\lambda^6$-sulfanone |
| 74S | 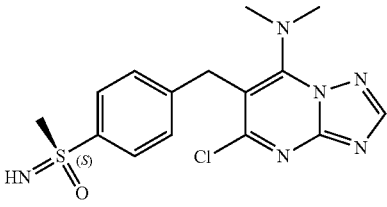 | (S)-(4-{[5-chloro-7-(dimethylamino)-[1,2,4]triazolo[1,5-a]pyrimidin-6-yl]methyl}phenyl)(imino)methyl-$\lambda^6$-sulfanone |
| 75 | 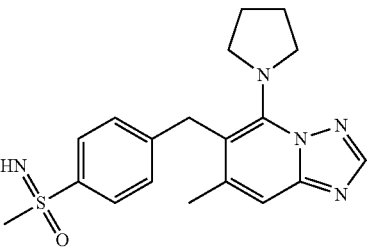 [SMILES: Cc1cc2ncnn2c(N2CCCC2)c1Cc1ccc(S(C)(=N)=O)cc1] | imino(methyl)(4-{[7-methyl-5-(pyrrolidin-1-yl)-[1,2,4]triazolo[1,5-a]pyridin-6-yl]methyl}phenyl)-$\lambda^6$-sulfanone |
| 76 | 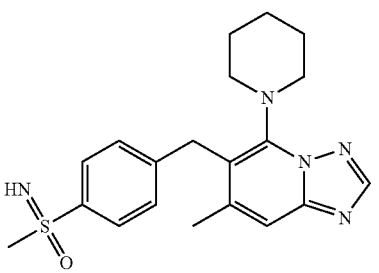 [SMILES: Cc1cc2ncnn2c(N2CCCCC2)c1Cc1ccc(S(C)(=N)=O)cc1] | imino(methyl)(4-{[7-methyl-5-(piperidin-1-yl)-[1,2,4]triazolo[1,5-a]pyridin-6-yl]methyl}phenyl)-$\lambda^6$-sulfanone |

TABLE 1-continued

| Compound No. | Structure | Name |
|---|---|---|
| 77 | 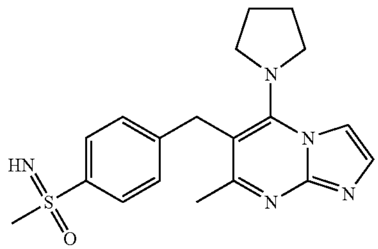 [SMILES: Cc1nc2nccn2c(N2CCCC2)c1Cc1ccc(S(C)(=N)=O)cc1] | imino(methyl)(4-{[7-methyl-5-(pyrrolidin-1-yl)imidazo[1,2-a]pyrimidin-6-yl]methyl}phenyl)-λ⁶-sulfanone |
| 78 | 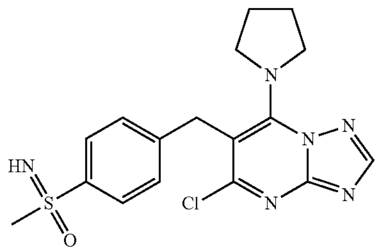 [SMILES: CS(=N)(=O)c1ccc(Cc2c(Cl)nc3ncnn3c2N2CCCC2)cc1] | (4-{[5-chloro-7-(pyrrolidin-1-yl)-[1,2,4]triazolo[1,5-a]pyrimidin-6-yl]methyl}phenyl)(imino)methyl-λ⁶-sulfanone |
| 79 | 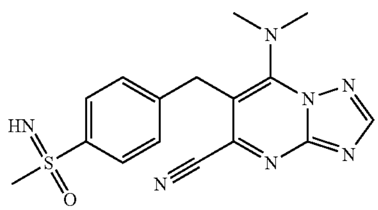 [SMILES: CN(C)c1c(Cc2ccc(S(C)(=N)=O)cc2)c(C#N)nc2ncnn12] | 7-(dimethylamino)-6-({4-[imino(methyl)oxo-λ⁶-sulfanyl]phenyl}methyl)-[1,2,4]triazolo[1,5-a]pyrimidine-5-carbonitrile |
| 80 | 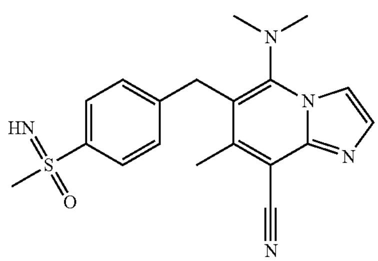 [SMILES: Cc1c(Cc2ccc(S(C)(=N)=O)cc2)c(N(C)C)n2ccnc2c1C#N] | 5-(dimethylamino)-6-({4-[imino(methyl)oxo-λ⁶-sulfanyl]phenyl}methyl)-7-methylimidazo[1,2-a]pyridine-8-carbonitrile |
| 80R | 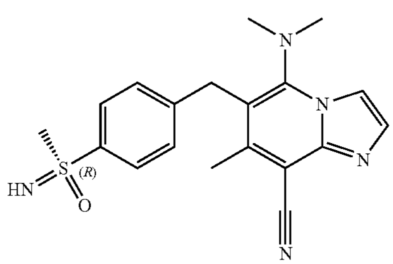 | (R)-5-(dimethylamino)-6-({4-[imino(methyl)oxo-λ⁶-sulfanyl]phenyl}methyl)-7-methylimidazo[1,2-a]pyridine-8-carbonitrile |
| 80S | 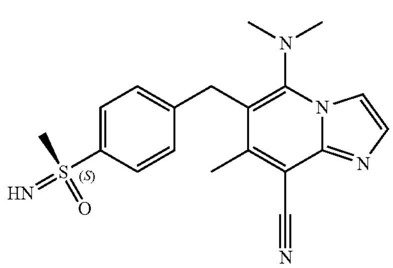 | (S)-5-(dimethylamino)-6-({4-[imino(methyl)oxo-λ⁶-sulfanyl]phenyl}methyl)-7-methylimidazo[1,2-a]pyridine-8-carbonitrile |

TABLE 1-continued

| Compound No. | Structure | Name |
|---|---|---|
| 81 | 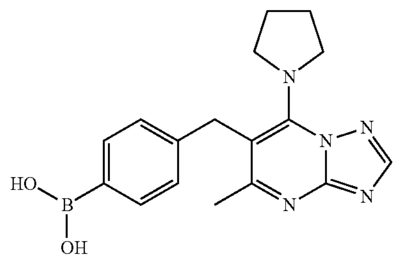 [SMILES: Cc1nc2ncnn2c(N2CCCC2)c1Cc1ccc(B(O)O)cc1] | (4-{[5-methyl-7-(pyrrolidin-1-yl)-[1,2,4]triazolo[1,5-a]pyrimidin-6-yl]methyl}phenyl)boronic acid |
| 82 | 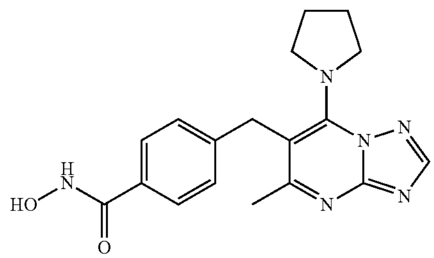 [SMILES: Cc1nc2ncnn2c(N2CCCC2)c1Cc1ccc(C(=O)NO)cc1] | N-hydroxy-4-{[5-methyl-7-(pyrrolidin-1-yl)-[1,2,4]triazolo[1,5-a]pyrimidin-6-yl]methyl}benzamide |
| 83 | 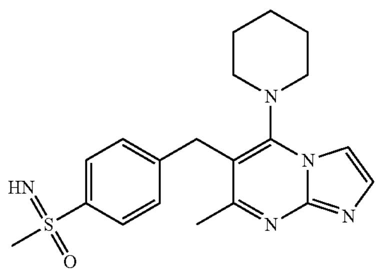 [SMILES: Cc1nc2nccn2c(N2CCCCC2)c1Cc1ccc(S(C)(=N)=O)cc1] | imino(methyl)(4-{[7-methyl-5-(piperidin-1-yl)imidazo[1,2-a]pyrimidin-6-yl]methyl}phenyl)-$\lambda^6$-sulfanone |
| 84 | 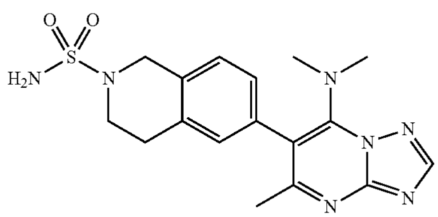 [SMILES: Cc1nc2ncnn2c(N(C)C)c1-c1ccc2c(c1)CCN(S(N)(=O)=O)C2] | 6-[7-(dimethylamino)-5-methyl-[1,2,4]triazolo[1,5-a]pyrimidin-6-yl]-1,2,3,4-tetrahydroisoquinoline-2-sulfonamide |
| 85 | 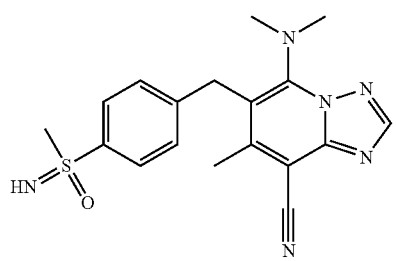 [SMILES: Cc1c(Cc2ccc(S(C)(=N)=O)cc2)c(N(C)C)n2ncnc2c1C#N] | 5-(dimethylamino)-6-({4-[imino(methyl)oxo-$\lambda^6$-sulfanyl]phenyl}methyl)-7-methyl-[1,2,4]triazolo[1,5-a]pyridine-8-carbonitrile |
| 85R | 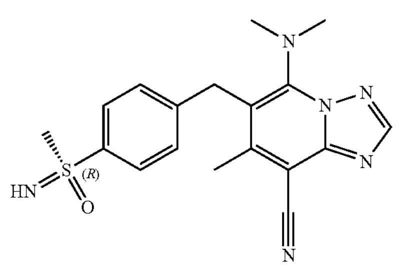 | (R)-5-(dimethylamino)-6-({4-[imino(methyl)oxo-$\lambda^6$-sulfanyl]phenyl}methyl)-7-methyl-[1,2,4]triazolo[1,5-a]pyridine-8-carbonitrile |

TABLE 1-continued

| Compound No. | Structure | Name |
|---|---|---|
| 85S | 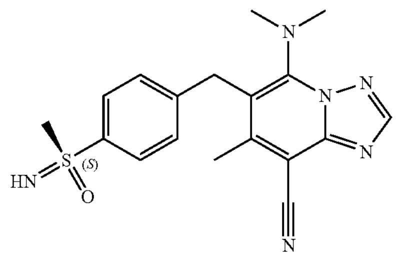 | (S)-5-(dimethylamino)-6-({4-[imino(methyl)oxo-λ⁶-sulfanyl]phenyl}methyl)-7-methyl-[1,2,4]triazolo[1,5-a]pyridine-8-carbonitrile |
| 86 | 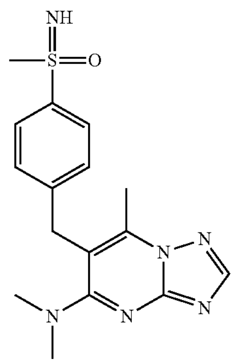 [SMILES: Cc1c(Cc2ccc(S(C)(=N)=O)cc2)c(N(C)C)nc2ncnn12] | (4-{[5-(dimethylamino)-7-methyl-[1,2,4]triazolo[1,5-a]pyrimidin-6-yl]methyl}phenyl)(imino)methyl-λ⁶-sulfanone |
| 87 | 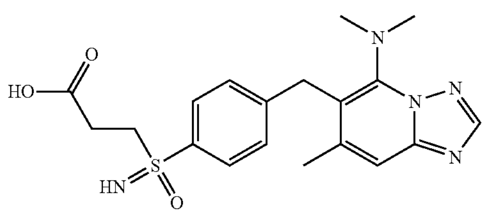 [SMILES: Cc1cc2ncnn2c(N(C)C)c1Cc1ccc(S(=N)(=O)CCC(=O)O)cc1] | 3-[(4-{[5-(dimethylamino)-7-methyl-[1,2,4]triazolo[1,5-a]pyridin-6-yl]methyl}phenyl)(imino)oxo-λ⁶-sulfanyl]propanoic acid |
| 88 | 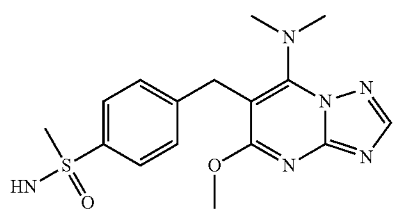 | (4-{[7-(dimethylamino)-5-methoxy-[1,2,4]triazolo[1,5-a]pyrimidin-6-yl]methyl}phenyl)(imino)methyl-λ⁶-sulfanone |
| 88R | 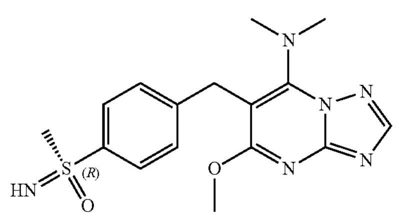 | (R)-(4-{[7-(dimethylamino)-5-methoxy-[1,2,4]triazolo[1,5-a]pyrimidin-6-yl]methyl}phenyl)(imino)methyl-λ⁶-sulfanone |
| 88S | 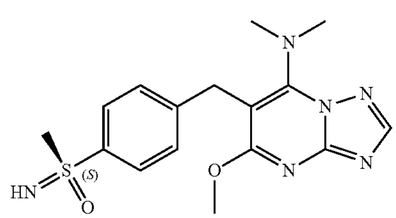 | (S)-(4-{[7-(dimethylamino)-5-methoxy-[1,2,4]triazolo[1,5-a]pyrimidin-6-yl]methyl}phenyl)(imino)methyl-λ⁶-sulfanone |

TABLE 1-continued

| Compound No. | Structure | Name |
|---|---|---|
| 89 | (structure) | [4-({7-amino-5-methyl-[1,2,4]triazolo[1,5-a]pyridin-6-yl}methyl)phenyl](imino)methyl-$\lambda^6$-sulfanone |

In some variations, any of the compounds described herein, such as a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or any variation thereof, or a compound of Table 1 may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

Any formula given herein, such as Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of X, Y, L, A, $R^{A1}$, $R^{A2}$, $R^{A3}$, $R^{A4}$, $R^{A5}$, $R^{A6}$, W, $R^{1a}$, $R^{1a1}$, $R^{1a2}$, $R^{1a3}$, $R^{1a4}$, $R^{1a5}$, $R^{1a6}$, $R^{2a}$, $R^{2a1}$, $R^{2a2}$, $R^{2a3}$, $R^{2a4}$, $R^{2a5}$, $R^{2a6}$, $R^{3a}$, $R^{3a1}$, $R^{3a2}$, $R^{3a3}$, $R^{3a4}$, $R^{3a5}$, $R^{3a6}$, $R^{3a7}$, $R^{4a}$, $R^{4a1}$, $R^{4a2}$, $R^{4a3}$, $R^{4a4}$, $R^{4a5}$, $R^{4a6}$, $R^{1b}$, $R^{1b1}$, $R^{1b2}$, $R^{1b3}$, $R^{1b4}$, $R^{1b5}$, $R^{1b6}$, $R^{2b}$, $R^{3b}$, $R^{3b1}$, $R^{3b2}$, $R^{3b3}$, $R^{3b4}$, $R^{3b5}$, $R^{3b6}$, $R^{4b}$, $R^{5b}$, $R^{6b}$, $R^{7b}$, $R^{8b}$, $R^{9b}$, $R^{10b}$, $R^{11b}$, $R^{12b}$, $R^{13b}$, $R^{14b}$, $R^{1c}$, $R^{1c1}$, $R^{1c2}$, $R^{1c3}$, $R^{1c4}$, $R^{1c5}$, $R^{1c6}$, $R^{1c7}$, $R^{1c8}$, $R^{2c}$, $R^{2c1}$, $R^{2c2}$, $R^{2c3}$, $R^{2c4}$, $R^{2c5}$, $R^{2c6}$, $R^{3c}$, $R^{3c1}$, $R^{3c2}$, $R^{3c3}$, $R^{3c4}$, $R^{3c5}$, $R^{3c6}$, $R^{1d}$, $R^{z1}$, $R^{z2}$, $R^{z3}$, $R^{z4}$, $R^{z5}$, $R^{z6}$, $R^{z7}$, $R^{z8}$, $a^1$, $a^2$, or $a^3$ provided herein can be combined with every other variation or embodiment of X, Y, L, A, $R^{A1}$, $R^{A2}$, $R^{A3}$, $R^{A4}$, $R^{A5}$, $R^{A6}$, W, $R^{1a}$, $R^{1a1}$, $R^{1a2}$, $R^{1a3}$, $R^{1a4}$, $R^{1a5}$, $R^{1a6}$, $R^{2a}$, $R^{2a1}$, $R^{2a2}$, $R^{2a3}$, $R^{2a4}$, $R^{2a5}$, $R^{2a6}$, $R^{3a}$, $R^{3a1}$, $R^{3a2}$, $R^{3a3}$, $R^{3a4}$, $R^{3a5}$, $R^{3a6}$, $R^{3a7}$, $R^{4a}$, $R^{4a1}$, $R^{4a2}$, $R^{4a3}$, $R^{4a4}$, $R^{4a5}$, $R^{4a6}$, $R^{1b}$, $R^{1b1}$, $R^{1b2}$, $R^{1b3}$, $R^{1b4}$, $R^{1b5}$, $R^{1b6}$, $R^{2b}$, $R^{3b}$, $R^{3b1}$, $R^{3b2}$, $R^{3b3}$, $R^{3b4}$, $R^{3b5}$, $R^{3b6}$, $R^{4b}$, $R^{5b}$, $R^{6b}$, $R^{7b}$, $R^{8b}$, $R^{9b}$, $R^{10b}$, $R^{11b}$, $R^{12b}$, $R^{13b}$, $R^{14b}$, $R^{1c}$, $R^{1c1}$, $R^{1c3}$, $R^{1c4}$, $R^{1c5}$, $R^{1c6}$, $R^{1c7}$, $R^{1c8}$, $R^{2c}$, $R^{2c1}$, $R^{2c2}$, $R^{2c3}$, $R^{2c4}$, $R^{2c5}$, $R^{2c6}$, $R^{3c}$, $R^{3c1}$, $R^{3c2}$, $R^{3c3}$, $R^{3c4}$, $R^{3c5}$, $R^{3c6}$, $R^{1d}$, $R^{z1}$, $R^{z2}$, $R^{z3}$, $R^{z4}$, $R^{z5}$, $R^{z6}$, $R^{z7}$, $R^{z8}$, $a^1$, $a^2$, or $a^3$ as if each combination had been individually and specifically described.

As used herein, when any variable occurs more than one time in a chemical formula, its definition on each occurrence is independent of its definition at every other occurrence.

Formula (I) includes all subformulae thereof. For example, Formula (I) includes compounds of Formula (I-1), (I-2), (I-3), (I-4), (Ia), (Ia1), (Ia2), (Ia3), (Ia4), (Ib), (Ib1), (Ic), (Ic1), (Id), (Ie), (If), or (Ig).

Compound names provided herein, including in Table 1, are provided by ChemDraw Professional 19.1. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds that are substantially pure.

Also provided are packaged pharmaceutical compositions, comprising a pharmaceutical composition as described herein and instructions for using the composition to treat a patient suffering from a disease or condition described herein.

Methods of Use

As described herein, the compounds of the present disclosure are inhibitors of ENPP1 enzymatic activity. In one aspect, the compounds and pharmaceutical compositions herein may be used to inhibit ENPP1. In another aspect, the compounds and pharmaceutical compositions herein may be used to treat or prevent a disease or condition in an individual.

The inhibitory activity of the compounds described herein against ENPP1 may be determined and measured by methods known in the art including, but not limited to, inhibition of ENPP1 hydrolysis of 2',3'-cGAMP (Cyclic guanosine monophosphate-adenosine monophosphate) (Mardjuki, R. et al. (2020), *Journal of Biological Chemistry*, 295(15), 4881-4892), inhibition of ENPP1 hydrolysis of pNP-TMP (p-nitrophenyl thymidine 5'-monophosphate), or inhibition of ENPP1 hydrolysis of pNP-AMP (p-nitrophenyl adenosine 5'-monophosphate) (Lee, S. et al. (2017), *Frontiers in Pharmacology* 8, 54).

In one aspect, provided herein is a method of inhibiting ENPP1 comprising contacting a cell with an effective amount of a compound or a pharmaceutical composition as described herein. In some embodiments, provided herein are methods of inhibiting ENPP1 comprising contacting a cell with an effective amount of a compound Formula (I), (I-1), (I-2), (I-3), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. In some embodiments, provided herein are methods of inhibiting ENPP1 comprising contacting a cell with an effective amount of a pharmaceutical composition comprising a compound a compound Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. In one variations of the aforementioned embodiments, the cell is contacted in vitro. In other variations of the aforementioned embodiments, the cell is contacted in vivo.

In another aspect, the compounds and pharmaceutical compositions herein may be used to treat or prevent a disease or condition in an individual, comprising administering an effective amount of a compound or a pharmaceutical composition as described herein. When used in a prophylactic manner, the compounds disclosed and/or described herein may prevent a disease or disorder from developing in an individual at risk of developing the disease or disorder, or lessen the extent of a disease or disorder that may develop.

In some embodiments, provided herein are methods of treating or preventing a disease or condition in an individual, comprising administering to the subject a therapeutically effective amount of a compound or a pharmaceutical composition as described herein. In some embodiments, provided herein are methods of treating or preventing a disease or condition in an individual, comprising administering to the subject a therapeutically effective amount of a compound Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. In some embodiments, provided herein are methods of treating or preventing a disease or condition in an individual, comprising administering to the subject a therapeutically effective amount of a pharmaceutical composition comprising a compound a compound Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof.

In some embodiments, the disease or condition is mediated by ENPP1. In some embodiments, the disease or condition is cancer. In some embodiments, the disease or condition is a bacterial or viral infection. In certain embodiments, the disease or condition is a bacterial infection. In certain other embodiments, the disease or condition is a viral infection. In some embodiments, the disease or condition is insulin resistance. In some embodiments, the disease or condition is type II diabetes. In some embodiments, the disease or condition is chondrocalcinosis. In some embodiments, the disease or condition is calcium pyrophosphate deposition disorder (CPPD). In some embodiments, the disease or condition is hypophosphatasia.

In some embodiments, provided are methods of treating or preventing cancer in an individual, comprising administering to the individual in need thereof a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. In some embodiments, provided are methods of treating or preventing cancer in a subject in need thereof comprising administering to the subject a therapeutically effective amount of at least one chemical entity as described herein. Also provided herein is the use of a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof in the manufacture of a medicament for treatment of a disease in a subject.

In some embodiments, provided herein are methods of treating cancer, comprising administering to an individual in need thereof a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. Also provided herein is the use of a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof in the manufacture of a medicament for treatment of a cancer.

In some embodiments, the provided are methods of treating a bacterial and/or viral infection in an individual, comprising administering to the individual in need thereof a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. Also provided herein is the use of a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof in the manufacture of a medicament for treatment of a bacterial and/or viral infection.

In some embodiments, provided are methods of treating insulin resistance in an individual, comprising administering to the individual in need thereof a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. Also provided herein is the use of a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof in the manufacture of a medicament for treatment of a insulin resistance.

In some embodiments, the provided are methods of treating type II diabetes, comprising administering to the individual in need thereof a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. Also provided herein is the use of a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof in the manufacture of a medicament for treatment of type II diabetes.

In some embodiments, provided are methods of treating chondrocalcinosis in an individual, comprising administering to the individual in need thereof a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. Also provided herein is the use of a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof in the manufacture of a medicament for treatment of chondrocalcinosis.

In some embodiments, provided are methods of treating calcium pyrophosphate deposition disorder (CPPD) in an individual, comprising administering to the individual in need thereof a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. Also provided herein is the use of a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof in the manufacture of a medicament for treatment of calcium pyrophosphate deposition disorder (CPPD).

In some embodiments, provided are methods of treating hypophosphatasia in an individual, comprising administering to the individual in need thereof a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof. Also provided herein is the use of a compound of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or a compound of Table 1, or a pharmaceutically acceptable salt thereof in the manufacture of a medicament for treatment of hypophosphatasia.

Dosages

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pennsylvania In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microtine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of any disease or condition described herein in an individual in need thereof. A kit may additionally contain any materials or equipment that may be used in the administration of the compound or composition, such as vials, syringes, or IV bags. A kit may also contain sterile packaging.

Combinations

The compounds and compositions described and/or disclosed herein may be administered alone or in combination with other therapies and/or therapeutic agents useful in the treatment of the aforementioned disorders.

The compounds and compositions described and/or disclosed herein may be combined with one or more other therapies to treat the diseases or conditions described herein, including but not limited to cancer, bacterial and/or viral infections, insulin resistance, type II diabetes, chondrocalcinosis, calcium pyrophosphate deposition disorder (CPPD), and hypophosphatasia.

General Synthetic Methods

Compounds of Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (I-1), (I-2), (I-3), (I-4), (Ia), (Ia1), (Ia2), (Ia3), (Ia4), (Ib), (Ib1), (Ic), (Ic1), (Id), (Ie), (If), or (Ig), or any variation thereof. Other compounds described herein may be prepared by similar methods.

In some embodiments, compounds provided herein may be synthesized according to Scheme 1, Scheme 2, Scheme 3, Scheme 4, and/or Scheme 5.

An exemplary route to the synthesis of compounds of the structure IX is outlined in Scheme 1. FG represents functional groups either defined by W, protected forms of W such as S(=O)(=N-Piv)$R^{1c}$, S(=O)(=N—CH$_2$(4-MeOPh))$R^{1c}$, diemethylpinacolatoboron, or PO$_3$Et$_2$, or functional groups that can be later transformed to W such as bromide, chloride, amino, hydroxy, and CO$_2$ alkyl.

Scheme 2.

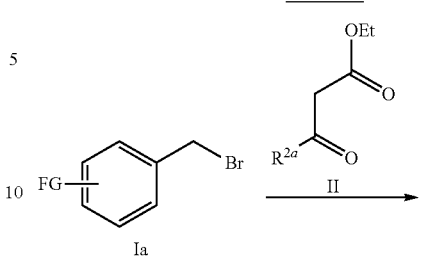

Scheme 1.

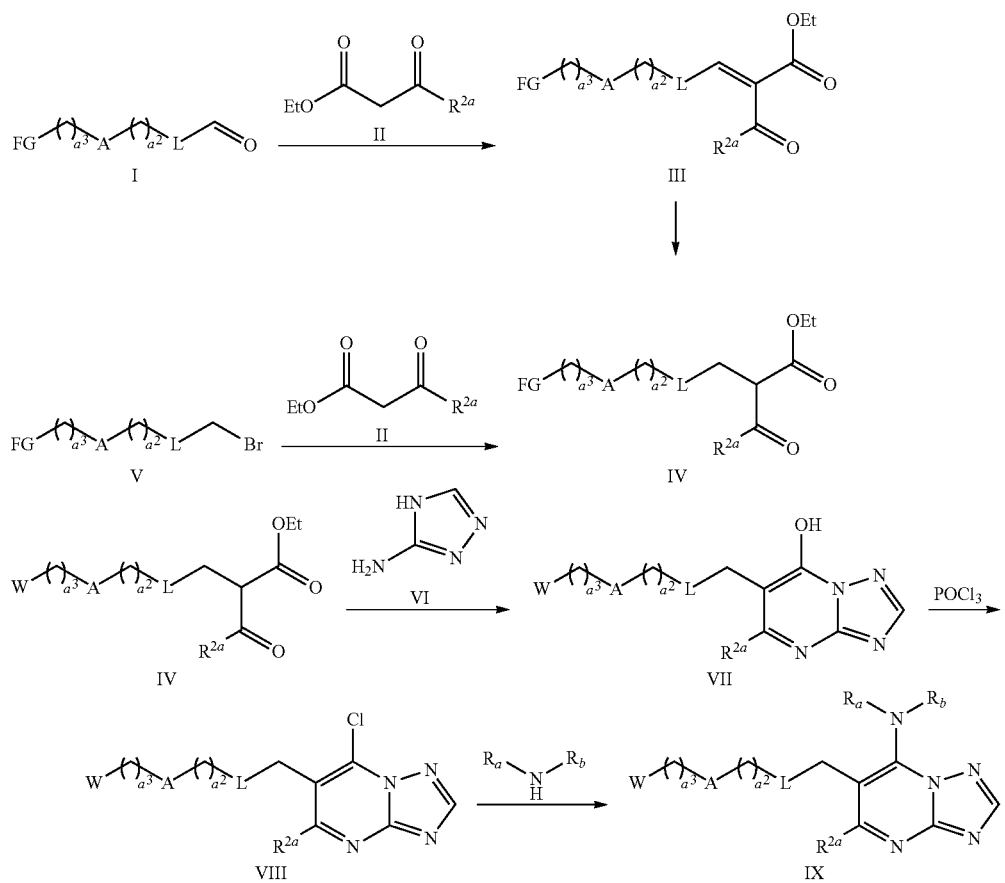

Intermediate IV may be prepared by condensation of aldehydes I with an acetoacetate II to provide intermediate III, that may be reduced, for example by hydrogenation in the presence of a catalyst like Pd(C), to provide IV. Alternatively, II may be alkylated with alkylating agents V in the presence of a base, like NaOEt. Intermediates IV are condensed with aminotriazole VI, for example by heating in acetic acid, to provide triazolopyrimidines VII. Treatment of VII with POCl$_3$ provides chloride VIII that can be reacted with amines, heterocycles, or azoles of formula NHR$^a$R$^b$ to further provide compounds IX, wherein —NR$^a$R$^b$ is the —NR$^{1b}$R$^{2b}$ of R$^{1a}$, or —R$^a$ and R$^b$ are taken together with the nitrogen atom to which they are attached to form the heteroaryl, heterocycloalkyl, or heterocycloalkenyl of R$^{1a}$.

-continued

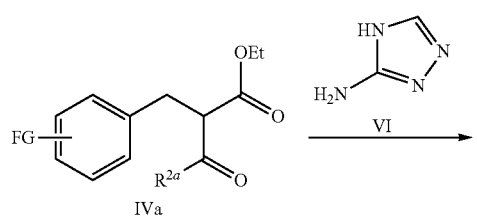

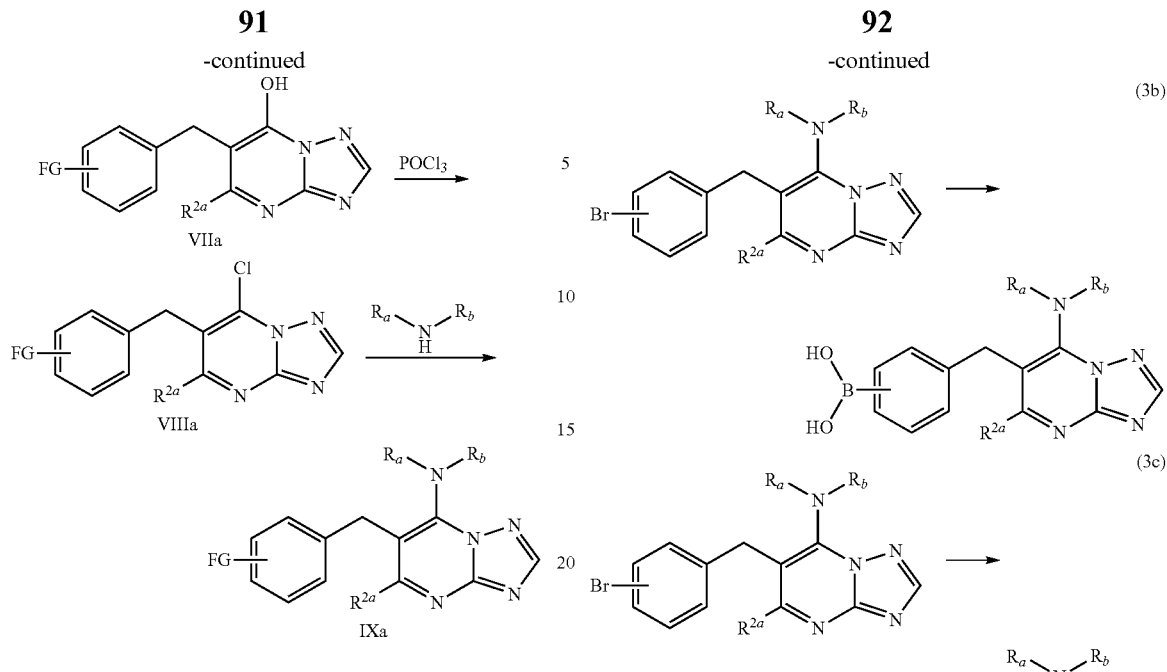

Scheme 2 summarizes the route to IXa, a subset of compounds IX, from benzyl bromides Ia following the route described in Scheme I.

When FG is an intermediate functional group that can be transformed into the moieties W, IXa can be further elaborated as described in Scheme 3. When FG is a thioether, sulfoximines may be prepared with an appropriate oxidant, such as $PhI(OAc)_2$, and an ammonia salt, such as $NH_4OAc$ (equation 3a). When FG is a halide, such as bromide, boronic acids may be prepared by, for example, cross-coupling with bispinacolatodiboron with a Pd-catalyst and a base such as $CsCO_3$, followed by hydrolysis (equation 3b). Phosphonates may also be prepared from IXa when FG is bromide by cross-coupling with $P(O)H(OEt)_2$ with a Pd-catalyst and a base such as $Et_3N$, followed by hydrolysis (equation 3c). When FG is —$NH_2$, treatment with a sulfamoylating agent, such as $ClSO_2NH_2$, will provide sulfamoyl ureas (equation 3d). When FG is a carboxylic acid, hydroxamic acids may be prepared by amidation with hydroxylamine (equation 3e). When FG is a bromide, phosphinic acids may be prepared by cross-coupling with $R^{2c}P(O)H(OEt)$ with a Pd-catalyst and base such as $iPr_2NEt$ (equation 3f).

Scheme 3.

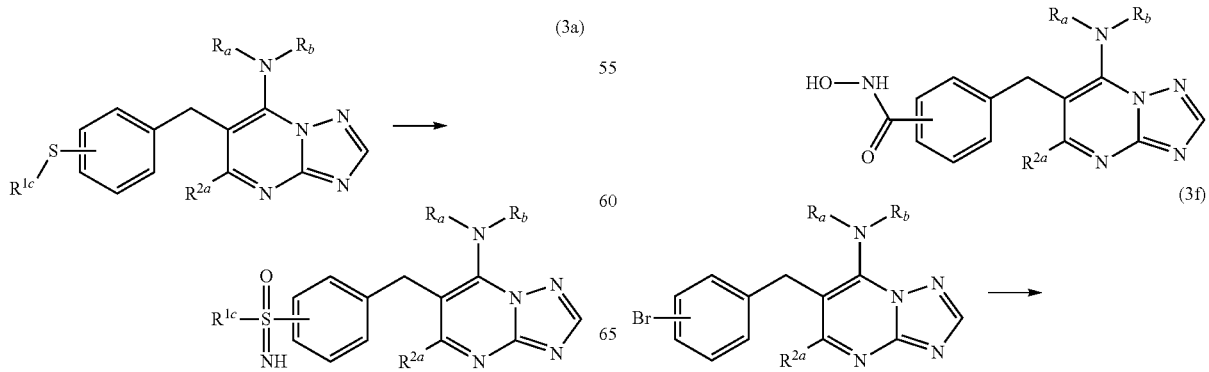

93

-continued

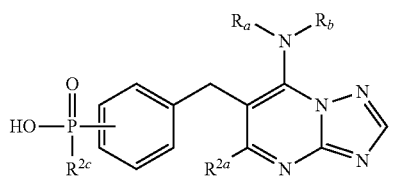

Scheme 4.

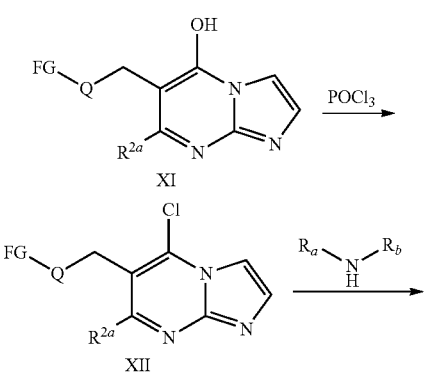

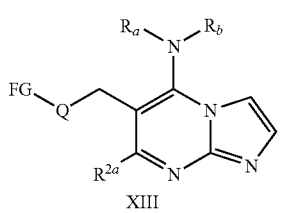

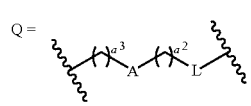

Imidazolopyrimidines XIII may be prepared via the route summarized in Scheme 4. Intermediates IV may be condensed with aminoimidazole X, for example by heating in acetic acid, to provide imidazolopyrimidines XI. Chlorination with POCl$_3$ and chloride displacement of XI (by way of chloride XII) will provide XIII

Scheme 5.

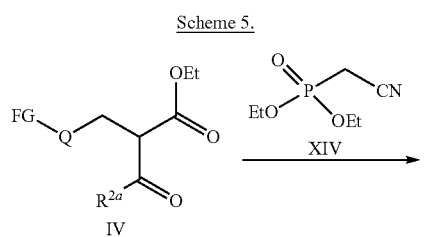

94

-continued

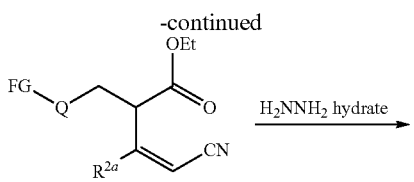

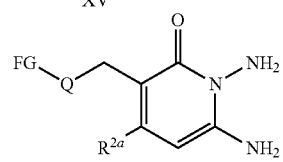

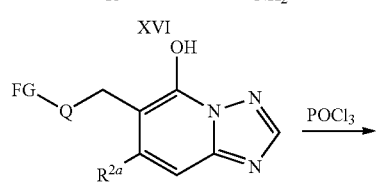

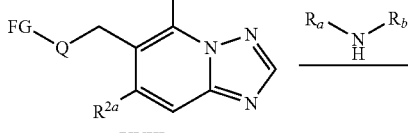

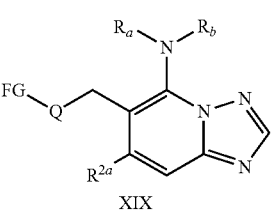

Triazolopyridines XIX may be prepared via the route outlined in Scheme 5. Intermediate IV may be condensed with diethyl(cyanomethyl)phosphonate XIV, for example by heating with K$_2$CO$_3$ in THF, to provide XV. Reaction of XV with hydrazine hydrate, for example by heating in EtOH, will provide XVI. Condensation of XVI with formaldehyde or a formaldehyde surrogate, such as trimethyl orthoformate and acetic acid, will provide XVII. Chlorination of XVII, for example with POCl$_3$, will yield chloride XVIII and chloride displacement of XVIII will provide XIX.

Enumerated Embodiments

1. A compound of Formula (I)

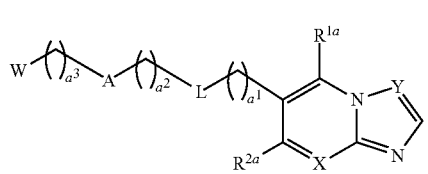

or a pharmaceutically acceptable salt thereof, wherein:
X is —N— or —CR$^{3a}$—;
Y is —N— or —CR$^{4a}$—;

$R^{1a}$ is hydrogen, halogen, cyano, $C_{1-3}$ alkyl, $C_{1-3}$ haloalkyl, aryl, heteroaryl, cycloalkyl, cycloalkenyl, heterocycloalkyl, or heterocycloalkenyl, wherein the $C_{1-3}$ alkyl, aryl, heteroaryl, cycloalkyl, cycloalkenyl, heterocycloalkyl, or heterocycloalkenyl of $R^{1a}$ is optionally substituted;

$R^{2a}$—$R^{4a}$ are each independently hydrogen, halogen, cyano, optionally substituted $C_{1-3}$ alkyl, $C_{1-3}$ haloalkyl, cycloalkyl, or —$OR^{3b}$;

L is a bond, —O—, —C(O)—, —$NR^{4b}$—, or —$CR^{5b}R^{6b}$—;

A is a bond, aryl, heteroaryl, cycloalkyl, cycloalkenyl, heterocycloalkyl, or heterocycloalkenyl, each of which is optionally substituted;

$R^{1b}$ and $R^{2b}$ are each independently hydrogen, optionally substituted $C_{1-3}$ alkyl, or cycloalkyl, $R^{3b}$—$R^{6b}$ are each independently hydrogen or optionally substituted $C_{1-3}$ alkyl; W is

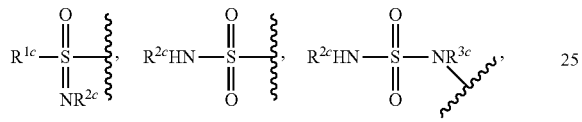

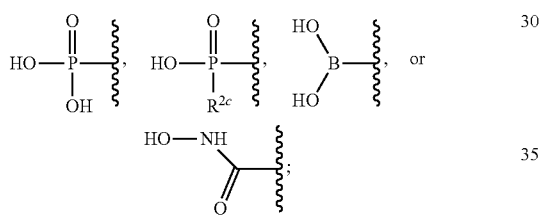

$R^{1c}$ is hydrogen, —$NHR^{1d}$, optionally substituted $C_{1-3}$ alkyl, $C_{1-3}$ haloalkyl, cycloalkyl, or heterocycloalkyl;

$R^{2c}$, $R^{3c}$, and $R^{1d}$ are each independently hydrogen or optionally substituted $C_{1-3}$ alkyl; and $a^1$, $a^2$, and $a^3$ are each independently 0, 1, or 2.

2. The compound of embodiment 1, or a pharmaceutically acceptable salt thereof, wherein W is

3. The compound of embodiment 2, or a pharmaceutically acceptable salt thereof, wherein $R^{1c}$ is methyl.

4. The compound of embodiment 1, or a pharmaceutically acceptable salt thereof, wherein W is

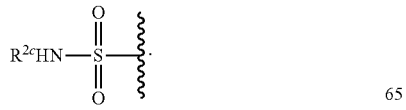

5. The compound of embodiment 1, or a pharmaceutically acceptable salt thereof, wherein W is

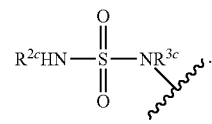

6. The compound of embodiment 1, or a pharmaceutically acceptable salt thereof, wherein W is

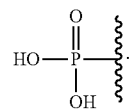

7. The compound of embodiment 1, or a pharmaceutically acceptable salt thereof, wherein W is

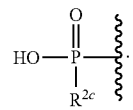

8. The compound of embodiment 1, or a pharmaceutically acceptable salt thereof, wherein W is

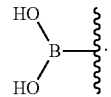

9. The compound of embodiment 1, or a pharmaceutically acceptable salt thereof, wherein W is

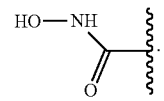

10. The compound of any one of embodiments 1-9, or a pharmaceutically acceptable salt thereof, wherein X is —N—.

11. The compound of any one of embodiments 1-9, or a pharmaceutically acceptable salt thereof, wherein X is —CH—

12. The compound of any one of embodiments 1-11, or a pharmaceutically acceptable salt thereof, wherein Y is —N—.

13. The compound of any one of embodiments 1-11, or a pharmaceutically acceptable salt thereof, wherein Y is —CH—.

14. The compound of any one of embodiments 1-13, or a pharmaceutically acceptable salt thereof, wherein $R^{1a}$ is —$NR^{1b}R^{2b}$.

15. The compound of any one of embodiments 1-13, or a pharmaceutically acceptable salt thereof, wherein $R^{1a}$ is optionally substituted heterocycloalkyl.

16. The compound of any one of embodiments 1-13, or a pharmaceutically acceptable salt thereof, wherein $R^{1a}$ is hydrogen, methyl,

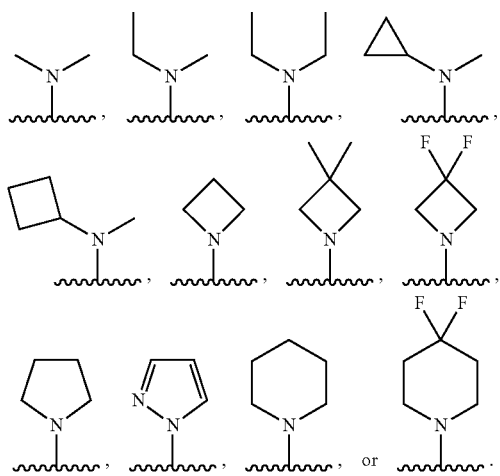

17. The compound of any one of embodiments 1-13, or a pharmaceutically acceptable salt thereof, wherein $R^{1a}$ is

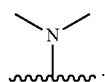

18. The compound of any one of embodiments 1-17, or a pharmaceutically acceptable salt thereof, wherein $R^{2a}$ is hydrogen, methyl, or ethyl.

19. The compound of any one of embodiments 1-17, or a pharmaceutically acceptable salt thereof, wherein $R^{2a}$ is methyl.

20. The compound of any one of embodiments 1-19, or a pharmaceutically acceptable salt thereof, wherein L is a bond.

21. The compound of any one of embodiments 1-19, or a pharmaceutically acceptable salt thereof, wherein L is —CH(CH$_3$)—.

22. The compound of any one of embodiments 1-21, or a pharmaceutically acceptable salt thereof, wherein A is aryl or heterocycloalkyl, each of which is optionally substituted.

23. The compound of any one of embodiments 1-21, or a pharmaceutically acceptable salt thereof, wherein A is

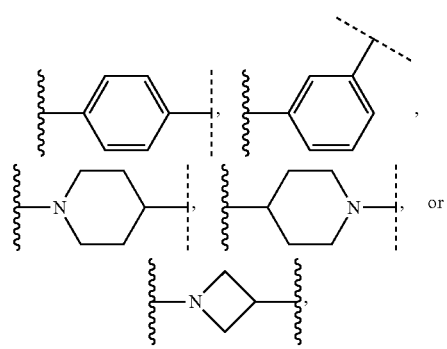

wherein <span style="font-family:cursive">∿∿∿</span> denotes the point of attachment to

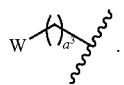

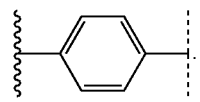

24. The compound of any one of embodiments 1-21, or a pharmaceutically acceptable salt thereof, wherein A is 25. The compound of any one of embodiments 1-24, or a pharmaceutically acceptable salt thereof, wherein $a^1$ is 1.

26. The compound of any one of embodiments 1-24, or a pharmaceutically acceptable salt thereof, wherein $a^1$ is 0.

27. The compound of any one of embodiments 1-26, or a pharmaceutically acceptable salt thereof, wherein $a^2$ is 0.

28. The compound of any one of embodiments 1-27, or a pharmaceutically acceptable salt thereof, wherein $a^3$ is 0.

29. The compound of any one of embodiments 1-27, or a pharmaceutically acceptable salt thereof, wherein $a^3$ is 2.

30. The compound of embodiment 1, or a pharmaceutically acceptable salt thereof, wherein the compound is selected from the group consisting of compounds of Table 1.

31. A pharmaceutical composition comprising a compound of any one of embodiments 1-30, or a pharmaceutically acceptable salt thereof, and a pharmaceutically acceptable carrier or excipient.

32. A method of inhibiting ENPP1 comprising contacting a cell with an effective amount of a compound of any one of embodiments 1-30, or a pharmaceutically acceptable salt thereof.

33. A method of treating cancer in a subject in need thereof, comprising administering to the subject a therapeutically effective amount of a compound of any one of embodiments 1-30, or a pharmaceutically acceptable salt thereof.

34. A method of treating a bacterial and/or viral infection in a subject in need thereof, comprising administering to the subject a therapeutically effective amount of a compound of any one of embodiments 1-30, or a pharmaceutically acceptable salt thereof.

35. A method of treating insulin resistance in a subject in need thereof, comprising administering to the subject a therapeutically effective amount of a compound of any one of embodiments 1-30, or a pharmaceutically acceptable salt thereof.

36. A method of treating type II diabetes in a subject in need thereof, comprising administering to the subject a therapeutically effective amount of a compound of any one of embodiments 1-30, or a pharmaceutically acceptable salt thereof.

37. A method of treating chondrocalcinosis in a subject in need thereof, comprising administering to the subject a therapeutically effective amount of a compound of any one of embodiments 1-30, or a pharmaceutically acceptable salt thereof.

38. A method of treating calcium pyrophosphate deposition disorder (CPPD) in a subject in need thereof, comprising administering to the subject a therapeutically effective amount of a compound of any one of embodiments 1-30, or a pharmaceutically acceptable salt thereof.

39. A method of treating hypophosphatasia in a subject in need thereof, comprising administering to the subject a therapeutically effective amount of a compound of any one of embodiments 1-30, or a pharmaceutically acceptable salt thereof.

Abbreviations dba: dibenzylidene acetone
dppf: 1,1'-bis(diphenylphosphino)ferrocene
DBU: 1,8-Diazabicyclo[5.4.0]undec-7-ene
DME: 1,2-dimethoxyethane
DMF: dimethylformamide
HATU: (1-[Bis(dimethylamino)methylene]-1H-1,2,3-triazolo[4,5-b]pyridinium 3-oxide hexafluorophosphate
HPLC: high-performance liquid chromatography
MTBE: methyl t-butyl ether
NBS: N-bromosuccinimide
NCS: N-chlorosuccinimide
NMP: N-methyl pyrrolidine
SFC: super-critical fluid chromatography
TFA: trifluoroacetic acid
THF: tetrahydrofuran
Xantphos: 4,5-Bis(diphenylphosphino)-9,9-dimethylxanthene Particular non-limiting examples are provided in the Example section below.

EXAMPLES

The following examples are offered to illustrate but not to limit the compositions, uses, and methods provided herein. The compounds are prepared using the general methods described above.

Synthetic Example S-001

Synthesis of (4-{[7-(dimethylamino)-5-methyl-[1,2,4]triazolo[1,5-α]pyrimidin-6-yl]methyl}phenyl)(imino)methyl-λ⁶-sulfanone (Compound 1)

Step 1: Synthesis of ethyl 2-(4-(methylthio)benzyl)-3-oxobutanoate

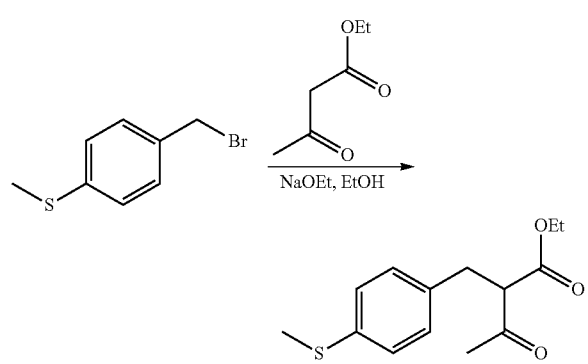

To a solution of ethyl 3-oxobutanoate (3.6 g, 28 mmol) in 45 mL of EtOH was added NaOEt (0.47 g, 6.9 mmol). The mixture was stirred at 20° C. for 10 min, then 1-(bromomethyl)-4-methylsulfanyl-benzene (1.5 g, 6.9 mmol) was added and stirred for 4 h at 80° C. The reaction mixture was concentrated and treated with 10 mL of water, and then extracted with EtOAc (10 mL×2). The combined extracts were concentrated and purified by silica chromatography (7-15% EtOAc in petroleum ether) to afford ethyl 2-(4-(methylthio)benzyl)-3-oxobutanoate (2.0 g) that was used directly in the next step.

Step 2: Synthesis of 5-methyl-6-(4-(methylthio)benzyl)-[1,2,4]triazolo[1,5-α]pyrimidin-7-ol

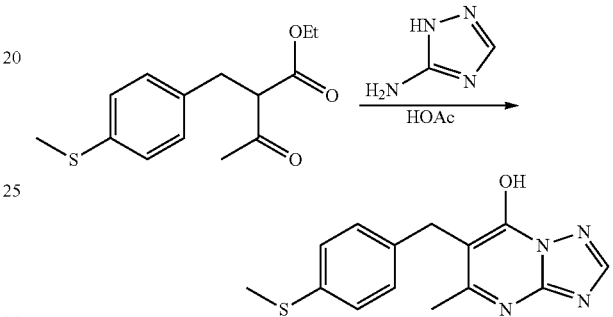

A mixture of ethyl 2-(4-(methylthio)benzyl)-3-oxobutanoate (2.8 g, 11 mmol) and 1H-1,2,4-triazol-5-amine (1.77 g, 21 mmol) in HOAc (1.2 mL) was stirred at 120° C. for 48 h. The reaction mixture was concentrated, triturated with 1:1 iPrOH:MTBE (30 mL) at 50° C. for 30 min and filtered to afford 5-methyl-6-(4-(methylthio)benzyl)-[1,2,4]triazolo[1,5-α]pyrimidin-7-ol (3.0 g).

Step 3: Synthesis of 7-chloro-5-methyl-6-(4-(methylthio)benzyl)-[1,2,4]triazolo[1,5-α]pyrimidine

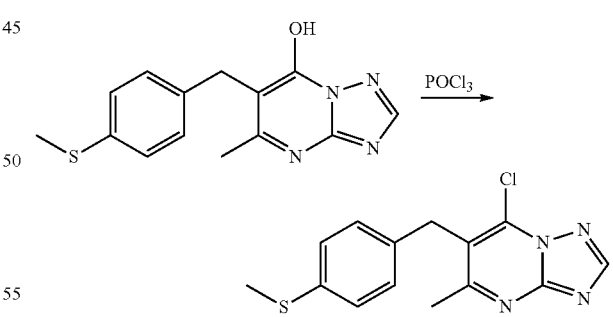

A solution of 5-methyl-6-(4-(methylthio)benzyl)-[1,2,4]triazolo[1,5-α]pyrimidin-7-ol (2.4 g, 8.4 mmol) in POCl₃ (24 mL, 260 mmol) was stirred at 120° C. for 12 h. The reaction mixture was concentrated to give a residue. The reaction mixture was adjusted to pH 7-8 by addition of saturated aqueous of NaHCO₃ and the precipitate filtered. The filter cake was washed with H₂O (20 mL×3). The solid was collected and dried to afford the compound 7-chloro-5-methyl-6-(4-(methylthio)benzyl)-[1,2,4]triazolo[1,5-α]pyrimidine (1.1 g).

Step 4: Synthesis of N,N,5-trimethyl-6-(4-(methylthio)benzyl)-[1,2,4]triazolo[1,5-α]pyrimidin-7-amine

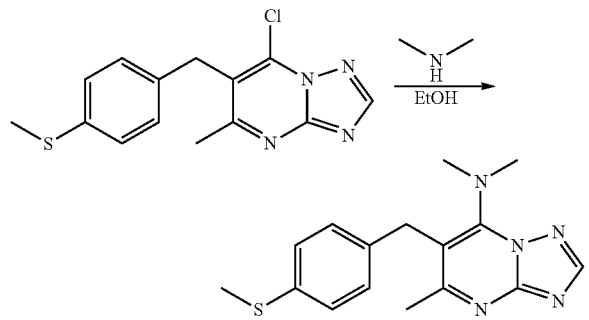

To a solution of 7-chloro-5-methyl-6-(4-(methylthio)benzyl)-[1,2,4]triazolo[1,5-α]pyrimidine (0.50 g, 1.6 mmol) in EtOH (5 mL) was added 33% dimethylamine (1.3 mL, 8.2 mmol). The reaction mixture was stirred at 25° C. for 12 h, concentrated, and then purified by silica chromatography (20-50% EtOAc in petroleum ether) to provide N,N,5-trimethyl-6-(4-(methylthio)benzyl)-[1,2,4]triazolo[1,5-α]pyrimidin-7-amine (0.2 g).

Step 5: Synthesis of (4-{[7-(dimethylamino)-5-methyl-[1,2,4]triazolo[1,5-α]pyrimidin-6-yl]methyl}phenyl)(imino)methyl-$\lambda^6$-sulfanone (Compound 1)

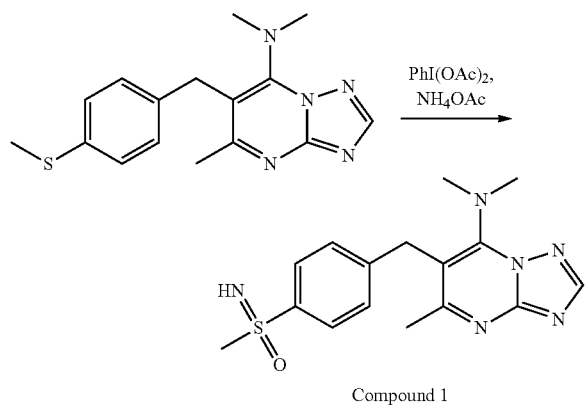

To a solution of N,N,5-trimethyl-6-(4-(methylthio)benzyl)-[1,2,4]triazolo[1,5-α]pyrimidin-7-amine (0.20 g, 0.64 mmol) in EtOH (2 mL) was added PhI(OAc)$_2$ (0.82 g, 2.6 mmol) and NH$_4$OAc (0.25 g, 3.2 mmol). The reaction mixture was stirred at 20° C. for 2 h, then was concentrated and purified by reverse-phase preparative HPLC (27-57% MeCN in H$_2$O, 10 mM NH$_4$HCO$_3$) to afford (4-{[7-(dimethylamino)-5-methyl-[1,2,4]triazolo[1,5-α]pyrimidin-6-yl]methyl}phenyl)(imino)methyl-$\lambda^6$-sulfanone (Compound 1) (10 mg). ESI MS m/z: 345 (M+H).

(3-{[7-(dimethylamino)-5-methyl-[1,2,4]triazolo[1,5-α]pyrimidin-6-yl]methyl}phenyl)(imino)methyl-$\lambda^6$-sulfanone (Compound 4) was prepared in the manner described for Compound 1 in Synthetic Example S-001 by using 1-(bromomethyl)-3-methylsulfanyl-benzene in place of 1-(bromomethyl)-4-methylsulfanyl-benzene in Step 1. ESI MS m/z: 345.0 (M+H).

Compounds in Table 2 were prepared in the same manner as Compound 1 in Synthetic Example S-001 by using the indicated β-keto ester in place of ethyl-3-oxobutanoate in Step 1, and the indicated amine in place of dimethylamine in step 4. Minor modifications to the procedure are indicated by the Conditions.

TABLE 2

| Compound | β-keto ester | Amine | Conditions | MS (m/z) |
|---|---|---|---|---|
| 8 | ethyl-3-oxobutanoate | pyrrolidine | | 371.2 (M + H) |
| 10 | ethyl-3-oxobutanoate | azetidine·HCl | Step 4: 2.5 equiv. Et$_3$N | 357.2 (M + H) |
| 12 | ethyl-3-oxobutanoate | N-ethylmethylamine | | 359.2 (M + H) |
| 16 | ethyl-3-oxobutanoate | piperidine | | 385.2 (M + H) |
| 18 | ethyl-3-oxobutanoate | pyrazole | Step 4: dioxane, 120° C. | 368.2 (M + H) |
| 38 | ethyl-3-oxobutanoate | N-ethyl-N-methylethylamine | | 373.2 (M + H) |
| 39 | ethyl-3-oxobutanoate | N-methylcyclopropylamine | | 371.2 (M + H) |
| 40 | ethyl-3-oxobutanoate | N-methylcyclobutylamine | | 385.2 (M + H) |
| 41 | ethyl-3-oxobutanoate | 3,3-difluoroazetidine | | 393.1 (M + H) |
| 42 | ethyl-3-oxobutanoate | 3,3-dimethylazetidine | | 385.2 (M + H) |
| 43 | ethyl-3-oxobutanoate | 4,4-difluoropiperidine | | 421.2 (M + H) |

TABLE 2-continued

| Compound | β-keto ester | Amine | Conditions | MS (m/z) |
|---|---|---|---|---|
| 44 | ethyl-3-oxobutanoate | (bicyclic NH) | | 397.2 (M + H) |
| 45 | ethyl-3-oxobutanoate | (bicyclic NH) | | 383.2 (M + H) |
| 46 | ethyl-3-oxobutanoate | (bicyclic NH) | | 397.2 (M + H) |
| 47 | ethyl-3-oxobutanoate | (bicyclic NH) | | 411.2 (M + H) |
| 48 | ethyl-3-oxobutanoate | (bicyclic NH) | | 383.2 (M + H) |
| 49 | ethyl 3-oxobutanoate | HN(CD$_3$)$_2$ HCl | Step 4: 2.5 equiv. Et3N | 351.2 (M + H) |
| 50 | ethyl 3-oxopentanoate | (pyrrolidine NH) | | 385.5 M + H) |
| 51 | ethyl 4,4,4-trifluoro-3-oxobutanoate | Me$_2$NH | | 399.1 (M + H) |
| 52 | ethyl 4,4,4-trifluoro-3-oxobutanoate | (piperidine NH) | | 439.2 (M + H) |
| 53 | ethyl 3-cyclopropyl-3-oxopropanoate | Me$_2$NH | | 371.2 (M + H) |

Synthetic Example S-002

Synthesis of 4-((7-(dimethylamino)-5-methyl-[1,2,4]triazolo[1,5-α]pyrimidin-6-yl)methyl)benzenesulfonamide (Compound 2)

Step 1: Synthesis of ethyl 2-[(4-bromophenyl)methyl]-3-oxo-butanoate

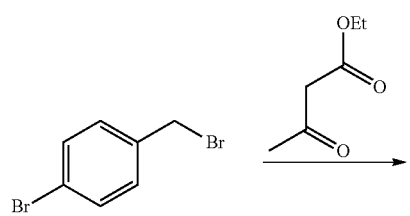

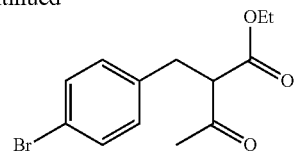

To a solution of 1-bromo-4-(bromomethyl)benzene (5.0 g, 20 mmol) in THF (30 mL) was added 60% NaH (880 mg, 22 mmol) at 0° C. in portions. After addition, the mixture was stirred at 0° C. for 0.5 h, and then ethyl 3-oxobutanoate (3.5 mL, 28 mmol) in THF (20 mL) was added dropwise at 0° C. The resulting mixture was stirred at 20° C. for 12 h, then it was poured into saturated NH$_4$Cl (30 mL) and extracted with EtOAc (2×30 mL). The organic phase was washed with brine (10 mL), dried over Na$_2$SO$_4$, concentrated, and purified by silica chromatography (10-50% EtOAc in Petroleum ether) to afford ethyl 2-[(4-bromophenyl)methyl]-3-oxo-butanoate (5.2 g).

Step 2: Synthesis of 6-(4-bromobenzyl)-5-methyl-[1,2,4]triazolo[1,5-α]pyrimidin-7-ol

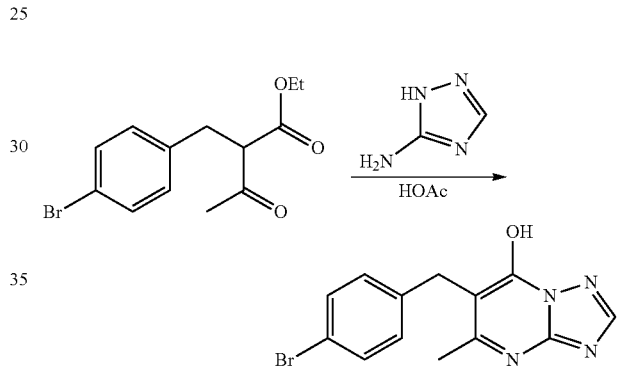

To a solution of ethyl 2-[(4-bromophenyl)methyl]-3-oxo-butanoate (3.0 g, 10 mmol) in HOAc (30 mL) was added 1H-1,2,4-triazol-5-amine (1.7 g, 20 mmol). The mixture was stirred at 130° C. for 12 h, concentrated and recrystallized from MTBE: iPrOH (1:1, 20 mL) to afford 6-(4-bromobenzyl)-5-methyl-[1,2,4]triazolo[1,5-α]pyrimidin-7-ol (3.1 g).

Step 3: Synthesis of 6-(4-bromobenzyl)-7-chloro-5-methyl-[1,2,4]triazolo[1,5-α]pyrimidine

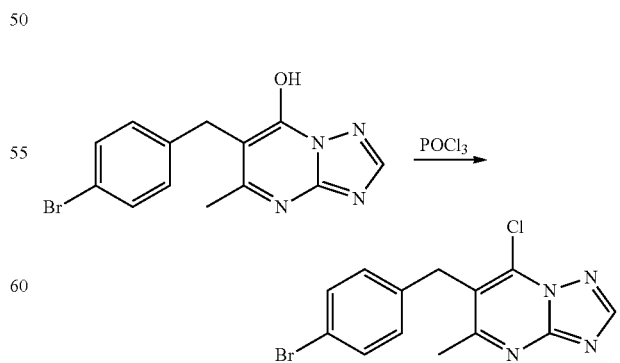

To a solution of 6-(4-bromobenzyl)-5-methyl-[1,2,4]triazolo[1,5-α]pyrimidin-7-ol (1.0 g, 3.1 mmol) was added POCl$_3$ (10 mL, 108 mmol). The mixture was stirred at 120°

C. for 12 h, concentrated, diluted with CH₂Cl (10 mL) and stirred 10 min. The mixture was washed with saturated aq. NaHCO₃ (10 mL) and brine (10 mL), dried by Na₂SO₄, filtered and concentrated to afford 6-(4-bromobenzyl)-7-chloro-5-methyl-[1,2,4]triazolo[1,5-α]pyrimidine (0.6 g).

Step 4: Synthesis of 6-(4-bromobenzyl)-N,N,5-trimethyl-[1,2,4]triazolo[1,5-α]pyrimidin-7-amine

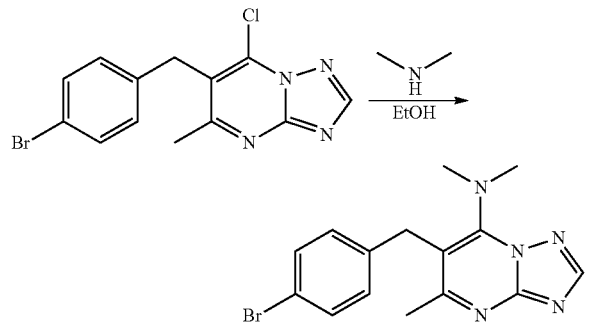

A mixture of 6-(4-bromobenzyl)-7-chloro-5-methyl-[1,2,4]triazolo[1,5-α]pyrimidine (600 mg, 1.8 mmol), 40% dimethylamine (0.45 mL, 3.6 mmol) and EtOH (10 mL) was purged with N₂ before being stirred at 20° C. for 12 h under an N₂ atmosphere. The reaction mixture was concentrated to afford 6-(4-bromobenzyl)-N,N,5-trimethyl-[1,2,4]triazolo[1,5-α]pyrimidin-7-amine (0.3 g).

Step 5: Synthesis of 6-(4-(benzylthio)benzyl)-N,N,5-trimethyl-[1,2,4]triazolo[1,5-α]pyrimidin-7-amine

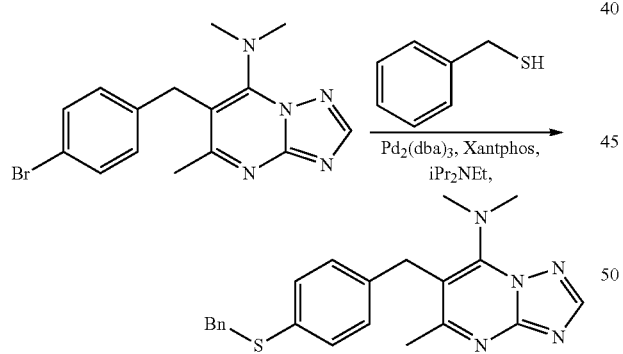

To a solution of 6-(4-bromobenzyl)-N,N,5-trimethyl-[1,2,4]triazolo[1,5-α]pyrimidin-7-amine (250 mg, 0.72 mmol) in dioxane (5 mL) was added phenylmethanethiol (0.16 mL, 1.4 mmol), Xantphos (42 mg, 72 μmol, 0.1 eq), Pd₂(dba)₃ (33 mg, 36.10 umol, 0.05 eq), iPr₂NEt (252 mg, 1.95 mmol, 339.59 uL). The mixture was stirred at 120° C. for 12 h under N₂ before being poured into water (30 mL) and extracted with EtOAc (2×30 mL). The combined extract was washed with brine (10 mL), dried over anhydrous Na₂SO₄, filtered, and concentrated to afford 6-(4-(benzylthio)benzyl)-N,N,5-trimethyl-[1,2,4]triazolo[1,5-α]pyrimidin-7-amine (480 mg).

Step 6: Synthesis of 4-((7-(dimethylamino)-5-methyl-[1,2,4]triazolo[1,5-α]pyrimidin-6-yl)methyl)benzenesulfonyl chloride

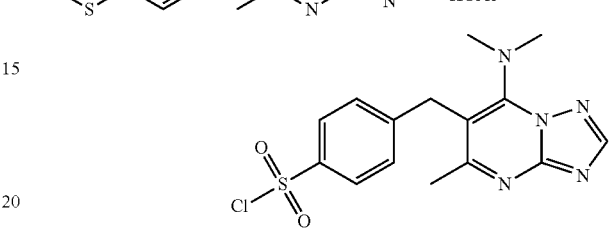

To a mixture of 6-(4-(benzylthio)benzyl)-N,N,5-trimethyl-[1,2,4]triazolo[1,5-α]pyrimidin-7-amine (430 mg, 1.1 mmol) in HOAc (4.5 mL)/H₂O (0.5 mL) was added NCS (442 mg, 3.3 mmol). The mixture was stirred at 20° C. for 2 h, then concentrated to afford 4-((7-(dimethylamino)-5-methyl-[1,2,4]triazolo[1,5-α]pyrimidin-6-yl)methyl)benzenesulfonyl chloride (550 mg).

Step 7: 4-((7-(dimethylamino)-5-methyl-[1,2,4]triazolo[1,5-α]pyrimidin-6-yl)methyl)benzenesulfonamide (Compound 2)

Compound 2

To a solution of 4-((7-(dimethylamino)-5-methyl-[1,2,4]triazolo[1,5-α]pyrimidin-6-yl)methyl)benzenesulfonyl chloride (100 mg, 0.27 mmol) in acetone (2 mL) was added 25% NH₃·H₂O (0.2 mL, 1.3 mmol). The mixture was stirred at 20° C. for 2 h before being concentrated and purified by reverse-phase preparative HPLC (15-45% MeCN in H₂O, 10 mM NH₄HCO₃)) to afford 4-((7-(dimethylamino)-5-methyl-[1,2,4]triazolo[1,5-α]pyrimidin-6-yl)methyl)benzenesulfonamide (Compound 2) (10 mg). ESI MS m/z: 347.1 (M+H).

Synthetic Example S-003

Synthesis of N-(3-{[7-(dimethylamino)-5-methyl-[1,2,4]triazolo[1,5-α]pyrimidin-6-yl]methyl}phenyl)aminosulfonamide (Compound 3)

Step 1: Synthesis of ethyl 2-(3-nitrobenzyl)-3-oxobutanoate

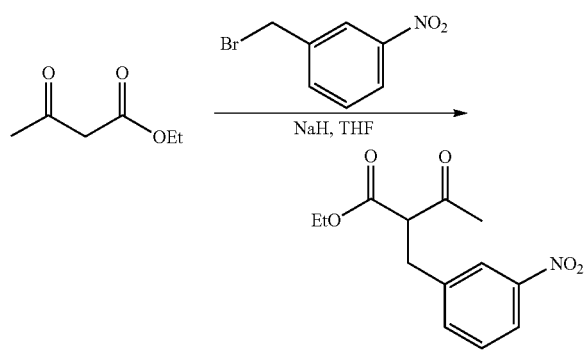

To a solution of ethyl 3-oxobutanoate (1.20 mL, 9.26 mmol) in THF (20.0 mL) was added 60% NaH (410 mg, 10 mmol) at 0° C. The reaction mixture was stirred at 0° C. for 10 min, 1-(bromomethyl)-3-nitrobenzene (2.0 g, 9.3 mmol) was added and the mixture was stirred at 20° C. for 12 h. The mixture was poured into 30 mL of water and extracted with EtOAc (30 mL×2). The combined organic layers were washed with brine (20 mL×2), dried over Na₂SO₄, filtered, and concentrated to give a residue. The residue was purified by silica chromatography (0-36% EtOAc/Petroleum ether) to afford ethyl 2-[(3-nitrophenyl)methyl]-3-oxo-butanoate (1.1 g).

Step 2: Synthesis of 5-methyl-6-(3-nitrobenzyl)-[1,2,4]triazolo[1,5-α]pyrimidin-7-ol

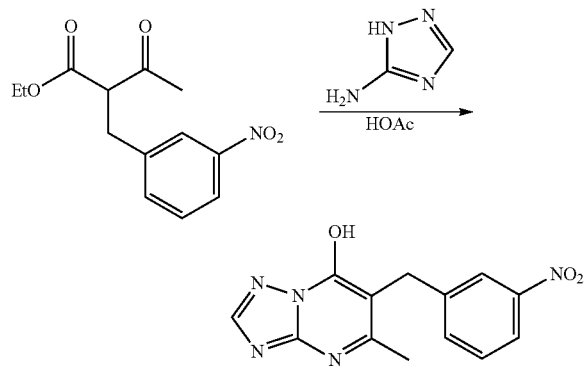

To a stirred solution of ethyl 2-[(3-nitrophenyl)methyl]-3-oxo-butanoate (1.0 mL, 3.4 mmol) in 10 mL of HOAc was added 1H-1,2,4-triazol-5-amine (570 mg, 6.8 mmol). The reaction mixture was stirred at 120° C. for 12 h, then concentrated under reduced pressure to give a residue. The mixture was triturated with MTBE (5.0 mL) and iPrOH (5.0 mL) at 50° C. for 30 min, filtered and concentrated to give 5-methyl-6-(3-nitrobenzyl)-[1,2,4]triazolo[1,5-α]pyrimidin-7-ol (1.1 g).

Step 3: Synthesis of 7-chloro-5-methyl-6-(3-nitrobenzyl)-[1,2,4]triazolo[1,5-α]pyrimidine

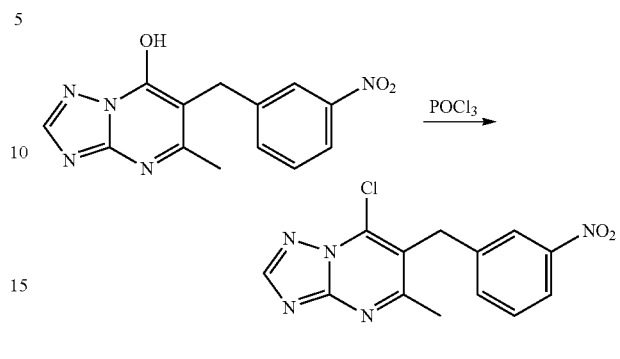

A mixture of 5-methyl-6-(3-nitrobenzyl)-[1,2,4]triazolo[1,5-α]pyrimidin-7-ol (0.55 g, 1.9 mmol) in POCl₃ (5.0 mL, 54 mmol) was stirred at 120° C. for 12 h. The reaction mixture was concentrated, 50 mL of CH₂Cl₂ added, and 2N aq. NaOH added until the pH was 7-8. The organic phase was separated and concentrated to provide 7-chloro-5-methyl-6-(3-nitrobenzyl)-[1,2,4]triazolo[1,5-α]pyrimidine (0.58 g) that was used without further purification.

Step 4: Synthesis of N,N,5-trimethyl-6-(3-nitrobenzyl)-[1,2,4]triazolo[1,5-α]pyrimidin-7-amine

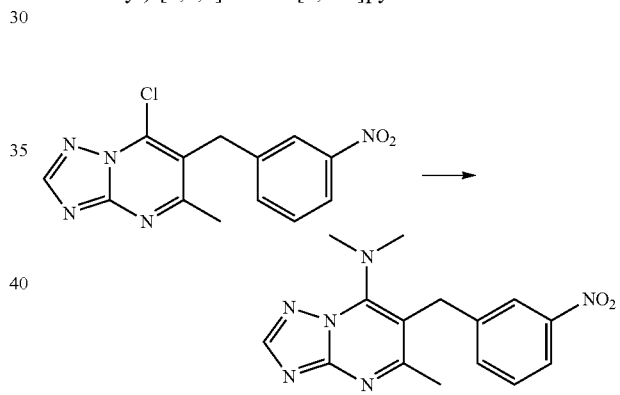

To a solution of 7-chloro-5-methyl-6-(3-nitrobenzyl)-[1,2,4]triazolo[1,5-α]pyrimidine (0.58 g, 1.9 mmol) in EtOH (10 mL) was added 40% Me₂NH (0.73 mL, 5.7 mmol). The mixture was stirred at 20° C. for 12 h, then was concentrated to give N,N,5-trimethyl-6-(3-nitrobenzyl)-[1,2,4]triazolo[1,5-α]pyrimidin-7-amine (0.59 g, crude) as a brown solid that was used without further purification Step 5: Synthesis of N,N,5-trimethyl-6-[(3-nitrophenyl)methyl]-[1, 2, 4]triazolo[1, 5-α]pyrimidin-7-amine

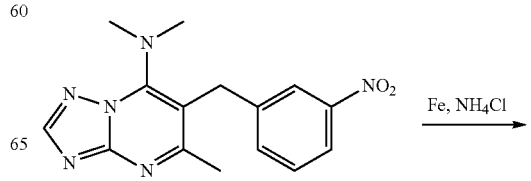

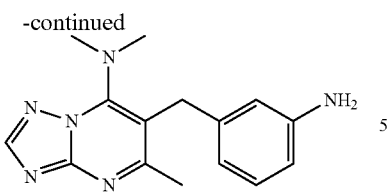

To a solution of 7-chloro-5-methyl-6-(3-nitrobenzyl)-[1,2,4]triazolo[1,5-α]pyrimidine (0.40 g, 1.3 mmol) in 20 mL of EtOH and 5 mL of H₂O was added iron powder (720 mg, 13 mmol) and NH₄Cl (340 mg, 6.4 mmol). After stirring at 80° C. for 12 h, the mixture was filtered and concentrated to provide 6-(3-aminobenzyl)-N,N,5-trimethyl-[1,2,4]triazolo[1,5-α]pyrimidin-7-amine (0.36 g) that was used without further purification.

Step 6: Synthesis of N-(3-{[7-(dimethylamino)-5-methyl-[1,2,4]triazolo[1,5-α]pyrimidin-6-yl]methyl}phenyl)aminosulfonamide (Compound 3)

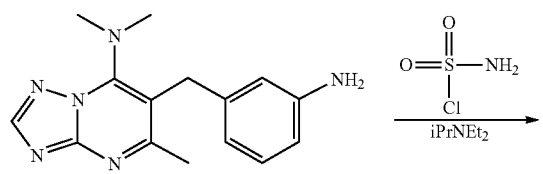

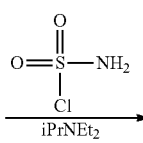

Compound 3

To a solution of 6-(3-aminobenzyl)-N,N,5-trimethyl-[1,2,4]triazolo[1,5-α]pyrimidin-7-amine (0.20 g, 0.71 mmol) in 3.0 mL of DMF was added iPrNEt₂ (0.62 mL, 3.5 mmol) and sulfamoyl chloride (163 mg, 1.4 mmol). The mixture was stirred at 20° C. for 12 h, poured into 10 mL of water, and extracted with EtOAc (10.0 mL×2). The combined organic layers were washed with brine (10 mL×2), dried over Na₂SO₄, filtered and concentrated, and purified by reverse-phase preparative HPLC (12-32% MeCN in H₂O, 0.04% HCl) to afford the compound N-(3-{[7-(dimethylamino)-5-methyl-[1,2,4]triazolo[1,5-α]pyrimidin-6-yl]methyl}phenyl)aminosulfonamide (Compound 3) (6.8 mg). ESI MS m/z: 362.0 (M+H).

Synthetic Example S-004

Synthesis of imino(methyl)(4-{[7-(pyrrolidin-1-yl)-[1,2,4]triazolo[1,5-α]pyrimidin-6-yl]methyl}phenyl)-λ⁶-sulfanone (Compound 54)

Step 1: Synthesis of ethyl 2-formyl-3-(4-methylsulfanylphenyl)propanoate

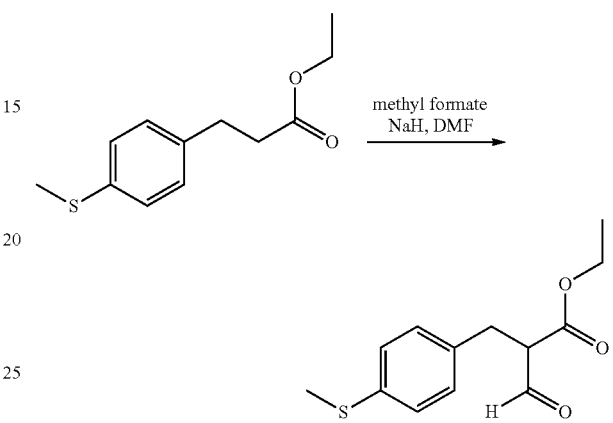

To a 0° C. mixture of ethyl 3-(4-methylsulfanylphenyl)propanoate (0.50 g, 2.2 mmol) and DMF (5.0 mL) was added 60% NaH (0.13 g, 3.3 mmol). The mixture was stirred at 0° C. for 1 h, and methyl formate (0.20 mg, 3.3 mmol) was added dropwise. The resulting mixture was stirred at 25° C. for 11 h. The mixture was poured into saturated aqueous NH₄Cl (20 mL), and the mixture was extracted with EtOAc (20 mL×2). The extracts were combined, washed with brine (10 mL), dried over Na₂SO₄, filtered, and concentrated to provide 0.50 g of ethyl 2-formyl-3-(4-methylsulfanylphenyl)propanoate.

Step 2: Synthesis of 6-[(4-methylsulfanylphenyl)methyl]-[1,2,4]triazolo[1,5-a]pyrimidin-7-ol

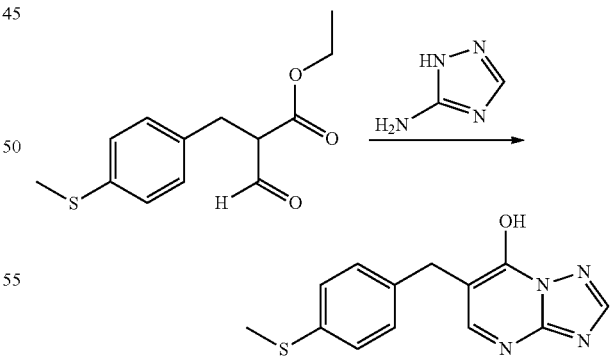

A degassed mixture of ethyl 2-formyl-3-(4-methylsulfanylphenyl)propanoate (0.55 g, 2.2 mmol), 1H-1,2,4-triazol-5-amine (0.37 g, 4.4 mmol), and HOAc (7.0 mL) was stirred at 120° C. for 12 h under N₂ atmosphere. The mixture was concentrated, and the residue was triturated with MTBE (20 mL) at 25° C. for 30 mins, then filtered and dried to provide 0.50 g of 6-[(4-methylsulfanylphenyl)methyl]-[1,2,4]triazolo[1,5-α]pyrimidin-7-ol.

Step 3: Synthesis of 7-chloro-6-[(4-methylsulfanylphenyl)methyl]-[1,2,4]triazolo[1,5-α]pyrimidine

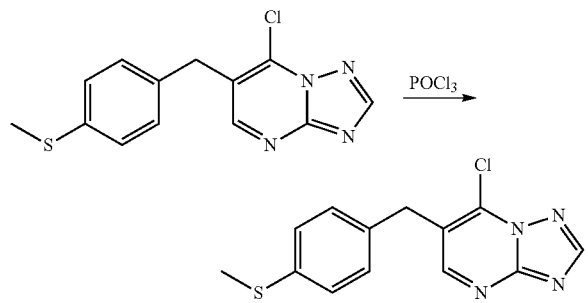

A mixture of 6-[(4-methylsulfanylphenyl)methyl]-[1,2,4]triazolo[1,5-α]pyrimidin-7-ol (0.35 g, 1.3 mmol) and POCl₃ (10 mL, 110 mmol) was stirred at 120° C. for 3 h. The mixture was concentrated and poured into water (10 mL). The aqueous phase was adjusted to pH 7-8 with aqueous NaOH and extracted with EtOAc (10 mL×2). The combined extracts were washed with brine (10 mL), dried over Na₂SO₄, filtered, and concentrated to provide 0.35 g of 7-chloro-6-[(4-methylsulfanylphenyl)methyl]-[1,2,4]triazolo[1,5-α]pyrimidine.

Step 4: Synthesis of 6-[(4-methylsulfanylphenyl)methyl]-7-pyrrolidin-1-yl-[1,2,4]triazolo[1,5-α]pyrimidine

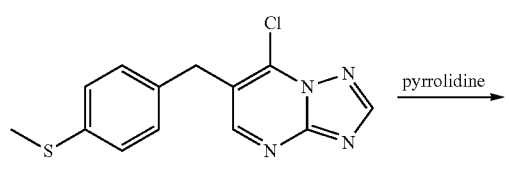

A mixture of 7-chloro-6-[(4-methylsulfanylphenyl)methyl]-[1,2,4]triazolo[1,5-α]pyrimidine (0.35 g, 1.2 mmol), EtOH (5.0 mL) and pyrrolidine (0.17 g, 2.4 mmol) was stirred at 25° C. for 12 h. The mixture was concentrated and purified by silica chromatography (50-100% EtOAc in petroleum ether) to provided 0.20 g of 6-[(4-methylsulfanylphenyl)methyl]-7-pyrrolidin-1-yl-[1,2,4]triazolo[1,5-α]pyrimidine.

Step 5: Synthesis of imino(methyl)(4-{[7-(pyrrolidin-1-yl)-[1,2,4]triazolo[1,5-α]pyrimidin-6-yl]methyl}phenyl)-λ⁶-sulfanone (Compound 54)

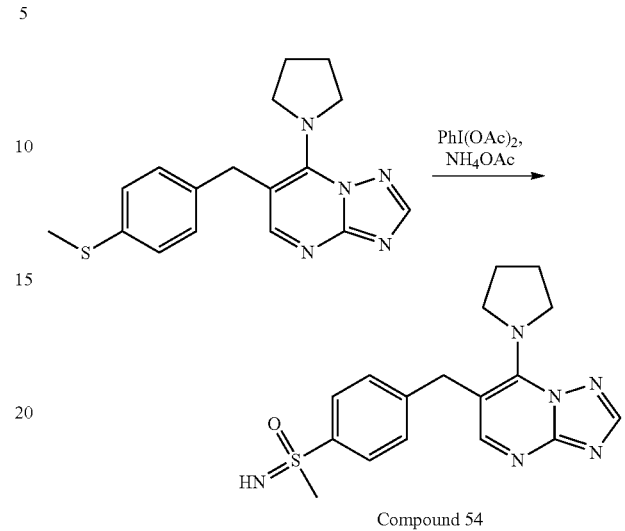

Compound 54

A mixture of 6-[(4-methylsulfanylphenyl)methyl]-7-pyrrolidin-1-yl-[1,2,4]triazolo[1,5-α]pyrimidine (0.20 g, 0.61 mmol), EtOH (3.0 mL), PhI(OAc)₂ (0.59 g, 1.8 mmol), and NH₄OAc (0.19 g, 2.5 mmol) was stirred at 25° C. for 2 h. The reaction was concentrated and purified by reverse-phase preparative HPLC (10-50% MeCN in H₂O, 10 mM NH₄HCO₃) to provide 0.19 g of imino(methyl)(4-{[7-(pyrrolidin-1-yl)-[1,2,4]triazolo[1,5-α]pyrimidin-6-yl]methyl}phenyl)-λ⁶-sulfanone (Compound 54). ESI MS m/z: 357.1 (M+H)

Synthetic Example S-005

Synthesis of benzyl(4-((7-(dimethylamino)-5-methyl-[1,2,4]triazolo[1,5-α]pyrimidin-6-yl)methyl)phenyl)(imino)-λ6-sulfanone (Compound 55)

Step 1: Synthesis of ethyl 2-[(4-bromophenyl)methyl]-3-oxo-butanoate

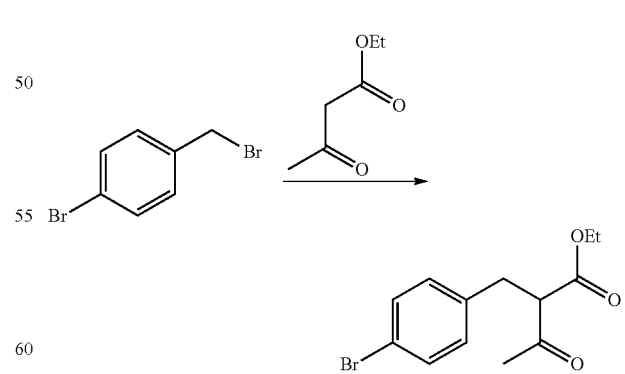

To a solution of 1-bromo-4-(bromomethyl) benzene (5.0 g, 20 mmol) in THF (30 mL) was added 60% NaH (880 mg, 22 mmol) at 0° C. in portions. After addition, the mixture was stirred at 0° C. for 0.5 h, and then ethyl 3-oxobutanoate (3.5 mL, 28 mmol) in THF (20 mL) was added dropwise at 0° C. The resulting mixture was stirred at 20° C. for 12 h, then it was poured into sat'd NH$_4$Cl (30 mL) and extracted with EtOAc (2×30 mL). The organic phase was washed with brine (10 mL), dried over Na$_2$SO$_4$, concentrated, and purified by silica chromatography (10-50% EtOAc:Petroleum ether) to afford ethyl 2-[(4-bromophenyl)methyl]-3-oxo-butanoate (5.2 g).

Step 2: Synthesis of 6-(4-bromobenzyl)-5-methyl-[1,2,4]triazolo[1,5-α]pyrimidin-7-ol

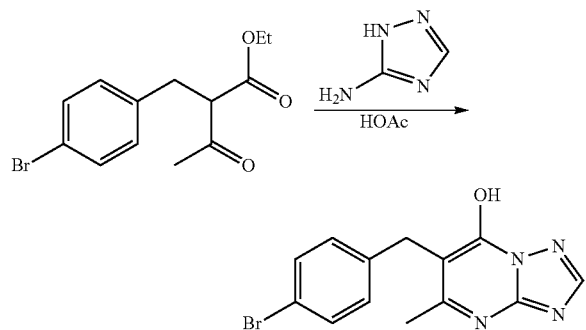 [SMILES: CCOC(=O)C(Cc1ccc(Br)cc1)C(C)=O ; Nc1ncn[nH]1 ; Cc1nc2ncnn2c(O)c1Cc1ccc(Br)cc1 ; "HOAc"]

To a solution of ethyl 2-[(4-bromophenyl) methyl]-3-oxo-butanoate (3.0 g, 10 mmol) in HOAc (30 mL) was added 1H-1,2,4-triazol-5-amine (1.7 g, 20 mmol). The mixture was stirred at 130° C. for 12 h, concentrated and recrystallized from MTBE: iPrOH (1:1, 20 mL) to afford 6-(4-bromobenzyl)-5-methyl-[1,2,4]triazolo[1,5-α]pyrimidin-7-ol (3.1 g).

Step 3: Synthesis of 6-(4-bromobenzyl)-7-chloro-5-methyl-[1,2,4]triazolo[1,5-α]pyrimidine

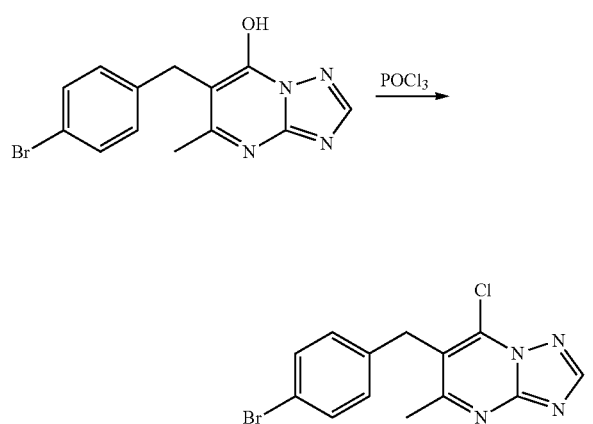

To a solution of 6-(4-bromobenzyl)-5-methyl-[1,2,4]triazolo[1,5-α]pyrimidin-7-ol (1.0 g, 3.1 mmol) was added POCl$_3$ (10 mL, 108 mmol). The mixture was stirred at 120° C. for 12 h, concentrated, diluted with CH$_2$Cl (10 mL) and stirred 10 min. The mixture was washed with saturated aq. NaHCO$_3$ (10 mL) and brine (10 mL), dried by Na$_2$SO$_4$, filtered and concentrated to afford 6-(4-bromobenzyl)-7-chloro-5-methyl-[1,2,4]triazolo[1,5-α]pyrimidine (0.6 g).

Step 4: Synthesis of 6-(4-bromobenzyl)-N,N,5-trimethyl-[1,2,4]triazolo[1,5-α]pyrimidin-7-amine

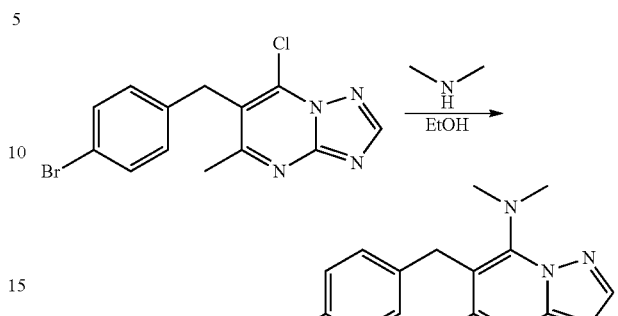

A mixture of 6-(4-bromobenzyl)-7-chloro-5-methyl-[1,2,4]triazolo[1,5-α]pyrimidine (600 mg, 1.8 mmol), 40% dimethylamine (0.45 mL, 3.6 mmol) and EtOH (10 mL) was purged with N$_2$ before being stirred at 20° C. for 12 h under an N$_2$ atmosphere. The reaction mixture was concentrated to afford 6-(4-bromobenzyl)-N,N,5-trimethyl-[1,2,4]triazolo[1,5-α]pyrimidin-7-amine (0.3 g).

Step 5: Synthesis of 6-(4-(benzylthio)benzyl)-N,N,5-trimethyl-[1,2,4]triazolo[1,5-α]pyrimidin-7-amine

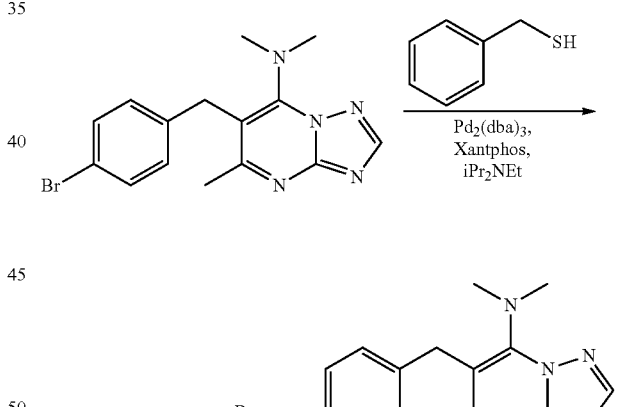

To a solution of 6-[(4-bromophenyl)methyl]-N,N,5-trimethyl-[1,2,4]triazolo[1,5-α]pyrimidin-7-amine (250 mg, 0.72 mmol) in dioxane (5 mL) was added phenylmethanethiol (0.16 mL, 1.4 mmol), Xantphos (42 mg, 72 µmol, 0.1 eq), Pd$_2$(dba)$_3$ (33 mg, 36.10 umol, 0.05 eq), and iPr$_2$NEt (252 mg, 1.95 mmol, 339.59 uL). The mixture was stirred at 120° C. for 12 h under N$_2$ before being poured into water (30 mL) and extracted with EtOAc (2×30 mL). The combined extract was washed with brine (10 mL), dried over anhydrous Na$_2$SO$_4$, filtered, and concentrated to afford 6-(4-(benzylthio)benzyl)-N,N,5-trimethyl-[1,2,4]triazolo[1,5-α]pyrimidin-7-amine (480 mg).

Step 6: Synthesis of benzyl(4-((7-(dimethylamino)-5-methyl-[1,2,4]triazolo[1,5-α]pyrimidin-6-yl)methyl)phenyl)(imino)-λ6-sulfanone (Compound 55)

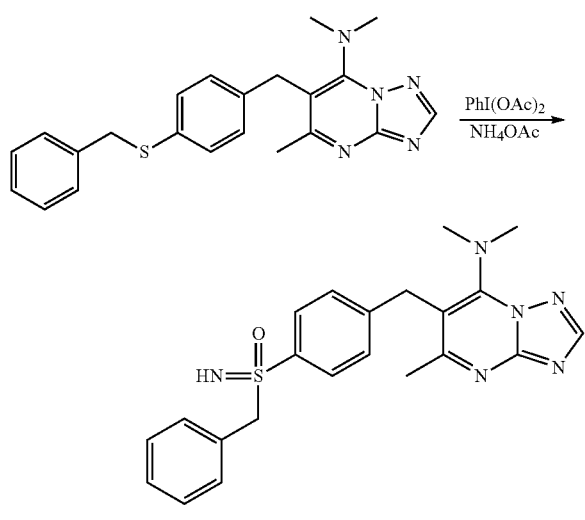

Compound 55

To a mixture of 6-[(4-benzylsulfanylphenyl)methyl]-N,N,5-trimethyl-[1,2,4]triazolo[1,5-α]pyrimidin-7-amine (0.08 g, 0.21 mmol), EtOH (5 mL), PhI(OAc)₂ (0.20 g, 0.62 mmol), and NH₄OAc (63 mg, 0.82 mmol). The mixture was stirred at 15° C. for 2 h then was concentrated and purified by preparative HPLC (20-50% MeCN in H₂O, 10 mM NH₄HCO₃) to provide 73 mg of benzyl(4-((7-(dimethylamino)-5-methyl-[1,2,4]triazolo[1,5-α]pyrimidin-6-yl)methyl)phenyl)(imino)-λ⁶-sulfanone (Compound 55). ESI MS m/z: 362.2 (M+H)

Compounds in Table 3 were prepared in two steps from 6-(4-bromobenzyl)-N,N,5-trimethyl-[1,2,4]triazolo[1,5-α]pyrimidin-7-amine and the indicated mercaptan in place of phenylmethanethiol in the manner described in Step 5 and Step 6 of Synthetic Example S-005.

TABLE 3

| Compound | Mercaptan | MS (m/z) |
|---|---|---|
| 56 | methyl 3-mercaptopropanoate | 417.1 (M + H) |
| 57 | ethanethiol | 359.2 (M + H) |
| 58 | BocNHCH₂CH₂SH | 474.2 (M + H) |
| 59 | 2-mercaptoethan-1-ol | 375.2 (M + H) |
| 60 | Methoxyethane-1-thiol | 389.2 (M + H) |
| 61 | 2-mercaptopropanenitrile | 331.2 (M + H) |
| 62 | ![oxetane-SH] | 387.2 (M + H) |
| 63 | Cyclopropane thiol | 371.2 (M + H) |
| 64 | N-(2-mercaptoethyl) acetamide | 416.2 (M + H) |

Synthetic Example S-006

Synthesis of 4-{[5-methyl-7-(pyrrolidin-1-yl)-[1,2,4]triazolo[1,5-α]pyrimidin-6-yl]methyl}benzene-1-sulfonamide (Compound 9)

Step 1: Synthesis of 6-[(4-Bromophenyl)methyl]-5-methyl-7-pyrrolidin-1-yl-[1,2,4]triazolo[1,5-α]pyrimidine

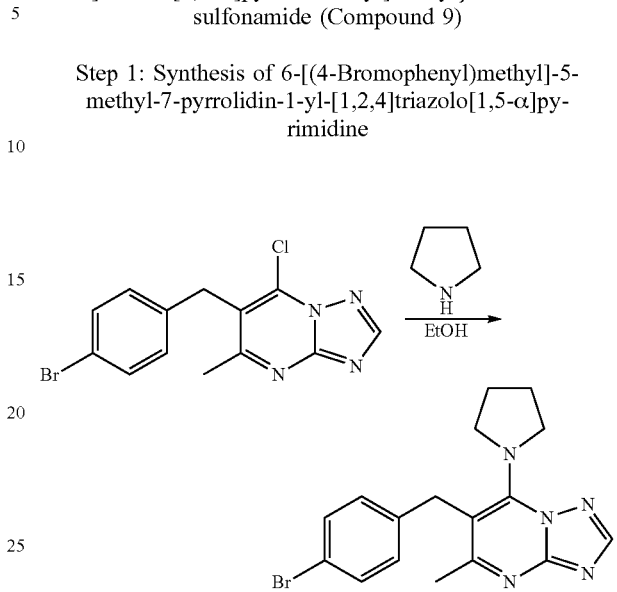

To a mixture of 6-[(4-bromophenyl)methyl]-7-chloro-5-methyl-[1,2,4]triazolo[1,5-α]pyrimidine (4.0 g, 12 mmol) and EtOH (50 mL) was added pyrrolidine (2.0 mL, 24 mmol). The mixture was stirred at 25° C. for 12 h, then was concentrated to provide 4.0 g of 6-[(4-bromophenyl)methyl]-5-methyl-7-pyrrolidin-1-yl-[1,2,4]triazolo[1,5-α]pyrimidine.

Step 2: Synthesis of 6-[(4-Benzylsulfanylphenyl)methyl]-5-methyl-7-pyrrolidin-1-yl-[1,2,4]triazolo[1,5-α]pyrimidine

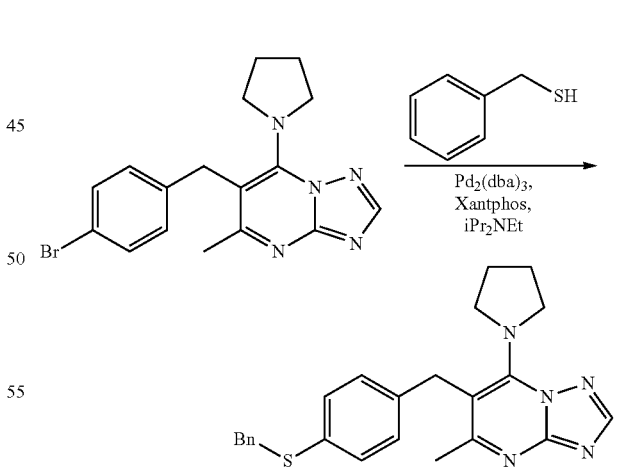

To a solution of 6-[(4-bromophenyl)methyl]-5-methyl-7-pyrrolidin-1-yl-[1,2,4]triazolo[1,5-α]pyrimidine (400 mg, 1.1 mmol) and 1,4-dioxane (5 mL) was added phenylmethanethiol (0.27 g, 2.2 mmol), Pd₂(dba)₃ (49 mg, 54 Xantphos (62 mg, 110 μmol), and iPr₂NEt (0.47 mL, 2.7 mmol). The mixture was stirred at 120° C. for 12 h, then was poured into 30 mL of water and extracted with EtOAc (2×30 mL). The combined extracts were washed with brine (10 mL), dried over anhydrous Na₂SO₄, concentrated, and purified by silica chromatography (25-50% EtOAc in petroleum ether) to provide 0.33 g of 6-[(4-benzylsulfanylphenyl)methyl]-5-methyl-7-pyrrolidin-1-yl-[1,2,4]triazolo[1,5-α]pyrimidine.

Step 3: Synthesis of 4-[(5-methyl-7-pyrrolidin-1-yl-[1,2,4]triazolo[1,5-α]pyrimidin-6-yl)methyl]benzenesulfonyl chloride

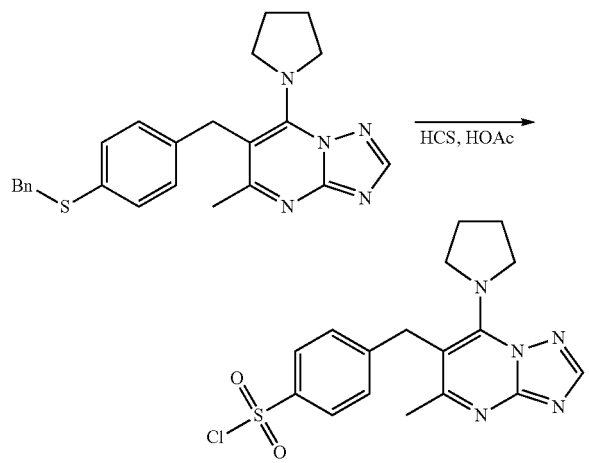

To a mixture of 6-[(4-benzylsulfanylphenyl)methyl]-5-methyl-7-pyrrolidin-1-yl-[1,2,4]triazolo[1,5-α]pyrimidine (150 mg, 0.36 mmol), HOAc (1.8 mL) and H₂O (0.2 mL) was added NCS (0.14 g, 1.1 mmol). The mixture was stirred at 20° C. for 2 h, then was concentrated and the residue washed with EtOAc. The EtOAc wash was concentrated to provide 130 mg of 4-[(5-methyl-7-pyrrolidin-1-yl-[1,2,4]triazolo[1,5-α]pyrimidin-6-yl)methyl]benzenesulfonyl chloride.

Step 4: Synthesis of 4-{[5-methyl-7-(pyrrolidin-1-yl)-[1,2,4]triazolo[1,5-α]pyrimidin-6-yl]methyl}benzene-1-sulfonamide (Compound 9)

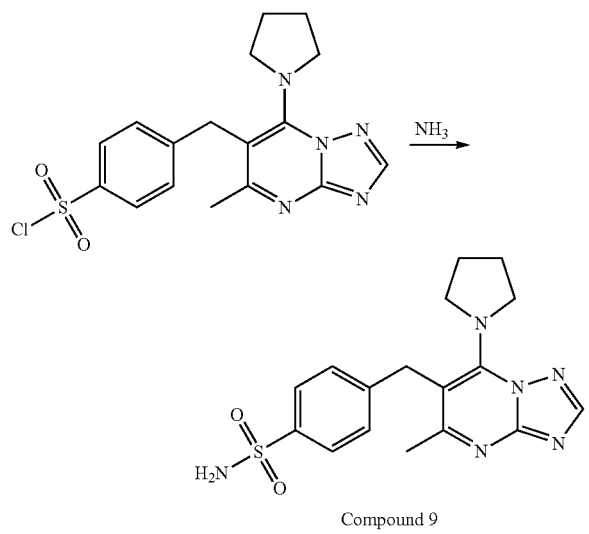

Compound 9

A mixture of 4-[(5-methyl-7-pyrrolidin-1-yl-[1,2,4]triazolo[1,5-α]pyrimidin-6-yl)methyl]benzenesulfonyl chloride (130 mg, 331.74 umol, 1.0 eq), acetone (2 mL), and NH₃·H₂O (25% solution, 3 mL, 20 mmol). The mixture was stirred at 20° C. for 2 h, then was concentrated and purified by preparative HPLC (15-45% MeCN in H₂O, 10 mM NH₄HCO₃) to provide 43 mg of 4-{[5-methyl-7-(pyrrolidin-1-yl)-[1,2,4]triazolo[1,5-α]pyrimidin-6-yl]methyl}benzene-1-sulfonamide (Compound 9). ESI MS m/z: 373.1 (M+H)

Synthetic Example S-007

Synthesis of 3-{[7-(dimethylamino)-5-methyl-[1,2,4]triazolo[1,5-α]pyrimidin-6-yl]methyl}benzene-1-sulfonamide (Compound 65)

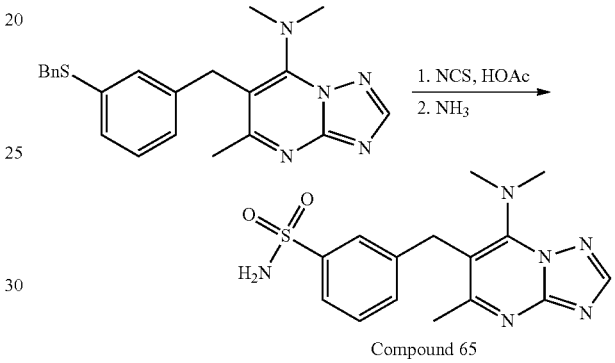

Compound 65

3-{[7-(dimethylamino)-5-methyl-[1,2,4]triazolo[1,5-α]pyrimidin-6-yl]methyl}benzene-1-sulfonamide (Compound 65) was prepared from 6-[(3-benzylsulfanylphenyl)methyl]-N,N,5-trimethyl-[1,2,4]triazolo[1,5-α]pyrimidin-7-amine in the same manner as Compound 2 in Synthetic Example S-002. 6-[(3-benzylsulfanylphenyl)methyl]-N,N,5-trimethyl-[1,2,4]triazolo[1,5-α]pyrimidin-7-amine was prepared from 3-bromobenzyl bromide and ethyl acetoacetate in the manner described for 6-(4-(benzylthio)benzyl)-N,N,5-trimethyl-[1,2,4]triazolo[1,5-α]pyrimidin-7-amine in Synthetic Example S-005. ESI MS m/z: 347.1 (M+H).

Synthetic Example S-008

Synthesis of imino(methyl)[(4-{[1,2,4]triazolo[1,5-α]pyrimidin-6-yl}phenyl)methyl]-λ⁶-sulfanone (Compound 66)

Step 1: Synthesis of 4,4,5,5-tetramethyl-2-(4-((methylthio)methyl)phenyl)-1,3,2-dioxaborolane

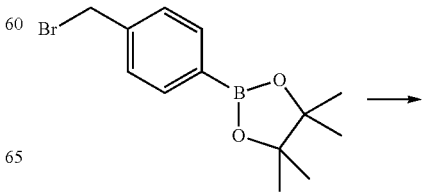

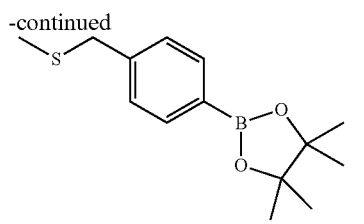

To a solution of 2-(4-(bromomethyl)phenyl)-4,4,5,5-tetramethyl-1,3,2-dioxaborolane (1.0 g, 3.4 mmol) in DMF (17 mL) was added NaSMe (0.24 g, 3.4 mmol) in small portions. The mixture was stirred overnight, then partitioned between ice-cold H$_2$O and EtOAc. The EtOAc extract was separated, washed with ice-cold H$_2$O (4×) and once with ice-cold brine, dried over Na$_2$SO$_4$, filtered and concentrated to provide 0.86 g of 4,4,5,5-tetramethyl-2-(4-((methylthio)methyl)phenyl)-1,3,2-dioxaborolane.

Step 2: Synthesis of 6-(4-((methylthio)methyl)phenyl)-[1,2,4]triazolo[1,5-α]pyrimidine

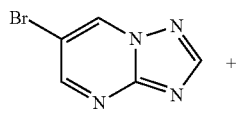

+

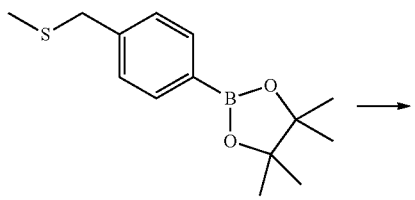

→

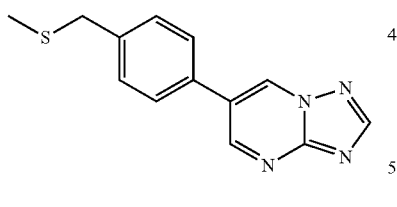

To a degassed mixture of 6-bromo-[1,2,4]triazolo[1,5-α]pyrimidine (30 mg, 0.15 mmol), 4,4,5,5-tetramethyl-2-(4-((methylthio)methyl)phenyl)-1,3,2-dioxaborolane (44 mg, 0.17 mmol), Na$_2$CO$_3$ (48 mg, 0.45 mmol), DME (1 mL), and H$_2$O (0.25 mL) and was added Pd$_2$(dba)$_3$ (6.9 mg, 7.5 μmol) and tri-tert-butylphosphine tetrafluoroborate (4.4 mg, 0.015 mmol). The reaction mixture was stirred for 3 h at 80° C., cooled, and diluted with water and CH$_2$Cl$_2$. The layers were separated, and the aqueous layer was extracted with CH$_2$Cl$_2$. The combined organic layers were concentrated and purified by silica chromatography (0-10% MeOH in CH$_2$Cl$_2$) to provide 12 mg of 6-(4-((methylthio)methyl)phenyl)-[1,2,4]triazolo[1,5-α]pyrimidine.

Step 3: Synthesis of imino(methyl)[(4-{[1,2,4]triazolo[1,5-α]pyrimidin-6-yl}phenyl)methyl]-λ$^6$-sulfanone (Compound 66)

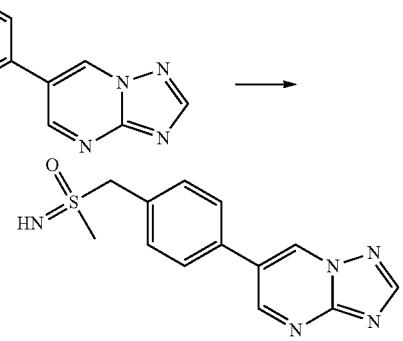

Compound 66

A mixture of 6-(4-((methylthio)methyl)phenyl)-[1,2,4]triazolo[1,5-α]pyrimidine (12 mg, 0.047 mmol), MeOH (0.5 mL), ammonium carbamate (5.5 mg, 0.070 mmol), and PhI(OAc)$_2$ (32 mg, 0.098 mmol) was stirred for 1 h. The mixture was purified by reverse-phase preparative HPLC (0-100% MeCN in H$_2$O, 10 mM NH$_4$HCO$_3$) to provide 0.9 mg imino(methyl)[(4-{[1,2,4]triazolo[1,5-α]pyrimidin-6-yl}phenyl)methyl]-λ$^6$-sulfanone (Compound 66). ESI MS m/z: 288.0 (M+H).

Synthetic Example S-009

Synthesis of imino(methyl)({4-[5-methyl-7-(pyrrolidin-1-yl)-[1,2,4]triazolo[1,5-α]pyrimidin-6-yl]phenyl}methyl)-λ6-sulfanone (Compound 67)

Step 1: Synthesis of 5-methyl-[1,2,4]triazolo[1,5-α]pyrimidin-7-ol

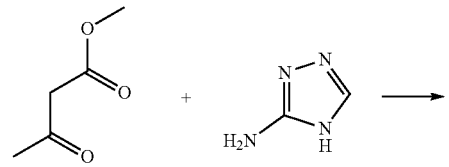

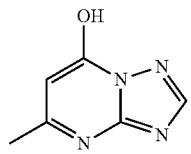

A mixture of 1H-1,2,4-triazol-5-amine (10 g, 120 mmol), HOAc (120 mL), and methyl 3-oxobutanoate (14 mL, 130 mmol) was stirred for 5 h at 120° C. The reaction mixture was cooled, concentrated, and then stirred in EtOAc for 10 minutes. The suspension was filtered, and the white solids were washed with EtOAc. The solids were collected and dried to obtain 5-methyl-[1,2,4]triazolo[1,5-α]pyrimidin-7-ol (18 g).

Step 2: Synthesis of 6-bromo-5-methyl-[1,2,4]triazolo[1,5-α]pyrimidin-7-ol

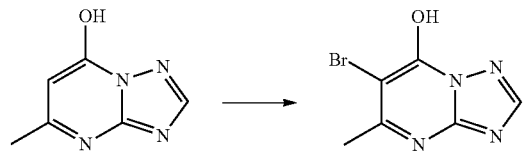

A mixture of 5-methyl-[1,2,4]triazolo[1,5-α]pyrimidin-7-ol (17 g, 120 mmol), NBS (21 g, 120 mmol), and CHCl3 (300 mL) was stirred at reflux for 2.5 h. The reaction mixture was cooled, the solids were filtered and washed with $CH_2Cl_2$ (3×) and dried to provide 6-bromo-5-methyl-[1,2,4]triazolo[1,5-α]pyrimidin-7-ol (25 g).

Step 3: Synthesis of 6-bromo-7-chloro-5-methyl-[1,2,4]triazolo[1,5-α]pyrimidine

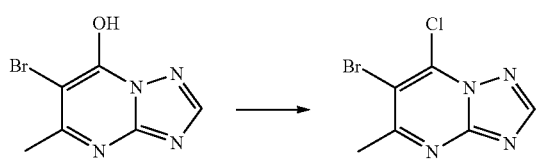

$POCl_3$ (163 mL, 1800 mmol) was added dropwise to 6-bromo-5-methyl-[1,2,4]triazolo[1,5-α]pyrimidin-7-ol (20 g, 87 mmol) and the resulting suspension was stirred at 105° C. overnight, then was concentrated. EtOAc and water were added, the pH of the aqueous layer was adjusted to >7 by addition of aqueous NaOH (4 M). The aqueous layer was extracted with EtOAc (3×), and the combined extracts were washed with brine, dried over $Na_2SO_4$, filtered and concentrated to provide 6-bromo-7-chloro-5-methyl-[1,2,4]triazolo[1,5-α]pyrimidine (14 g, 49 mmol.

Step 4: Synthesis of 6-bromo-5-methyl-7-(pyrrolidin-1-yl)-[1,2,4]triazolo[1,5-α]pyrimidine

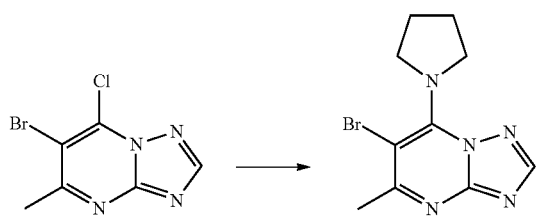 [SMILES: Cc1nc2ncnn2c(Cl)c1Br ; Cc1nc2ncnn2c(N2CCCC2)c1Br]

Pyrrolidine (0.062 mL, 0.75 mmol) was added dropwise to a stirring mixture of 6-bromo-7-chloro-5-methyl-[1,2,4]triazolo[1,5-α]pyrimidine (0.077 g, 0.30 mmol) and MeCN (2.0 mL). The resulting mixture was stirred for 1 h, then was purified by silica chromatography (10-100% EtOAc in heptane) to provide 82 mg of 6-bromo-5-methyl-7-(pyrrolidin-1-yl)-[1,2,4]triazolo[1,5-α]pyrimidine.

Step 5: Synthesis of 5-methyl-6-(4-((methylthio)methyl)phenyl)-7-(pyrrolidin-1-yl)-[1,2,4]triazolo[1,5-α]pyrimidine

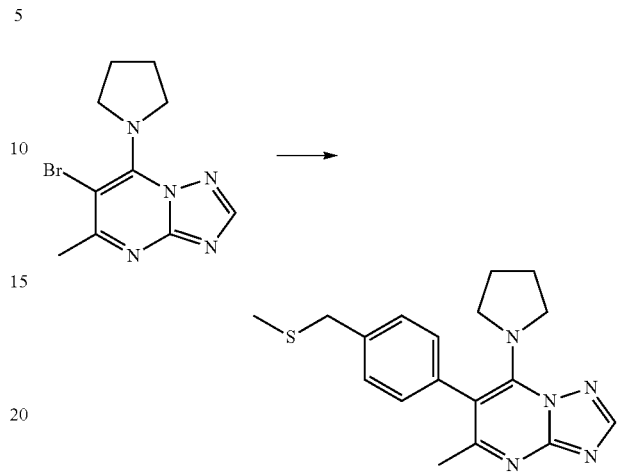

To a degassed mixture 6-bromo-5-methyl-7-(pyrrolidin-1-yl)-[1,2,4]triazolo[1,5-α]pyrimidine (80 mg, 0.31 mmol), 4,4,5,5-tetramethyl-2-(4-((methylthio)methyl)phenyl)-1,3,2-dioxaborolane (82 mg, 0.31 mmol), $Na_2CO_3$ (90 mg, 0.85 mmol), DME (2 mL), and $H_2O$ (0.5 mL) and was added $Pd_2(dba)_3$ (13 mg, 14 μmol) and tri-tert-butylphosphine tetrafluoroborate (8.2 mg, 0.028 mmol). The reaction mixture was stirred for 12 h at 80° C., cooled, and diluted with water and $CH_2Cl_2$. The layers were separated, and the aqueous layer was extracted twice with $CH_2Cl_2$. The combined organic layers were concentrated and purified by silica chromatography (0-10% MeOH in $CH_2Cl_2$) to provide 25 mg of 5-methyl-6-(4-((methylthio)methyl)phenyl)-7-(pyrrolidin-1-yl)-[1,2,4]triazolo[1,5-α]pyrimidine.

Step 6: Synthesis of imino(methyl)[(4-{[1,2,4]triazolo[1,5-α]pyrimidin-6-yl}phenyl)methyl]-$\lambda^6$-sulfanone (Compound 67)

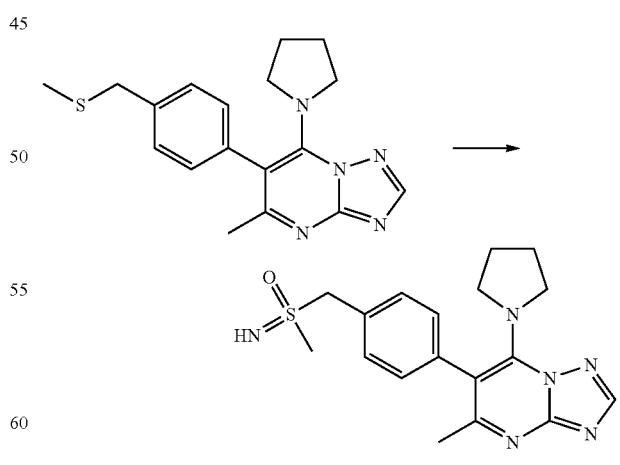

Compound 67

A mixture of 5-methyl-6-(4-((methylthio)methyl)phenyl)-7-(pyrrolidin-1-yl)-[1,2,4]triazolo[1,5-α]pyrimidine (25 mg, 0.027 mmol), MeOH (0.5 mL), ammonium carbamate (3.2 mg, 0.041 mmol), and PhI(OAc)$_2$ (18 mg, 0.057 mmol) was stirred for 1 h. Purification by reverse-phase HPLC (5-100% MeCN in water, 10 mM NH$_4$HCO$_3$) provided imino(methyl)(4-(5-methyl-7-(pyrrolidin-1-yl)-[1,2,4]triazolo[1,5-α]pyrimidin-6-yl)benzyl)-λ$^6$-sulfanone (Compound 67) (2.8 mg). ESI MS m/z: 371.2 (M+H).

Synthetic Example S-010

Synthesis of (2-{4-[7-(dimethylamino)-5-methyl-[1,2,4]triazolo[1,5-α]pyrimidin-6-yl]phenyl}ethyl)(imino)methyl-λ$^6$-sulfanone (Compound 68)

Step 1: Synthesis of 4,4,5,5-tetramethyl-2-(4-(2-(methylthio)ethyl)phenyl)-1,3,2-dioxaborolane

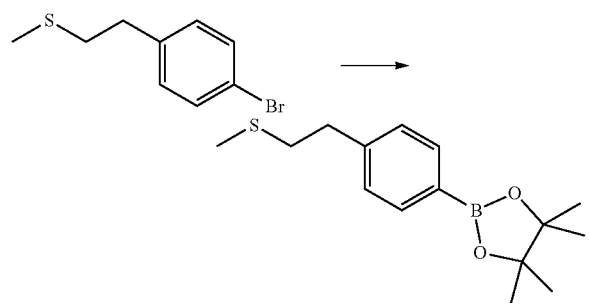

To a degassed mixture of (4-bromophenethyl)(methyl) sulfane (1.8 g, 7.6 mmol), bis(pinacolato)diboron (2.1 g, 8.3 mmol), KOAc (2.2 g, 23 mmol), and 1,4-dioxane (35 mL) was added Pd(dppf)Cl$_2$ (0.28 g, 0.38 mmol). The resulting mixture was stirred overnight at 85° C., cooled and filtered through celite. EtOAc and water were added to the filtrate. The aqueous layer was extracted with EtOAc (3×). The organic layers were combined, washed with brine, dried over Na$_2$SO$_4$, filtered, concentrated, and purified by silica chromatography (10-90% EtOAc in heptane) to obtain 1.4 g of 4,4,5,5-tetramethyl-2-(4-(2-(methylthio)ethyl)phenyl)-1,3,2-dioxaborolane.

Step 2: Synthesis of 6-bromo-N,N,5-trimethyl-[1,2,4]triazolo[1,5-α]pyrimidin-7-amine

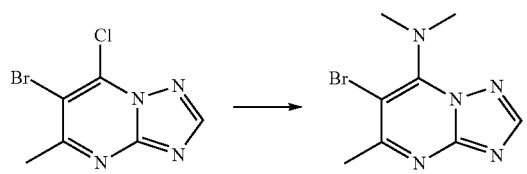

A mixture of 6-bromo-7-chloro-5-methyl-[1,2,4]triazolo[1,5-α]pyrimidine (600 mg, 2.4 mmol), MeCN (20 mL), Et$_3$N (1.0 mL, 7.3 mmol), and Me$_2$NH HCl (400 mg, 4.9 mmol) was stirred overnight, concentrated, and partitioned between EtOAc and H$_2$O. The layers were separated, and the aqueous layer was extracted with EtOAc (2×). The extracts were combined, washed with brine, dried over Na$_2$SO$_4$, filtered, concentrated, and purified by silica chromatography (0-10% MeOH in CH$_2$Cl$_2$) to provide 6-bromo-N,N,5-trimethyl-[1,2,4]triazolo[1,5-α]pyrimidin-7-amine (620 mg).

Step 3: Synthesis of N,N,5-trimethyl-6-(4-(2-(methylthio)ethyl)phenyl)-[1,2,4]triazolo[1,5-α]pyrimidin-7-amine

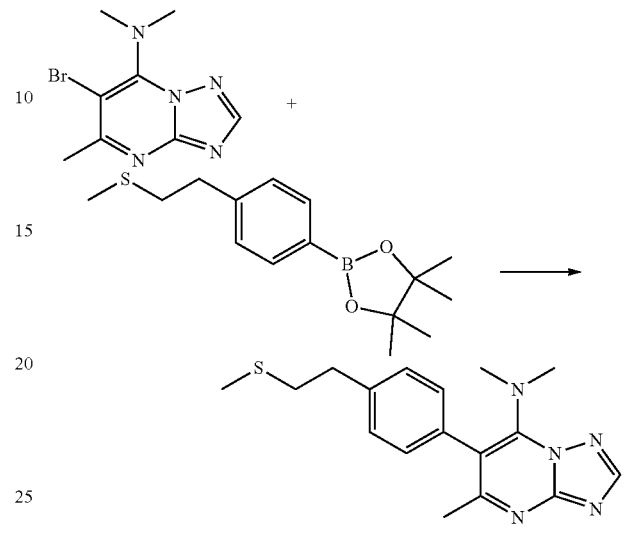

To a degassed mixture of 6-bromo-N,N,5-trimethyl-[1,2,4]triazolo[1,5-α]pyrimidin-7-amine (80 mg, 0.31 mmol), 4,4,5,5-tetramethyl-2-(4-(2-(methylthio)ethyl)phenyl)-1,3,2-dioxaborolane (130 mg, 0.47 mmol), Na$_2$CO$_3$ (99 mg, 0.94 mmol), DME (4 mL), and H$_2$O (1.0 mL) was added Pd$_2$(dba)$_3$ (14 mg, 0.016 mmol) and (t-Bu)$_3$P HBF$_4$ (9.1 mg, 0.031 mmol) and the mixture was stirred at 80° C. for 12 h. The reaction mixture was diluted with water and CH$_2$Cl$_2$, the aqueous layer was extracted with CH$_2$Cl$_2$, the extracts were combined, concentrated, and purified by silica chromatography (1-10% MeOH in CH$_2$Cl$_2$) to provide 50 mg of N,N,5-trimethyl-6-(4-(2-(methylthio)ethyl)phenyl)-[1,2,4]triazolo[1,5-α]pyrimidin-7-amine.

Step 4: Synthesis of (2-{4-[7-(dimethylamino)-5-methyl-[1,2,4]triazolo[1,5-α]pyrimidin-6-yl]phenyl}ethyl)(imino)methyl-λ$^6$-sulfanone (Compound 68)

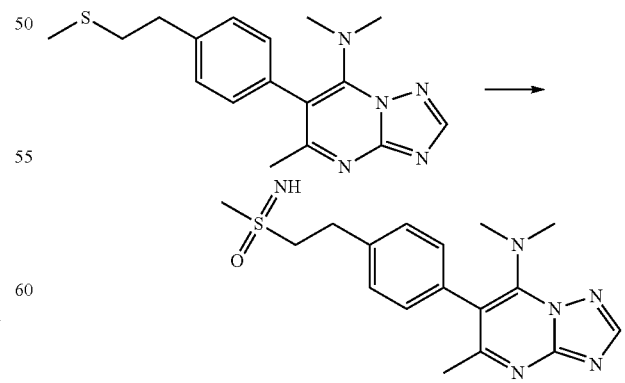

Compound 68

A mixture of N,N,5-trimethyl-6-(4-(2-(methylthio)ethyl)phenyl)-[1,2,4]triazolo[1,5-α]pyrimidin-7-amine (50 mg, 0.11 mmol), MeOH (1 mL), and ammonium carbamate (13 mg, 0.16 mmol), and PhI(OAc)$_2$ (73 mg, 0.23 mmol) was stirred for 1 h. Purification by reverse phase preparative HPLC (5-100% MeCN in H$_2$O, NH$_4$HCO$_3$) delivered 11 mg of (2-{4-[7-(dimethylamino)-5-methyl-[1,2,4]triazolo[1,5-α]pyrimidin-6-yl]phenyl}ethyl)(imino)methyl-λ$^6$-sulfanone (Compound 68). ESI MS m/z: 359.2 (M+H).

Synthetic Example 5-011

Synthesis of 7-[7-(dimethylamino)-5-methyl-[1,2,4]triazolo[1,5-α]pyrimidin-6-yl]-1,2,3,4-tetrahydroisoquinoline-2-sulfonamide (Compound 69)

Step 1: Synthesis of tert-butyl 7-(7-(dimethylamino)-5-methyl-[1,2,4]triazolo[1,5-α]pyrimidin-6-yl)-3,4-dihydroisoquinoline-2(1H)-carboxylate

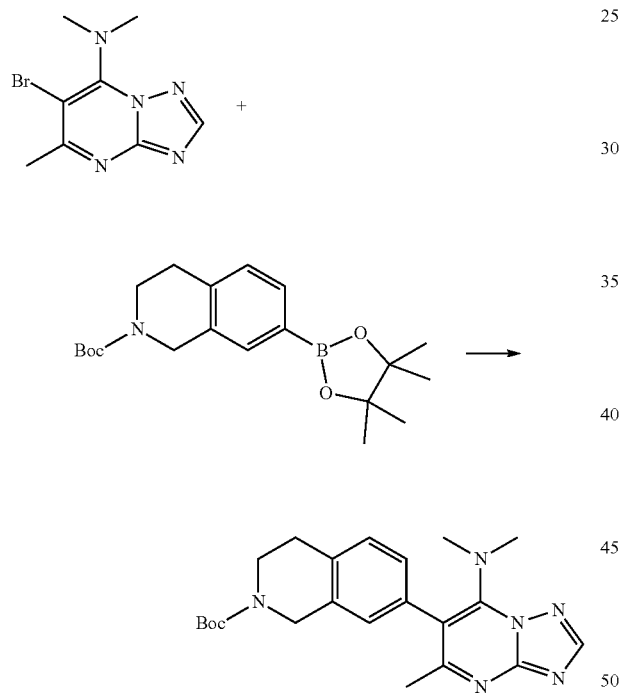

To a degassed mixture of 6-bromo-N,N,5-trimethyl-[1,2,4]triazolo[1,5-α]pyrimidin-7-amine (500 mg, 2.0 mmol), tert-butyl 7-(4,4,5,5-tetramethyl-1,3,2-dioxaborolan-2-yl)-3,4-dihydroisoquinoline-2(1H)-carboxylate (1.8 g, 2.9 mmol), Na$_2$CO$_3$ (620 mg, 5.9 mmol), DME (10 mL), and H$_2$O (2.500 mL) were added Pd$_2$(dba)$_3$ (89 mg, 0.098 mmol) and tri-tert-butylphosphine HBF$_4$ (57 mg, 0.20 mmol) and the mixture was stirred for 12 h at 85° C. The reaction mixture was cooled, diluted with H$_2$O and CH$_2$Cl$_2$ and the layers were separated. The aqueous layer was extracted with CH$_2$Cl$_2$. The combined extracts were concentrated and purified by flash column chromatography (0-10% MeOH in CH$_2$Cl$_2$) to obtain 100 mg of tert-butyl 7-(7-(dimethylamino)-5-methyl-[1,2,4]triazolo[1,5-α]pyrimidin-6-yl)-3,4-dihydroisoquinoline-2(1H)-carboxylate.

Step 2: Synthesis of 7-[7-(dimethylamino)-5-methyl-[1,2,4]triazolo[1,5-α]pyrimidin-6-yl]-1,2,3,4-tetrahydroisoquinoline-2-sulfonamide (Compound 69)

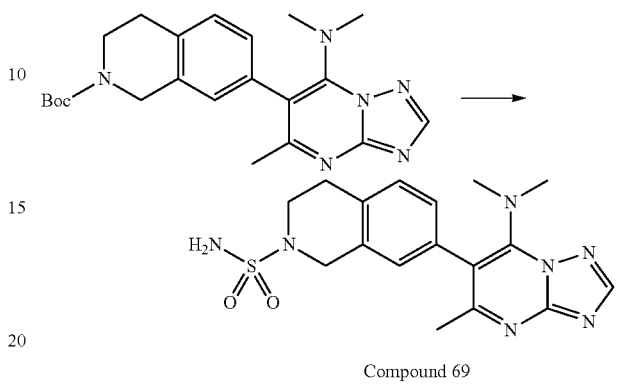

Compound 69

A mixture of tert-butyl 7-(7-(dimethylamino)-5-methyl-[1,2,4]triazolo[1,5-α]pyrimidin-6-yl)-3,4-dihydroisoquinoline-2(1H)-carboxylate (100 mg, 0.20 mmol), CH$_2$Cl$_2$ (3 mL), and 4 M HCl in dioxane (0.50 mL, 2.0 mmol) was stirred for 1.5 h, then was concentrated. The resulting residue, pyridine (1 mL), Et$_3$N (0.13 mL, 0.94 mmol), and sulfamide (36 mg, 0.38 mmol) were stirred for 12 h at 80° C. The mixture was concentrated and purified by reverse phase HPLC (5-50% MeCN in H$_2$O, 10 mM NH$_4$HCO$_3$) to provide 5.1 mg of 7-(7-(dimethylamino)-5-methyl-[1,2,4]triazolo[1,5-α]pyrimidin-6-yl)-3,4-dihydroisoquinoline-2(1H)-sulfonamide (Compound 69). ESI MS m/z: 388.2.

6-[7-(dimethylamino)-5-methyl-[1,2,4]triazolo[1,5-α]pyrimidin-6-yl]-1,2,3,4-tetrahydroisoquinoline-2-sulfonamide (Compound 84) was prepared in the manner described in Synthetic Example 5-011 for Compound 69 by replacing 7-(4,4,5,5-tetramethyl-1,3,2-dioxaborolan-2-yl)-3,4-dihydroisoquinoline-2(1H)-carboxylate with tert-butyl 6-(4,4,5,5-tetramethyl-1,3,2-dioxaborolan-2-yl)-3,4-dihydroisoquinoline-2(1H)-carboxylate. ESI MS m/z: 388.2 (M+H).

Synthetic Example S-012

Synthesis of imino(methyl)[4-({5-methyl-[1,2,4]triazolo[1,5-α]pyrimidin-6-yl}methyl)phenyl]-λ6-sulfanone (Compound 70)

Step 1: Synthesis of 5-methyl-6-(4-(methylthio)benzyl)-[1,2,4]triazolo[1,5-α]pyrimidine

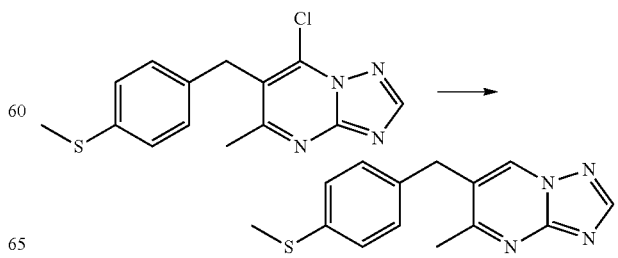

A degassed mixture of 7-chloro-5-methyl-6-(4-(methylthio)benzyl)-[1,2,4]triazolo[1,5-α]pyrimidine (250 mg, 0.82 mmol), EtOH (4.1 mL), Na₂CO₃ (87 mg, 0.82 mmol, and 10% palladium on carbon (190 mg, 0.90 mmol) was stirred under 5 bar of H₂ gas for 12 h. The reaction mixture was purged with N₂, filtered, and the filtrate concentrated. The resulting residue was purified by silica chromatography (5-80% EtOAc in heptanes) to provide 120 mg of 5-methyl-6-(4-(methylthio)benzyl)-[1,2,4]triazolo[1,5-α]pyrimidine.

Step 2: Synthesis of imino(methyl)[4-({5-methyl-[1,2,4]triazolo[1,5-α]pyrimidin-6-yl}methyl)phenyl]-λ6-sulfanone (Compound 70)

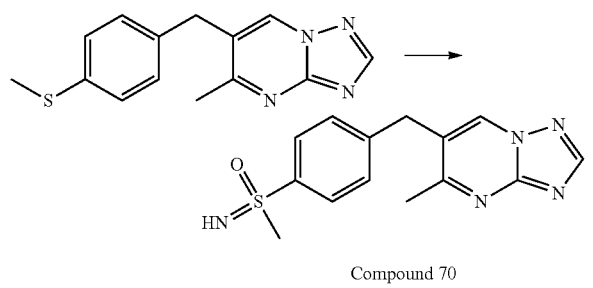

Compound 70

Imino(methyl)[4-({5-methyl-[1,2,4]triazolo[1,5-α]pyrimidin-6-yl}methyl)phenyl]-λ$^6$-sulfanone (Compound 70) was prepared from 5-methyl-6-(4-(methylthio)benzyl)-[1,2,4]triazolo[1,5-α]pyrimidine in the manner described in Step 6 of Synthetic Example S-009. ESI MS m/z: 302.0 (M+H).

Synthetic Example S-013

Synthesis of [4-({7-cyclopropyl-5-methyl-[1,2,4]triazolo[1,5-α]pyrimidin-6-yl}methyl)phenyl](imino)methyl-λ6-sulfanone (Compound 71)

Step 1: Synthesis of 7-cyclopropyl-5-methyl-6-(4-(methylthio)benzyl)-[1,2,4]triazolo[1,5-α]pyrimidine

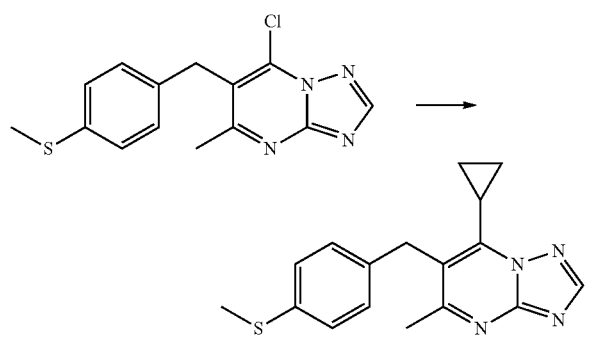

To a degassed mixture of 7-chloro-5-methyl-6-(4-(methylthio)benzyl)-[1,2,4]triazolo[1,5-α]pyrimidine (100 mg, 0.33 mmol), cyclopropylboronic acid (28 mg, 0.33 mmol), K₃PO₄ (170 mg, 0.82 mmol), and THF (1.6 mL) was added PdCl₂(dppf)CH₂Cl₂ (27 mg, 0.033 mmol). The mixture was stirred at 100° C. for 1 h in a microwave reactor. After cooling, H₂O and EtOAc were added, the layers separated, and the aqueous phase extracted with EtOAc (3×). The extracts were combined, washed with brine, dried over Na₂SO₄, filtered, concentrated, and purified by silica chromatography (25-75% EtOAc in heptane) to provide 51 mg of 7-cyclopropyl-5-methyl-6-(4-(methylthio)benzyl)-[1,2,4]triazolo[1,5-α]pyrimidine.

Step 2: Synthesis of [4-({7-cyclopropyl-5-methyl-[1,2,4]triazolo[1,5-α]pyrimidin-6-yl}methyl)phenyl](imino)methyl-λ6-sulfanone (Compound 71)

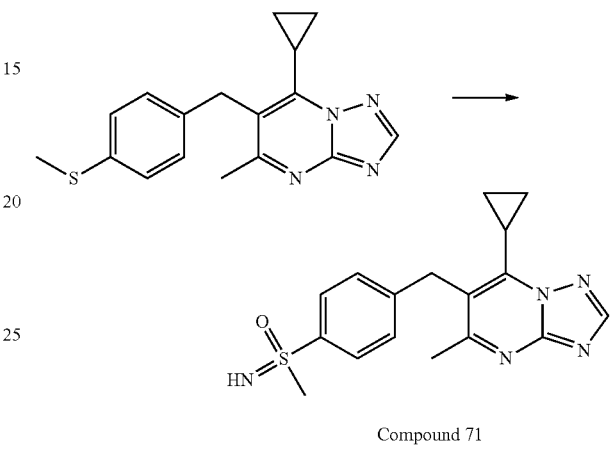

Compound 71

[4-({7-cyclopropyl-5-methyl-[1,2,4]triazolo[1,5-α]pyrimidin-6-yl}methyl)phenyl](imino)methyl-λ$^6$-sulfanone (Compound 71) was prepared from 7-cyclopropyl-5-methyl-6-(4-(methylthio)benzyl)-[1,2,4]triazolo[1,5-α]pyrimidine in the manner described in Step 6 of Synthetic Example S-009. ESI MS m/z: 342.2 (M+H).

Synthetic Example S-014

Synthesis of [4-({5,7-dimethyl-[1,2,4]triazolo[1,5-α]pyrimidin-6-yl}methyl)phenyl](imino)methyl-λ6-sulfanone (Compound 26)

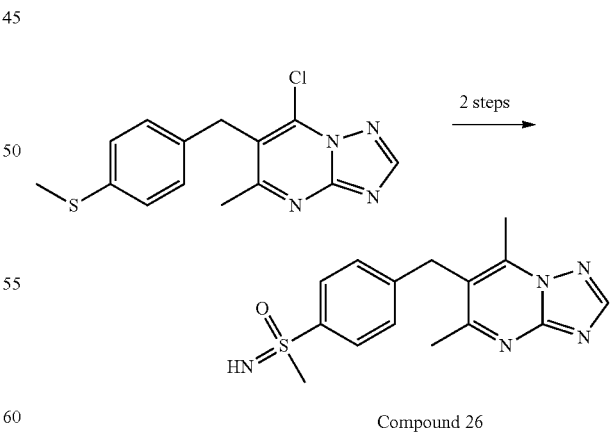

Compound 26

[4-({5,7-dimethyl-[1,2,4]triazolo[1,5-α]pyrimidin-6-yl}methyl)phenyl](imino)methyl-λ$^6$-sulfanone (Compound 26) was prepared from 7-chloro-5-methyl-6-(4-(methylthio)benzyl)-[1,2,4]triazolo[1,5-α]pyrimidine in the manner described for Compound 71 with the replacement of cyclopropylboronic acid with methylboronic acid in Step 1 in Synthetic Example S-013. ESI MS m/z: 316.0 (M+H).

Synthetic Example S-015

Synthesis of 3-[(4-{[7-(dimethylamino)-5-methyl-[1,2,4]triazolo[1,5-α]pyrimidin-6-yl]methyl}phenyl)(imino)oxo-$\lambda^6$-sulfanyl]propanoic acid (Compound 72)

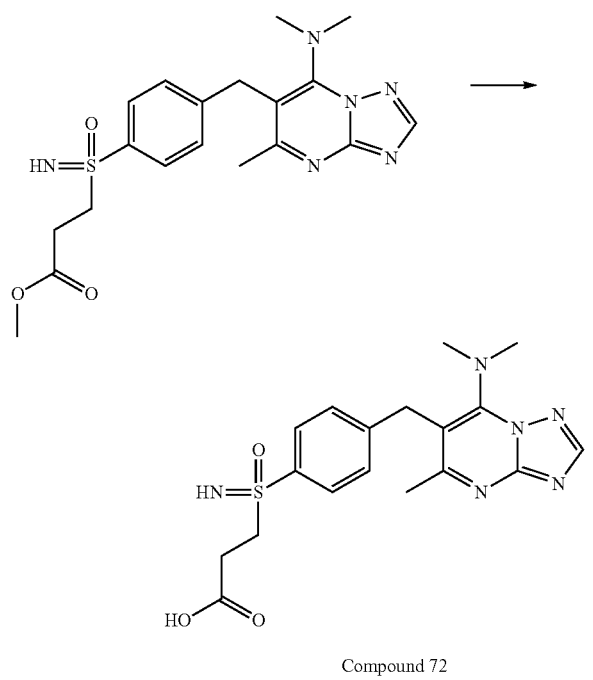

Compound 72

A mixture of methyl 3-(4-((7-(dimethylamino)-5-methyl-[1,2,4]triazolo[1,5-α]pyrimidin-6-yl)methyl)phenylsulfonimidoyl)propanoate (86 mg, 0.21 mmol), 1 mL of HOAc and conc. HCl (1.0 mL, 6.2 mmol) was stirred for 1 h. The mixture was purfied by preparative HPLC (5-40% H₂O in MeCN, 0.1% HCO₂H) to provide 17 mg of 3-[(4-{[7-(dimethylamino)-5-methyl-[1,2,4]triazolo[1,5-α]pyrimidin-6-yl]methyl}phenyl)(imino)oxo-$\lambda^6$-sulfanyl]propanoic acid (Compound 72). ESI MS m/z: 403.2 (M+H)⁺.

Synthetic Example S-016

Synthesis of (2-aminoethyl)(4-{[7-(dimethylamino)-5-methyl-[1,2,4]triazolo[1,5-α]pyrimidin-6-yl]methyl}phenyl)imino-$\lambda^6$-sulfanone (Compound 73)

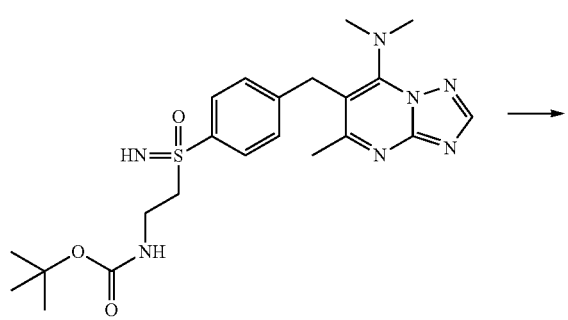

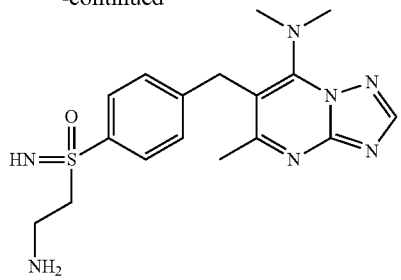

Compound 73

A mixture of tert-butyl (2-(4-((7-(dimethylamino)-5-methyl-[1,2,4]triazolo[1,5-α]pyrimidin-6-yl)methyl)phenylsulfonimidoyl)ethyl)carbamate (250 mg, 0.52 mmol), 2.9 mL of CH₂Cl₂, and TFA (1.20 mL, 16 mmol) was stirred for 2 h. The mixture was concentrated and purified twice by preparative HPLC (0-40% H₂O in MeCN with 0.1% NH₄HCO₃) to provide 50 mg of (2-aminoethyl)(4-{[7-(dimethylamino)-5-methyl-[1,2,4]triazolo[1,5-α]pyrimidin-6-yl]methyl}phenyl)imino-$\lambda^6$-sulfanone (Compound 73). ESI MS m/z: 374.2 (M+H).

Synthetic Example S-017

Synthesis of (4-{[5-(dimethylamino)-7-methyl-[1,2,4]triazolo[1,5-α]pyridin-6-yl]methyl}phenyl)(imino)methyl-$\lambda^6$-sulfanone (Compound 28)

Step 1. Synthesis of ethyl 4-cyano-3-methyl-2-(4-(methylthio)benzyl)but-3-enoate

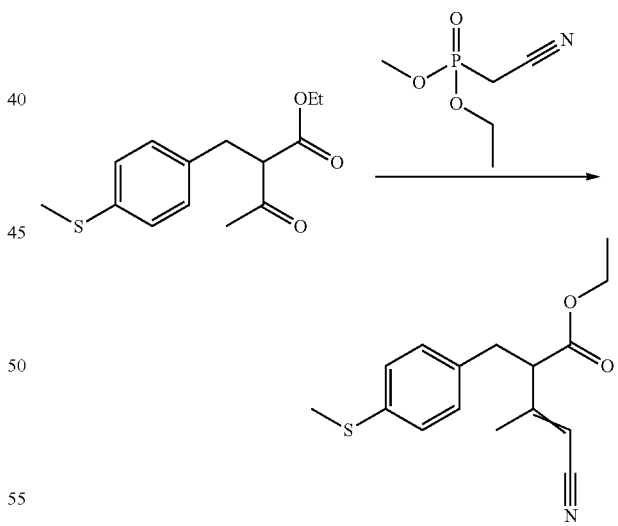

To a 0° C. mixture of diethyl (cyanomethyl)phosphonate (1.0 mL, 12 mmol), THF (30 mL), was added KOtBu (1.7 M in THF; 6.8 mL, 12 mmol) was added dropwise over 5 min. The mixture was warmed to room temperature over 25 min, then cooled back to 0° C., and ethyl 2-(4-(methylthio)benzyl)-3-oxobutanoate (3.0 g, 10 mmol) in 10 mL of THF was added dropwise. The cold bath was removed, and the mixture was stirred for 36 h before being heated to 70° C. for 6 h. Water was added, and the mixture partially concentrated. The mixture was extracted with CH₂Cl₂, dried over Na$_2$SO$_4$, filtered, concentrated and purified by silica chromatography (20-100% CH$_2$Cl$_2$ in heptane) to provide 3.0 g of ethyl 4-cyano-3-methyl-2-(4-(methylthio)benzyl)but-3-enoate.

Step 2. Synthesis of 1,6-diamino-4-methyl-3-(4-(methylthio)benzyl)pyridin-2(1H)-one

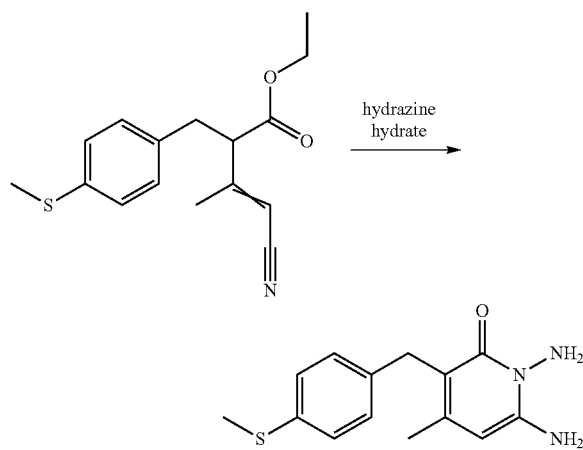

A mixture of ethyl 4-cyano-3-methyl-2-(4-(methylthio)benzyl)but-3-enoate (3.0 g, 8.2 mmol), EtOH (24 mL), and hydrazine hydrate (2.0 mL, 41 mmol) was stirred at 80° C. for 2 h. Additional hydrazine hydrate (0.52 mL, 11 mmol) was added and the heating was continued for 24 h. The mixture was cooled to 0 C and the precipitate was isolated by filtration. The solid was washed with EtOH and heptane, then dried. The solid was triturated with hot MeOH to provide 0.88 g of 1,6-diamino-4-methyl-3-(4-(methylthio)benzyl)pyridin-2(1H)-one.

Step 3. Synthesis 7-methyl-6-(4-(methylthio)benzyl)-[1,2,4]triazolo[1,5-α]pyridin-5-ol

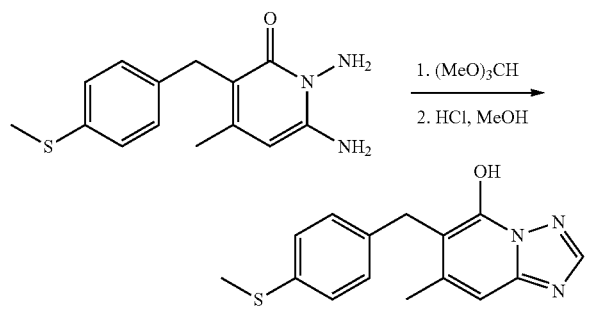

A mixture of 1,6-diamino-4-methyl-3-(4-(methylthio)benzyl)pyridin-2(1H)-one (0.96 g, 3.0 mmol), HOAc (20 mL), and trimethyl orthoformate (3.3 mL, 30 mmol) was stirred at 100° C. for 2h. The mixture cooled and concentrated. The resulting residue was mixed with 150 mL CH$_2$Cl$_2$ and 100 mL of 25% saturated aqueous NaHCO$_3$. The organic phase was separated, and the aqueous wash was extracted twice with CH$_2$Cl$_2$. These extracts were combined, dried over Na$_2$SO$_4$, filtered and concentrated to provide 0.67 g of a mixture of products that included 7-methyl-6-(4-(methylthio)benzyl)-[1,2,4]triazolo[1,5-α]pyridin-5-ol, 7-methyl-6-(4-(methylthio)benzyl)-5-oxo-[1,2,4]triazolo[1,5-α]pyridine-1(5H)-carbaldehyde, and a dimeric species with mass of 580 amu. The mixture was mixed with methanol 25 mL of MeOH, 2.5 mL of 10 M HCl (25 mmol) was added dropwise before being heated at 75° C. for 2 h. The mixture was cooled to room temperature and stirred for 16 h. An additional 10 M HCl (1.2 mL, 12.00 mmol) was added and the mixture was heated at 75° C. for 2 h. The mixture was concentrated to provide 0.68 g of 7-methyl-6-(4-(methylthio)benzyl)-[1,2,4]triazolo[1,5-α]pyridin-5-ol with 90% purity.

Step 4: Synthesis of 5-chloro-7-methyl-6-(4-(methylthio)benzyl)-[1,2,4]triazolo[1,5-α]pyridine

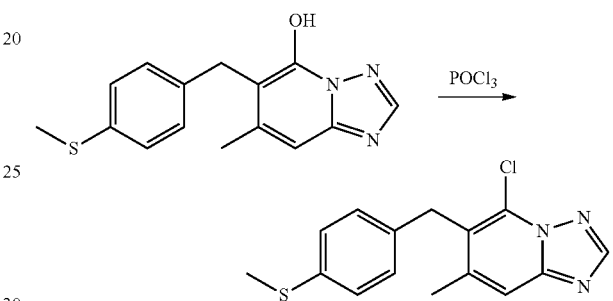

A mixture of 7-methyl-6-(4-(methylthio)benzyl)-[1,2,4]triazolo[1,5-α]pyridin-5(1H)-one (0.68 g, 2.2 mmol) and POCl$_3$ (20 mL, 220 mmol) was heated at 100° C. for 30 min. A drop of DMF was added and heating continued for 15 h. The mixture was cooled and Et$_3$N (0.60 mL, 4.3 mmol) was added and the mixture was heated to 120° C. for 3 h, POCl$_3$ added (10 mL, 110 mmol) and heating continued for 20 h. The mixture was concentrated and mixed with CH$_2$Cl$_2$ and ice along with aqueous NaHCO$_3$ until the pH was basic. The layers were separated, and the aqueous layer extracted twice with CH$_2$Cl$_2$. The extracts were combined and dried over Na$_2$SO$_4$, filtered, concentrated, and purified by silica chromatography (0-100% in CH$_2$Cl$_2$) to provide 390 mg of 5-chloro-7-methyl-6-(4-(methylthio)benzyl)-[1,2,4]triazolo[1,5-α]pyridine.

Step 5: Synthesis of N,N,7-trimethyl-6-(4-(methylthio)benzyl)-[1,2,4]triazolo[1,5-α]pyridin-5-amine

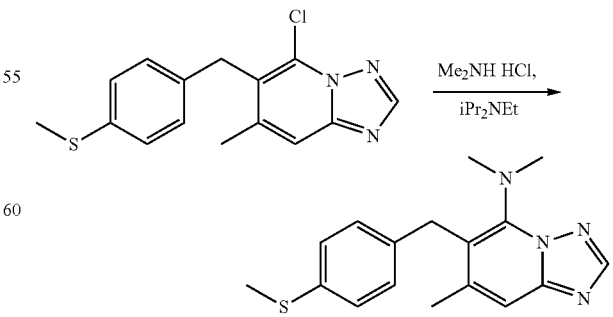

A mixture of 5-chloro-7-methyl-6-(4-(methylthio)benzyl)-[1,2,4]triazolo[1,5-α]pyridine (62 mg, 0.20 mmol), DMF (2.0 mL), dimethylamine hydrochloride (0.25 g, 3.0 mmol) and iPr₂NEt (0.52 mL, 3.0 mmol) was heated in a reaction block to 150° C. for 65 h. The mixture was purified by preparative HPLC (5-100% MeCN in water, 10 mM NH₄HCO₃) to provide 45 mg of N,N,7-trimethyl-6-(4-(methylthio)benzyl)-[1,2,4]triazolo[1,5-α]pyridin-5-amine.

Step 5: Synthesis of (4-{[5-(dimethylamino)-7-methyl-[1,2,4]triazolo[1,5-α]pyridin-6-yl]methyl}phenyl)(imino)methyl-λ⁶-sulfanone (Compound 28)

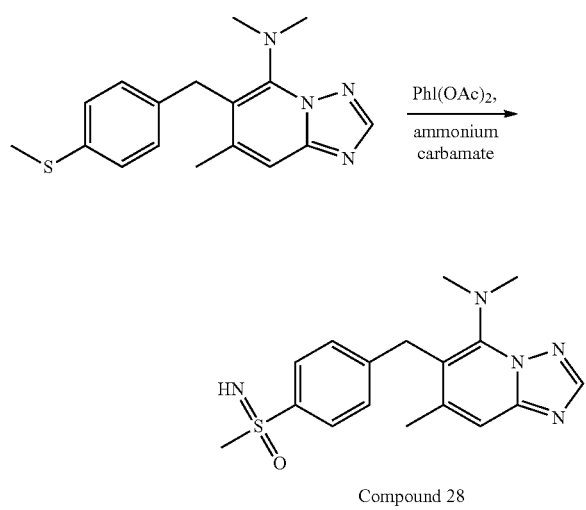

Compound 28

To an ice-cold mixture of N,N,7-trimethyl-6-(4-(methylthio)benzyl)-[1,2,4]triazolo[1,5-α]pyridin-5-amine (45 mg, 0.14 mmol) and MeOH (4.2 mL) were added ammonium carbamate (22 g, 0.28 mmol) and PhI(OAc)₂ (91 mg, 0.28 mmol). The mixture was stirred at room temperature for 1 h. The mixture was concentrated and purified by reverse phase HPLC (5-50% MeCN in H₂O, 0.1% NH₄HCO₃) to provide 44 mg of (4-{[5-(dimethylamino)-7-methyl-[1,2,4]triazolo[1,5-α]pyridin-6-yl]methyl}phenyl)(imino)methyl-λ⁶-sulfanone (Compound 28). ESI MS m/z: 344.2.

Compounds in Table 4 were prepared in two steps from 5-chloro-7-methyl-6-(4-(methylthio)benzyl)-[1,2,4]triazolo[1,5-α]pyridine and the amine in place of dimethylamine hydrochloride and iPr₂NEt in the manner described in Step 4 and Step 5 of Synthetic Example S-017.

TABLE 4

| Compound | Amine | Conditions | MS (m/z) |
|---|---|---|---|
| 75 | Pyrrolidine | Step 1: solvent = NMP, 200° C. | 339.2 (M + H) |
| 76 | Piperidine | Step 1: solvent = NMP, 200° C. | 353.2 (M + H) |

Synthetic Example S-018

Synthesis of (4-{[5-(dimethylamino)-7-methylimidazo[1,2-α]pyrimidin-6-yl]methyl}phenyl)(imino)methyl-λ⁶-sulfanone (Compound 29)

Step 1: Synthesis of 7-methyl-6-(4-(methylthio)benzyl)imidazo[1,2-α]pyrimidin-5-ol

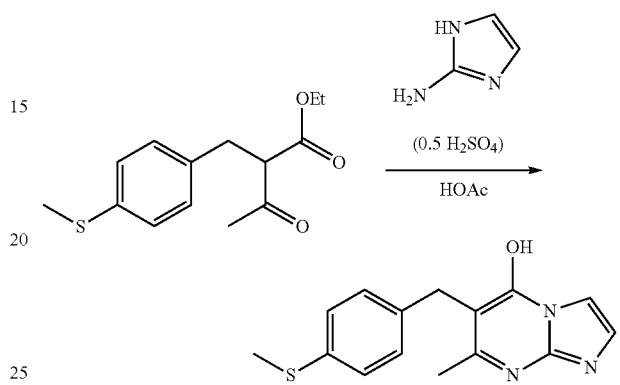

A mixture of ethyl 2-(4-(methylthio)benzyl)-3-oxobutanoate (1.5 g, 5.0 mmol), 1H-imidazol-2-amine hemisulfate (0.73 g, 2.8 mmol), HOAc (10 mL) was stirred in a sealed vessel at 120° C. for 24 h, then at 140° C. for 15 h. The mixture was evaporated, and the residue was partitioned between H₂O and CH₂Cl₂ and NaHCO₃ added until the pH was basic. The organic phase separated, and the aqueous phase extracted twice with CH₂Cl₂. The extracts were combined, dried over sodium sulfate, filtered, and concentrated. The mixture was suspended in 10 mL CH₂Cl₂ and filtered through a sintered glass filter. The filtrate was concentrated and purified by silica chromatography (20-100% CH₂Cl₂ in heptane, then 0-3% MeOH in CH₂Cl₂) to provide 275 mg of (4-{[5-(dimethylamino)-7-methylimidazo[1,2-α]pyrimidin-6-yl]methyl}phenyl)(imino)methyl-λ⁶-sulfanone with 80% purity. This material was dissolved in CH₂Cl₂ and washed with 0.5 N HCl, dried over Na₂SO₄, filtered and concentrated to provide 230 mg of 7-methyl-6-(4-(methylthio)benzyl)imidazo[1,2-α]pyrimidin-5-ol.

Step 2: Synthesis of 5-chloro-7-methyl-6-(4-(methylthio)benzyl)imidazo[1,2-α]pyrimidine

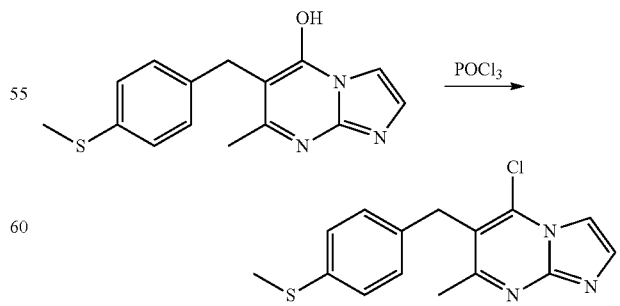

A mixture of 7-methyl-6-(4-(methylthio)benzyl)imidazo[1,2-α]pyrimidin-5-ol (0.23 g, 0.80 mmol), POCl₃ (7.5 mL, 80 mmol), one drop of DMF was stirred at 120° C. for 15 h. The mixture was concentrated and mixed with $CH_2Cl_2$ and ice. After the ice had melted, the pH was adjusted to basic with saturated aqueous sodium bicarbonate. The mixture was extracted with $CH_2Cl_2$ and the extract was dried over $Ns_2SO_4$, filtered, concentrated and purified by silica chromatography (0-100% EtOAc in $CH_2Cl_2$) to provide 158 mg of 5-chloro-7-methyl-6-(4-(methylthio)benzyl)imidazo[1,2-α]pyrimidine.

Step 3. Synthesis of N,N,7-trimethyl-6-(4-(methylthio)benzyl)imidazo[1,2-α]pyrimidin-5-amine

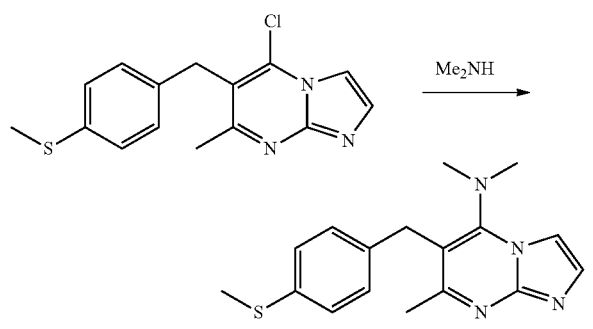

A sealed mixture of 5-chloro-7-methyl-6-(4-(methylthio)benzyl)imidazo[1,2-α]pyrimidine (64 mg, 0.20 mmol), THF (5 mL), $Me_2NH$ (2M in THF; 0.50 mL, 1.0 mmol) was stirred for 1 h, and additional $Me_2NH$ (1.0 mL, 2.0 mmol) was added the mixture stirred for 65 h. Additional $Me_2NH$ (2.0 mL, 4.0 mmol) was added, and the mixture heated at 100° C. for 20 h. Additional $Me_2NH$ (2.0 mL, 4.0 mmol) was added and the mixture heated at 120° C. for 7 h, followed by 100° C. for 16 h. The mixture was concentrated and purified by silica chromatography (0-3% MeOH in $CH_2Cl_2$) to provide 63 mg of N,N,7-trimethyl-6-(4-(methylthio)benzyl)imidazo[1,2-α]pyrimidin-5-amine.

Step 4. Synthesis of (4-{[5-(dimethylamino)-7-methylimidazo[1,2-α]pyrimidin-6-yl]methyl}phenyl)(imino)methyl-λ⁶-sulfanone (Compound 29)

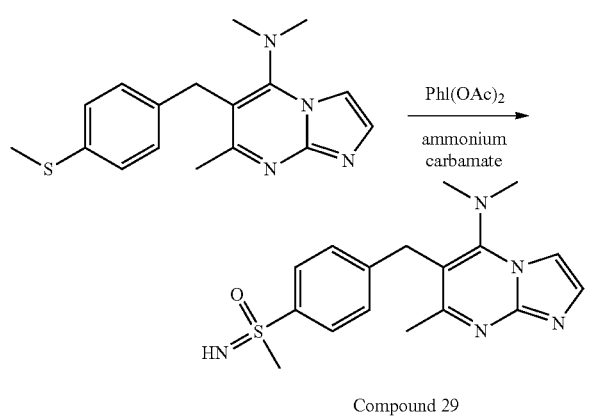

To an ice-cold mixture of N,N,7-trimethyl-6-(4-(methylthio)benzyl)imidazo[1,2-α]pyrimidin-5-amine (62 mg, 0.18 mmol) and MeOH (3.6 mL) were added ammonium carbamate (28 mg, 0.36 mmol) and $PhI(OAc)_2$ (0.12 g, 0.36 mmol). The mixture was stirred at room temperature for 1 h. The mixture was concentrated and purified by reverse phase HPLC (5-40% MeCN in $H_2O$, 10 mM $NH_4HCO_3$) to provide 28 mg of pure product along with mixed fractions. Purification of the mixed fractions by SFC (Waters Acquity UPC2 Torus 2-PIC, 35° C., 170 bar, 2-50% 20 mM $NH_3$ in MeOH/$CO_2$) provided an additional 13 mg of (4-{[5-(dimethylamino)-7-methylimidazo[1,2-α]pyrimidin-6-yl]methyl}phenyl)(imino)methyl-λ⁶-sulfanone (Compound 29). ESI MS m/z: 344.2.

Synthetic Example S-019

Synthesis of imino(methyl)(4-{[7-methyl-5-(pyrrolidin-1-yl)-[1,2,4]triazolo[1,2-α]pyridin-6-yl]methyl}phenyl)-λ⁶-sulfanone (Compound 77)

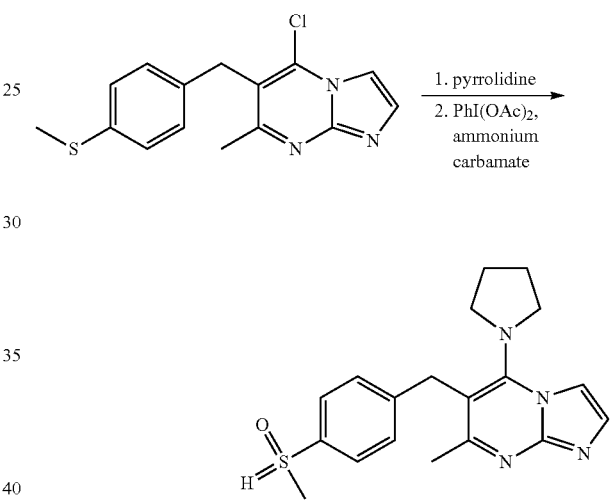

Compound 77

A mixture of 5-chloro-7-methyl-6-(4-(methylthio)benzyl)imidazo[1,2-α]pyrimidine (48 mg, 0.15 mmol), NMP (2.50 mL), and pyrrolidine (62 μL, 0.75 mmol) was heated to 200° C. for 2.5 h in a microwave reactor. Purification by preparative HPLC (5-60% MeCN in $H_2O$, 10 mM $NH_4HCO_3$) provided 40 mg of 7-methyl-6-(4-(methylthio)benzyl)-5-(pyrrolidin-1-yl)imidazo[1,2-α]pyrimidine that was combined with MeOH (4.6 mL), cooled in an ice-bath, and ammonium carbamate (18 mg, 0.23 mmol) and $PhI(OAc)_2$ (78 mg, 0.24 mmol) were added. The mixture was stirred at room temperature for 1 h. It was concentrated and purified by SFC (Waters Acquity UPC2 Torus 2-PIC, 35° C., 170 bar, 2-50% 20 mM $NH_3$ in MeOH/$CO_2$) to provide 24 mg of imino(methyl)(4-{[7-methyl-5-(pyrrolidin-1-yl)-[1,2,4]triazolo[1,2-α]pyridin-6-yl]methyl}phenyl)-λ⁶-sulfanone (Compound 77). ESI MS m/z: 370.2 (M+H).

Imino(methyl)(4-{[7-methyl-5-(piperidin-1-yl)imidazo[1,2-α]pyrimidin-6-yl]methyl}phenyl)-λ⁶-sulfanone (Compound 83) was prepared in the manner described in Synthetic Example S-019 (Compound 77) by substituting piperidine for pyrrolidine. ESI MS m/z: 384.2 (M+H).

Synthetic Example S-020

Synthesis of (4-{[5-chloro-7-(dimethylamino)-[1,2,4]triazolo[1,5-α]pyrimidin-6-yl]methyl}phenyl)(imino)methyl-$\lambda^6$-sulfanone (Compound 74)

Step 1. Synthesis of diethyl 2-(4-(methylthio)benzyl)malonate

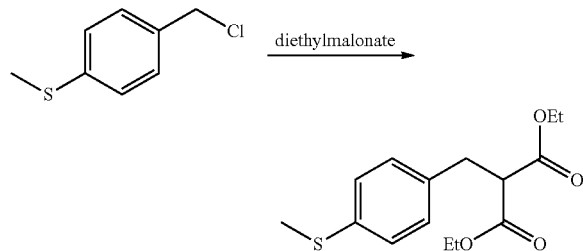

Diethyl malonate (1.5 mL, 10 mmol) was added to a 0° C. mixture of 60% NaH (0.61 g, 15 mmol) and THF (30 mL). The mixture was stirred for 30 min at room temperature before being cooled to 0° C. and a mixture of (4-(chloromethyl)phenyl)(methyl)sulfane (1.8 g, 10 mmol) and THF (10 mL) was slowly added. The resulting mixture was stirred for 30 min at 0° C., and 12 h at room temperature, and 6 h at 50° C. Aqueous KHSO₄ (0.5 M) was added, and the mixture was extracted by EtOAc (3×). The extracts were combined, washed with brine, dried over Na₂SO₄, filtered, and concentrated. Purification by silica chromatography (2-10% EtOAc in heptane) provided 0.95 g of diethyl 2-(4-(methylthio)benzyl)malonate.

Step 2. Synthesis of 6-(4-(methylthio)benzyl)-[1,2,4]triazolo[1,5-α]pyrimidine-5,7-diol

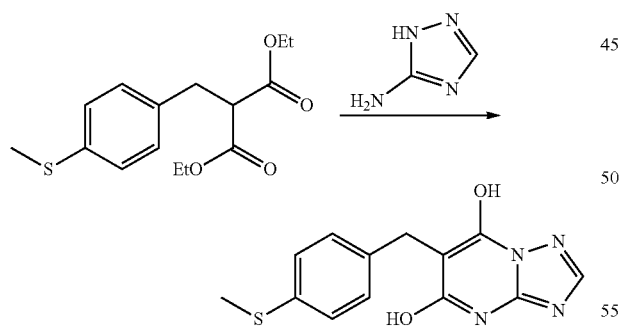

DBU (1.3 mL, 8.3 mmol) was added dropwise to a mixture of 3-amino-1H-1,2,4-triazole (278 mg, 3.31 mmol) and diethyl 2-(4-(methylthio)benzyl)malonate (0.95 g, 2.8 mmol), DMF (5 mL). The resulting mixture was stirred overnight at 120° C. The mixture was concentrated, dissolved in H₂O, and 2M HCl was added until the pH was 2. The resulting precipitate was filtered, and the solid residue was washed with H₂O and EtOH then dried to provide 0.5 g of 6-(4-(methylthio)benzyl)-[1,2,4]triazolo[1,5-α]pyrimidine-5,7-diol.

Step 3. Synthesis of 5,7-dichloro-6-(4-(methylthio)benzyl)-[1,2,4]triazolo[1,5-α]pyrimidine

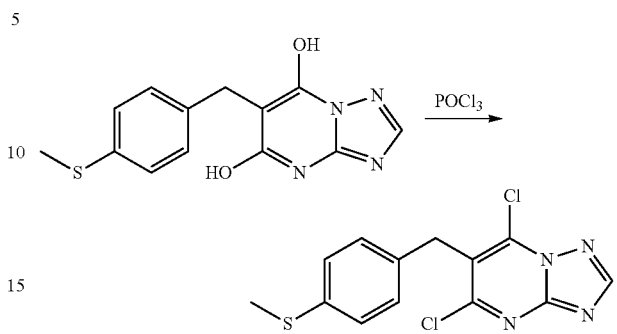

POCl₃ (3.2 mL, 35 mmol) was added dropwise to 6-(4-(methylthio)benzyl)-[1,2,4]triazolo[1,5-α]pyrimidine-5,7-diol (0.5 g, 1.7 mmol) and the mixture was stirred at 105° C. overnight. The mixture was concentrated, co-evaporated with toluene, and H₂O added. The pH was adjusted to 7 by addition of saturated aqueous NaHCO₃, and the mixture extracted with EtOAc (3×). The combined extracts were washed with brine, dried over Na₂SO₄, filtered, and concentrated. Purification by silica chromatography (5-100% EtOAc in heptane) provided 380 mg of 5,7-dichloro-6-(4-(methylthio)benzyl)-[1,2,4]triazolo[1,5-α]pyrimidine.

Step 4. Synthesis of 5-chloro-N,N-dimethyl-6-(4-(methylthio)benzyl)-[1,2,4]triazolo[1,5-α]pyrimidin-7-amine

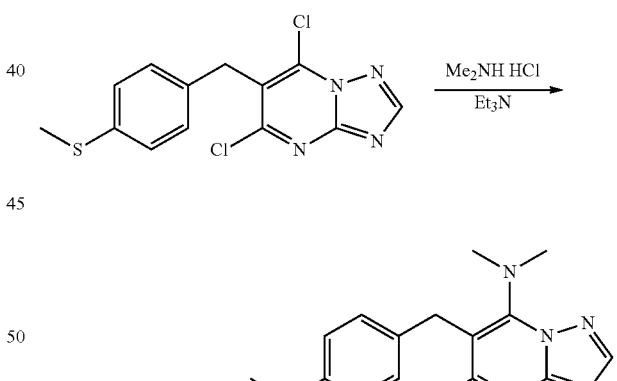

A mixture of 5,7-dichloro-6-(4-(methylthio)benzyl)-[1,2,4]triazolo[1,5-α]pyrimidine (0.38 g, 1.2 mmol), MeCN (10 mL), Et₃N (0.38 mL, 2.7 mmol), and dimethylamine hydrochloride (0.12 g, 1.5 mmol) was stirred for 1 h. The mixture was concentrated, mixed with water, and extracted with CH₂Cl₂ (3×). The combined extracts were concentrated and purified by silica chromatography (5-100% EtOAc in heptane) to provide 0.33 g of 5-chloro-N,N-dimethyl-6-(4-(methylthio)benzyl)-[1,2,4]triazolo[1,5-α]pyrimidin-7-amine.

Step 5. Synthesis of (4-((5-chloro-7-(dimethyl-amino)-[1,2,4]triazolo[1,5-α]pyrimidin-6-yl)methyl)phenyl)(imino)(methyl)-λ⁶-sulfanone (Compound 74)

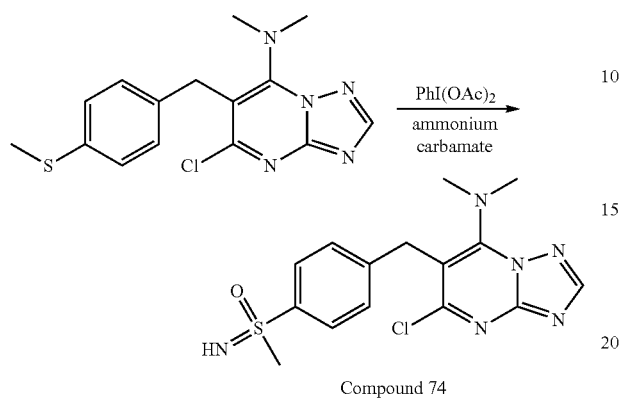

Compound 74

A mixture of 5-chloro-N,N-dimethyl-6-(4-(methylthio)benzyl)-[1,2,4]triazolo[1,5-α]pyrimidin-7-amine (330 mg, 0.989 mmol), MeOH (4 mL), ammonium carbamate (0.12 g, 1.5 mmol) and PhI(OAc)₂ (0.64 g, 2.0 mmol) was stirred for 1 h. The mixture was concentrated and purified by silica chromatography (5-100% EtOAc in heptane, then 50-80% [9:1 MeOH/CH₂Cl₂] in EtOAc) to obtain 0.30 g of (4-((5-chloro-7-(dimethylamino)-[1,2,4]triazolo[1,5-α]pyrimidin-6-yl)methyl)phenyl)(imino)(methyl)-λ⁶-sulfanone (Compound 74). ESI MS m/z: 365.1 (M+H).

(4-{[5-chloro-7-(pyrrolidin-1-yl)-[1,2,4]triazolo[1,5-α]pyrimidin-6-yl]methyl}phenyl)(imino)methyl-λ⁶-sulfanone (Compound 78) was prepared in the manner described in Synthetic Example S-020 (Compound 74) by substituting pyrrolidine for dimethylamine hydrochloride. ESI MS m/z: 391.1 (M+H).

Synthetic Example S-021

Synthesis of 7-(dimethylamino)-6-({4-[imino(methyl)oxo-λ⁶-sulfanyl]phenyl}methyl)-[1,2,4]triazolo[1,5-α]pyrimidine-5-carbonitrile (Compound 79)

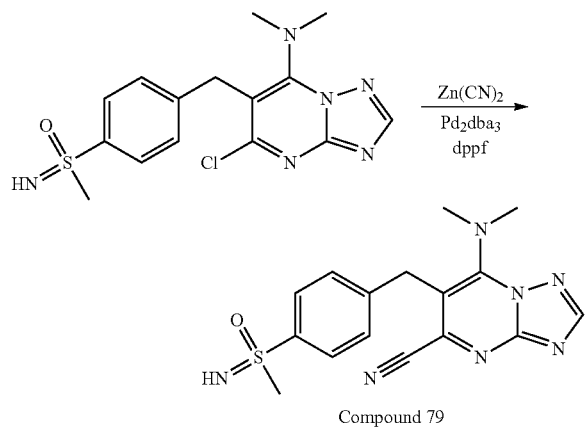

Compound 79

A mixture of (4-((5-chloro-7-(dimethylamino)-[1,2,4]triazolo[1,5-α]pyrimidin-6-yl)methyl)phenyl)(imino)(methyl)-λ⁶-sulfanone (35 mg, 0.096 mmol), Zn(CN)₂ (11 mg, 0.096 mmol), DMF (1 mL), and H₂O (0.01 mL) was degassed with nitrogen for 5 min. Pd₂(dba)₃ (4.4 mg, 4.8 μmol) and dppf (5.3 mg, 9.6 μmol) were added and the resulting mixture was stirred overnight at 100° C. The reaction mixture was filtered and the filtrate was purified by reverse phase HPLC (5-40% MeCN in H₂O, 0.1% NH₄HCO₃) to provide 15 mg of 7-(dimethylamino)-6-({4-[imino(methyl)oxo-λ⁶-sulfanyl]phenyl}methyl)-[1,2,4]triazolo[1,5-α]pyrimidine-5-carbonitrile (Compound 79). ESI MS m/z: 356.1 (M+H).

Synthetic Example S-022

Synthesis of 5-(dimethylamino)-6-({4-[imino(methyl)oxo-λ⁶-sulfanyl]phenyl}methyl)-7-methyl-imidazo[1,2-α]pyridine-8-carbonitrile (Compound 80)

Step 1: Synthesis of 5-hydroxy-7-methyl-6-(4-(methylthio)benzyl)imidazo[1,2-α]pyridine-8-carbonitrile

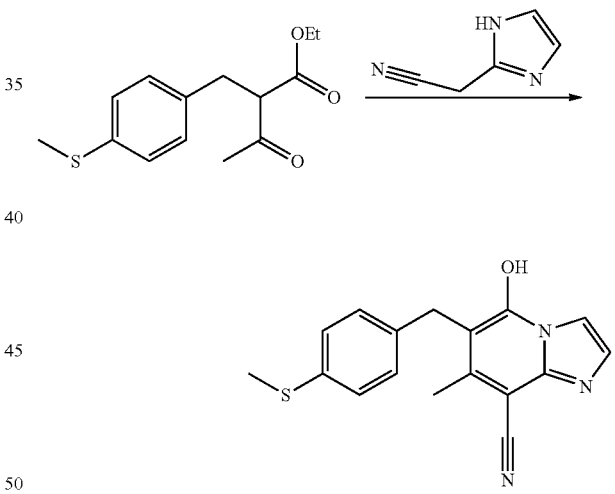

A mixture of 2-(4-(methylthio)benzyl)-3-oxobutanoate (0.45 g, 1.5 mmol), 2-(1H-imidazol-2-yl)acetonitrile (0.19 g, 1.8 mmol) and NH₄OAc (0.58 g, 7.5 mmol) was stirred at 130° C. for 4 h The mixture was cooled and partitioned between 50 mL of H₂O and 50 mL of CH₂Cl₂. The precipitate was filtered, washed with water and CH₂Cl₂, and dried to provide 268 mg of 5-hydroxy-7-methyl-6-(4-(methylthio)benzyl)imidazo[1,2-α]pyridine-8-carbonitrile. The organic portion of the filtrate was concentrated and the residue was purified by silica chromatography (0-5% MeOH in CH₂Cl₂) to provide an additional 40 mg of 5-hydroxy-7-methyl-6-(4-(methylthio)benzyl)imidazo[1,2-α]pyridine-8-carbonitrile.

Step 2: Synthesis of 5-chloro-7-methyl-6-(4-(methylthio)benzyl)imidazo[1,2-α]pyridine-8-carbonitrile

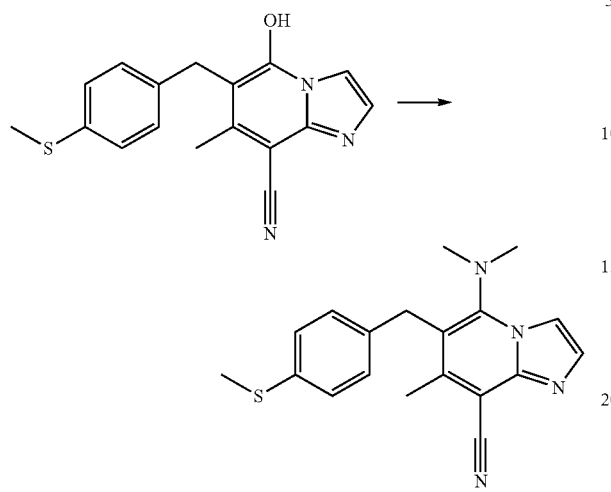

A mixture of 5-hydroxy-7-methyl-6-(4-(methylthio)benzyl)imidazo[1,2-α]pyridine-8-carbonitrile (73 mg, 0.20 mmol) and POCl₃ (1.9 mL, 20 mmol) was heated to 120° C. for 2 h. The mixture was cooled, concentrated to provide 85 mg of 5-chloro-7-methyl-6-(4-(methylthio)benzyl)imidazo[1,2-α]pyridine-8-carbonitrile with 85% purity.

Step 3: Synthesis 5-(dimethylamino)-7-methyl-6-(4-(methylthio)benzyl)imidazo[1,2-α]pyridine-8-carbonitrile

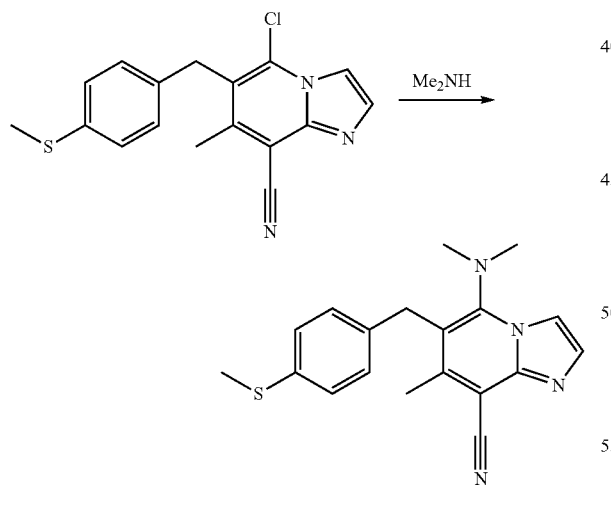

A mixture of 5-chloro-7-methyl-6-(4-(methylthio)benzyl)imidazo[1,2-α]pyridine-8-carbonitrile (85 mg, 0.20 mmol) and 2M Me₂NH in THF (2.0 mL, 3.0 mmol) was heated to 120° C. for 2h in a microwave reactor. The mixture was concentrated and purified by silica chromatography (0-3% MeOH in CH₂Cl₂), then by reverse phase HPLC (5-70% MeCN in H₂O, 0.1% NH₄HCO₃) to provide 174 mg of 5-(dimethylamino)-7-methyl-6-(4-(methylthio)benzyl)imidazo[1,2-α]pyridine-8-carbonitrile.

Step 4: Synthesis of 5-(dimethylamino)-6-({4-[imino(methyl)oxo-$\lambda^6$-sulfanyl]phenyl}methyl)-7-methylimidazo[1,2-α]pyridine-8-carbonitrile (Compound 80)

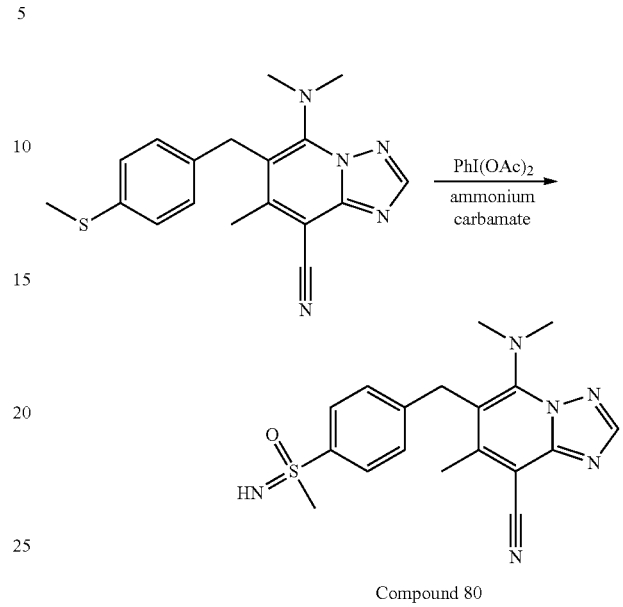

Compound 80

To an ice-cold mixture of 5-(dimethylamino)-7-methyl-6-(4-(methylthio)benzyl)imidazo[1,2-α]pyridine-8-carbonitrile (59 mg, 0.17 mmol) and MeOH (5.2 mL) was added ammonium carbamate (27 mg, 0.35 mmol) and PhI(OAc)₂ (0.12 g, 0.37 mmol). The mixture was stirred for 1 h at room temperature, concentrated, and purified by preparative HPLC (5-40% MeCN in H₂O, 0.1% NH₄HCO₃) to provide 50 mg of 5-(dimethylamino)-6-({4-[imino(methyl)oxo-$\lambda^6$-sulfanyl]phenyl}methyl)-7-methylimidazo[1,2-α]pyridine-8-carbonitrile (Compound 80). ESI MS m/z: 368.2 (M+H).

Synthetic Example S-023

Synthesis of 4-{[7-(dimethylamino)-5-methyl-[1,2,4]triazolo[1,5-α]pyrimidin-6-yl]methyl}piperidine-1-sulfonamide (Compound 15)

Step 1: Synthesis of tert-butyl 4-(2-(ethoxycarbonyl)-3-oxobutyl)piperidine-1-carboxylate

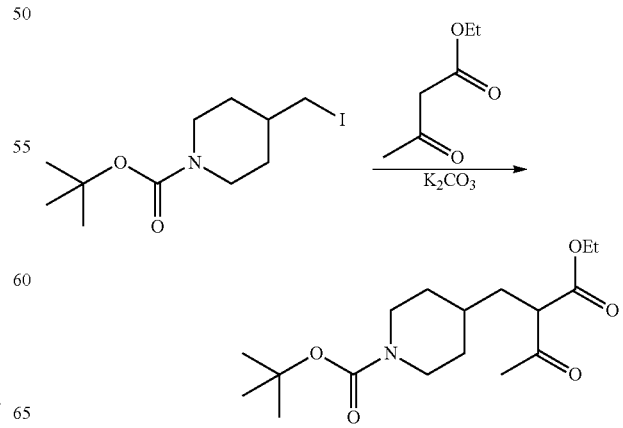

To a mixture of ethyl acetoacetate (1.0 mL, 7.9 mmol), DMF (20 mL), and $K_2CO_3$ (2.2 g, 16 mmol) was added dropwise tert-butyl 4-(iodomethyl)piperidine-1-carboxylate (2.8 g, 8.7 mmol) and the mixture was stirred for 40 h. Aqueous $KHSO_4$ (0.5 M) was added and the mixture was extracted with EtOAc (3×). The combined extracts were washed with brine, dried over $Na_2SO_4$, filtered, concentrated, and purified by silica chromatography (10% $CH_2Cl_2$ in heptane) to provide 1.3 g of tert-butyl 4-(2-(ethoxycarbonyl)-3-oxobutyl)piperidine-1-carboxylate.

Step 2: Synthesis of tert-butyl 4-((7-hydroxy-5-methyl-[1,2,4]triazolo[1,5-α]pyrimidin-6-yl)methyl)piperidine-1-carboxylate

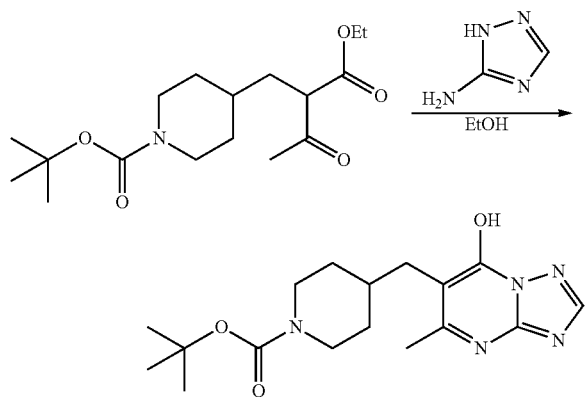

A mixture of tert-butyl 4-(2-(ethoxycarbonyl)-3-oxobutyl)piperidine-1-carboxylate (1.3 g, 3.8 mmol), EtOH (10 mL), and 3-amino-1H-1,2,4-triazole (0.40 g, 4.8 mmol) was stirred for 36 h at 80° C. The mixture was concentrated and combined with fresh EtOH (10 mL) and 3-amino-1H-1,2,4-triazole (0.16 g, 1.9 mmol) and heated at 80° C. for 2 days. The mixture was concentrated and purified by silica chromatography (0-10% MeOH in $CH_2Cl_2$) to provide 0.93 g of tert-butyl 4-((7-hydroxy-5-methyl-[1,2,4]triazolo[1,5-α]pyrimidin-6-yl)methyl)piperidine-1-carboxylate.

Step 3: Synthesis of 6-((1-benzylpiperidin-4-yl)methyl)-5-methyl-[1,2,4]triazolo[1,5-α]pyrimidin-7-ol

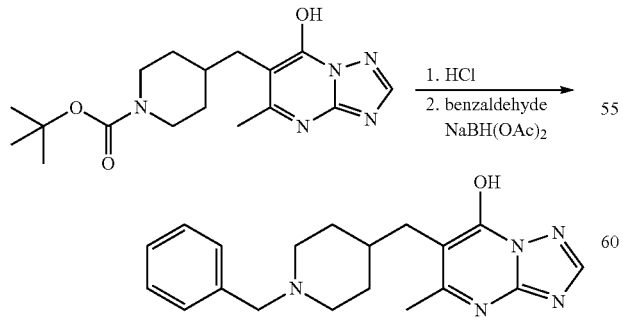

A mixture of tert-butyl 4-((7-hydroxy-5-methyl-[1,2,4]triazolo[1,5-α]pyrimidin-6-yl)methyl)piperidine-1-carboxylate (930 mg, 2.7 mmol), $CH_2Cl_2$ (15 mL), and 4M HCl in dioxane (6.7 mL, 27 mmol) was stirred for 1.5 h, then concentrated to provide 0.88 g of 5-methyl-6-(piperidin-4-ylmethyl)-[1,2,4]triazolo[1,5-α]pyrimidin-7-ol dihydrochloride. The residue was stirred with $CH_2CL_2$ (1 mL), MeOH (10 mL), benzaldehyde (1.1 mL, 11 mmol), and $NaBH(OAc)_3$ (4.7 g, 22 mmol) overnight. DMF (0.5 mL) was added the mixture heated at 50° C. for 3 h. Additional $NaBH(OAc)_3$ (2.3 g, 11 mmol) was added and the mixture stirred at 50° C. overnight. Additional $NaBH(OAc)_3$ (2.3 g, 11 mmol) was added and the mixture was stirred at 50° C. for 48 h. After concentration, water was added, and the mixture extracted twice with EtOAc. The aqueous phase was concentrated, then purified by reverse phase HPLC (5-100% MeCN in $H_2O$, 10 mM $NH_4HCO_3$) to provide 110 mg of 64(1-benzylpiperidin-4-yl)methyl)-5-methyl-[1,2,4]triazolo[1,5-α]pyrimidin-7-ol.

Step 4: Synthesis of 6-((1-benzylpiperidin-4-yl)methyl)-7-chloro-5-methyl-[1,2,4]triazolo[1,5-α]pyrimidine

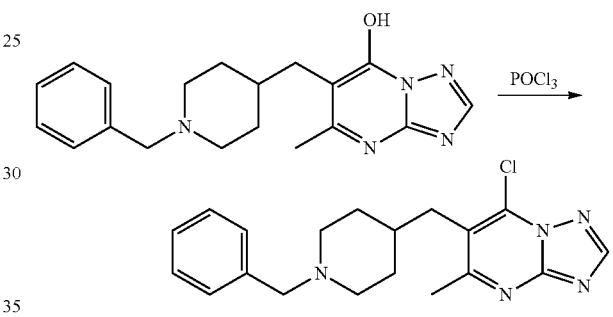

$POCl_3$ (0.61 mL, 6.5 mmol) was added dropwise to 6-((1-benzylpiperidin-4-yl)methyl)-5-methyl-[1,2,4]triazolo[1,5-α]pyrimidin-7-ol (110 mg, 0.33 mmol) and the resulting mixture was stirred at 90° C. overnight. The mixture was cooled and concentrated. Saturated aqueous $NaHCO_3$ was added and the mixture was extracted with $CH_2Cl_2$ (3×). The combined extracts were concentrated to provide 110 mg of 64(1-benzylpiperidin-4-yl)methyl)-7-chloro-5-methyl-[1,2, 4]triazolo[1,5-α]pyrimidine.

Step 4: Synthesis of 6-((1-benzylpiperidin-4-yl)methyl)-N,N,5-trimethyl-[1,2,4]triazolo[1,5-α]pyrimidin-7-amine

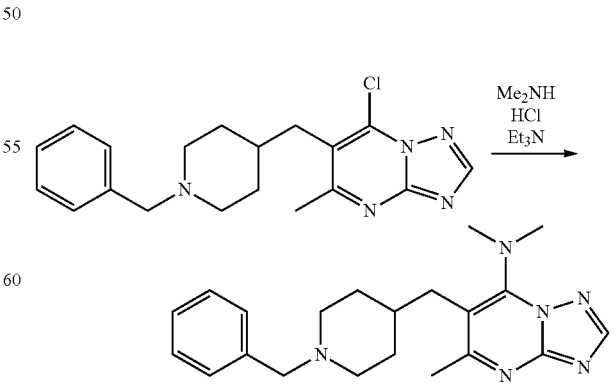

A mixture of 6-((1-benzylpiperidin-4-yl)methyl)-7-chloro-5-methyl-[1,2,4]triazolo[1,5-α]pyrimidine (110 mg, 0.31 mmol), MeCN (3 mL), Et₃N (0.22 mL, 1.6 mmol) and dimethylamine hydrochloride (76 mg, 0.93 mmol) was stirred for 4 h. Additional dimethylamine hydrochloride (50 mg, 0.62 mmol) and Et₃N (0.13 mL, 0.93 mmol) were added and the reaction mixture was stirred overnight, concentrated, and mixed with H₂O. The mixture was extracted with CH₂Cl₂ (3×). The extracts were combined and concentrated to provide 110 mg of 6-((1-benzylpiperidin-4-yl)methyl)-N,N,5-trimethyl-[1,2,4]triazolo[1,5-α]pyrimidin-7-amine.

Step 5: Synthesis of N,N,5-trimethyl-6-(piperidin-4-ylmethyl)-[1,2,4]triazolo[1,5-α]pyrimidin-7-amine

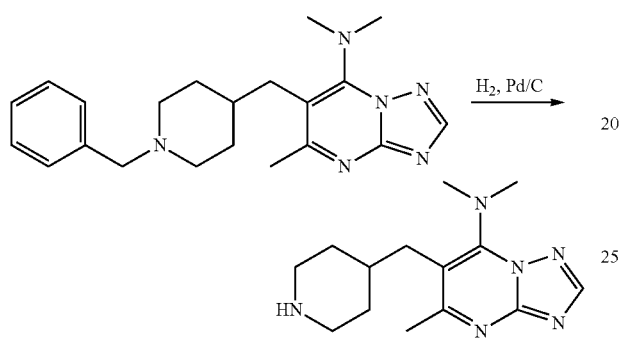

Hydrogen was bubbled through a degassed mixture of 6-((1-benzylpiperidin-4-yl)methyl)-N,N,5-trimethyl-[1,2,4]triazolo[1,5-α]pyrimidin-7-amine (80 mg, 0.22 mmol) MeOH (2 mL), and Pd—C (23 mg, 0.022 mmol) for 5 minutes. The mixture was stirred for 3 h under a H₂ atmosphere. Additional Pd—C (12 mg, 11 µmol) was added, and H₂ was bubbled through the mixture. The resulting reaction mixture was stirred overnight, filtered, and the filtrate concentrated to provide 60 mg of N,N,5-trimethyl-6-(piperidin-4-ylmethyl)-[1,2,4]triazolo[1,5-α]pyrimidin-7-amine.

Step 6: Synthesis of 4-{[7-(dimethylamino)-5-methyl-[1,2,4]triazolo[1,5-α]pyrimidin-6-yl]methyl}piperidine-1-sulfonamide (Compound 15)

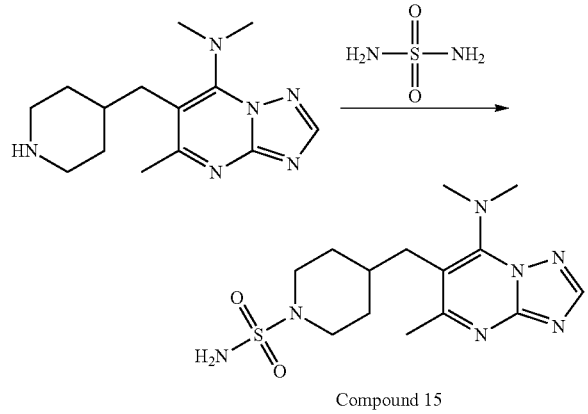

Compound 15

A mixture of N,N,5-trimethyl-6-(piperidin-4-ylmethyl)-[1,2,4]triazolo[1,5-α]pyrimidin-7-amine (50 mg, 0.18 mmol), pyridine (1 mL), and sulfamide (53 mg, 0.55 mmol) was stirred overnight at 80° C. Additional sulfamide (35 mg, 0.36 mmol) and iPr₂NEt (0.095 mL, 0.55 mmol) were added and the resulting mixture was stirred for 3 h at 100° C. The mixture was concentrated and purified by reverse phase HPLC (0-15% MeCN in H₂O, 10 mM NH₄HCO₃) to provide 24 mg of 4-((7-(dimethylamino)-5-methyl-[1,2,4]triazolo[1,5-α]pyrimidin-6-yl)methyl)piperidine-1-sulfonamide (Compound 15). ESI MS m/z: 354.3 (M+H).

Synthetic Example S-024

Synthesis of (4-{[5-methyl-7-(pyrrolidin-1-yl)-[1,2,4]triazolo[1,5-α]pyrimidin-6-yl]methyl}phenyl) phosphonic acid (Compound 36)

Step 1: Synthesis of 6-[(4-diisopropoxyphosphorylphenyl)methyl]-5-methyl-7-pyrrolidin-1-yl-[1,2,4]triazolo[1,5-α]pyrimidine

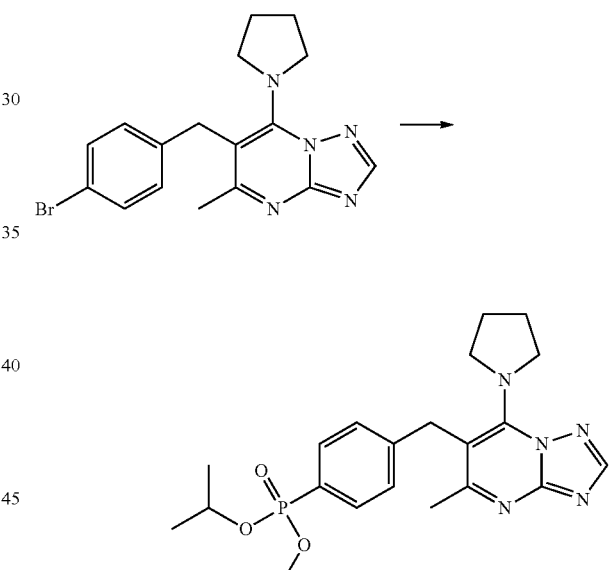

To a mixture of 6-[(4-bromophenyl)methyl]-5-methyl-7-pyrrolidin-1-yl-[1,2,4]triazolo[1,5-α]pyrimidine (200 mg, 0.54 mmol), toluene (3 mL), 2-isopropoxyphosphonoyloxypropane (0.11 g, 0.67 mmol) and Pd(dppf)Cl₂ (39 mg, 54 µmol) was added a mixture of Et₃SiH (0.17 mL, 1.1 mmol), Et₃N (0.22 g, 1.6 mmol), and CH₂Cl₂ (0.5 mL). The resulting mixture was stirred at 90° C. for 12 h before being cooled to room temperature, poured to water (30 mL) and extracted with EtOAc (2×30 mL). The combined extracts were washed with brine (10 mL), dried over Na₂SO₄, and concentrated to provide 0.24 g of 6-[(4-diisopropoxyphosphorylphenyl)methyl]-5-methyl-7-pyrrolidin-1-yl-[1,2,4]triazolo[1,5-α]pyrimidine.

Step 2: Synthesis of (4-{[5-methyl-7-(pyrrolidin-1-yl)-[1,2,4]triazolo[1,5-α]pyrimidin-6-yl]methyl}phenyl)phosphonic acid (Compound 36)

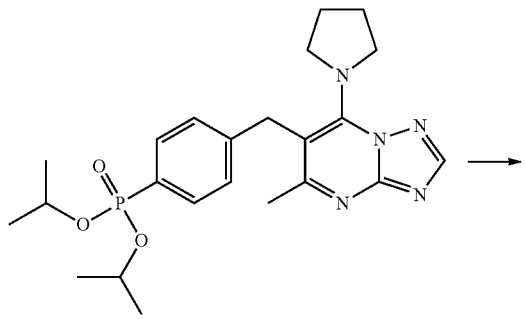

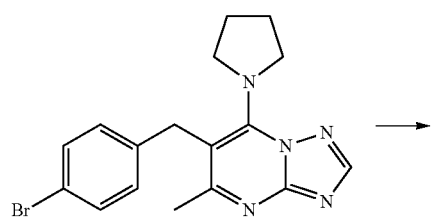

Compound 36

A mixture of 6-[(4-diisopropoxyphosphorylphenyl)methyl]-5-methyl-7-pyrrolidin-1-yl)-[1,2,4]triazolo[1,5-α]pyrimidine (300 mg, 0.66 mmol) and HCl (6 M, 3.0 mL) was stirred at 100° C. for 2 h under an $N_2$ atmosphere. The reaction mixture was concentrated and purified by preparative HPLC (1-30% MeCN in $H_2O$, 0.04% HCl) to provide 32 mg of (4-{[5-methyl-7-(pyrrolidin-1-yl)-[1,2,4]triazolo[1,5-α]pyrimidin-6-yl]methyl}phenyl)phosphonic acid (Compound 36). ESI MS m/z: 374.0 (M+H).

(4-{[7-(dimethylamino)-5-methyl-[1,2,4]triazolo[1,5-α]pyrimidin-6-yl]methyl}phenyl)phosphonic acid (Compound 5) was prepared in the manner described in Synthetic Example S-024 for Compound 36 by replacing 6-[(4-bromophenyl)methyl]-5-methyl-7-pyrrolidin-1-yl)-[1,2,4]triazolo[1,5-α]pyrimidine with 6-(4-bromobenzyl)-N,N,5-trimethyl-[1,2,4]triazolo[1,5-α]pyrimidin-7-amine in step 1. ESI MS m/z: 346.1 (M+H).

Synthetic Example S-025

Synthesis of (4-{[5-methyl-7-(pyrrolidin-1-yl)-[1,2,4]triazolo[1,5-α]pyrimidin-6-yl]methyl}phenyl)boronic acid (Compound 81)

Step 1: Synthesis of 5-methyl-7-pyrrolidin-1-yl-6-[[4-(4,4,5,5-tetramethyl-1,3,2-dioxaborolan-2-yl)phenyl]methyl]-[1,2,4]triazolo[1,5-α]pyrimidine

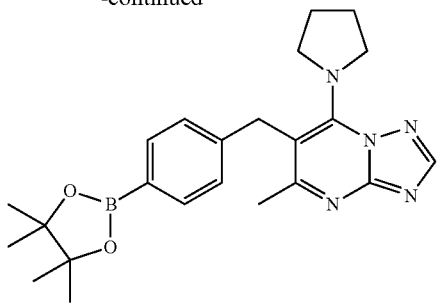

A mixture of 6-[(4-bromophenyl)methyl]-5-methyl-7-pyrrolidin-1-yl-[1,2,4]triazolo[1,5-α]pyrimidine (0.40 g, 1.1 mmol), in dioxane (5 mL), bispinacolatodiboron (0.41 g, 1.6 mmol), KOAc (0.32 g, 3.2 mmol), and Pd(dppf)Cl$_2$ (0.16 g, 0.21 mmol) was stirred at 100° C. for 12 h. The mixture was cooled, poured to water (30 mL), and extracted with EtOAc (2×30 mL). The combined extracts were washed with brine (10 mL), dried over Na$_2$SO$_4$, concentrated to provide 0.45 g of 5-methyl-7-pyrrolidin-1-yl-6-[[4-(4,4,5,5-tetramethyl-1,3,2-dioxaborolan-2-yl)phenyl]methyl]-[1,2,4]triazolo[1,5-α]pyrimidine.

Step 2: Synthesis of [4-[(5-methyl-7-pyrrolidin-1-yl-[1,2,4]triazolo[1,5-α]pyrimidin-6-yl)methyl]phenyl]boronic acid (Compound 81)

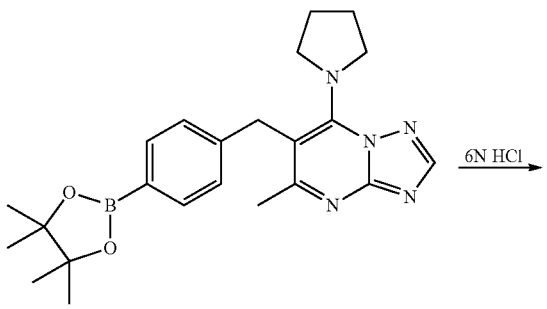

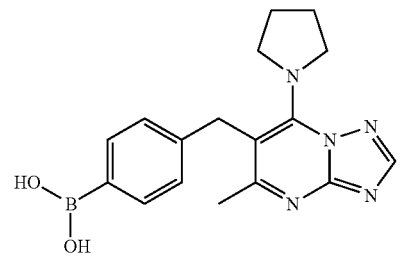

Compound 81

A mixture of 5-methyl-7-pyrrolidin-1-yl-6-[[4-(4,4,5,5-tetramethyl-1,3,2-dioxaborolan-2-yl)phenyl]methyl]-[1,2,4]triazolo[1,5-α]pyrimidine (0.30 mg, 0.72 mmol), THF (2.0 mL), and 6N HCl (8.6 mL) was stirred at 20° C. for 1 h. Aqueous NaOH (2 M) was added to adjust the pH to 7 and the mixture purified by preparative HPLC (10-40% MeCN in H$_2$O, 10 mM NH$_4$HCO$_3$) to provide 42 mg of [4-[(5-methyl-7-pyrrolidin-1-yl-[1,2,4]triazolo[1,5-α]pyrimidin-6-yl)methyl]phenyl]boronic acid (Compound 81). ESI MS m/z: 338.1 (M+H).

Synthetic Example S-026

Synthesis of N-hydroxy-4-{[5-methyl-7-(pyrrolidin-1-yl)-[1,2,4]triazolo[1,5-α]pyrimidin-6-yl]methyl}benzamide (Compound 82)

Step 1: Synthesis of methyl 4-[(5-methyl-7-pyrrolidin-1-yl-[1,2,4]triazolo[1,5-α]pyrimidin-6-yl)methyl]benzoate

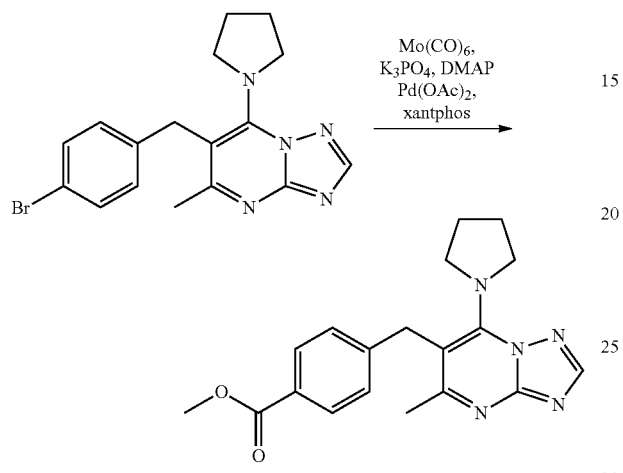

A mixture of 6-[(4-bromophenyl)methyl]-5-methyl-7-pyrrolidin-1-yl-[1,2,4]triazolo[1,5-α]pyrimidine (0.50 g, 1.3 mmol), dioxane (5 mL), MeOH (5 mL), Mo(CO)$_6$ (45 mg, 0.34 mmol), K$_3$PO$_4$ (0.29 g, 1.3 mmol), DMAP (82 mg, 0.67 mmol), Xantphos (77 mg, 0.13 mmol) and Pd(OAc)$_2$ (15 mg, 67.16 μmol) was stirred at 120° C. for 3 h in a microwave reactor. The mixture was filtered and concentrated to provide 0.70 g of methyl 4-[(5-methyl-7-pyrrolidin-1-yl-[1,2,4]triazolo[1,5-α]pyrimidin-6-yl)methyl]benzoate.

Step 2: Synthesis of 4-[(5-methyl-7-pyrrolidin-1-yl-[1,2,4]triazolo[1,5-α]pyrimidin-6-yl)methyl]benzoic acid

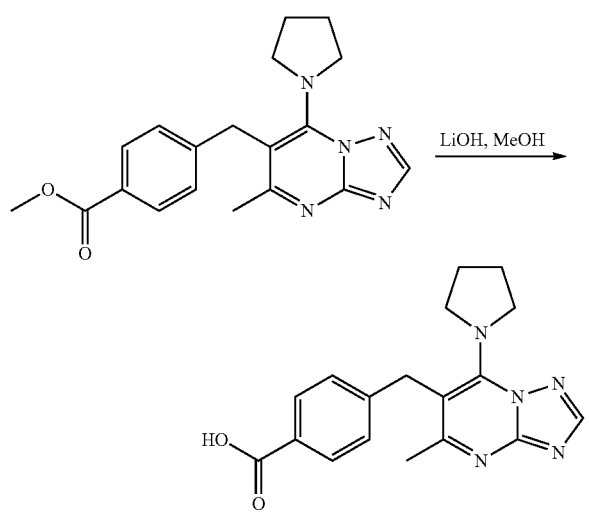 [SMILES: COC(=O)c1ccc(Cc2c(C)nc3ncnn3c2N2CCCC2)cc1 ; Cc1nc2ncnn2c(N2CCCC2)c1Cc1ccc(C(=O)O)cc1]

A mixture of methyl 4-[(5-methyl-7-pyrrolidin-1-yl-[1,2,4]triazolo[1,5-α]pyrimidin-6-yl)methyl]benzoate (0.50 g, 1.4 mmol), MeOH (2 mL), THF (2 mL), LiOH (0.17 g, 7.1 mmol), H$_2$O (8 mL) was stirred at 20° C. for 2 h. The mixture was concentrated to provide 110 mg of 4-[(5-methyl-7-pyrrolidin-1-yl-[1,2,4]triazolo[1,5-α]pyrimidin-6-yl)methyl]benzoic acid.

Step 3: Synthesis of N-hydroxy-4-{[5-methyl-7-(pyrrolidin-1-yl)-[1,2,4]triazolo[1,5-α]pyrimidin-6-yl]methyl}benzamide (Compound 82)

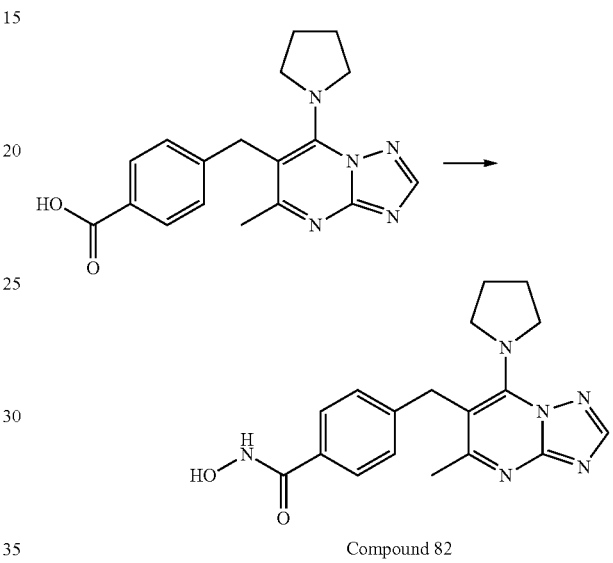

Compound 82

A mixture of 4-[(5-methyl-7-pyrrolidin-1-yl-[1,2,4]triazolo[1,5-α]pyrimidin-6-yl)methyl]benzoic acid (50 mg, 0.15 mmol), DMF (3 mL), iPr$_2$NEt (0.13 mL, 0.74 mmol), HATU (0.11 g, 0.30 mmol) was stirred for 15 min, and NH$_2$OH·HCl (15 mg, 0.22 mmol) was added. After stirring at 20° C. for 12 h, the mixture was concentrated, and purified by preparative HPLC (15-50% MeCN in H$_2$O, 10 mM NH$_4$HCO$_3$) to provide 12 mg of N-hydroxy-4-{[5-methyl-7-(pyrrolidin-1-yl)-[1,2,4]triazolo[1,5-α]pyrimidin-6-yl]methyl}benzamide (Compound 82). ESI MS m/z: 353.1 (M+H).

Synthetic Example S-027

Synthesis of 5-(dimethylamino)-6-({4-[imino(methypoxo-λ$^6$-sulfanyl]phenyl}methyl)-7-methyl-[1,2,4]triazolo[1,5-a]pyridine-8-carbonitrile (Compound 85)

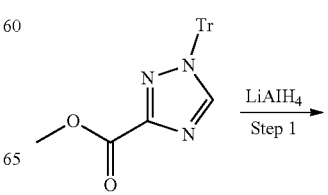

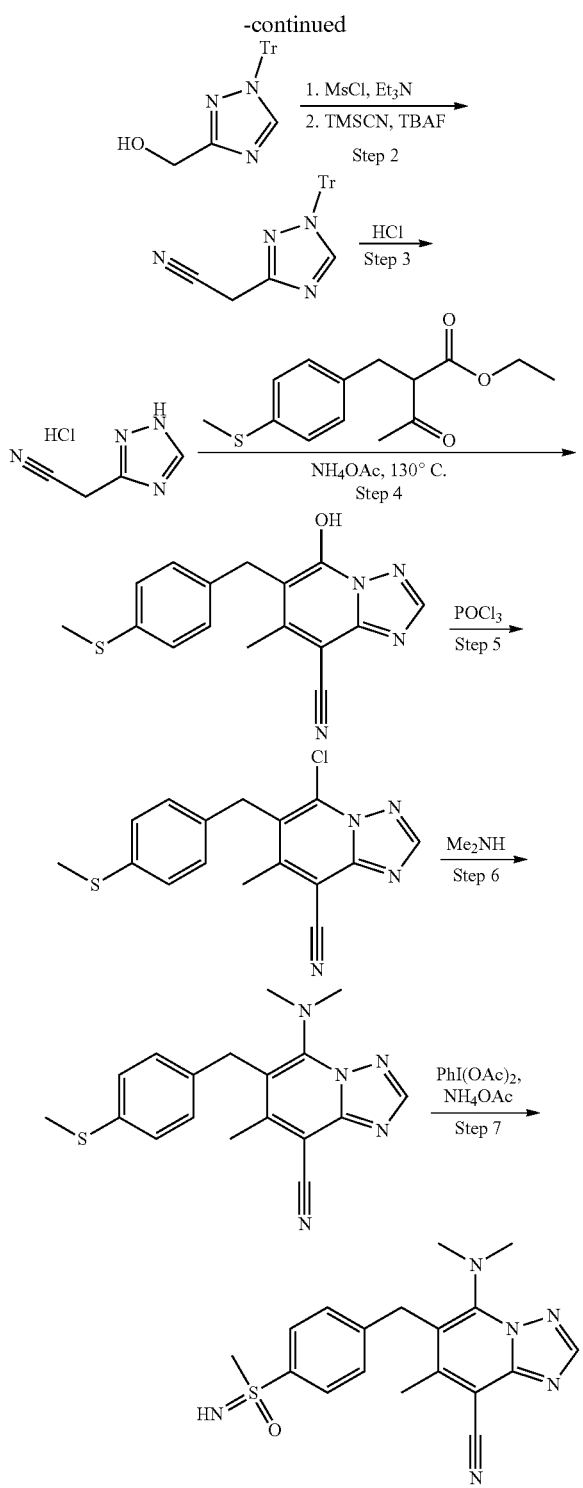

Step 1: LiAlH₄ (4.3 g, 114 mmol) was added in portions to a mixture of methyl 1-trityl-1H-1,2,4-triazole-3-carboxylate (28 g, 76 mmol) and THF (400 mL) at 0° C., and the mixture was stirred at 0° C. for 0.5 h, and then at 20° C. for 4 h. To the mixture was added dropwise 2M aqueous NaOH (8 mL) and Na₂SO₄ (80 g) with stirring at 0° C. The mixture was filtered and the filtrate was concentrated, and triturated with EtOAc (40 mL) at 20° C. for 15 min to provide (1-trityl-1H-1,2,4-triazol-3-yl)methanol (12 g).

Step 2: MSCl (8.9 mL, 115 mmol) was added dropwise into a mixture of (1-trityl-1H-1,2,4-triazol-3-yl)methanol (13 g, 38 mmol), Et₃N (7.0 mL, 50 mmol), and CH₂Cl₂ (200 mL) at 0° C. The mixture was stirred at 20° C. for 1 h and poured into ice-water (100 mL), extracted with CH₂Cl₂ (80×2 mL). The extracts were combined, washed with water (80 mL×2) and brine (80 mL), dried over Na₂SO₄, filtered and concentrated to provide (1-trityl-1H-1,2,4-triazol-3-yl) methyl methanesulfonate (15 g). This material was combined with TMSCN (9.6 mL, 77 mmol), MeCN (50 mL), and THF (50 mL), and TBAF (1 M, 65 mL) was added and the mixture was stirred at 80° C. for 2 h, concentrated, and purified by silica chromatography (0-70% THF in petroleum ether) to provide 2-(1-trityl-1H-1,2,4-triazol-3-yl)acetonitrile (8 g).

Step 3: A mixture of 2-(1-trityl-1H-1,2,4-triazol-3-yl) acetonitrile (2.6 g, 7.4 mmol) and HCl/dioxane (4 M, 13 mL) was stirred at 20° C. for 12 h. The mixture was concentrated, triturated with MTBE (10 mL) at 30° C. for 15 min, filtered, and the filtered cake was washed with additional MTBE (1 mL×3) to provide 2-(1H-1,2,4-triazol-3-yl)acetonitrile hydrochloride (1.0 g).

Step 4: A mixture of ethyl 2-(4-(methylthio)benzyl)-3-oxobutanoate (1 g, 3.8 mmol), 2-(1H-1,2,4-triazol-3-yl) acetonitrile hydrochloride (0.45 g, 3.1 mmol), and NH₄OAc (0.75 g, 9.7 mmol) was stirred at 130° C. for 12 h. The mixture was cooled to 20° C., combined with saturated NaHCO₃ (20 mL) and MTBE (5 mL) and ground to give a suspension. The suspension was triturated with MTBE (10 mL) at 30° C. for 15 min and filtered to provide 5-hydroxy-7-methyl-6-(4-(methylthio)benzyl)-[1,2,4]triazolo[1,5-a] pyridine-8-carbonitrile (1.6 g).

Step 5: A mixture of 5-hydroxy-7-methyl-6-(4-(methylthio)benzyl)-[1,2,4]triazolo[1,5-a]pyridine-8-carbonitrile (1.6 g, 5.2 mmol) and POCl₃ (8 mL, 86 mmol) was stirred at 120° C. for 12 h. The mixture concentrated, and aqueous saturated NaHCO₃ was added to provide a suspension. The suspension was filtered, and the filter cake was washed with water (5 mL×3) and petroleum ether (10 mL). The solid was further triturated with petroleum ether (30 mL) at 45° C. for 15 min, filtered and the filtered cake was washed with petroleum ether (5 mL×2) to provide 5-chloro-7-methyl-6-(4-(methylthio)benzyl)-[1,2,4]triazolo[1,5-a]pyridine-8-carbonitrile (0.55 g).

Step 6: A mixture of 5-chloro-7-methyl-6-(4-(methylthio) benzyl)-[1,2,4]triazolo[1,5-a]pyridine-8-carbonitrile (0.55 g, 1.7 mmol), 40 aqueous Me₂NH (2.2 mL, 43 mmol), iPr₂NEt (0.88 mL 5.1 mmol), EtOH (30 mL), and THF (20 mL) was stirred at 40° C. for 12 h. The mixture was concentrated to provide crude 5-(dimethylamino)-7-methyl-6-(4-(methylthio)benzyl)-[1,2,4]triazolo[1,5-a]pyridine-8-carbonitrile (0.70 g).

Step 7: A mixture of crude 5-(dimethylamino)-7-methyl-6-(4-(methylthio)benzyl)-[1,2,4]triazolo[1,5-a] pyridine-8-carbonitrile (0.70 g, <2.1 mmol), NH₄OAc (1 g, 13 mmol), PhI(OAc)₂ (2.6 g, 8.1 mmol), and EtOH (40 mL) was stirred at 20° C. for 6 h, then at 40° C. for 12 h. The mixture was concentrated and purified by preparative HPLC (20-50% MeCN in H₂O (10 mM NH₄HCO₃)) to provide 5-(dimethylamino)-6-({4-[imino(methyl)oxo-$\lambda^6$-sulfanyl] phenyl}methyl)-7-methyl-[1,2,4]triazolo[1,5-a]pyridine-8-carbonitrile (Compound 85) (0.36 g). ESI MS m/z: 369.1 (M+H).

Synthetic Example S-028

Synthesis of (4-{[5-(dimethylamino)-7-methyl-[1,2,4]triazolo[1,5-a]pyrimidin-6-yl]methyl}phenyl)(imino)methyl-λ⁶-sulfanone (Compound 86)

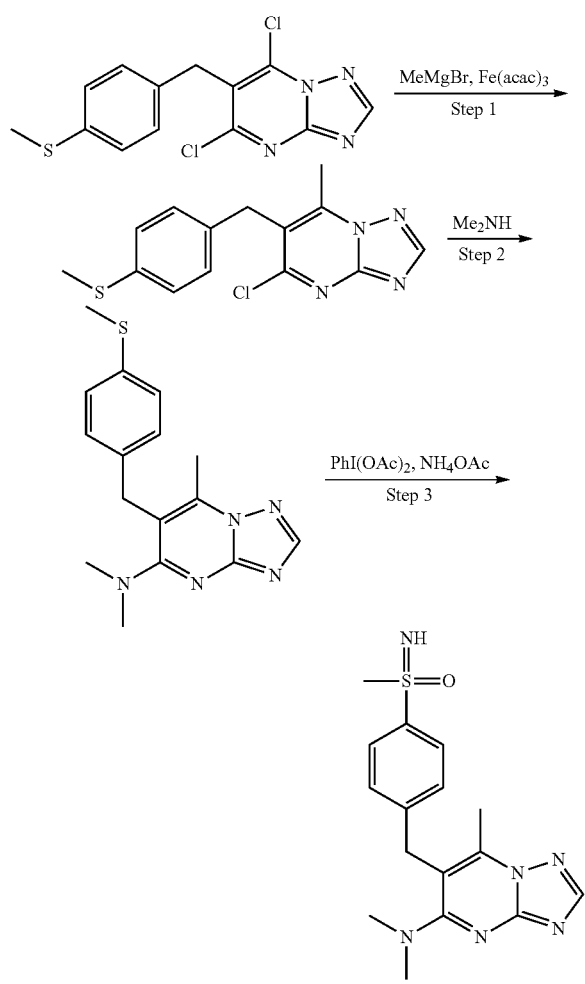

Step 1: To a mixture of 5,7-dichloro-6-[(4-methylsulfanylphenyl)methyl]-[1,2,4]triazolo[1,5-a]pyrimidine (0.50 g, 1.5 mmol). THF (10 mL), and NMP (1 mL) was added tris[(Z)-1-methyl-3-oxo-but-1-enoxy]iron (54 mg) in one portion and bromo(methyl)magnesium (3 M, 0.51 mL), slowly at 0° C. The mixture was stirred at 20° C. for 12 h, and a 10:1 mixture of saturated NH₄Cl and aqueous NH₄OH was added. The mixture was concentrated, combined with H₂O (10 mL) and extracted with EtOAc (10 mL×2). The extracts were combined, washed with brine (10 mL), dried over Na₂SO₄, filtered, and concentrated, and purified by preparative HPLC (20-60% MeCN in H₂O (0.2% formic acid)) to provide 5-chloro-7-methyl-6-[(4-methyl sulfanylphenyl)methyl]-[1,2,4]triazolo[1,5-a]pyrimidine (10 mg).

Step 2: A degassed mixture of 5-chloro-7-methyl-6-[(4-methylsulfanylphenyl)methyl]-[1,2,4]triazolo[1,5-a]pyrimidine (10 mg, 33 μmol), 40% aqueous Me₂NH (11 mg, 98 μmol), EtOH (2.0 mL) was stirred at 20° C. for 2 h under an N₂ atmosphere. The reaction was poured into water (10 mL), and extracted with EtOAc (2×10 mL). The extracts were combined, washed with brine (10 mL), dried over Na₂SO₄, and concentrated to provide N,N,7-trimethyl-6-[(4-methylsulfanylphenyl)methyl]-[1,2,4]triazolo[1,5-a]pyrimidin-5-amine (10 mg).

Step 3: A mixture of N,N,7-trimethyl-6-[(4-methylsulfanylphenyl)methyl]-[1,2,4]triazolo[1,5-a]pyrimidin-5-amine (10 mg, 32 μmol), EtOH (1.0 mL), PhI(OAc)₂ (31 mg, 96 μmol) and NH₄OAc (9.8 mg, 0.13 mmol) was stirred for 1 h. The mixture was concentrated and purified by preparative HPLC (1-40% MeCN in H₂O (0.2% formic acid)) to provide N,N,7-trimethyl-6-[[4-(methylsulfonimidoyl)phenyl]methyl]-[1,2,4]triazolo[1,5-a]pyrimidin-5-amine (Compound 86) (5.1 mg). ESI MS m/z=345.1 (M+H).

Synthetic Example S-029

Synthesis of 3-[(4-{[5-(dimethylamino)-7-methyl-[1,2,4]triazolo[1,5-a]pyridin-6-yl]methyl}phenyl)(imino)oxo-λ⁶-sulfanyl]propanoic acid (Compound 87)

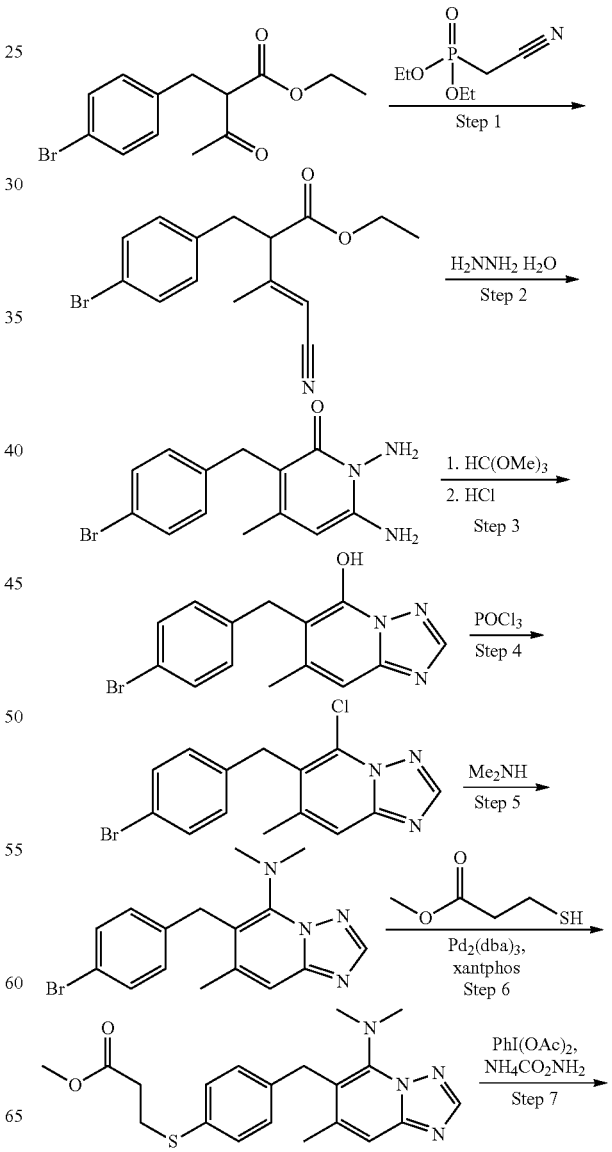

-continued

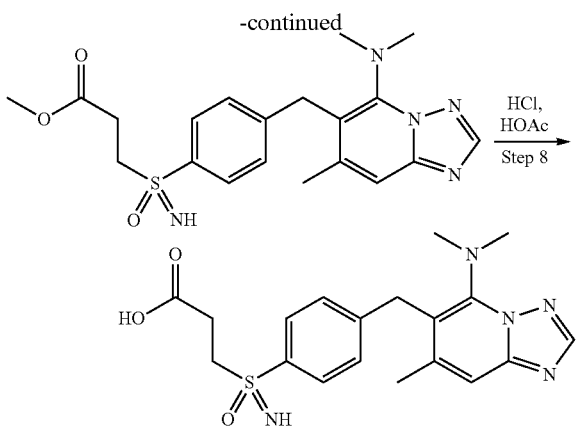

Step 1: A mixture of 2-diethoxyphosphorylacetonitrile (3.0 mL, 19 mmol), THF (50 mL), and $K_2CO_3$ (1.6 g, 11 mmol) was stirred for 10 min, and ethyl 2-[(4-bromophenyl)methyl]-3-oxo-butanoate (2.8 g, 9.4 mmol) and additional 2-diethoxyphosphorylacetonitrile (3.0 mL, 19 mmol) were added. The resulting mixture was stirred at 80° C. for 12 h. The mixture was concentrated, $H_2O$ was added (50 mL), and the mixture was extracted with EtOAc (2×50 mL). The extracts were combined, washed with brine (30 mL×2), dried over anhydrous $Na_2SO_4$, filtered, concentrated, and purified by silica chromatography (0-30% EtOAc in petroleum ether) to provide ethyl (E)-2-[(4-bromophenyl)methyl]-4-cyano-3-methyl-but-3-enoate (5.0 g).

Step 2: To a mixture of ethyl (E)-2-[(4-bromophenyl)methyl]-4-cyano-3-methyl-but-3-enoate (5.0 g, 16 mmol), EtOH (50 mL) was added hydrazine hydrate (6.2 mL, 124 mmol). The mixture was stirred at 80° C. for 12 h, concentrated, and crystallized from EtOH (10 mL) to provide 1,6-diamino-3-[(4-bromophenyl)methyl]-4-methyl-pyridin-2-one (3.5 g).

Step 3: A mixture of 1,6-diamino-3-[(4-bromophenyl)methyl]-4-methyl-pyridin-2-one (3.0 g, 9.7 mmol), AcOH (10 mL), methylorthoformate (11 mL, 97 mmol) was stirred at 130° C. for 1 h. The mixture was concentrated to provide 6-[(4-bromophenyl)methyl]-7-methyl-5-oxo-[1,2,4]triazolo[1,5-a]pyridine-1-carbaldehyde (3.0 g, 8.7 mmol), that was combined with MeOH (5 mL), and 39% HCl (5.5 mL, 60 mmol). The mixture was stirred at 100° C. for 6 h and concentrated to provide 6-[(4-bromophenyl)methyl]-7-methyl-[1,2,4]triazolo[1,5-a]pyridin-5-ol (3.0 g).

Step 4: A degassed mixture of 6-[(4-bromophenyl)methyl]-7-methyl-[1,2,4]triazolo[1,5-a]pyridin-5-ol (3.0 g, 9.4 mmol) and $POCl_3$ (30 mL, 323 mmol) was stirred at 120° C. for 24 h under an $N_2$ atmosphere. The mixture was concentrated, poured into saturated aqueous $NaHCO_3$ (30 mL), and the resulting precipitate was filtered and triturated with MTBE to provide 6-[(4-bromophenyl)methyl]-5-chloro-7-methyl-[1,2,4]triazolo[1,5-a]pyridine (2.2 g).

Step 5: A mixture of 6-[(4-bromophenyl)methyl]-5-chloro-7-methyl-[1,2,4]triazolo[1,5-a]pyridine (0.6 g, 1.8 mmol), DMF (10 mL), 40% aqueous $Me_2NH$ (1.1 mL, 8.9 mmol), and $iPr_2NEt$ (0.62 mL, 3.6 mmol) was stirred at 170° C. in a microwave reactor for 4 h. The mixture was poured into $H_2O$ (30 mL) and extracted with EtOAc (2×30 mL). The extracts were combined, washed with brine (10 mL), dried over $Na_2SO_4$, filtered, concentrated, and purified by silica chromatography (0-10% MeOH in $CH_2Cl_2$) to provide 6-[(4-bromophenyl)methyl]-N,N,7-trimethyl-[1,2,4]triazolo[1,5-a]pyridin-5-amine (0.54 g).

Step 6: A degassed mixture of 6-[(4-bromophenyl)methyl]-N,N,7-trimethyl-[1,2,4]triazolo[1,5-a]pyridin-5-amine (0.74 g, 2.1 mmol), methyl 3-sulfanylpropanoate (0.70 mL, 6.4 mmol), $Pd_2(dba)_3$ (0.39 g, 0.43 mmol), Xantphos (0.12 g, 0.21 mmol), $iPr_2NEt$ (1.1 mL, 6.4 mmol), and dioxane (10 mL) was stirred at 120° C. for 12 h under an $N_2$ atmosphere. The reaction was poured into water (30 mL) and extracted with EtOAc (2×30 mL). The extracts were combined, washed with brine (10 mL), dried over $Na_2SO_4$, filtered, concentrated, and purified by silica chromatography (0-10% MeOH in $CH_2Cl_2$) to provide methyl 3-[4-[[5-(dimethylamino)-7-methyl-[1,2,4]triazolo[1,5-a]pyridin-6-yl]methyl]phenyl]sulfanylpropanoate (0.80 g).

Step 7: A mixture of methyl 3-[4-[[5-(dimethylamino)-7-methyl-[1,2,4]triazolo[1,5-a]pyridin-6-yl]methyl]phenyl]sulfanylpropanoate (0.70 g, 1.8 mmol), EtOH (10 mL), $PhI(OAc)_2$ (1.8 g, 5.5 mmol), and $NH_4OAc$ (0.56 g, 7.3 mmol) was stirred at 20° C. for 2 h. The mixture was concentrated and purified by silica chromatography (0-10% MeOH in $CH_2Cl_2$) to provide methyl 3-[[4-[[5-(dimethylamino)-7-methyl-[1,2,4]triazolo[1,5-a]pyridin-6-yl]methyl]phenyl]sulfonimidoyl]propanoate (0.48 g).

Step 8: A mixture of methyl 3-[[4-[[5-(dimethylamino)-7-methyl-[1,2,4]triazolo[1,5-a]pyridin-6-yl]methyl]phenyl]sulfonimidoyl]propanoate (0.4 g, 0.96 mmol), HOAc (0.5 mL), and 6 M HCl (3.5 mL) was stirred at 40° C. for 1 h, and was concentrated and purified by preparative HPLC (1-40% MeCN in $H_2O$ (0.2% formic acid)) to provide 3-[[4-[[5-(dimethylamino)-7-methyl-[1,2,4]triazolo[1,5-a]pyridin-6-yl]methyl]phenyl]sulfonimidoyl] propanoic acid (Compound 87) (0.10 g). ESI MS m/z=402.1 (M+H).

Synthetic Example S-030

Synthesis of (4-{[7-(dimethylamino)-5-methoxy-[1,2,4]triazolo[1,5-a]pyrimidin-6-yl]methyl}phenyl)(imino)methyl-$\lambda^6$-sulfanone (Compound 88)

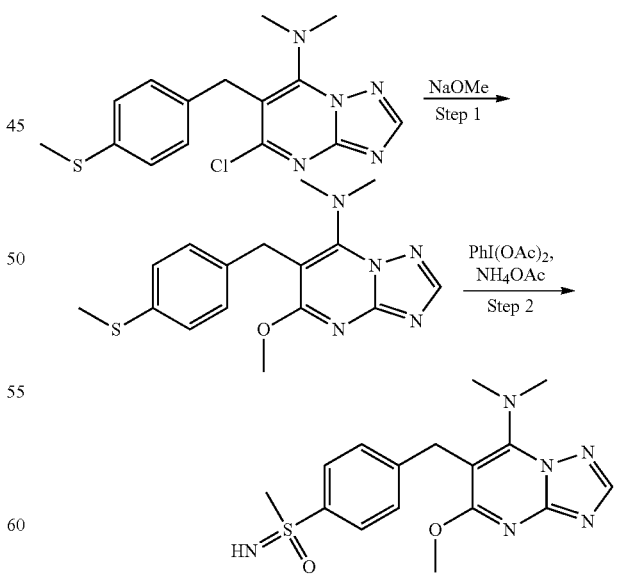

Step 1: A degassed mixture of 5-chloro-N,N-dimethyl-6-[(4-methylsulfanylphenyl)methyl]-[1,2,4]triazolo[1,5-a]pyrimidin-7-amine (0.45 g, 1.4 mmol), NaOMe (0.22 g, 4.0 mmol), and MeOH (15 mL) was stirred at 20° C. for 1 h under an N₂ atmosphere. The mixture was poured into saturated aqueous NH₄Cl (50 mL) and extracted with EtOAc (2×30 mL). The extracts were combined, washed with brine (10 mL), dried over Na₂SO₄, and concentrated to provide 5-methoxy-N,N-dimethyl-6-[(4-methylsulfanylphenyl)methyl]-[1,2,4]triazolo[1,5-a]pyrimidin-7-amine (0.45 g).

Step 2: A mixture of 5-methoxy-N,N-dimethyl-6-[(4-methylsulfanylphenyl)methyl]-[1,2,4]triazolo[1,5-a]pyrimidin-7-amine (0.45 g, 1.4 mmol), EtOH (10 mL), PhI(OAc)₂ (1.3 g, 4.1 mmol), and NH₄OAc (0.42 mg, 5.5 mmol) was stirred at 20° C. for 1 h, then was concentrated and purified by preparative HPLC (15-35% MeCN in water (0.2% formic acid)) to afford compound (4-{[7-(dimethylamino)-5-methoxy-[1,2,4]triazolo[1,5-a]pyrimidin-6-yl]methyl}phenyl)(imino)methyl-λ⁶-sulfanone (Compound 88) (38 mg). ESI MS m/z=361.1 (M+H).

Synthetic Example S-031

Synthesis of [4-({7-amino-5-methyl-[1,2,4]triazolo[1,5-a]pyridin-6-yl}methyl)phenyl](imino)methyl-λ⁶-sulfanone (Compound 89)

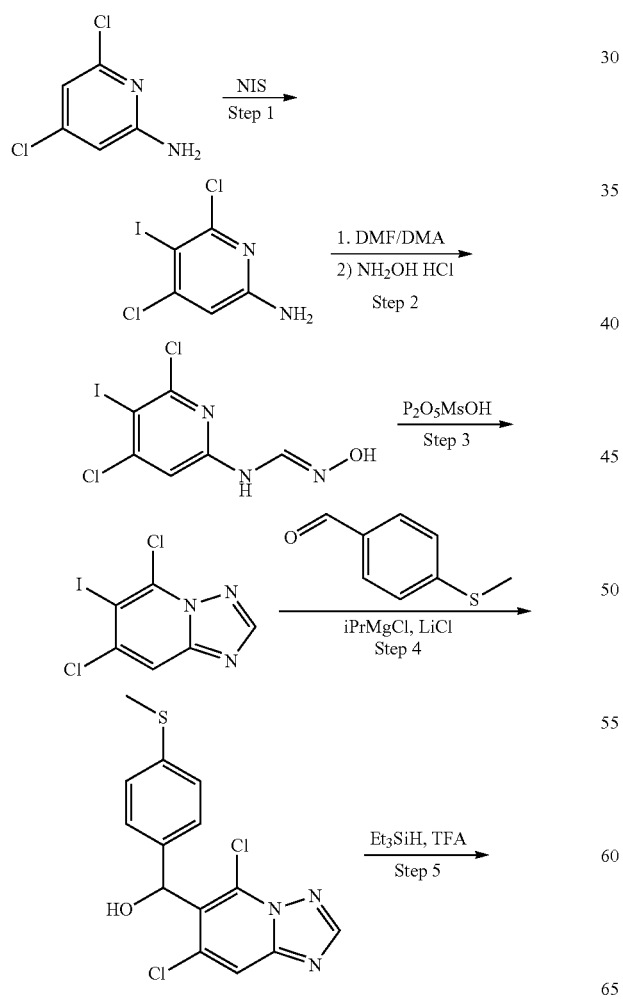
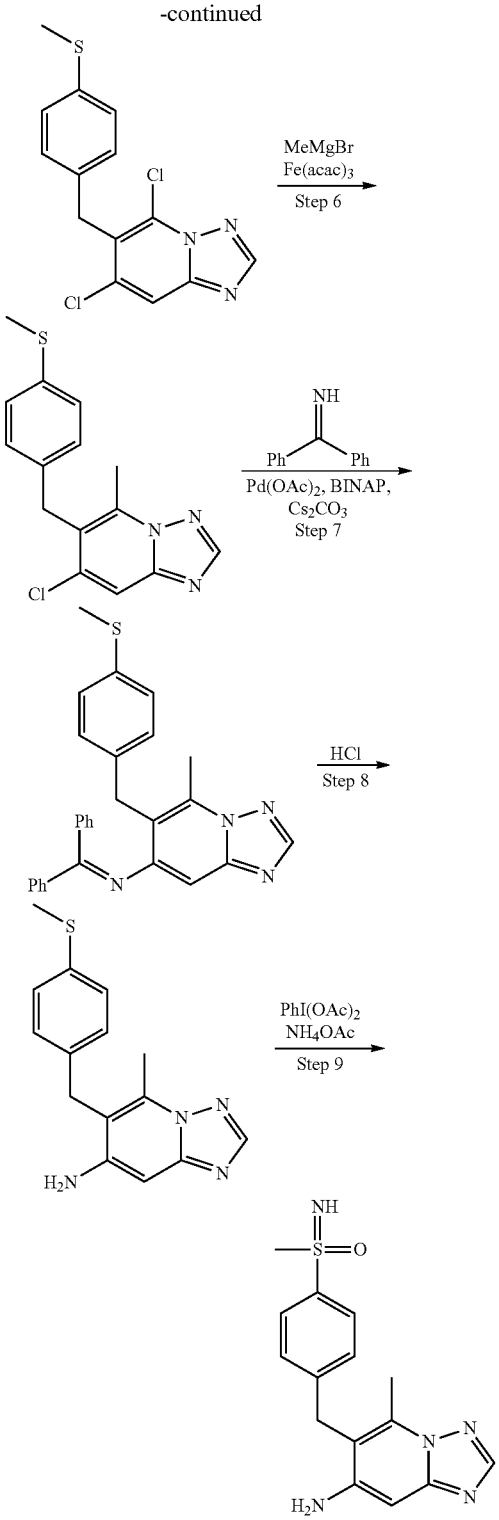

Step 1: A degassed mixture of 4,6-dichloropyridin-2-amine (5.0 g, 31 mmol), NIS (7.6 g, 34 mmol), and DMF (50 mL) was stirred at 50° C. for 2 h under an N₂ atmosphere. The mixture was concentrated and purified by silica chromatography (0-100% EtOAc in petroleum ether) to provide 4,6-dichloro-5-iodo-pyridin-2-amine (12 g).

Step 2: To a mixture of 4,6-dichloro-5-iodo-pyridin-2-amine (8.0 g, 28 mmol) and EtOH (100 mL) was added DMF-DMA (4.8 mL, 36 mmol). The mixture was stirred at 85° C. for 75 min, then was concentrated and dissolved in MeOH (70 mL). Hydroxylamine hydrochloride (2.9 g, 42 mmol) was added, and the mixture was stirred for 1 h, then was concentrated, and triturated with water for 20 min. N-(4,6-dichloro-5-iodo-2-pyridyl)-N'-hydroxy-formamidine was collected by filtration (6.8 g, 21 mmol).

Step 3: A mixture of N-(4,6-dichloro-5-iodo-2-pyridyl)-N'-hydroxy-formamidine (6.8 g, 21 mmol), dissolved into Eaton's Reagent ($P_2O_5$ MsOH, 30 mL) was stirred at 105° C. for 20 min. The mixture was cooled to room temperature, diluted with $H_2O$, and $K_2CO_3$ added to adjust the pH to 8. The solid was collected by filtration to provide 5,7-dichloro-6-iodo-[1,2,4]triazolo[1,5-a]pyridine (7 g).

Step 4: To a mixture of 5,7-dichloro-6-iodo-[1,2,4]triazolo[1,5-a]pyridine (4.0 g, 13 mmol, 1.0 eq) and THF (20 mL) was added iPrMgCl—LiCl (1.3 M, 12 mL). The mixture was stirred at 20° C. for 1 h, then was cooled to −10° C., and 4-(methylthio)benzaldehyde (2.1 g, 14 mmol) was added. The mixture was stirred at 0° C. for 20 min, combined with $NH_4Cl$ (40 mL), and extracted with EtOAc (30×4 mL). The extracts were dried over $Na_2SO_4$, filtered, concentrated, and purified by silica chromatography (0-20% (1:1 THF/EtOAc) in petroleum ether) to provide (5,7-dichloro-[1,2,4]triazolo[1,5-a]pyridin-6-yl)(4-(methylthio)phenyl)methanol (0.74 g).

Step 5: A mixture of (5,7-dichloro-[1,2,4]triazolo[1,5-a]pyridin-6-yl)(4-(methylthio)phenyl)methanol (0.74 g, 2.2 mmol), $Et_3SiH$ (2.5 mL, 16 mmol), and TFA (5 mL) was stirred at 20° C. for 12 h. The reaction was concentrated, combined with EtOAc (20 mL) and $H_2O$ (10 mL), $NaHCO_3$ was added to adjust the pH to 7, and the phases were separated. The organic phase washed with saturated $NaHCO_3$ (10 mL) and brine (10 mL×2), dried over $Na_2SO_4$, filtered, concentrated, and triturated with petroleum ether/MTBE at 20° C. for 30 min to provide 5,7-dichloro-6-[(4-methylsulfanylphenyl)methyl]-[1,2,4]triazolo[1,5-a]pyridine (0.55 g).

Step 6: To a mixture of 5,7-dichloro-6-(4-(methylthio)benzyl)-[1,2,4]triazolo[1,5-a]pyridine (0.50 g, 1.5 mmol), THF (25 mL), and NMP (2.5 mL) was added dropwise tris[(Z)-1-methyl-3-oxo-but-1-enoxy]iron (55 mg, 0.16 mmol) and bromo(methyl)magnesium (3 M, 0.66 mL) under nitrogen gas at 0° C. The mixture was stirred at 20° C. for 12 h and saturated aqueous $NH_4Cl$ (20 mL) was added at 0° C. The mixture was extracted with EtOAc (20 mL×3). The extracts were combined, washed brine (20 mL×3), dried over $Na_2SO_4$, filtered, concentrated, and purified by silica chromatography (0-15% (1:1 THF/EtOAc) in petroleum ether) to provide 7-chloro-5-methyl-6-(4-(methylthio)benzyl)-[1,2,4]triazolo[1,5-a]pyridine (0.35 g).

Step 7: To a degassed mixture of 7-chloro-5-methyl-6-(4-(methylthio)benzyl)-[1,2,4]triazolo[1,5-a]pyridine (0.10 g, 0.33 mmol), diphenylmethanimine (0.10 g, 0.55 mmol), $Cs_2CO_3$ (0.50 g, 1.5 mmol), and toluene (10 mL) was added BINAP (55 mg, 88 µmol) and $Pd(OAc)_2$ (36 mg, 0.16 mmol). The mixture was stirred under $N_2$ at 140° C. for 12 h, then was filtered through celite, and the filter cake was washed with THF (10 mL×2). The filtrate was concentrated and purified by silica chromatography (0-25% (1:1 THF/EtOAc) in petroleum ether) to provide N-(diphenylmethylene)-5-methyl-6-(4-(methylthio)benzyl)-[1,2,4]triazolo[1,5-a]pyridin-7-amine (79 mg).

Step 8: HCl/MeOH (4 M, 0.5 mL) was added slowly to a mixture of N-(diphenylmethylene)-5-methyl-6-(4-(methylthio)benzyl)-[1,2,4]triazolo[1,5-a]pyridin-7-amine (79 mg, 0.18 mmol) in $CH_2Cl_2$ (2 mL) stirring at 0° C. The mixture was stirred at 20° C. for 1 h, concentrated, combined with EtOAc (10 mL), and the pH was adjusted to 7 with saturated $NaHCO_3$. The mixture was extracted with THF/EtOAc (1/1, 20 mL). The extract was washed with brine (8 mL×2), dried over $Na_2SO_4$, filtered, concentrated, and purified by silica chromatography (0-80% (1:1 THF/EtOAc) in petroleum ether) to provide 5-methyl-6-(4-(methylthio)benzyl)-[1,2,4]triazolo[1,5-a]pyridin-7-amine (30 mg).

Step 9: A mixture of 5-methyl-6-(4-(methylthio)benzyl)-[1,2,4]triazolo[1,5-a]pyridin-7-amine (20 mg, 70 µmol), EtOH (2 mL), $PhI(OAc)_2$ (70 mg, 0.22 mmol), $NH_4OAc$ (24 mg, 0.31 mmol). The mixture was stirred at 20° C. for 2 h, concentrated, and purified by preparative HPLC (1-35% MeCN in $H_2O$ (10 mM $NH_4HCO_3$)) to provide [4-({7-amino-5-methyl-[1,2,4]triazolo[1,5-a]pyridin-6-yl}methyl)phenyl](imino)methyl-$\lambda^6$-sulfanone (Compound 89) (2.1 mg). ESI MS m/z=316.1 (M+H).

Table 5 describes chiral separation conditions for specific examples where supercritical $CO_2$ is the non-polar co-solvent. Table 6 shows NMR data for compounds of Table 1.

TABLE 5

| | SFC Separation Conditions | | | | |
|---|---|---|---|---|---|
| Example | Conditions | First | ee % | Second | ee % |
| 1 | Phenomenex Cellulose-2 (100 × 4.6 mm 5 µm) 2.5 mL/min, 35° C.; BPR: 170 bar $CO_2$ 50% [10 mM $NH_3$ in MeOH] | 1a | >99 | 1b | >99 |
| 8 | Phenomenex Cellulose-2 (100 × 4.6 mm 5 µm) 2.5 mL/min, 35° C.; BPR: 170 bar $CO_2$ 5-50% [20 mM $NH_3$ in MeOH] | 8a | >99 | 8b | >99 |
| 16 | Phenomenex Cellulose-2 (100 × 4.6 mm, 5 µm) 2.5 mL/min, 35° C.; BPR: 170 bar $CO_2$ 5-50% [20 mM $NH_3$ in MeOH] | 16a | >99 | 16b | >99 |
| 28 | Chiralpak IC (100 × 4.6 mm, 5 µm) 2.5 mL/min, 35° C.; BPR: 170 bar $CO_2$ 5-50% [20 mM $NH_3$ in MeOH] | 28a | >99 | 28b | >99 |

TABLE 5-continued

| | SFC Separation Conditions | | | | |
|---|---|---|---|---|---|
| Example | Conditions | First | ee % | Second | ee % |
| 29 | Phenomenex Cellulose-2 (100 × 4.6 mm, 5 μm) 2.5 mL/min, 35° C.; BPR: 170 bar $CO_2$ 50% [20 mM $NH_3$ in MeOH] | 29a | >99 | 29b | >99 |
| 49 | Phenomenex Amylose-1 (100 × 4.6 mm, 5 μm) 2.5 mL/min, 35° C.; BPR: 170 bar $CO_2$ 5-50% [20 mM $NH_3$ in MeOH] | 49a | >99 | 49b | 94 |
| 72 | Daicel Chiralpak AS (250 × 30 mm, 10 μM) 40% [0.1% $NH_3/H_2O$ in EtOH] | 72a | >99 | 72b | 97.1 |
| 74 | Phenomenex Cellulose-2 (100 × 4.6 mm, 5 μm) 2.5 mL/min, 35° C.; BPR: 170 bar $CO_2$ 5-50% [20 mM $NH_3$ in MeOH] | 74a | >99 | 74b | >99 |
| 80 | Phenomenex Cellulose-2 (100 × 4.6 mm, 5 μm) 2.5 mL/min, 35° C.; BPR: 170 bar $CO_2$ 5-50% [20 mM $NH_3$ in MeOH] | 80a | >99 | 80b | >99 |
| 85 | Daicel Chiralpak AS (250 × 30 mm, 10 μM) 35% [0.1% $NH_3/H_2O$ in EtOH] | 85a | >99 | 85a | >99 |
| 88 | Daicel Chiralpak AS (250 × 30 mm, 10 μM) 50% [0.1% $NH_3/H_2O$ in iPrOH] | 88a | >99 | 88b | >99 |

TABLE 6

| | NMR data | |
|---|---|---|
| Compound | Solvent | $^1$H NMR (400 MHz) δ |
| 1 | MeOD | 8.37 (s, 1H), 7.95-7.97 (m, 2H), 7.42-7.74 (m, 2H), 4.36 (s, 2H), 3.12-3.31 (m, 9H), 2.45 (s, 3H) |
| 2 | DMSO-d$^6$ | 8.47 (s, 1 H), 7.76 (d, J = 8.38 Hz, 2 H), 7.38 (d, J = 8.25 Hz, 2 H), 7.32 (s, 2 H), 4.27 (s, 2 H), 3.05 (s, 6 H), 2.37 (m, 3 H) |
| 3 | DMSO-d$^6$ | 9.35 (s, 1H), 8.53 (s, 1H), 7.25-7.15(m, 1H), 7.12-6.96 (m, 3H), 6.87 (s, 1H), 6.78 (br d, J = 7.38 Hz, 1H), 4.13 (s, 2H), 3.07 (s, 6H), 2.39 (s, 3H) |
| 4 | DMSO-d$^6$ | 8.47 (s, 1 H), 7.71-7.82 (m, 2 H), 7.53 (t, J = 7.60 Hz, 1 H), 7.45 (br d, J = 7.60 Hz, 1 H), 4.28 (s, 2 H), 4.19 (s, 1 H), 3.04 (s, 9 H), 2.40 (s, 3 H). |
| 5 | DMSO-d$^6$ | 8.73 (s, 1H), 7.61 (dd, J = 12.76, 8.00 Hz, 2H), 7.27 (dd, J = 7.94, 2.94 Hz, 2H), 4.24 (s, 2H), 3.10 (s, 6H), 2.39 (s, 3H) |
| 8 | CDCl$_3$ | 8.30 (s, 1H), 7.99-7.93 (m, 2H), 7.33-7.28 (m, 2H), 4.27 (s, 2H), 3.78-3.70 (m, 4H), 3.12 (s, 3H), 2.69 (s, 1H), 2.49 (s, 3H), 1.98-1.89 (m, 4H) |
| 9 | DMSO-d$^6$ | 8.39 (s, 1 H) 7.74 (d, J = 8.33 Hz, 2 H) 7.28-7.38 (m, 4 H) 4.27 (s, 2 H) 3.67-3.75 (m, 4 H) 2.36 (s, 2 H) 2.33-2.39 (m, 1 H) 2.07 (s, 1 H) 1.75-1.87 (m, 4 H) |
| 10 | CDCl$_3$ | 8.16 (s, 1H), 8.01-7.95 (m, 2H), 7.31-7.27 (m, 2H), 4.81 (t, J = 7.9 Hz, 4H), 4.15 (s, 2H), 3.13 (s, 3H), 2.70 (s, 1H), 2.41-2.29 (m, 5H) |
| 12 | CDCl$_3$ | 8.37 (s, 1H), 7.98-7.92 (m, 2H), 7.30-7.26 (m, 2H), 4.27 (s, 2H), 3.44 (q, J = 7.2 Hz, 2H), 3.11 (d, J = 1.1 Hz, 3H), 3.02 (s, 3H), 2.68 (s, 1H), 2.49 (s, 3H), 1.09 (t, J = 7.1 Hz, 3H) |
| 15 | DMSO-d$^6$ | 8.42 (s, 1H), 6.67 (s, 2H), 3.42 (d, J = 11.7 Hz, 2H), 3.07 (s, 6H), 2.69 (d, J = 7.0 Hz, 2H), 2.59 (s, 3H), 2.41 (t, J = 11.5 Hz, 2H), 1.63 (d, J = 12.6 Hz, 2H), 1.45 (s, 1H), 1.29 (tt, J = 12.8, 6.5 Hz, 2H) |
| 16 | CDCl$_3$ | 8.35 (s, 1H), 7.98-7.92 (m, 2H), 7.31-7.28 (m, 2H), 4.25 (s, 2H), 3.43-3.35 (m, 4H), 3.12 (s, 3H), 2.69 (s, 1H), 2.48 (s, 3H), 1.68 (s, 6H) |
| 18 | DMSO-d$^6$ | 8.62 (s, 1H), 8.43 (d, J = 2.7 Hz, 1H), 7.95 (d, J = 1.5 Hz, 1H), 7.83-7.77 (m, 2H), 7.45-7.39 (m, 2H), 6.69(t, J = 2.3 Hz, 1H), 4.20 (s, 2H), 4.16 (s, 1H), 3.03 (s, 3H), 2.49 (s, 3H) |
| 26 | DMSO-d$^6$ | 8.57 (s, 1H), 7.86-7.79 (m, 2H), 7.40-7.34 (m, 2H), 4.32 (s, 2H), 4.16 (s, 1H), 3.03 (s, 3H), 2.80 (s, 3H), 2.47 (s, 3H) |

TABLE 6-continued

NMR data

| Compound | Solvent | $^1$H NMR (400 MHz) δ |
|---|---|---|
| 28 | DMSO-d$^6$ | 8.43 (s, 1H), 7.86-7.78 (sym. m, 2H), 7.59 (d, J = 1.3 Hz, 1H), 7.34-7.26 (sym. m, 2H), 4.32 (s, 2H), 4.13 (s, 1H), 3.03 (s, 3H), 2.90 (s, 6H), 2.22 (d, J = 1.0 Hz, 3H) |
| 29 | DMSO-d$^6$ | 7.88-7.81 (m, 2H), 7.71 (d, J = 1.5 Hz, 1H), 7.60 (d, J = 1.5 Hz, 1H), 7.39-7.32 (m, 2H), 4.23 (s, 2H), 4.15 (s, 1H), 3.04 (d, J = 1.0 Hz, 3H), 2.89 (s, 6H), 2.32 (s, 3H) |
| 36 | DMSO-d$^6$ | 8.68 (s, 1 H) 7.62 (dd, J = 12.72, 8.11 Hz, 2 H) 7.29 (dd, J = 8.00, 3.18 Hz, 2 H) 4.28 (s, 2 H) 3.86-3.93 (m, 4 H) 2.40 (s, 3 H) 1.76-1.85 (m, 4 H) |
| 38 | DMSO-d$^6$ | 8.50 (s, 1H), 7.87-7.80 (m, 2H), 7.39-7.31 (m, 2H), 4.30 (s, 2H), 4.17 (s, 1H), 3.40 (q, J = 7.1 Hz, 4H), 3.04 (s, 3H), 2.36 (s, 3H), 0.91 (t, J = 7.1 Hz, 6H) |
| 39 | DMSO-d$^6$ | 8.47 (s, 1H), 7.87-7.79 (m, 2H), 7.38-7.30 (m, 2H), 4.27 (s, 2H), 4.15 (s, 1H), 3.12 (tt, J = 6.6, 3.5 Hz, 1H), 3.05-3.01 (m, 3H), 2.98 (s, 3H), 2.43 (s, 3H), 0.54-0.44 (m, 2H), 0.31-0.23 (m, 2H) |
| 40 | DMSO-d$^6$ | 8.46 (s, 1H), 7.87-7.81 (m, 2H), 7.41-7.35 (m, 2H), 4.23 (s, 2H), 4.20-4.09 (m, 2H), 3.03 (s, 3H), 2.92 (s, 3H), 2.40 (s, 3H), 1.99-1.85 (m, 4H), 1.60-1.34 (m, 2H) |
| 41 | DMSO-d$^6$ | 8.36 (s, 1H), 7.92-7.84 (m, 2H), 7.46-7.39 (m, 2H), 5.09 (t, J = 12.6 Hz, 4H), 4.21-4.12 (m,3H), 3.06 (s, 2H), 2.30 (s, 3H) |
| 42 | DMSO-d$^6$ | 8.25 (s, 1H), 7.91-7.84 (m, 2H), 7.43-7.36 (m, 2H), 4.46-4.38 (m, 4H), 4.18 (s, 1H), 4.14 (s, 2H), 3.07-3.01 (m, 3H), 2.24 (s, 3H), 1.17 (s, 6H) |
| 43 | DMSO-d$^6$ | 8.52 (s, 1H), 7.87-7.81 (m, 2H), 7.44-7.37 (m, 2H), 4.28 (s, 2H), 4.17 (s, 1H), 3.49-3.41 (m, 4H), 3.04 (s, 3H), 2.39 (s, 3H), 2.17-2.02 (m, 4H) |
| 44 | DMSO-d$^6$ | 8.40 (s, 1H), 7.92-7.85 (m, 2H), 7.47-7.39 (m, 2H), 4.88-4.80 (m, 2H), 4.20 (s, 1H), 4.16 (s, 2H), 3.07 (s, 3H), 2.24 (s, 3H), 1.88-1.77 (m, 4H), 1.57-1.46 (m, 4H) |
| 45 | DMSO-d$^6$ | 8.36 (s, 1H), 7.89-7.83 (m, 2H), 7.45-7.38 (m, 2H), 4.92 (d, J = 6.8 Hz, 1H), 4.25 (s, 2H), 4.17 (s, 1H), 3.74 (s, 2H), 3.05 (s, 3H), 2.88 (dt, J = 6.6, 3.2 Hz, 1H), 2.32 (s, 3H), 2.02-1.93 (m, 2H), 1.44 (dd, J = 4.6, 1.9 Hz, 2H) |
| 46 | DMSO-d$^6$ | 8.53 (s, 1H), 7.86-7.80 (m, 2H), 7.44-7.37 (m, 2H), 4.34 (s, 2H), 4.16 (s, 1H), 3.68-3.59 (m, 4H), 3.03 (s, 3H), 2.44-2.35 (m, 5H), 2.12 (qd, J = 6.1, 2.4 Hz, 2H), 1.71-1.60 (m, 2H) |
| 47 | DMSO-d$^6$ | 8.45 (s, 1H), 7.87-7.80 (m, 2H), 7.41-7.34 (m, 2H), 4.22 (s, 2H), 4.17 (s, 1H), 3.91 (dd, J = 9.8, 2.5 Hz, 2H), 3.55 (dd, J = 9.5, 1.8 Hz, 2H), 3.05 (s, 3H), 2.36 (s, 3H), 1.52 (ddd, J = 6.6, 4.9, 2.0 Hz, 2H), 0.57-0.47 (m, 2H) |
| 48 | DMSO-d$^6$ | 8.40 (s, 1H), 7.90-7.82 (m, 2H), 7.47-7.39 (m, 2H), 4.55-4.45 (m, 2H), 4.19 (s, 3H), 3.06 (s, 3H), 2.27 (s, 3H), 2.10-2.00 (m, 2H), 2.00-1.86 (m, 2H), 1.83-1.67 (m, 3H), 1.59-1.39 (m, 3H) |
| 51 | MeOH-d$^4$ | 8.57 (s, 1H), 7.94 (d, J = 8.38 Hz, 2H), 7.39 (d, J = 8.50 Hz, 2H), 4.47 (s, 2H), 4.11 (dd, J = 8.00, 7.13Hz, 1H), 3.13 (s, 3H), 3.07 (s, 6H), 1.33 (td, J = 7.07, 0.88 Hz, 1H) |
| 52 | MeOH-d$^4$ | 8.60 (s, 1H), 7.95 (d, J = 8.38 Hz, 2H), 7.40 (d, J = 8.38 Hz, 2H), 4.47 (s, 2H), 3.38 (br d, J = 5.25 Hz, 4H), 3.15 (s, 3H), 1.66 (br s, 6H) |
| 53 | DMSO-d$^6$ | 8.42 (s, 1 H), 7.86 (d, J = 8.4 Hz, 2 H), 7.45 (d, J = 8.4 Hz, 2 H), 4.42 (s, 2 H), 4.16 (s, 1 H), 3.04 (s, 9 H), 1.95-2.03 (m, 1 H), 1.04-1.10 (m, 2 H), 0.90 (dd, J = 7.6, 3.2 Hz, 2 H). |
| 54 | DMSO-d$^6$ | 8.41 (s, 1 H) 8.33 (s, 1 H) 7.84 (m, J = 8.38 Hz, 2 H) 7.34 (m, J = 8.25 Hz, 2 H) 4.34 (s, 2 H) 4.16 (s, 1 H)3.85 (br t, J = 6.50 Hz, 4 H) 3.03 (s, 3 H) 1.75 (br t, J = 6.44 Hz, 4 H) |
| 55 | DMSO-d$^6$ | 2.35 (s, 3 H) 3.02 (s, 6 H) 4.20-4.26 (m, 3 H) 4.43 (s, 2 H) 7.00 (d, J = 7.25 Hz, 2 H) 7.13-7.30 (m, 5 H) 7.54 (d, J = 8.38 Hz, 2 H) 8.45 (s, 1 H) |
| 57 | DMSO-d$^6$ | 8.46 (s, 1H), 7.83-7.75 (m, 2H), 7.40 (d, J = 8.1 Hz, 2H), 4.27 (s, 2H), 4.14 (s, 1H), 3.09 (q, J = 7.3 Hz, 2H), 3.03 (s, 6H), 2.36 (s, 3H), 1.03 (t, J = 7.3 Hz, 3H) |
| 59 | DMSO-d$^6$ | 8.46 (s, 1H), 7.81 (d, J = 8.3 Hz, 2H), 7.39 (d, J = 8.2 Hz, 2H), 4.82 (br, 1H), 4.27 (s, 3H), 3.65-3.56 (m, 2H), 3.26 (td, J = 6.7, 2.9 Hz, 2H), 3.03 (s, 6H), 2.36 (s, 3H) |
| 60 | DMSO-d$^6$ | 8.46 (s, 1H), 7.84-7.77 (m, 2H), 7.41-7.34 (m, 2H), 4.27 (s, 2H), 4.24 (s, 1H), 3.62-3.48 (m, 2H), 3.38 (t, J = 6.2 Hz, 2H), 3.03 (s, 3H), 3.03 (s, 6H), 2.36 (s, 3H) |
| 61 | DMSO-d$^6$ | 8.45 (s, 1H), 7.61-7.54 (m, 2H), 7.36-7.28 (m, 2H), 6.23 (s, 2H), 4.24 (s, 1H), 3.04 (s, 6H), 2.36 (s, 3H) |
| 62 | DMSO-d$^6$ | 8.46 (s, 1H), 7.84-7.78 (m, 2H), 7.44-7.37 (m, 2H), 4.72-4.55 (m, 6H), 4.27 (s, 2H), 3.01 (s, 6H), 2.35 (s, 3H). |
| 63 | DMSO-d$^6$ | 8.46 (s, 1H), 7.83-7.76 (m, 2H), 7.42-7.35 (m, 2H), 4.27 (s, 2H), 4.16 (s, 1H), 3.03 (s, 6H), 2.64 (tq, J = 8.0, 4.7, 4.1 Hz, 1H), 2.36 (s, 3H), 1.15-1.01 (m, 1H), 0.99-0.80 (m, 3H) |

TABLE 6-continued

| Compound | Solvent | ¹H NMR (400 MHz) δ |
|---|---|---|
| 64 | DMSO-d⁶ | 8.46 (s, 1H), 7.84 (s, 1H), 7.80 (d, J = 8.4 Hz, 2H), 7.40 (d, J = 8.1 Hz, 2H), 4.35 (s, 1H), 4.27 (s, 2H), 3.27-3.20 (m, 4H), 3.03 (s, 6H), 2.36 (s, 3H), 1.63 (s, 3H) |
| 65 | DMSO-d⁶ | 8.46 (s, 1H), 7.69 (br d, J = 7.2 Hz, 1H), 7.57 (s, 1H), 7.54-7.49 (m, 1H), 7.48-7.43 (m, 1H), 7.33 (br s, 2H), 4.26 (s, 2H), 3.03 (s, 6H), 2.39 (s, 3H) |
| 66 | DMSO-d⁶ | 9.82 (d, J = 2.5 Hz, 1H), 9.31 (d, J = 2.5 Hz, 1H), 8.73 (s, 1H), 7.95-7.88 (m, 2H), 7.67-7.55 (m, 2H), 4.49 (d, J = 13.2 Hz, 1H), 4.43 (d, J = 13.2 Hz, 1H), 3.70 (s, 1H), 2.81 (s, 3H) |
| 67 | DMSO-d⁶ | 8.36 (s, 1H), 7.58-7.47 (m, 2H), 7.44-7.30 (m, 2H), 4.51-4.37 (m, 2H), 3.67 (s, 1H), 3.41 (q, J = 3.2, 2.8 Hz, 4H), 2.77 (s, 3H), 2.12 (s, 3H), 1.73-1.61 (m, 4H) |
| 68 | DMSO-d⁶ | 8.45 (s, 1H), 7.44 (d, J = 8.1 Hz, 2H), 7.34 (d, J = 8.1 Hz, 2H), 3.72 (s, 1H), 3.41 (dd, J = 9.2, 7.2 Hz, 2H), 3.10 (td, J = 7.8, 4.6 Hz, 2H), 2.91 (s, 3H), 2.75 (s, 6H), 2.24 (s, 3H) |
| 69 | DMSO-d⁶ | 8.45 (s, 1H), 7.30 (d, J = 8.3 Hz, 1H), 7.23-7.17 (m, 2H), 6.95 (s, 2H), 4.32-4.16 (m, 2H), 3.31-3.25 (m, 2H), 2.99 (t, J = 6.1 Hz, 2H), 2.76 (s, 6H), 2.26 (s, 3H) |
| 70 | DMSO-d⁶ | 9.24 (s, 1H), 8.57 (s, 1H), 7.90-7.82 (m, 2H), 7.52-7.45 (m, 2H), 4.23 (s, 2H), 4.18 (s, 1H), 3.04 (d, J = 1.1 Hz, 3H), 2.46 (s, 3H) |
| 71 | DMSO-d⁶ | 8.52 (s, 1H), 7.89-7.80 (m, 2H), 7.43-7.34 (m, 2H), 4.46 (s, 2H), 4.17 (s, 1H), 3.04 (s, 3H), 2.44 (s, 3H), 2.35 (tt, J = 8.7, 5.6 Hz, 1H), 1.69-1.61 (m, 2H), 1.17-1.08 (m, 2H) |
| 72 | DMSO-d⁶ | 12.46 (br, 1H), 8.47 (s, 1H), 7.81 (d, J = 8.3 Hz, 2H), 7.42 (d, J = 8.2 Hz, 2H), 4.28 (s, 2H), 3.66-3.41 (m, 4H), 3.03 (s, 6H), 2.48 (s, 1H), 2.36 (s, 3H) |
| 73 | DMSO-d⁶ | 8.46 (s, 1H), 7.82-7.75 (m, 2H), 7.43-7.36 (m, 2H), 4.35-4.15 (m, 3H), 3.15 (td, J = 6.8, 3.2 Hz, 2H), 3.03 (s, 6H), 2.71 (tt, J = 9.9, 4.8 Hz, 1H), 2.36 (s, 3H), 1.66 (br, 1H) |
| 74 | DMSO-d⁶ | 8.55 (s, 1H), 7.85 (d, J = 8.2 Hz, 2H), 7.46 (d, J = 8.1 Hz, 2H), 4.32 (s, 2H), 4.18 (s, 1H), 3.11 (s, 6H), 3.05 (s, 3H) |
| 75 | DMSO-d⁶ | 8.42 (s, 1H), 7.86-7.78 (m, 2H), 7.59 (d, J = 1.2 Hz, 1H), 7.31 (d, J = 8.3 Hz, 2H), 4.31 (s, 2H), 4.14 (s, 1H), 3.32-3.24 (m, 4H), 3.02 (s, 3H), 2.23 (d, J = 1.0 Hz, 3H), 2.01-1.93 (m, 4H) |
| 76 | DMSO-d⁶ | 8.40 (s, 1H), 7.86-7.79 (m, 2H), 7.57 (d, J = 1.1 Hz, 1H), 7.31 (d, J = 8.3 Hz, 2H), 4.33 (s, 2H), 4.14 (s, 1H), 3.76-3.53 (m, 2H), 3.02 (s, 3H), 2.92-2.74 (m, 2H), 2.24 (d, J = 1.0 Hz, 3H), 1.82-1.67 (m, 1H), 1.67-1.53 (m, 2H), 1.53-1.24 (m, 3H) |
| 77 | DMSO-d⁶ | 7.87-7.80 (sym. m, 2H), 7.65 (d, J = 1.6 Hz, 1H), 7.60 (d, J = 1.5 Hz, 1H), 7.39-7.32 (sym. m, 2H), 4.21 (s, 2H), 4.16 (s, 1H), 3.31-3.22 (sym. m, 4H), 3.04 (d, J = 1.1 Hz, 3H), 2.33 (s, 3H), 1.95-1.88 (sym. m, 4H) |
| 78 | DMSO-d⁶ | 8.47 (s, 1H), 7.85 (d, J = 8.3 Hz, 2H), 7.45 (d, J = 8.3 Hz, 2H), 4.39 (s, 2H), 4.18 (s, 1H), 3.89-3.81 (m, 4H), 3.05 (s, 3H), 1.82-1.74 (m, 4H). |
| 79 | DMSO-d⁶ | 8.71 (s, 1H), 7.87 (d, J = 8.3 Hz, 2H), 7.49 (d, J = 8.1 Hz, 2H), 4.46 (s, 2H), 4.21 (s, 1H), 3.14 (s, 6H), 3.06 (s, 3H) |
| 80 | DMSO-d⁶ | 7.94 (d, J = 1.3 Hz, 1H), 7.86-7.79 (m, 2H), 7.66 (d, J = 1.3 Hz, 1H), 7.35 (apparent d, J = 8.3 Hz, 2H), 4.25 (s, 2H), 4.15 (s, 1H), 3.04 (d, J = 1.0 Hz, 3H), 2.86 (s, 6H), 2.34 (s, 3H) |
| 83 | DMSO-d⁶ | 7.87-7.80 (m, 2H), 7.68 (d, J = 1.6 Hz, 1H), 7.60 (d, J = 1.5 Hz, 1H), 7.35 (apparent d, J = 8.2 Hz, 2H), 4.25 (s, 2H), 4.17 (s, 1H), 3.33-3.22 (m, 2H), 3.04 (d, J = 1.1 Hz, 3H), 3.02-2.89 (m, 2H), 2.30 (s, 3H), 1.74-1.43 (m, 6H) |
| 81 | DMSO-d⁶ | 8.38 (s, 1 H) 7.97 (s, 2 H) 7.71 (d, J = 7.89 Hz, 2 H) 7.10 (d, J = 7.89 Hz, 2 H) 4.19 (s, 2 H) 3.67-3.75 (m, 4 H) 2.37 (s, 3 H) 1.74- 1.84 (m, 4 H) |
| 82 | DMSO-d⁶ | 8.38 (s, 1 H) 7.68 (d, J = 8.33 Hz, 2 H) 7.23 (d, J = 8.11 Hz, 2 H) 4.23 (s, 2 H) 3.66-3.77 (m, 4 H) 2.37 (s, 3 H) 1.79 (dt, J = 6.41, 3.48 Hz, 4 H) |
| 84 | DMSO-d⁶ | 8.45 (s, 1H), 7.31 (d, J = 7.9 Hz, 1H), 7.24-7.15 (m, 2H), 6.95 (s, 2H), 4.36-4.19 (m, 2H), 3.29-3.22 (m, 2H), 2.97 (t, J = 5.6 Hz, 2H), 2.76 (s, 6H), 2.26 (s, 3H) |
| 85 | DMSO-d⁶ | 8.58 (s, 1H), 7.83 (d, J = 8.4 Hz, 2H), 7.37 (d, J = 8.4 Hz, 2H), 4.32 (s, 2H), 4.15 (s, 1H), 3.04 (s, 3H), 2.97 (s, 6H), 2.40 (s, 3H) |
| 86 | DMSO-d⁶ | 8.28-8.35 (m, 1 H) 7.85-7.94 (m, 2 H) 7.41-7.52 (m, 2 H) 4.24-4.29 (m, 2 H) 4.19 (s, 1 H) 3.05-3.10 (m, 3 H) 2.88-2.94 (m, 6 H) 2.46-2.48 (s, 3 H) |
| 87 | DMSO-d⁶ | 8.43 (s, 1 H) 7.79 (d, J = 8.25 Hz, 2 H) 7.60 (s, 1 H) 7.32 (d, J = 8.25 Hz, 2 H) 4.32 (s, 2 H) 2.89 (s, 6 H) 2.43-2.49 (m, 4 H) 2.24 (s, 3 H) |
| 88 | DMSO-d⁶ | 8.31-8.38 (m, 1 H) 7.79-7.88 (m, 2 H) 7.34-7.46 (m, 2 H) 4.13 (br s, 1 H) 4.12 (s, 2 H) 3.89-3.94 (m, 3 H) 3.04 (s, 3 H) 3.02 (s, 6 H) |

TABLE 6-continued

NMR data

| Compound | Solvent | $^1$H NMR (400 MHz) δ |
|---|---|---|
| 89 | DMSO-d$^6$ | 8.17 (s, 1H), 7.91 (d, J = 8.4 Hz, 2H), 7.44 (d, J = 8.4 Hz, 2H), 6.32 (s, 1H), 4.35 (s, 2H), 3.98 (s, 2H), 3.08 (s, 3 H) 2.71 (s, 3H), 2.63 (br s, 1H) |

Biological Example B-1

Inhibition of ENPP1 Hydrolysis of 2',3'-cGAMP (Assay 1)

Test compounds were plated in a 3× dilution scheme in a 384 well plate. To 50 nL of test compound in DMSO was added 2.5 μL ENPP-1 ECD in Assay Buffer (Tris-HCl pH 8.0 (50 mM), NaCl (150 mM), and 0.01% Triton X-100 in water (2.5 nM final concentration). Enzyme was omitted in control wells reserved to define maximum inhibition (max). Control wells were reserved to define no inhibition (min), and DMSO was used in place of compound solution. The plate was centrifuged for 30 s, and the mixture was incubated for 30 min. 2.5 μL of 2,3-cGAMP in Assay Buffer (final conc: 24 μM; $K_M$=24 μM) was added and the plate was centrifuged and incubated for 30 min. AMP-Glo™ Reagent I (Promega Corp.; 5 μL) was added, the plate was centrifuged for 1 min and incubated for 60 min. AMP Detection solution (100 μL) was added to each well, the plate centrifuged and incubated for 60 min. Luminescence was measured with an Envision plate reader, and % Inhibition was calculated for each well as: (([max−min]−[test−min])/[max−min]. IC$_{50}$ values were calculated from concentration vs. % Inhibition data via a four-parameter variable slope model and converted to $K_I$ values via the Cheng/Prusoff Equation ($K_I$=(IC$_{50}$−[ENPP1]/2)/(1+[substrate]/$K_M$). The known ENPP1 inhibitor 6-[(3-aminophenyl)methyl]-N,N,5-trimethyl-[1,2,4]triazolo[1,5-a]pyrimidin-7-amine has a $K_I$ of 110 nM in this assay. The following are the $K_{IS}$ for select compounds of this invention:

Biological Example B-2

Inhibition of ENPP1 hydrolysis of AMP p-nitrophenyl ester on MDA-MB-231 cells (Assay 2)

ENPP1 is normally expressed on the human metastatic breast cancer cell line MDA-MB-231. Hydrolysis of the p-nitrophenyl ester of AMP (pNP-AMP), an isostere of ATP, is selectively catalyzed by ENPP1 in the supernatant of MDA-MB-231 cell cultures. Inhibition of the hydrolysis of pNP-AMP by MDA-MB-231 at pH 7.4 and 37° C. is a good model of physiologically relevant activity of membrane-bound ENPP1 at disease-relevant expression levels.

MDA-MB-231 cells were harvested using TypLE Express Enzyme digestion and suspended in 100 μL of Leibovitz's L-15 Medium, 20% FBS, seeding the cells in a 96-well assay plate with 4.5×10$^4$ cells/well. Cells were incubated at 37 C with 1% CO$_2$ for 24 h. In a separate dilution plate, 2× of top dose of compound was prepared in phenol-red free 1640 medium without FBS and then 1:3 serial diluted in the same medium. The cell culture medium of L15 medium was aspirated carefully and cells were washed with PBS once, and 50 μL per well of test compound or DMSO blank are added to the assay plate. Substrate mix (50 μL; 0.5 mM pNP-AMP in phenol-red free 1640 media without FBS) was added for a pNP-AMP final concentration of 0.25 mM. The system was incubated at 37° C. for 3h. Release of para-nitrophenol was measured by absorbance at 405 nM on an Envision plate reader, and % Inhibition was calculated for each well as: (([max−min]−[test−min])/[max−min]. IC$_{50}$ values were calculated from concentration vs. % Inhibition data via a four-parameter variable slope model and converted to apparent $K_I$ ($K_{I,app}$) values via the Cheng/Prusoff Equation ($K_I$=IC$_{50}$/(1+[substrate]/$K_M$)). The known ENPP1 inhibitor 6-[(3-aminophenyl)methyl]-N,N,5-trimethyl-[1,2,4]triazolo[1,5-a]pyrimidin-7-amine has a $K_{I,app}$ of 1,400 nM in this assay. The following are the $K_{I,app}$ values for select compounds of this invention:

Results for biological assays are provided in Table 7. For Assay 1, $K_I$ values, A: ≥300 nM; B: <300 but>3 nM; C: ≤3 nM; for Assay 2, $K_{I,app}$ values, D: >10 nM; E: ≤10 nM. A more detailed and expanded summary of results for Assays 1 and 2 is provided below in Table 8.

TABLE 7

| Compound | Assay 1 | Assay 2 |
|---|---|---|
| 1 | C | E |
| 1a | B | |
| 1b | C | E |
| 2 | C | D |
| 3 | B | |
| 4 | A | |
| 5 | C | E |
| 8 | C | E |
| 8a | C | E |
| 8b | B | |
| 9 | C | D |
| 10 | B | D |
| 12 | C | D |
| 15 | B | |
| 16 | C | D |
| 16a | C | D |
| 16b | B | |
| 18 | B | |
| 26 | B | |
| 28 | C | E |
| 28a | C | E |
| 28b | B | |
| 29 | C | D |
| 29a | C | E |
| 29b | B | |
| 36 | C | E |
| 38 | B | |
| 39 | B | |
| 40 | B | |
| 41 | B | |
| 42 | B | |
| 43 | B | |
| 44 | B | |
| 45 | B | |
| 46 | B | |
| 47 | B | |
| 48 | C | |
| 49 | C | E |
| 49a | C | E |
| 49b | C | |
| 50 | C | D |

TABLE 7-continued

| Compound | Assay 1 | Assay 2 |
|---|---|---|
| 51 | B | |
| 52 | B | |
| 53 | C | E |
| 54 | C | D |
| 55 | C | |
| 57 | C | E |
| 59 | C | D |
| 60 | C | E |
| 61 | C | |
| 62 | C | |
| 63 | C | |
| 64 | C | E |
| 65 | B | |
| 66 | A | |
| 67 | A | |
| 68 | B | |
| 69 | B | |
| 70 | B | |
| 71 | B | |
| 72 | C | E |
| 73 | C | E |
| 74 | C | E |
| 74a | C | E |
| 74b | B | |
| 75 | C | D |
| 76 | C | D |
| 77 | C | |
| 78 | C | D |
| 79 | C | D |
| 80 | C | E |
| 80a | C | E |
| 80b | B | |
| 81 | C | D |
| 82 | C | D |
| 83 | C | |
| 84 | A | |

TABLE 8

| Compound | Assay 1 $K_I$ (nM) | Assay 2 $K_{I, app}$ (nM) |
|---|---|---|
| 1 | 0.109 | 7.47 |
| 1a | 13.4 | |
| 1b | 0.015 | 1.67 |
| 2 | 0.158 | 14.4 |
| 3 | 222 | |
| 4 | 537 | |
| 5 | 0.851 | 7.94 |
| 8 | 0.0718 | 7.79 |
| 8a | 0.054 | 9.73 |
| 8b | 13.4 | |
| 9 | 0.569 | 32.4 |
| 10 | 3.12 | 224 |
| 12 | 0.479 | 48.9 |
| 15 | 495 | |
| 16 | 0.0814 | 14.9 |
| 16a | 0.0627 | 11.9 |
| 16b | 3.17 | |
| 18 | 6.99 | |
| 26 | 13.6 | |
| 28 | <0.027 | 1.06 |
| 28a | 0.00806 | 0.56 |
| 28b | 10 | |
| 29 | 0.252 | 12.2 |
| 29a | 0.106 | 3.15 |
| 29b | 42.2 | |
| 36 | 0.512 | 5.68 |
| 38 | 37.9 | |
| 39 | 30.8 | |
| 40 | 27 | |
| 41 | 10.8 | |
| 42 | 4.05 | |
| 43 | 100 | |
| 44 | 23.2 | |
| 45 | 9.83 | |
| 46 | 40.6 | |
| 47 | 50.9 | |
| 48 | 2.65 | |
| 49 | 0.0621 | 4.7 |
| 49a | 0.0236 | 1.59 |
| 49b | 0.356 | |
| 50 | 0.254 | 15.7 |
| 51 | 5.56 | |
| 52 | 4.85 | |
| 53 | 0.0347 | 1.11 |
| 54 | 1.71 | 74.7 |
| 55 | 0.0295 | 1.65 |
| 57 | 0.06 | 9.59 |
| 59 | 0.165 | 11.5 |
| 60 | 0.0862 | 6.25 |
| 61 | 0.375 | |
| 62 | 0.19 | |
| 63 | 0.0363 | |
| 64 | 0.0667 | 4.41 |
| 65 | 181 | |
| 66 | >1500 | |
| 67 | 660 | |
| 68 | 200 | |
| 69 | 122 | |
| 70 | 179 | |
| 71 | 4 | |
| 72 | 0.0285 | 0.769 |
| 72a | 0.00881 | 0.505 |
| 72b | 0.982 | |
| 73 | 0.167 | 7.7 |
| 74 | 0.103 | 7.13 |
| 74a | 0.0523 | 1.34 |
| 74b | 9.97 | |
| 75 | 0.315 | 36.7 |
| 76 | 0.535 | 38.6 |
| 77 | 0.465 | |
| 78 | 0.265 | 24.1 |
| 79 | 2.86 | 74.4 |
| 80 | 0.0443 | 2.54 |
| 80a | 0.016 | 0.589 |
| 80b | 43 | |
| 81 | 0.817 | 13.5 |
| 82 | 1.16 | 69.9 |
| 83 | 0.0978 | |
| 84 | 672 | |
| 85 | 0.0287 | 0.724 |
| 85a | 0.00604 | 0.298 |
| 85b | 11.1 | |
| 86 | 0.138 | 8.29 |
| 87 | 0.0184 | 0.447 |
| 88 | 0.0267 | 0.322 |
| 88a | 0.00586 | 0.222 |
| 88b | >15 | |
| 89 | 28 | |

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiments, methods, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

What is claimed is:

1. A compound of Formula (I-4):

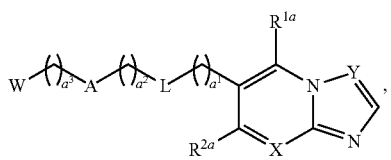

or a pharmaceutically acceptable salt thereof, wherein:
X is —N— or —CR$^{3a}$—;
Y is —N— or —CR$^{4a}$—;
R$^{1a}$ is hydrogen, halogen, cyano, C$_{1-3}$ alkyl, C$_{1-3}$ haloalkyl, —NR$^{1b}$R$^{2b}$, aryl, heteroaryl, cycloalkyl, cycloalkenyl, heterocycloalkyl, or heterocycloalkenyl, wherein the C$_{1-3}$ alkyl, aryl, heteroaryl, cycloalkyl, cycloalkenyl, heterocycloalkyl, or heterocycloalkenyl of R$^{1a}$ is optionally substituted, wherein the C$_{1-3}$ alkyl is optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, —NR$^{1a1}$R$^{1a2}$, —OR$^{1a3}$, —NR$^{1a4}$C(O)R$^{1a5}$, and —C(O)OR$^{1a6}$, wherein R$^{1a1}$-R$^{1a6}$ are each independently hydrogen or C$_{1-6}$ alkyl;
R$^{2a}$ is hydrogen, halogen, cyano, optionally substituted C$_{1-3}$ alkyl, C$_{1-3}$ haloalkyl, —NR$^{7b}$R$^{8b}$, cycloalkyl, or —OR$^{3b}$;
R$^{3a}$ is hydrogen, halogen, cyano, C$_{1-3}$ alkyl, C$_{1-3}$ haloalkyl, —NR$^{9b}$R$^{10b}$, cycloalkyl, or —OR$^{11b}$, wherein the C$_{1-3}$ alkyl is optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, —NR$^{3a1}$R$^{3a2}$, —OR$^{3a3}$, —NR$^{3a4}$C(O)R$^{3a5}$, and —C(O)OR$^{3a6}$, wherein R$^{3a1}$-R$^{3a6}$ are each independently hydrogen or C$_{1-6}$ alkyl;
R$^{4a}$ is hydrogen, halogen, cyano, C$_{1-3}$ alkyl, C$_{1-3}$ haloalkyl, —NR$^{12b}$R$^{13b}$, or —OR$^{14b}$, wherein the C$_{1-3}$ alkyl is optionally substituted with one, two, three, four, five, or more substituents selected from the group consisting of deuterium, halo, cyano, C$_{1-6}$ alkyl, C$_{6-14}$ aryl, 4- to 14-membered heteroaryl, C$_{3-10}$ cycloalkyl, C$_{3-10}$ cycloalkenyl, 3- to 18-membered heterocycloalkyl, 3- to 18-membered heterocycloalkenyl, —NR$^{4a1}$R$^{4a2}$, and —OR$^{4a3}$, wherein R$^{4a1}$-R$^{4a3}$ are each independently hydrogen or C$_{1-6}$ alkyl;
L is a bond, —O—, —NR$^{4b}$—, or —CR$^{5b}$R$^{6b}$—;
A is a bond, aryl, heteroaryl, cycloalkyl, cycloalkenyl, heterocycloalkyl, or heterocycloalkenyl, each of which is optionally substituted with one, two, three, four, five, or more substituents selected from the group consisting of deuterium, halo, cyano, C$_{1-6}$ alkyl, C$_{3-10}$ cycloalkyl, C$_{3-10}$ cycloalkenyl, 3- to 18-membered heterocycloalkyl, —NR$^{A1}$R$^{A2}$, —OR$^{A3}$, —NR$^{A4}$C(O)R$^{A5}$, and —C(O)OR$^{A6}$, wherein R$^{A1}$-R$^{A6}$ are each independently hydrogen or C$_{1-6}$ alkyl;
R$^{1b}$ and R$^{2b}$ are each independently hydrogen, optionally substituted C$_{1-3}$ alkyl, or cycloalkyl;
R$^{3b}$—R$^{14b}$ are each independently hydrogen or optionally substituted C$_{1-3}$ alkyl;
W is

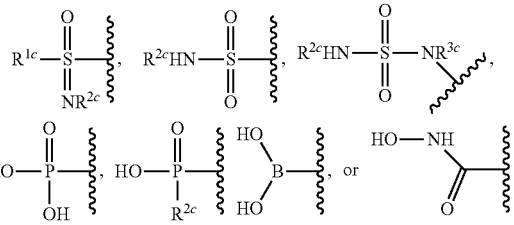

R$^{1c}$ is hydrogen, —NHR$^{1d}$, optionally substituted C$_{1-3}$ alkyl, C$_{1-3}$ haloalkyl, cycloalkyl, or heterocycloalkyl;
R$^{2c}$, R$^{3c}$, and R$^{1d}$ are each independently hydrogen or optionally substituted C$_{1-3}$ alkyl; and
a$^1$, a$^2$, and a$^3$ are each independently 0, 1, or 2,
wherein when A is a bond and L is a bond, then a$^1$ is 1 or 2; and
wherein when W is

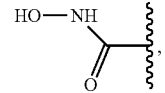

then A is not a bond and X is not CH.

2. The compound of claim 1, or a pharmaceutically acceptable salt thereof, wherein W is

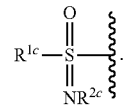

3. The compound of claim 2, or a pharmaceutically acceptable salt thereof, wherein R$^{1c}$ is methyl.

4. The compound of claim 1, or a pharmaceutically acceptable salt thereof, wherein W is

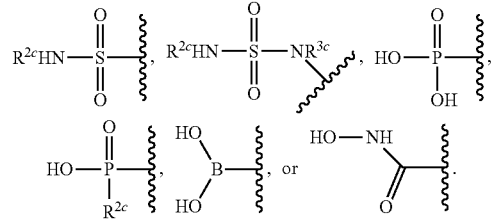

5. The compound of claim 1, or a pharmaceutically acceptable salt thereof, wherein X is —N—.

6. The compound of claim 1, or a pharmaceutically acceptable salt thereof, wherein X is —CR$^{3a}$—, wherein R$^{3a}$ is hydrogen or cyano.

7. The compound of claim 1, or a pharmaceutically acceptable salt thereof, wherein Y is —N—.

8. The compound of claim 1, or a pharmaceutically acceptable salt thereof, wherein Y is —CH—.

9. The compound of claim 1, or a pharmaceutically acceptable salt thereof, wherein $R^{1a}$ is —$NR^{1b}R^{2b}$.

10. The compound of claim 1, or a pharmaceutically acceptable salt thereof, wherein $R^{1a}$ is hydrogen, methyl,

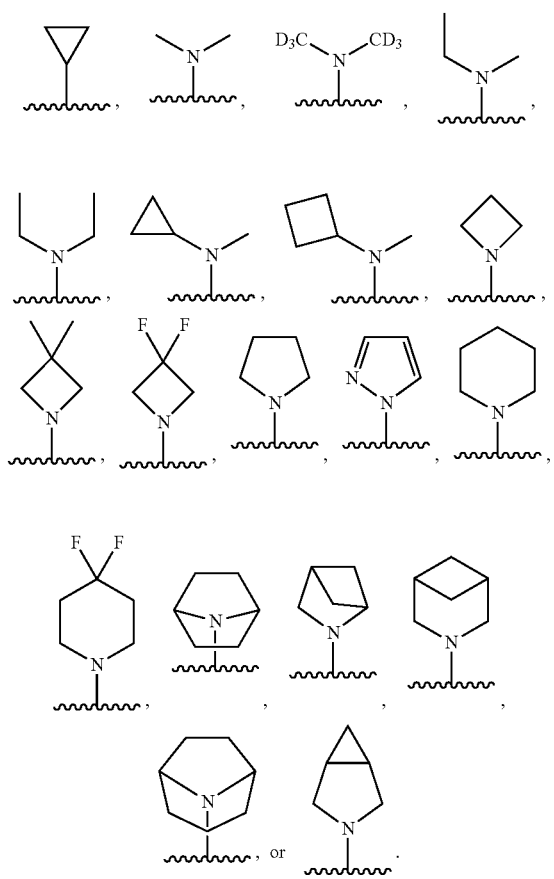

11. The compound of claim 1, or a pharmaceutically acceptable salt thereof, wherein $R^{1a}$ is

12. The compound of claim 1, or a pharmaceutically acceptable salt thereof, wherein $R^{2a}$ is hydrogen, methyl, ethyl, trifluoromethyl, cyclopropyl, chloro, cyano, dimethylamino, methoxy, or amino.

13. The compound of claim 1, or a pharmaceutically acceptable salt thereof, wherein $R^{2a}$ is methyl or methoxy.

14. The compound of claim 1, or a pharmaceutically acceptable salt thereof, wherein L is a bond.

15. The compound of claim 1, or a pharmaceutically acceptable salt thereof, wherein A is aryl or heterocycloalkyl, each of which is optionally substituted.

16. The compound of claim 1, or a pharmaceutically acceptable salt thereof, wherein A is

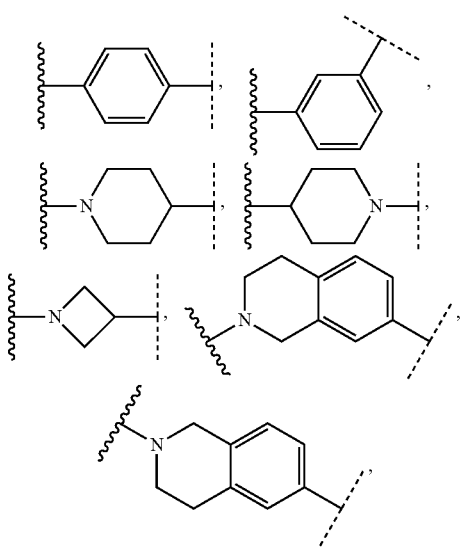

wherein ～～ denotes the point of attachment to

17. The compound of claim 1, or a pharmaceutically acceptable salt thereof, wherein A is

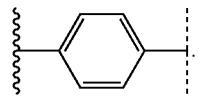

18. The compound of claim 1, or a pharmaceutically acceptable salt thereof, wherein $a^1$ is 1, $a^2$ is 0, and $a^3$ is 0; $a^1$ is 0, $a^2$ is 0, and $a^3$ is 2; $a^1$ is 0, $a^2$ is 0, and $a^3$ is 0; $a^1$ is 1, $a^2$ is 1, and $a^3$ is 2; or $a^1$ is 0, $a^2$ is 0, and $a^3$ is 1.

19. The compound of claim 1, or a pharmaceutically acceptable salt thereof, wherein the compound is selected from the group consisting of:

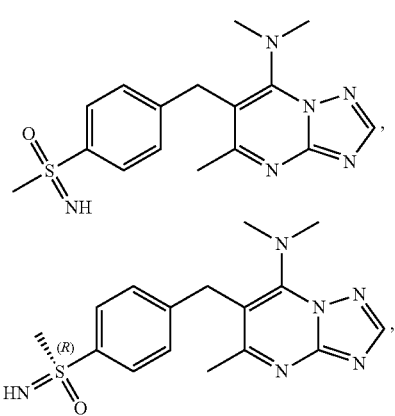

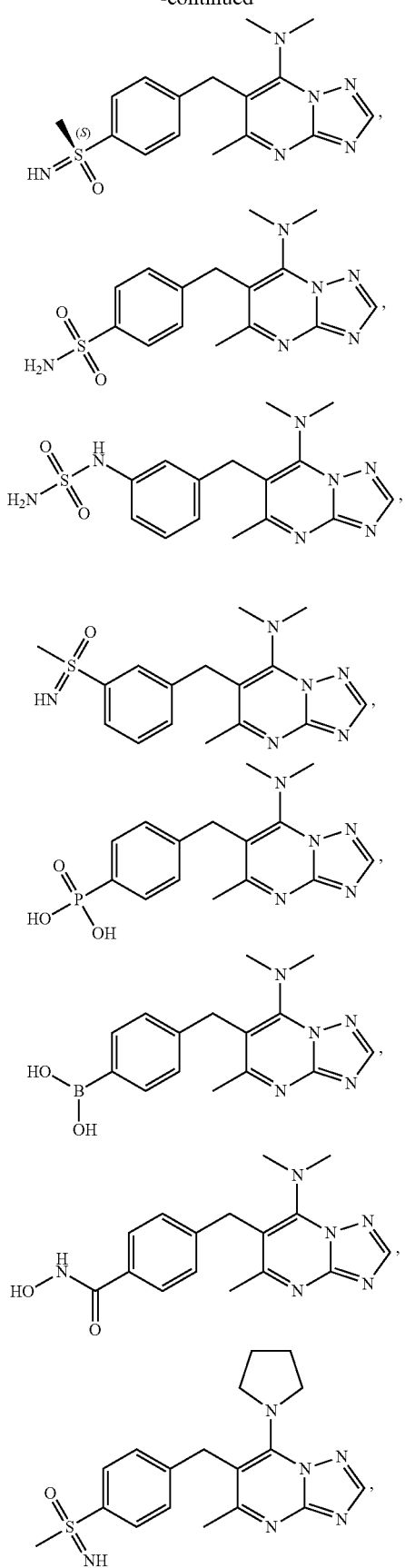
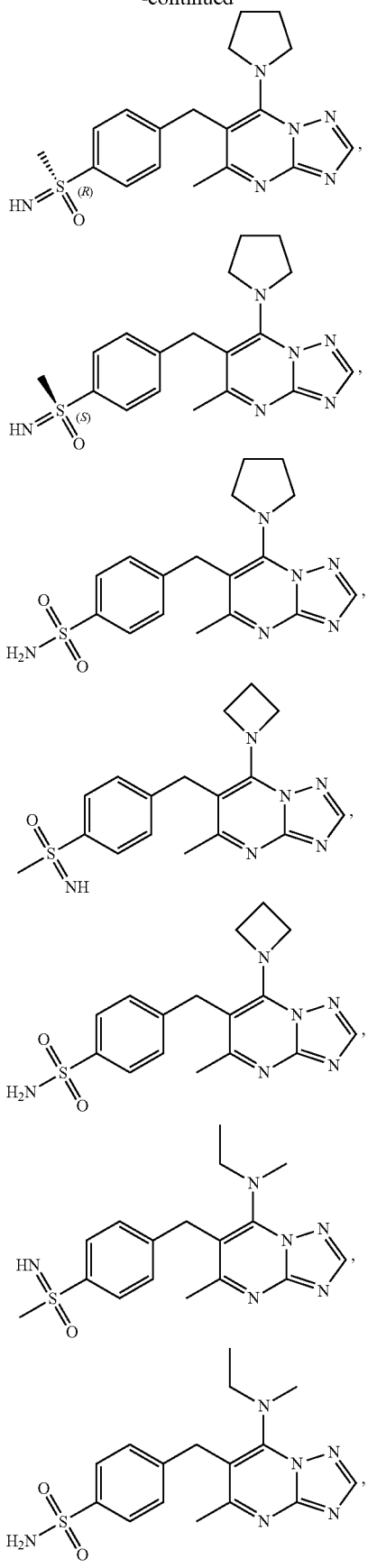

-continued
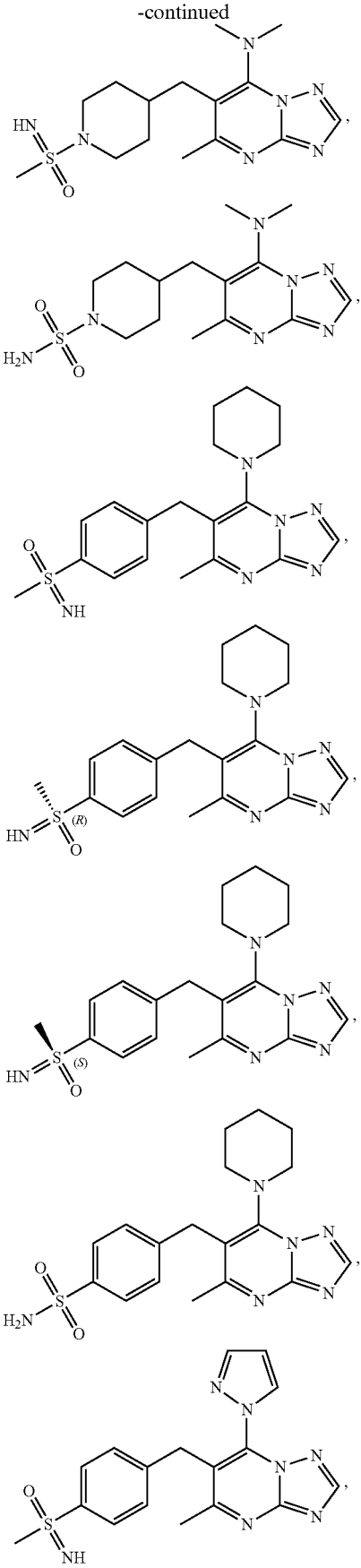
-continued
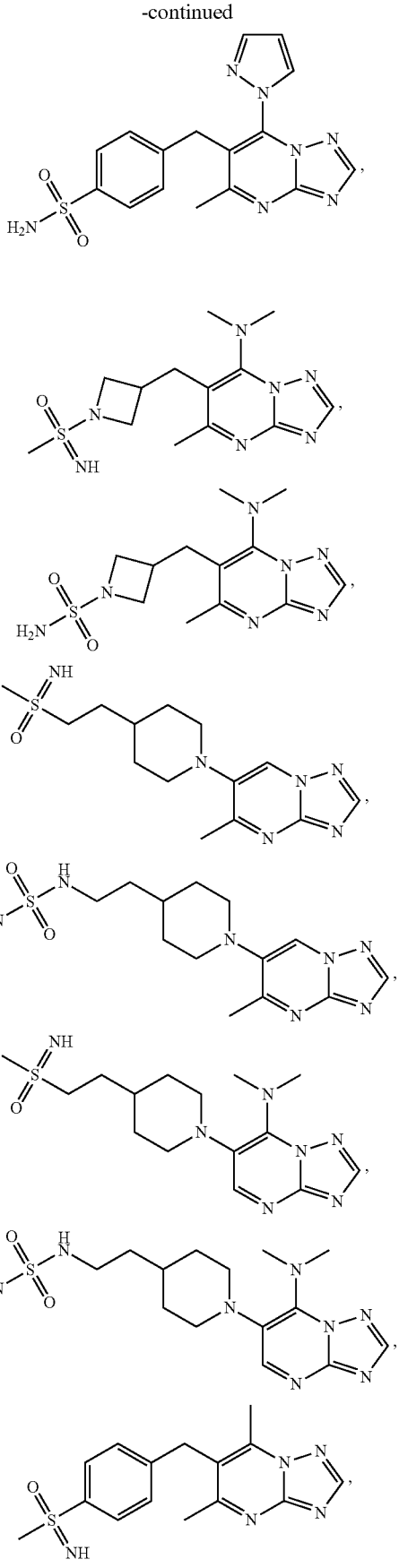

-continued
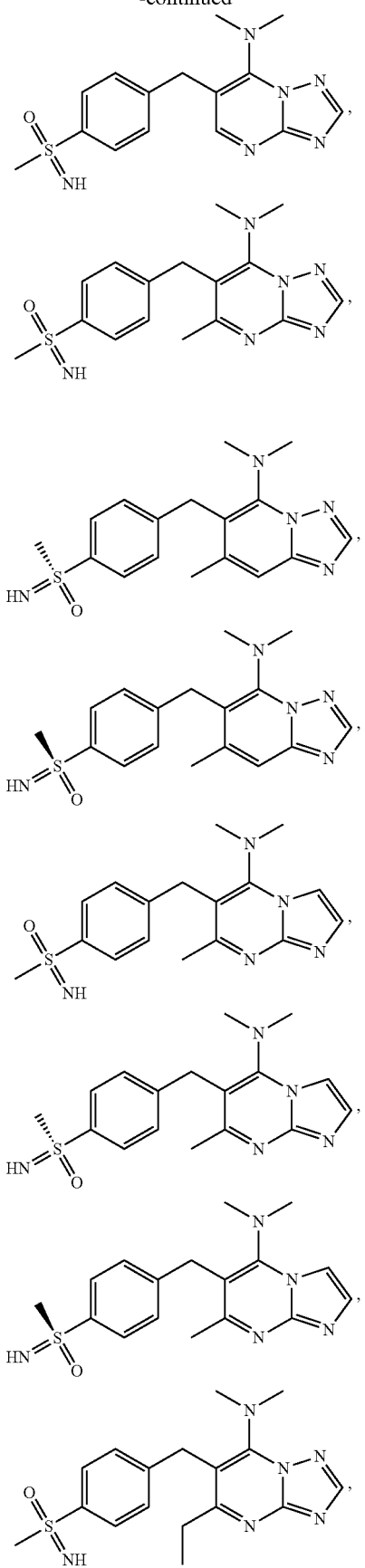
-continued
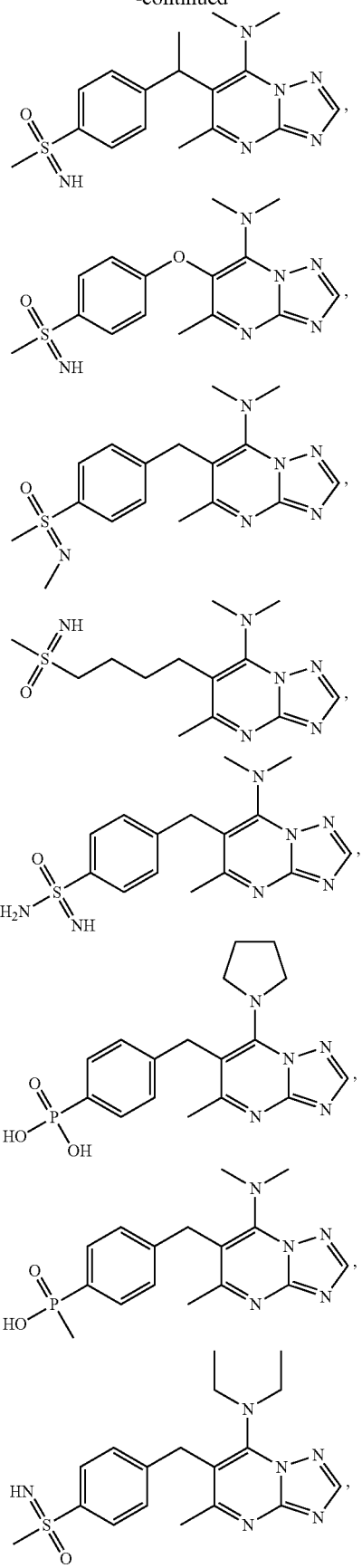

181
-continued
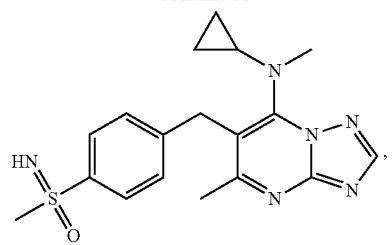
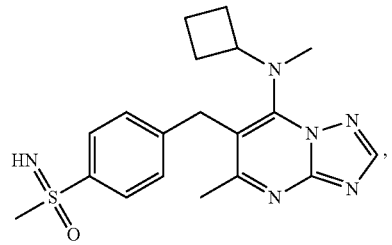
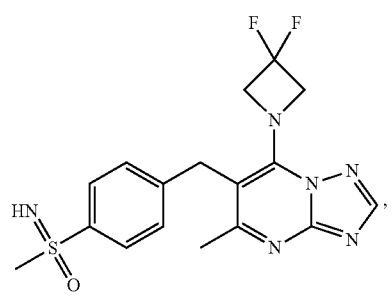
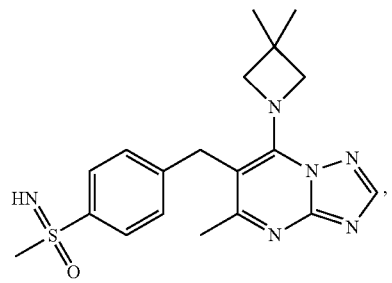
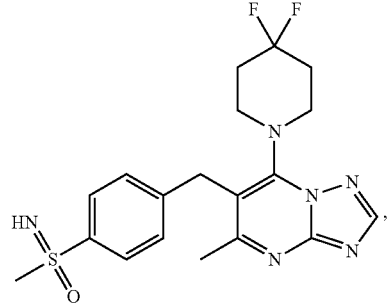
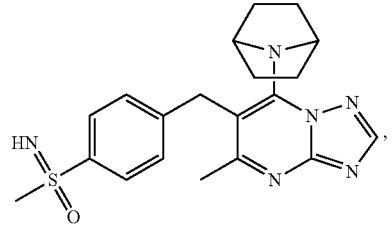
182
-continued
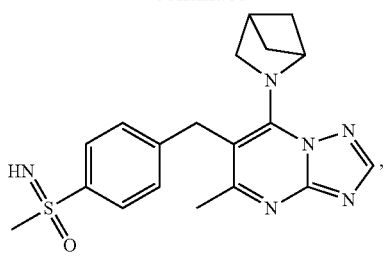
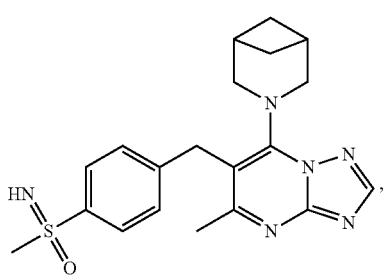
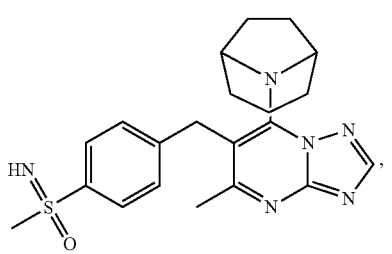
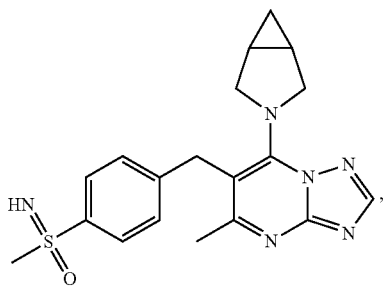
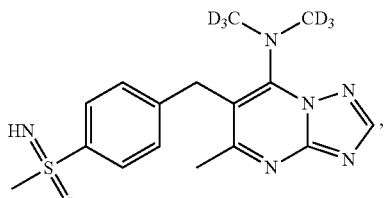
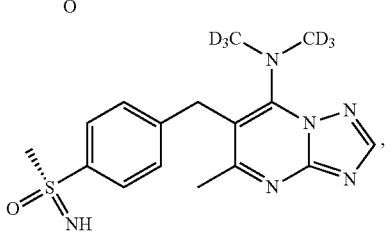
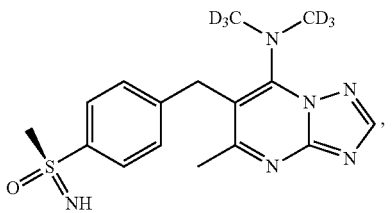

183
-continued
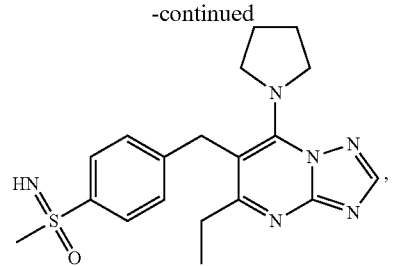
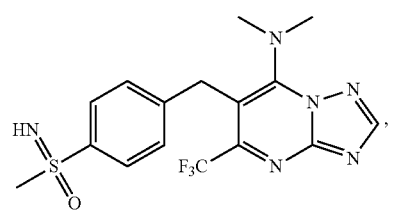
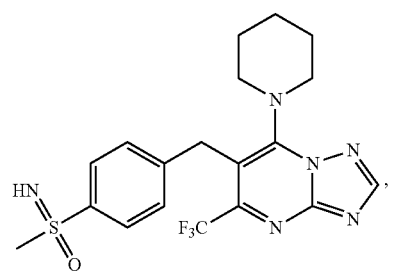
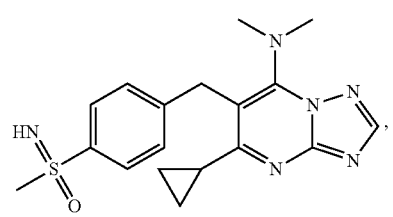
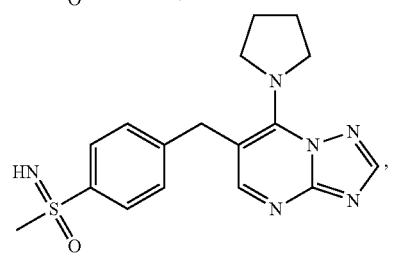
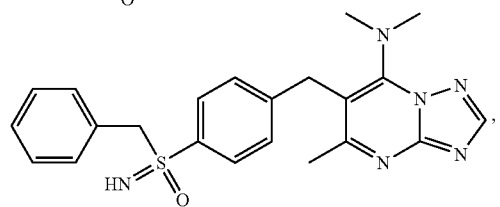
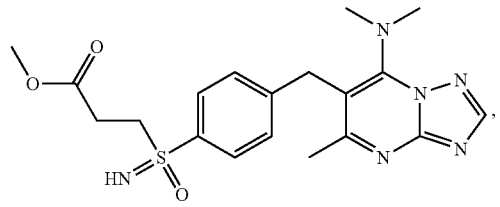
184
-continued
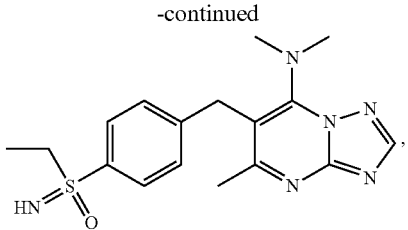
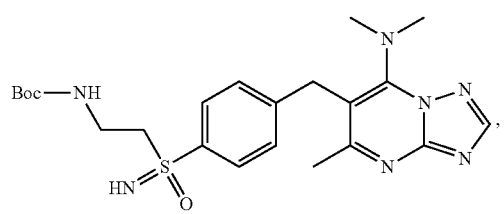
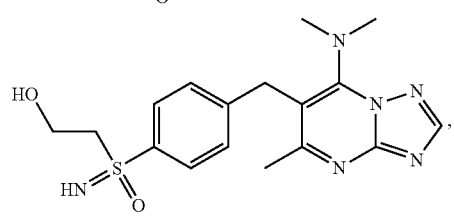
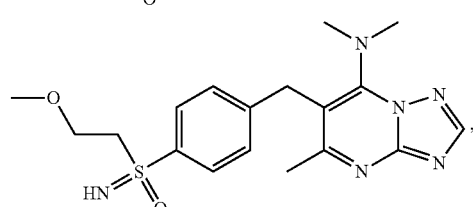
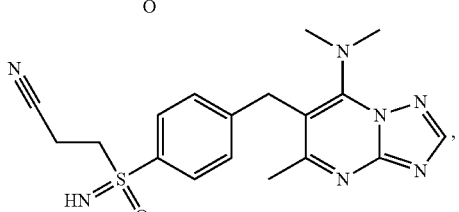
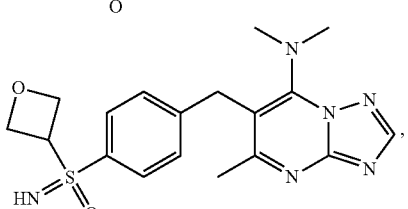
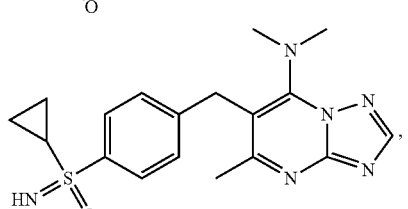
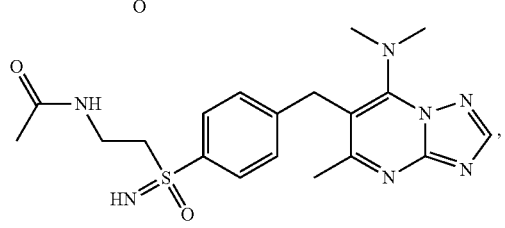

185
-continued
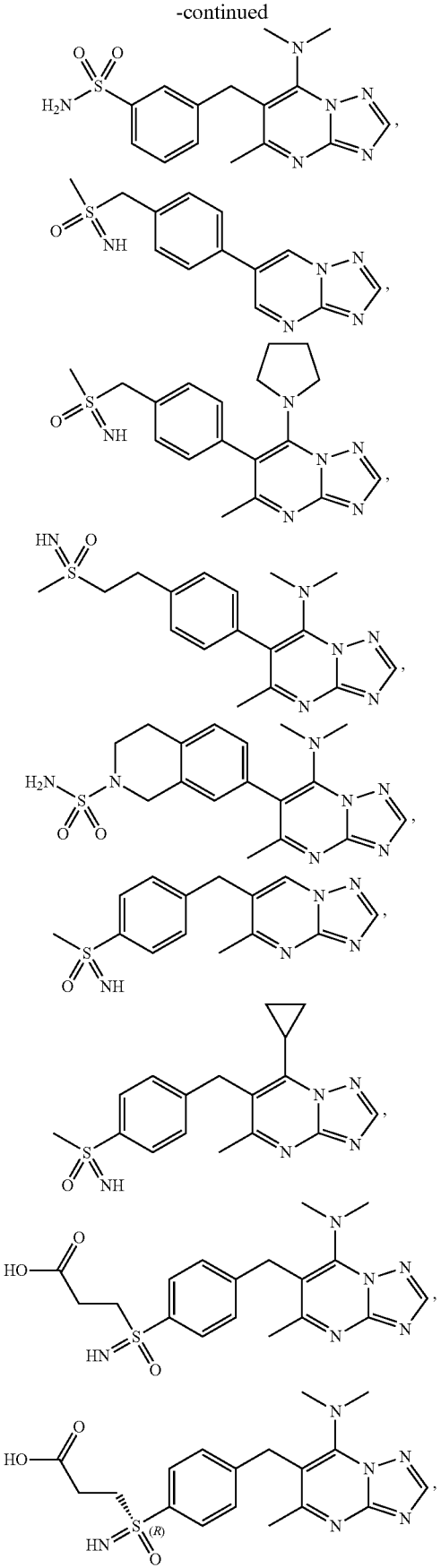
186
-continued
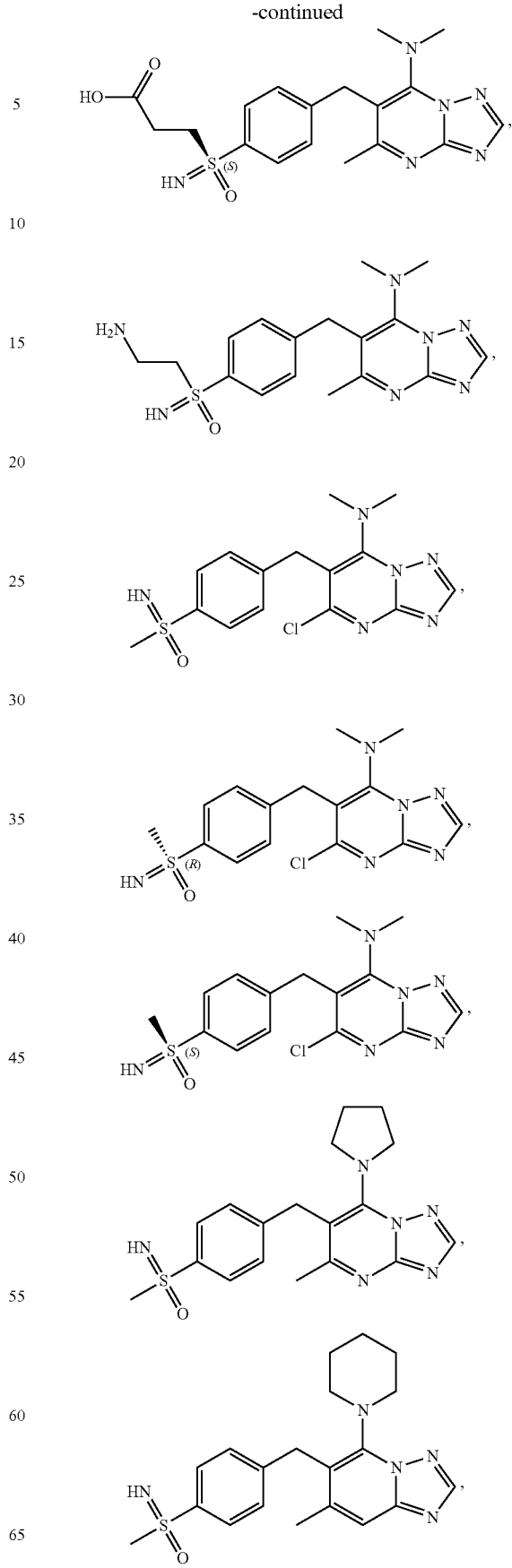

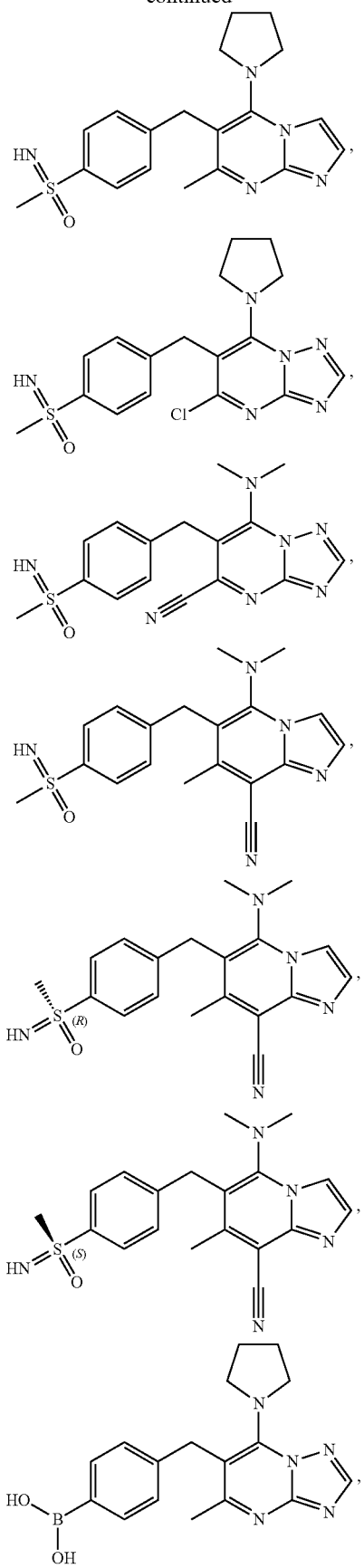
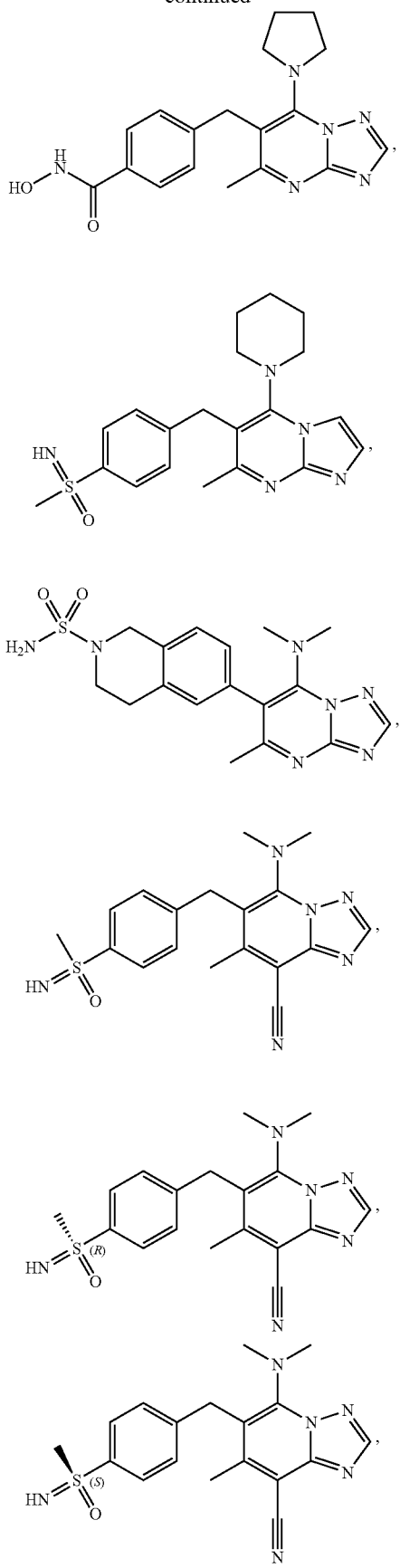

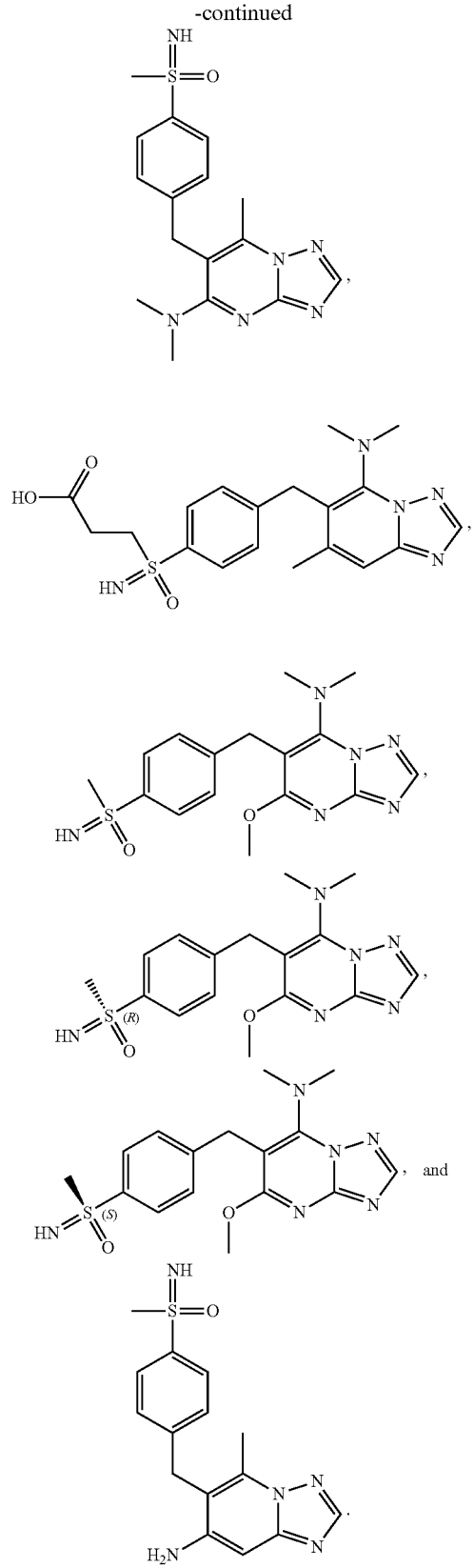
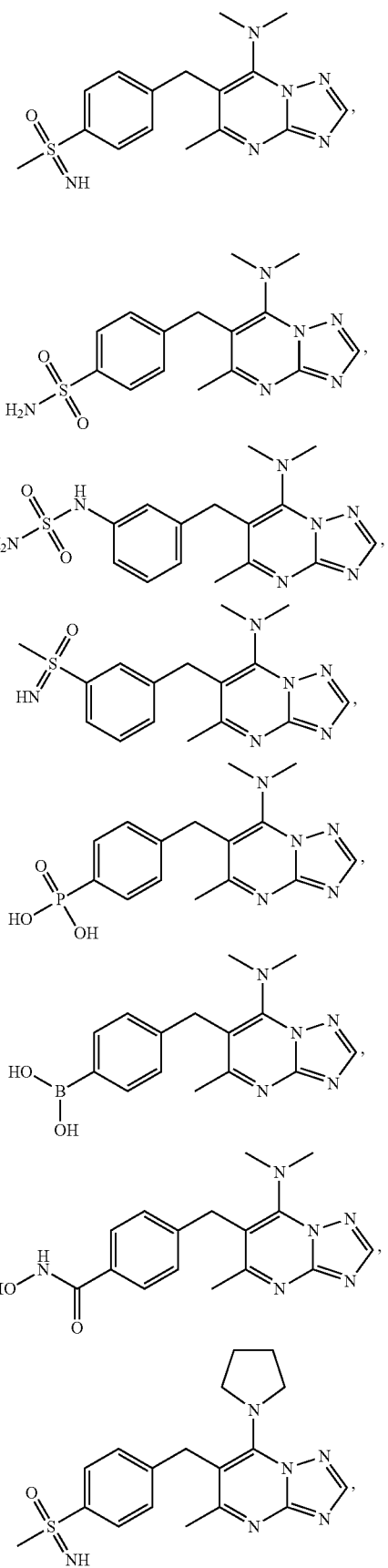
20. A compound, or a pharmaceutically acceptable salt thereof, wherein the compound is selected from the group consisting of:

191
-continued
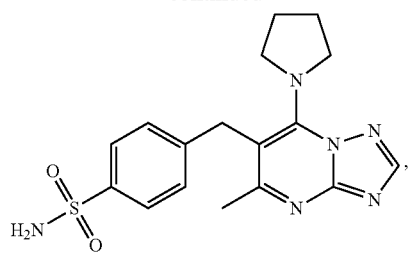
192
-continued
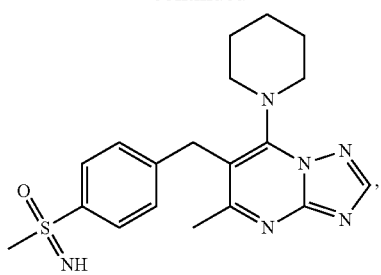
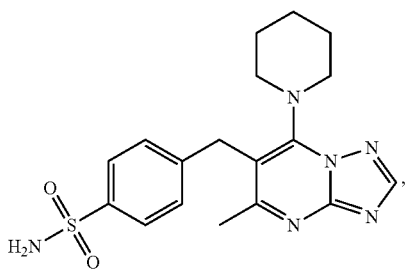
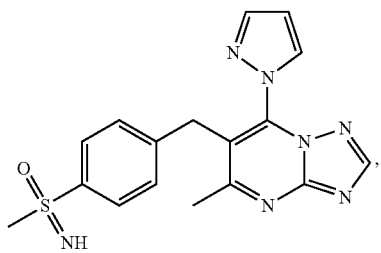
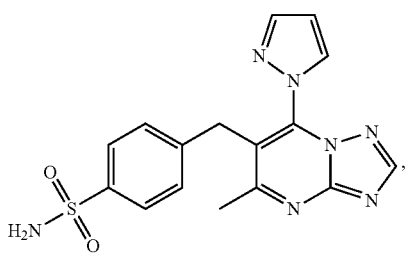
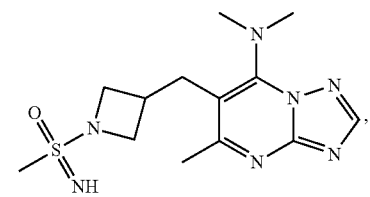
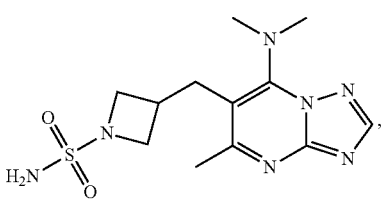
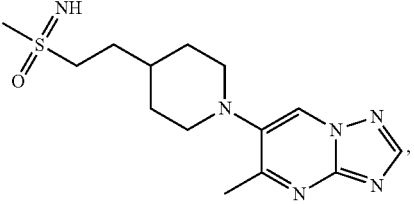

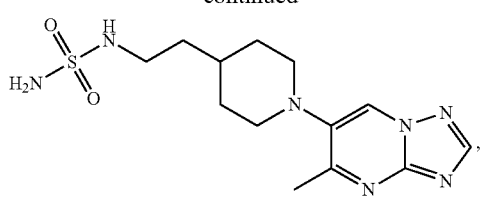
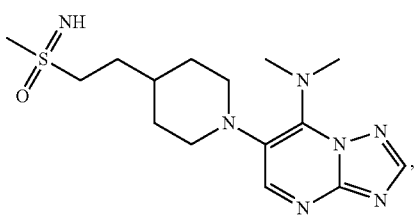
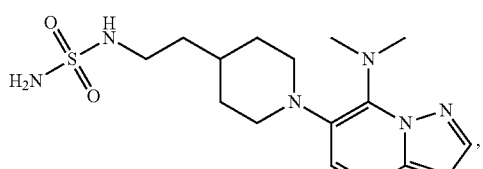
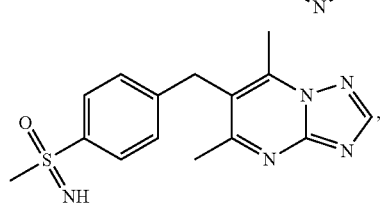
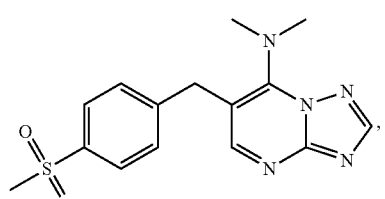
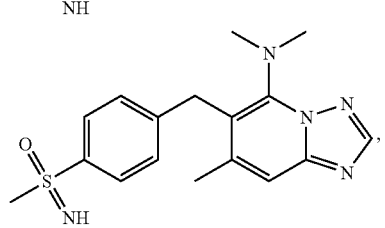
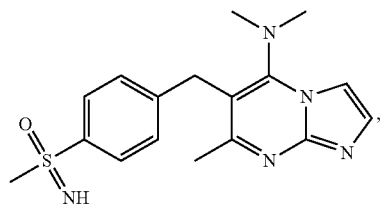
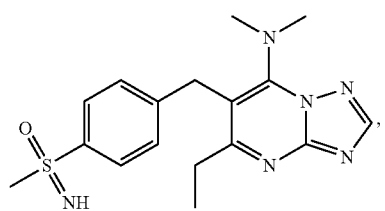
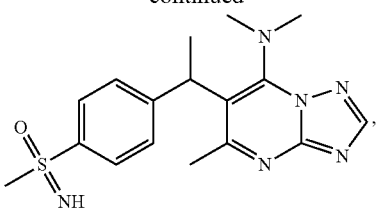
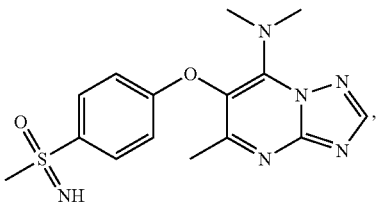
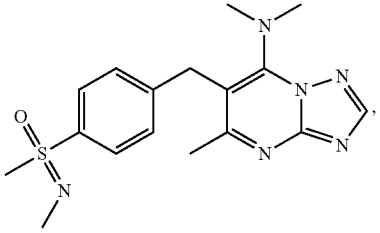
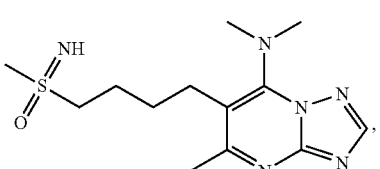
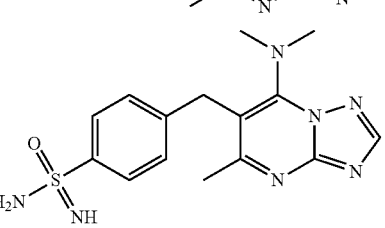
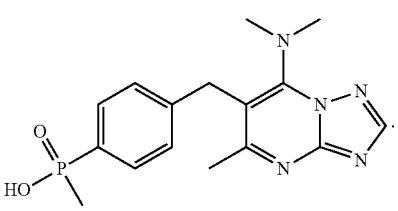
and
21. A compound, or a pharmaceutically acceptable salt thereof, wherein the compound is selected from the group consisting of:

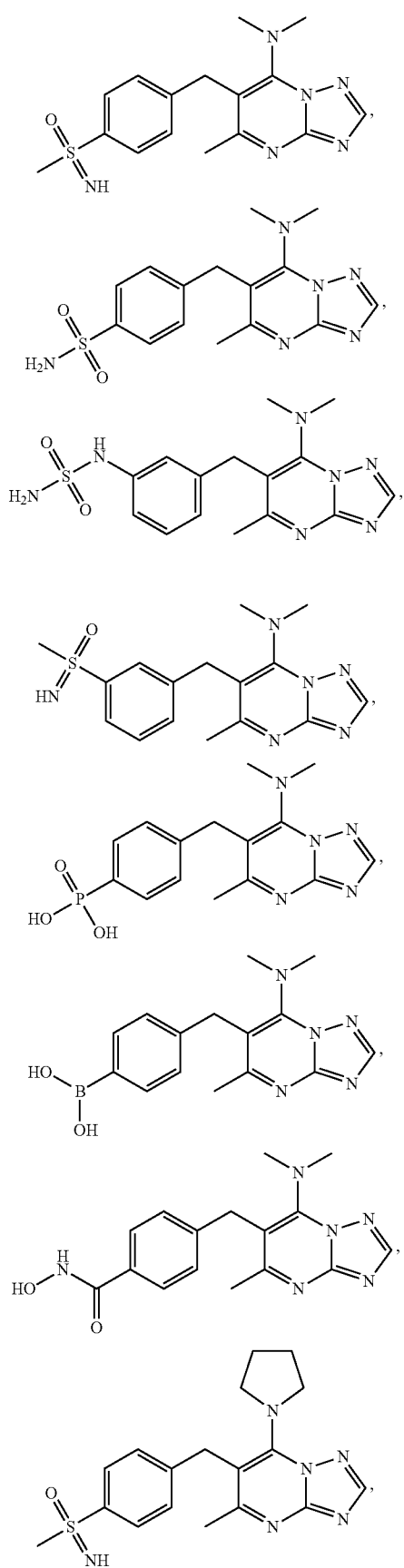
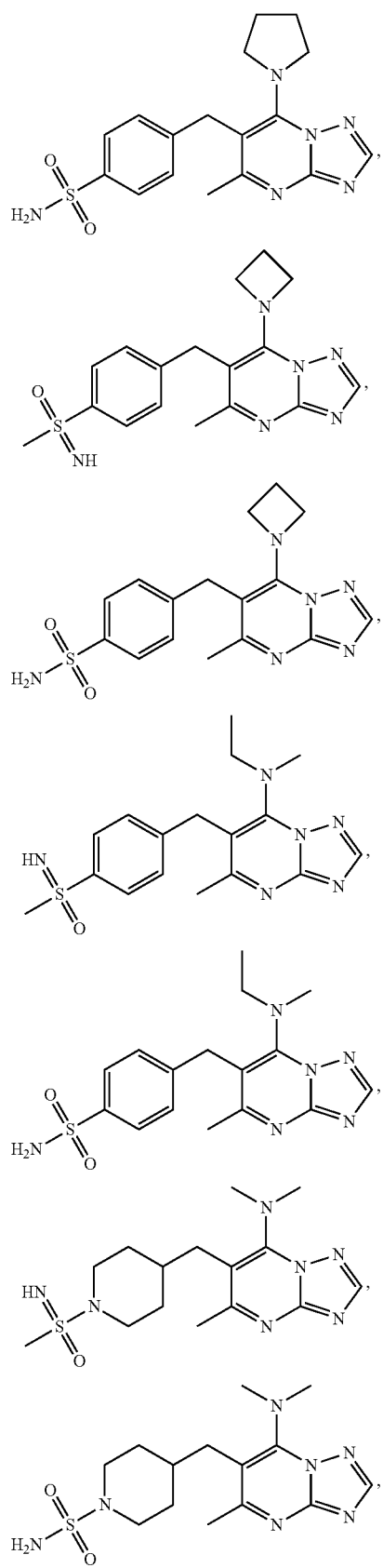

197
-continued
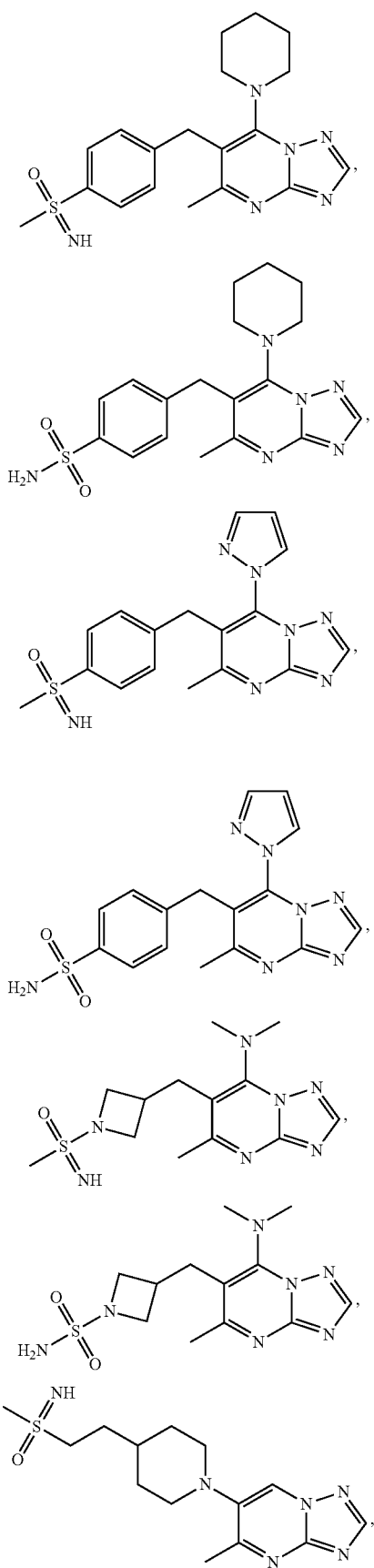
198
-continued
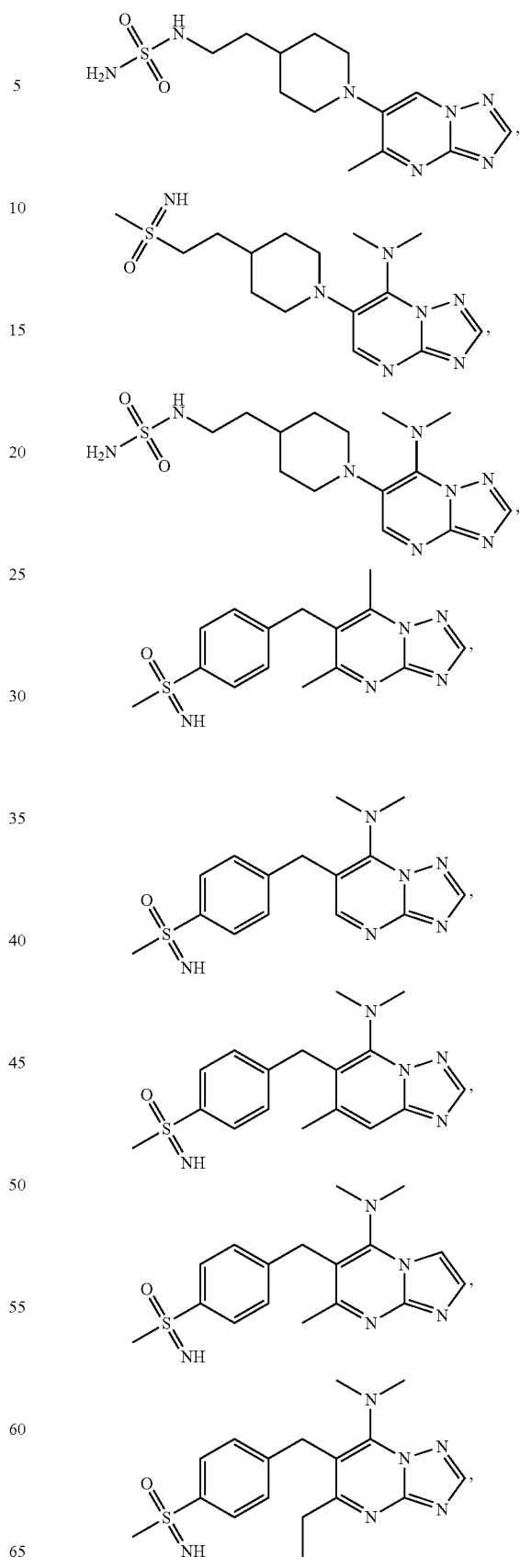

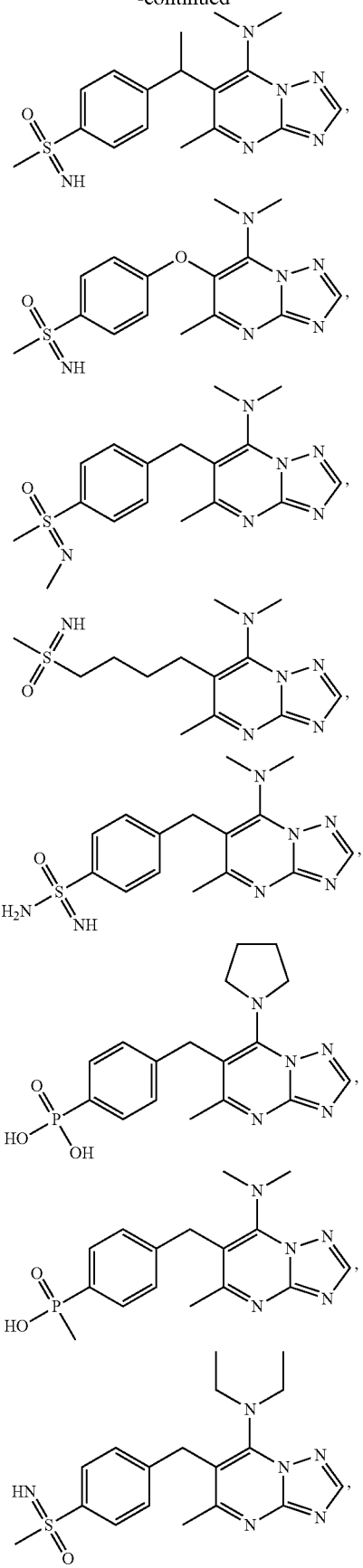
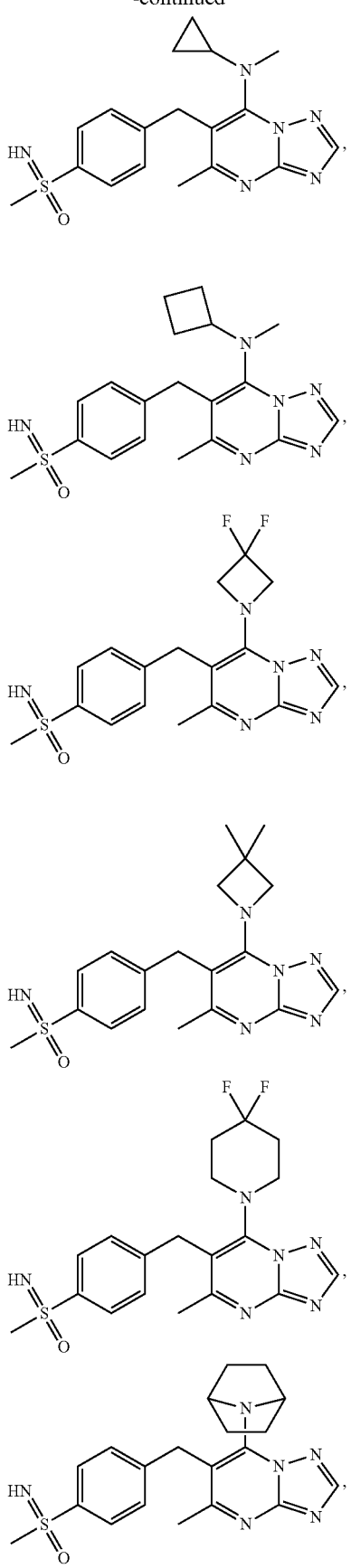

201
-continued
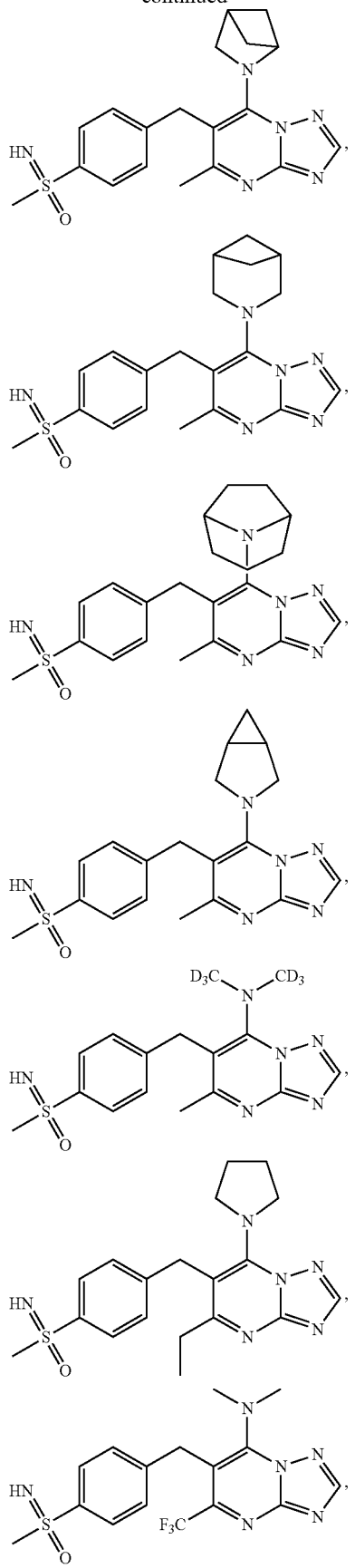
202
-continued
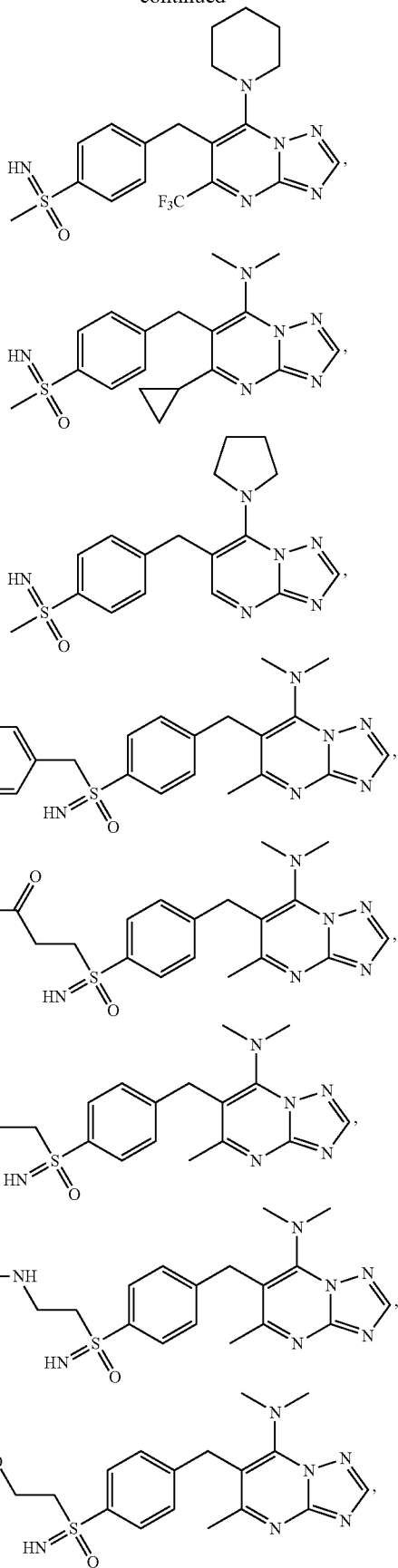

203
-continued
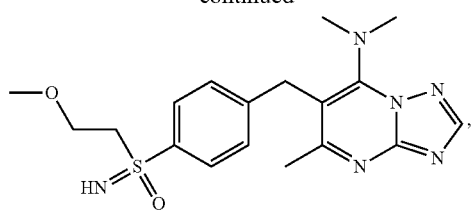
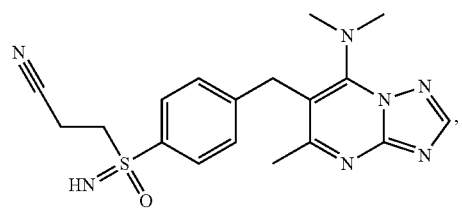
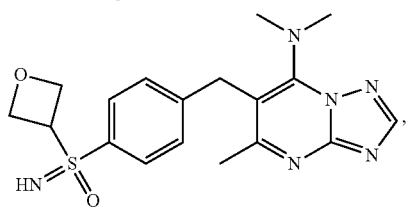
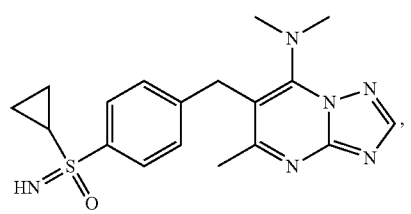
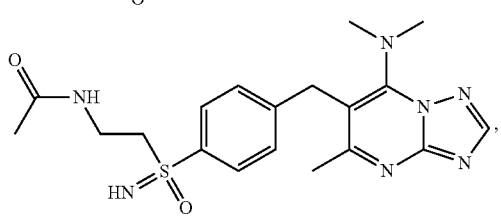
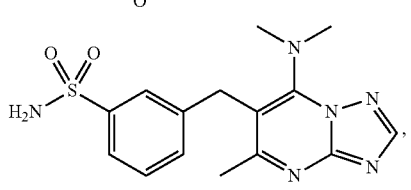
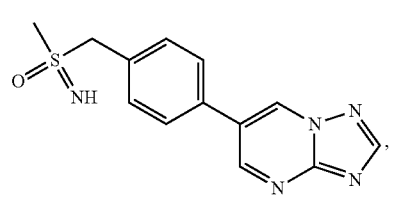
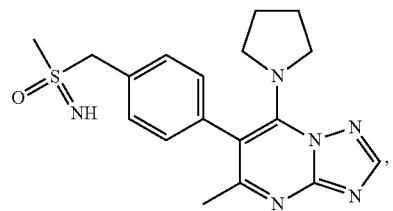
204
-continued
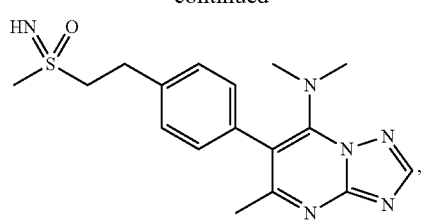
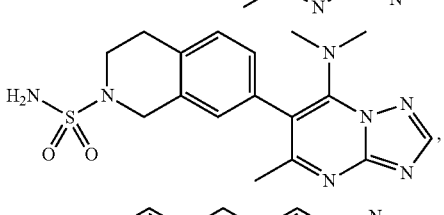
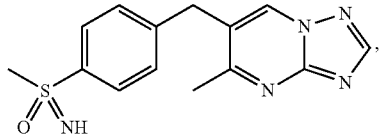
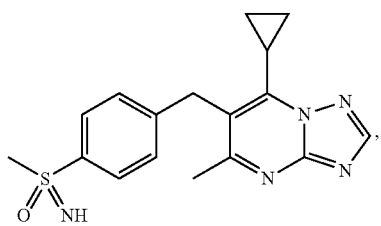
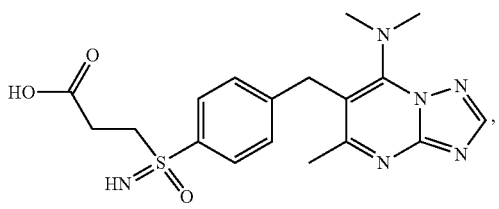
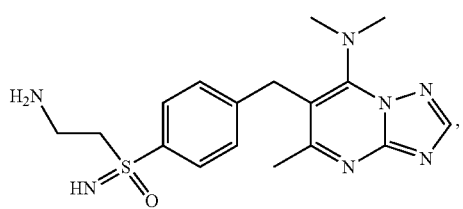
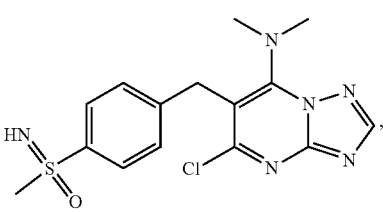
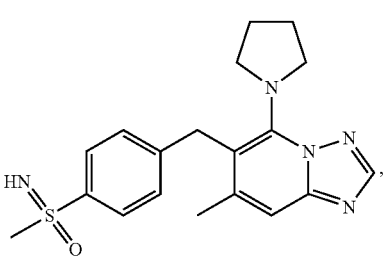

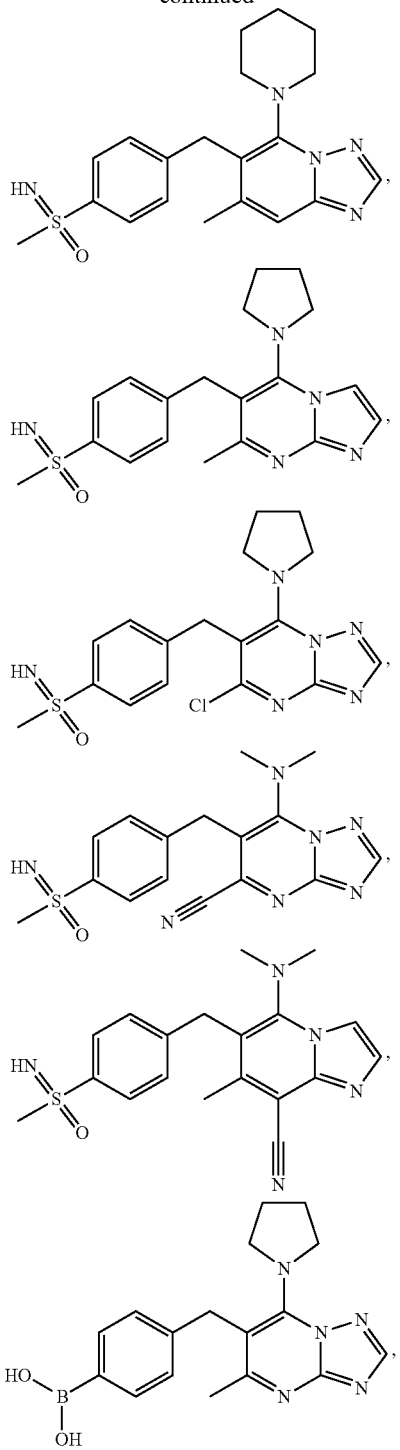

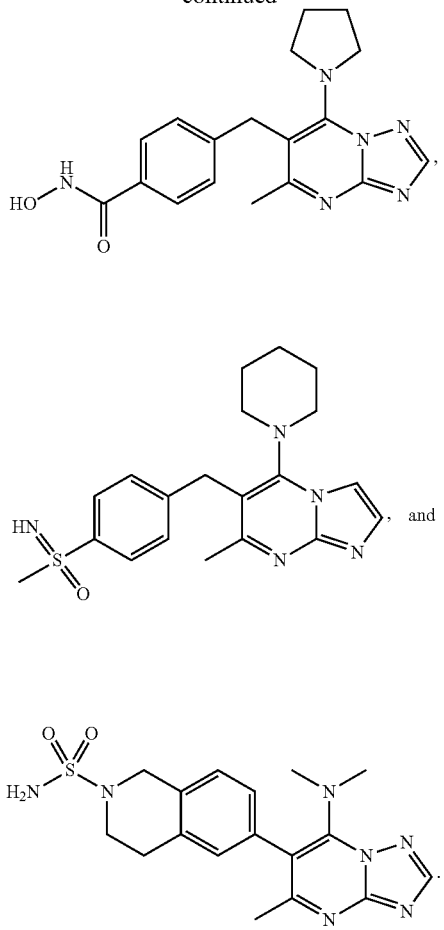

22. A pharmaceutical composition comprising a compound of claim 1, or a pharmaceutically acceptable salt thereof, and a pharmaceutically acceptable carrier or excipient.

23. A method of inhibiting ENPP1, the method comprising contacting a cell with an effective amount of a compound of claim 1, or a pharmaceutically acceptable salt thereof.

24. A method of treating chondrocalcinosis, calcium pyrophosphate deposition disorder (CPPD), or hypophosphatasia in a subject in need thereof, the method comprising administering to the subject a therapeutically effective amount of a compound of claim 1, or a pharmaceutically acceptable salt thereof.

* * * * *